US010022356B2

(12) United States Patent
Wang et al.

(10) Patent No.: US 10,022,356 B2
(45) Date of Patent: Jul. 17, 2018

(54) COMPOUNDS FOR TREATMENT OF CANCER

(71) Applicant: UNIVERSITY OF TENNESSEE RESEARCH FOUNDATION, Knoxville, TN (US)

(72) Inventors: Jin Wang, Memphis, TN (US); Jianjun Chen, Knoxville, TN (US); Duane D. Miller, Collierville, TN (US); Wei Li, Germantown, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 14/773,265

(22) PCT Filed: Mar. 5, 2014

(86) PCT No.: PCT/US2014/020858
§ 371 (c)(1),
(2) Date: Sep. 4, 2015

(87) PCT Pub. No.: WO2014/138279
PCT Pub. Date: Sep. 12, 2014

(65) Prior Publication Data
US 2016/0015688 A1 Jan. 21, 2016

Related U.S. Application Data

(60) Provisional application No. 61/772,885, filed on Mar. 5, 2013.

(51) Int. Cl.
| *A61K 31/42* | (2006.01) |
| *A61K 31/44* | (2006.01) |
| *A61K 31/335* | (2006.01) |
| *A61K 31/4178* | (2006.01) |
| *A61K 31/337* | (2006.01) |
| *A61K 31/437* | (2006.01) |
| *A61K 31/506* | (2006.01) |
| *A61K 31/519* | (2006.01) |
| *A61K 31/4174* | (2006.01) |
| *A61K 31/4164* | (2006.01) |
| *A61K 31/435* | (2006.01) |

(52) U.S. Cl.
CPC ........ *A61K 31/4178* (2013.01); *A61K 31/337* (2013.01); *A61K 31/4174* (2013.01); *A61K 31/437* (2013.01); *A61K 31/506* (2013.01); *A61K 31/519* (2013.01); *A61K 31/335* (2013.01); *A61K 31/4164* (2013.01); *A61K 31/42* (2013.01); *A61K 31/435* (2013.01)

(58) Field of Classification Search
CPC .... A61K 31/435; A61K 31/42; A61K 31/335; A61K 31/4164
USPC ................ 514/377, 379, 449, 300
See application file for complete search history.

(56) References Cited

U.S. PATENT DOCUMENTS

| 6,706,717 | B2 | 3/2004 | Barrish et al. |
| 8,822,513 | B2* | 9/2014 | Lu .......................... A61K 31/425 514/370 |
| 9,029,408 | B2* | 5/2015 | Miller ................... C07D 233/02 514/370 |
| 9,334,242 | B2* | 5/2016 | Lu ........................ A61K 31/425 |
| 9,447,049 | B2* | 9/2016 | Li ....................... A61K 31/4164 |
| 2003/0144329 | A1 | 7/2003 | Pfahl et al. |
| 2004/0192743 | A1 | 9/2004 | Mjalli |
| 2004/0248957 | A1 | 12/2004 | Lockhart |
| 2004/0267017 | A1 | 12/2004 | Bierer et al. |
| 2005/0131014 | A1 | 7/2005 | Collini et al. |
| 2006/0189618 | A1 | 8/2006 | Pelletier |
| 2006/0252793 | A1 | 11/2006 | Ameriks et al. |
| 2007/0155807 | A1 | 7/2007 | Miller et al. |
| 2008/0125418 | A1 | 5/2008 | Babin et al. |
| 2008/0146555 | A1 | 6/2008 | Caligiuri et al. |
| 2009/0326020 | A1 | 12/2009 | Miller et al. |
| 2011/0257196 | A1 | 10/2011 | Lu et al. |
| 2012/0053185 | A1 | 3/2012 | Coopersmith et al. |
| 2012/0071524 | A1 | 3/2012 | Lu et al. |
| 2012/0196879 | A1 | 8/2012 | Dumble et al. |
| 2013/0297049 | A1 | 11/2013 | Morita |

FOREIGN PATENT DOCUMENTS

| EP | 0 513 387 | 11/1992 |
| EP | 0 499 987 | 3/2000 |
| WO | WO 03/027085 | 4/2003 |
| WO | WO 2007096259 A1 * | 8/2007 ........... C07D 233/76 |

(Continued)

OTHER PUBLICATIONS

Li et al., "Orally Bioavailable Tubulin Antagonists for Paclitaxel-Refractory Cancer", Pharmaceutical Research, vol. 29, No. 11, pp. 3053-3063 (2012).*
Wang et al., "Novel Tubulin Polymerization Inhibitors Overcome Multidrug Resistance and Reduce Melanoma Lung Metastasis", Pharmaceutical Research, vol. 29, No. 11, pp. 3040-3052 (2012).*
International Search Report PCT/US14/20858 dated Jun. 23, 2014.
Lee, L et al. "The Safety, Pharmacokinetcs, and Pharmacodynamics of Single Oral Doses of RO5068760, and MEK inhibitor, in Healthy Volunteers; Assessment of Target Suppression" The Journal of Clinical Pharmacology [Abstract], 2010, vol. 50, Iss 12; pp. 1397-1405; [retrieved May 7, 2014]. Retrieved from the Internet: URL:http://onlinelibrary.wiley.com/dol/10.1177/0091270010361254/abstract:abstract.

(Continued)

Primary Examiner — Kevin E Weddington
(74) Attorney, Agent, or Firm — Mark S. Cohen; Pearl Cohen Zedek Latzer Baratz LLP

(57) ABSTRACT

The present invention relates to pharmaceutical compositions for treating cancer comprising BRAF inhibitors, (e.g. vemurafenib) and/or MEK inhibitor, (e.g. trametinib, RO5068760), in combination with anti-tubulin compounds of the invention or other known tubulin inhibitors, and using such compositions for treating cancer such as melanoma, drug-resistant cancer, and cancer metastasis.

4 Claims, 26 Drawing Sheets

(56) References Cited

FOREIGN PATENT DOCUMENTS

| WO | WO 2007/132867 | | 11/2007 |
|---|---|---|---|
| WO | WO 2008/038955 | | 4/2008 |
| WO | WO 2011/047238 | A1 | 4/2011 |
| WO | WO 2011/109059 | | 9/2011 |
| WO | WO 2012/135781 | | 4/2012 |
| WO | WO 2012/136776 | A1 | 10/2012 |
| WO | WO 2005/086902 | | 9/2015 |

OTHER PUBLICATIONS

Sapna P. Patel Et Al: "Clinical Responses to Selumetinib (Azd6244, Arry-142886)-Based Combination Therapy Stratified by Gene Mutations in Patients With Metastatic Melanoma", Cancer. , vol. 119, No. 4, Sep. 12, 2012 (Sep. 12, 2012), pp. 799-805.
N. K. Haass Et Al: "The Mitogen-Activated Protein/Extracellular Signal-Regulated Kinase Kinase Inhibitor Azd6244 (Arry-142886) Induces Growth Arrest in Melanoma Cells and Tumor Regression When Combined With Docetaxel". Clinical Cancer Research. vol. 14. No. 1. Jan. 1, 2008 (Jan. 1, 2008), pp. 230-239.
Anna Tesei Et Al: Ii Low-Dose Taxotere Enhances the Ability of Sorafenib to Induce Apoptosis in Gastric Cancer Models. Journal of Cellular and Molecular Medicine. Vo1. 15. No. 2. Feb. 1, 2011 (Feb. 1, 2011), pp. 316-326.
R. N. Amaria Et Al: "Therapeutic Options in Cutaneous Melanoma: Latest Developments". Therapeutic Advances in Medical Oncologyenglandjan 2016. Vo1. 3. No. 5. Sep. 1, 2011 (Sep. 1, 2011). pp. 245-225.
Jianjun Chen Et Al: "Discovery of Novel 2-Aryl-4-Benzoyl-Imidazole (Abi Iii) Analogues Targeting Tubulin Polymerization as Antiproliferative Agents". Journal of Medicinal Chemistry. Vo1. 55. No. 16. Aug. 23, 2012 (Aug. 23, 2012). pp. 7285-7289.
Chien-Ming Li Et Al: "Orally Bioavailable Tubulin Antagonists for Paclitaxel-Refractory Cancer". Pharmaceutical Research. Kluwer Academic Publishers-Plenum Publishers. NI. vol. 29. No. 11. Jul. 4, 2012 (Jul. 4, 2012). pp. 3053-3063.
J. Wang Et Al: "Synergistic Combination of Novel Tubulin Inhibitor Abi-274 and Vemurafenib Overcomes Vemurafenib Acquired Resistance in Brafv600e Melanoma". Molecular Cancer Therapeutics. vol. 13. No. 1. Nov. 18, 2013 (Nov. 18, 2013). pp. 16-26.
Greg Barsh Et Al: "Xviii Paspcr 2013 Advances in Melanocyte and Melanoma Biology President Local Organizing Committee Past-President and Ifpcs Representative" Uw Hospital & Clinics. Sep. 1, 2013 (Sep. 1, 2013). Retrieved From the Internet: Url:Http// Onlinelibrary.Wiley.Com/Store/10.1111 Retrieved on Feb. 13, 2014 p. 762-783.
Supplementary European Search Report for European Application No. 14760577.8 dated Dec. 14, 2016.
Office Action for Russian Application No. 2013112871 dated Jul. 28, 2015.
Office Action and English translation issued for Chinese application No. 201480025267.4 dated Oct. 21, 2016.
Bellina, F et al., Novel imidazole-based combretastatin A-4 analogues: Evaluation of their in vitro antitumor activity and molecular modeling study of their binding to the colchicine site of tubulin, Bioorganic & Medicinal Chemistry Letters 16, pp. 5757-5762, 2006.
Office Action and English translation issued for Chinese application No. 201480025267.4 dated Jun. 20, 2017.
International Search Report PCT/US15/29270 dated Sep. 21, 2015.
Office Action for corresponding U.S. Appl. No. 15/309,357 dated Jun. 21, 2017.
Lu et al, "Design, Synthesis, and Biological Evaluation of Stable Colchicine Binding Site Tubulin Inhibitors as Potential Anticancer Agents" Jornal of Medicinal Chemistry 2014, 57, pp. 7355-7366.
Office Action and English translation issued for Korean application No. 10-2016-7017425 dated Feb. 3, 2017.
Office Action and English translation issued for Chinese application No. 201410828197.8 dated Feb. 20, 2017.
Tucker, J. A. et al., "Structure-Activity Relationships of Acyloxyamidine Cytomegalovirus DNA Polymerase Inhibitors", Bioorganic and Medicinal Chemistry, 8, pp. 601-615, 2000.
Office Action corresponding Canadian application No. 2,728,118 dated Nov. 6, 2015.
Office Action corresponding to Indian application No. 8978/ DELNP/2010 dated Nov. 26, 2015.
Stenhagen et al. Studies of Hydrocarbons structurally related to Phthiocerol, Journal Biological Chemistry, 1950, vol. 183, pp. 223-229; p. 224.
Roy et al. Thiazole and oxazole peptides: biosynthesis and molecular machinery. Natural Product Reports, 1999, vol. 16, pp. 249-263; p. 249, scheme 1.
Office Action for corresponding Israel application No. 239672 dated Nov. 15, 2015.
Terasawa, K. "Cytotoxic Activity of 5-Benzoylimidazole and Related Compounds Against Human Oral Tumor Cell Lines" Anticancer Research (2001) 21:1081-1086.
European Search Report for European Application No. 15168526.0 dated Nov. 27, 2015.
Office Action for corresponding Australian application No. 2015227531 dated May 26, 2016.
Schubert et al: "Kristallin-flussige Hydroxypyrazine", Zeitschrift Fuer Chemie (Stuttgart) vol. 4, 1964, p. 228.
Mahboobi, S. et al., "Synthesis of Naturally Occurring Pyrazine and Imidazole Alkaloids from Botryllus", Monatshefte for Chemie, 135, pp. 333-342, 2004 Canada.
Khalili B et al: "Novel one-pot synthesis of (4 or 5)-aryl-2-aryloyl (1 H)-imidazoles in water and tauto-isomerization study using NMR", Tetrahedron, vol. 65, No. 34, Aug. 22, 2009, pp. 6882-6887.
Schubert H et al: "N-Alkyl-Uno N-Alkoxyderivate Des 3-Hydroxy-2,5 Diphenyld-Pyrazine", Journal Fuer Praktische Chemie (Leipzig) vol. 33, 1966, pp. 265-276.
Schubert et al: "Phasenbeziehungen zwischen imidazdylketonen und Hydroxypyrazinen", Journal Fuer Praktische Chemie (Leipzig) vol. 24, 1964, pp. 125-130.
Office Action European application No. 10 847 61.6 dated Jun. 16, 2016.
Office Action for corresponding JP Application No. 2015-561618 dated Nov. 21, 2017.
Patel et al. "Clinical Responses to Selumetinib (AZD6244; ARRY-142886)-Based Combination Therapy Startified by Gene Mutations in Patients With Metastatic Melanoma" Cancer, Feb. 2013, vol. 119, No. 4, pp. 799-805.
Haass et al. "The Mitogen-Activated Protein/Extracellular Signal-Regulated Kinase Kinase Inhibitor AZD6244 (ARRY-142886) Induces Growth Arrest in Melanoma Cells and Tumor Regression When Combined with Docetaxel" Clin. Cancer. Res., 2008, vol. 14(1), pp. 230-239.
Tesei et al. "Low-dose taxotere enhances the ability of sarafenib to induce apoptosis in gastric cancer models" J. Cell. Mol. Med., 2011, vol. 15(2), pp. 316-326.
Chen et al. "Discovery of Novel 2-Aryl-4-benzoyl (ABI-III) Analogues Targeting Tubulin Polymerization as Antiproliferative Agents" J. Med. Chem., 2012, vol. 55, pp. 7285-7289.
Wang et al. "Novel Tubulin Polymerization Inhibitors Overcome Multidrug Resistance and Reduce Melanoma Lung Metastasis" Pharm. Res., 2012, vol. 29(11), pp. 3053-3063.
Lee et al. "The Safety Tolerability, Pharmacokinetics,and Parmacodynamics of Single Oral Doses of RO5068760, an MEK Inhibitor, in Healthy Volunteers: Assessment of Target Suppression" J. Clin. Pharmacol., 2010, vol. 50, pp. 1397-1405.
Extended European Search Report Corresponding to EP patent No. 15789494.0 dated Dec. 8, 2017.
Yan Lu et al., "An Overview of Tubulin Inhibitors that Interact with the Colchicine Binding Site" Pharm Res 2012 pp. 2943-2971 Published online Jul. 20, 2017 Springer Science + Business Media, LLC.
Office Action for corresponding U.S. Appl. No. 15/270,359 dated Oct. 6, 2017.

* cited by examiner

Compound 12q

Compound 70a

Compound 70f

Compound 70m

A

B

C

A

B

C

D

COMPOUNDS FOR TREATMENT OF CANCER

FIELD OF THE INVENTION

The present invention relates to pharmaceutical compositions for treating cancer comprising BRAF inhibitors, (e.g. vemurafenib) and/or MEK inhibitor, (e.g. trametinib, RO5068760), in combination with anti-tubulin compounds of the invention or other known tubulin inhibitors, and using such compositions for treating cancer such as melanoma, drug-resistant cancer, and cancer metastasis.

BACKGROUND OF THE INVENTION

Cancer is the second most common cause of death in the United States, exceeded only by heart disease. In the United States, cancer accounts for 1 of every 4 deaths. The 5-year relative survival rate for all cancer patients diagnosed in 1996-2003 is 66%, up from 50% in 1975-1977 (*Cancer Facts & Figures* American Cancer Society: Atlanta, Ga. (2008)). The rate of new cancer cases decreased by an average 0.6% per year among men between 2000 and 2009 and stayed the same for women. From 2000 through 2009, death rates from all cancers combined decreased on average 1.8% per year among men and 1.4% per year among women. This improvement in survival reflects progress in diagnosing at an earlier stage and improvements in treatment. Discovering highly effective anticancer agents with low toxicity is a primary goal of cancer research.

Microtubules are cytoskeletal filaments consisting of αβ-tubulin heterodimers and are involved in a wide range of cellular functions, including shape maintenance, vesicle transport, cell motility, and division. Tubulin is the major structural component of the microtubules and a well verified target for a variety of highly successful anti-cancer drugs. Compounds that are able to interfere with microtubule-tubulin equilibrium in cells are effective in the treatment of cancers. Anticancer drugs like taxol and vinblastine that are able to interfere with microtubule-tubulin equilibrium in cells are extensively used in cancer chemotherapy.

Unfortunately, microtubule-interacting anticancer drugs in clinical use share two major problems, resistance and neurotoxicity.

Malignant melanoma is the most dangerous form of skin cancer, accounting for about 75% of skin cancer deaths. The incidence of melanoma is rising steadily in Western populations. The number of cases has doubled in the past 20 years. Around 160,000 new cases of melanoma are diagnosed worldwide each year, and it is more frequent in males and Caucasians. According to a WHO Report, about 48,000 melanoma-related deaths occur worldwide per year.

Currently there is no effective way to treat advanced/metastatic melanoma. It is highly resistant to current chemotherapy, radiotherapy, and immunotherapy. Advanced/metastatic melanoma has a very poor prognosis, with a median survival rate of 6 months and a 5-year survival rate of less than 5%.

Various chemotherapy agents are used, including dacarbazine (also termed DTIC), immunotherapy (with interleukin-2 (IL-2) or interferon (IFN)), as well as local perfusion, are used by different centers. The overall success in metastatic melanoma is quite limited. IL-2 (Proleukin) is the first new therapy approved for the treatment of metastatic melanoma in 20 years. However, it provides only less than 5% of complete remission in patients. In recent years, great efforts have been attempted in fighting advanced melanoma. Neither combinations of DTIC with other chemotherapy drugs (e.g., cisplatin, vinblastine, and carmustine) nor adding interferon-α2b to DTIC have shown a survival advantage over DTIC treatment alone. Most recently, clinical trials with antibodies and vaccines to treat advanced melanoma also failed to demonstrate satisfactory efficacy. Ipilimumab (Yervoy®) is a drug that uses your immune system to fight melanoma. Ipilimumab is used to treat advanced melanoma that has spread beyond its original location. Targeted therapy uses medications designed to target specific vulnerabilities in cancer cells.

The discovery of the BRAF mutation in ~60% of melanoma patients and the FDA approved BRAF inhibitors (BRAFi; e.g. vemurafenib and dabrafenib (GSK2118436)) and a MEK inhibitor (MEKi; e.g. trametinib (GSK1120212), RO5068760) have shown impressive clinical responses in the treatment of $BRAF^{V600}$ mutant melanomas. The upfront use of BRAFi+MEKi combination is highly effective during initial therapy, but due to tumor heterogeneity and activations of alternative pathways, resistance develops within ~9 months leading to recurrent disease and death of patients.

Vemurafenib (Zelboraf®) is a targeted therapy approved to treat advanced melanoma that cannot be treated with surgery or melanoma that has spread through the body. With regard to melanoma, vemurafenib only treats tumors that have a certain genetic mutation ($BRAF^{V600}$). Likewise, vemurafenib and other BRAF inhibitors may be active in a variety of BRAF mutant cancers. Examples in which B-RAF is mutated at a high frequency include melanoma (30-60%), thyroid cancer (30-50%), colorectal cancer (5-20%), ovarian cancer (~30%), and other cancers (1-3%) (Wellbrock C, Karasarides M, Marais R. "The Raf Protein Takes Centre Stage". *Nat. Rev.* (2004) 5: 875-885).

The sustained clinical activity of vemurafenib in patients with $BRAF^{V600}$ mutant melanoma is limited by the rapid development of acquired resistance (Lee J T, Li L, Brafford P A, et al. "PLX4032, a potent inhibitor of the B-Raf V600E oncogene, selectively inhibits V600E-positive melanomas." *Pigment Cell Melanoma Res*. (2010) 23: 820-827; Yang H, Higgins B, Kolinsky K, et al. "RG7204 (PLX4032), a selective BRAFV600E inhibitor, displays potent antitumor activity in preclinical melanoma models". *Cancer Res.* (2010) 70: 5518-5527; Yang H, Higgins B, Kolinsky K, et al. "Antitumor activity of BRAF inhibitor vemurafenib in pre-clinical models of BRAF-mutant colorectal cancer". *Cancer Res*. (2012) 72: 779-789.). The mechanisms of resistance development have been widely investigated (Little A S, Smith P D, Cook S J. "Mechanisms of acquired resistance to ERK1/2 pathway inhibitors". *Oncogene* (2013) 32(10): 1207-1215; Bollag G, Hirth P, Tsai J, et al. "Clinical efficacy of a RAF inhibitor needs broad target blockade in BRAF-mutant melanoma". *Nature* (2010) 467: 596-599; Flaherty K T. "Targeting metastatic melanoma". *Annu Rev Med*. (2012) 63: 171-183; Su F, Bradley W D, Wang Q, et al. "Resistance to selective BRAF inhibition can be mediated by modest upstream pathway activation". *Cancer Res*. (2012) 72: 969-978.). Many different mechanisms have been proposed in the literature, including intrinsic resistance to BRAFi, the amplification of the BRAF oncogene (Shi H, Moriceau G, Kong X, et al. "Melanoma whole-exome sequencing identifies (V600E)B-RAF amplification-mediated acquired B-RAF inhibitor resistance." *Nat. Commun*. (2012) 3: 724), up-regulation or activating mutations of downstream MEK kinases, the upregulation of CRAF expression (Montagut C, Sharma S V, Shioda T, et al. "*Elevated CRAF as a potential mechanism of acquired resistance to BRAF inhibition in melanoma*". *Cancer Res*. (2008) 68: 4853-4861), oncogenic activation of NRAS (Nazarian R, Shi H, Wang Q, et al. "Melanomas acquire resistance to B-RAF(V600E) inhibition by RTK or N-RAS upregulation". *Nature* (2010) 468: 973-977), up-regulated EGFR-SFK-STAT3 pathway (Girotti M R, Pedersen M, Sanchez-Laorden B, et al. "Inhibiting EFG receptor or SRC family kinase signaling overcomes BRAF inhibitor resistance in melanoma." *Cancer Discov.* (2013) 3(2): 158-167), gatekeeper mutations (Whittaker S, Kirk R, Hayward R, et al. "Gatekeeper mutations mediate resistance to BRAF-targeted therapies." *Sci. Transl. Med.* (2010) 2: 35ra41; Balzano D, Santaguida S, Musacchio A, Villa F. "A general framework for inhibitor resistance in protein kinases." *Chem. Biol.* (2011) 18: 966-975; Sierra J R, Cepero V, Giordano S. "Molecular mechanisms of acquired resistance to tyrosine kinase targeted therapy." *Mol. Cancer* (2010) 9: 75), upregulation of growth factor receptors such as insulin-like growth factor 1 receptor (IFG1R)(Villanueva J, Vultur A, Lee J T, et al. "Acquired resistance to BRAF inhibitors mediated by a RAF kinase switch in melanoma can be overcome by cotargeting MEK and IGF-1R/PI3K". *Cancer Cell* (2010) 18: 683-695) or platelet-derived growth factor receptor (PDGFR), and several other resistance mechanisms (Wilson T R, Fridlyand J, Yan Y, et al. "Widespread potential for growth-factor-driven resistance to anti-cancer kinase inhibitors". *Nature* (2012) 487: 505-509; Straussman R, Morikawa T, Shee K, et al. "Tumour microenvironment elicits innate resistance to RAF inhibitors through HGF secretion". *Nature* (2012) 487: 500-504). Several methods to maintain phosphorylated extracellular-signal-related kinase 1 and 2 (p-ERK1/2) levels in the presence of BRAF inhibitor drugs have been described, including ERKkinase 1 (MEK1) mutation, recruitment of alternative MEK1/2 activators, RAS mutation or up-regulation of receptor tyrosine kinases (RTKs). Thus in many cases, vemurafenib-resistant cells are cross-resistant to MEK inhibitors (Little A S, Smith P D, Cook S J. "Mechanisms of acquired resistance to ERK1/2 pathway inhibitors". *Oncogene* (2013) 32(10): 1207-1215; Atefi M, von Euw E, Attar N, et al. "Reversing melanoma cross-resistance to BRAF and MEK inhibitors by co-targeting the AKT/mTOR pathway." *PLoS One* (2011) 6: e28973; Poulikakos P I, Persaud Y, Janakiraman M, et al. "RAF inhibitor resistance is mediated by dimerization of aberrantly spliced BRAF (V600E)" *Nature* (2011) 480: 387-390). Because one of the major acquired vemurafenib-resistant mechanisms is sustained downstream MEK/ERK activation, the combination of BRAFi+MEKi that target elements within the RAF-MEK-ERK pathway has attracted the most attention leading to FDA approval of dabrafenib+trametinib combination in 2013. However, due to tumor heterogeneity and activations of alternative pathways in melanoma, resistance to this combination treatment develops in an average of 9.4 months, and it has little clinical activity once resistance develops.

Drug combination using agents with distinct anti-cancer mechanisms can enhance tumor response and patient survival, especially in the treatment of advanced cancer patients (Carrick S, Parker S, Wilcken N, et al. "Single agent versus combination chemotherapy for metastatic breast cancer". *Cochrane Database Syst. Rev.* 2005: CD003372; Fassnacht M, Terzolo M, Allolio B, et al. "Combination chemotherapy in advanced adrenocortical carcinoma". *N. Engl. J. Med.* (2012) 366: 2189-2197; Pannu V, Karna P, Sajja H K, et al. "Synergistic antimicrotubule therapy for prostate cancer". *Biochem. Pharmacol.* (2011) 81: 478-487). Although the combinations of vemurafenib with agents targeting the same mitogen-activated protein kinase (MAPK) pathway such as MEK or ERK inhibitors have been extensively investigated and have shown clinical efficacy (Greger J G, Eastman S D, Zhang V, et al. "Combinations of BRAF, MEK, and PI3K/mTOR inhibitors overcome acquired resistance to the BRAF inhibitor GSK2118436 dabrafenib, mediated by NRAS or MEK mutations" *Mol. Cancer Ther.* (2012) 11: 909-920; Patel S P, Lazar A J, Papadopoulos N E, et al. "Clinical responses to selumetinib (AZD6244; ARRY-142886)-based combination therapy stratified by gene mutations in patients with metastatic melanoma". *Cancer* (2013) 119(4): 799-805; Flaherty K T, Infante J R, Daud A, et al. "Combined BRAF and MEK inhibition in melanoma with BRAF V600 mutations". *N. Engl. J. Med.* (2012) 367: 1694-1703), they can only arrest cells in the $G_0/G_1$ phase. Such combination strategies are unlikely effective in dealing with resistant cells that can escape from this cell cycle arrest.

Chronically selected vemurafenib-resistant human melanoma cells (e.g., A375RF21) could not be blocked on the $G_0/G_1$ phase by vemurafenib at the effective concentration to sensitive parental cell line (i.e., A375), and the vemurafenib-resistant cells readily progressed into the $G_2/M$ phase (FIG. 2A). Thus, a combination of vemurafenib with a compound that strongly induces subsequent $G_2/M$ phase block should successfully capture the vemurafenib resistant cells leaking from $G_0/G_1$ arrest, thus produce strong synergy.

Recently, a novel class of anti-mitotic agents, represented by the scaffold of 2-aryl-4-benzoyl-imidazoles (ABIs) has been discovered (Chen J, Li C M, Wang J, et al. "Synthesis and antiproliferative activity of novel 2-aryl-4-benzoyl-imidazole derivatives targeting tubulin polymerization". *Bioorg. Med. Chem.* (2011) 19: 4782-4795; Chen J, Wang Z, Li C M, et al. "Discovery of novel 2-aryl-4-benzoyl-imidazoles targeting the colchicines binding site in tubulin as potential anticancer agents". *J. Med. Chem.* (2010) 53: 7414-7427; Chen J, Ahn S, Wang J, et al. "Discovery of novel 2-aryl-4-benzoyl-imidazole (ABI-III) analogues targeting tubulin polymerization as antiproliferative agents". *J. Med. Chem.* (2012) 55: 7285-7289; Li C M, Lu Y, Chen J, et al. "Orally bioavailable tubulin antagonists for paclitaxel-refractory cancer". *Pharm. Res.* (2012) 29: 3053-3063). These compounds presented anti-proliferation $IC_{50}$ values at the low nanomolar (nM) range in several human and mouse melanoma cell lines. They bind to tubulin at colchicine binding site. Compared with many existing tubulin inhibitors such as paclitaxel and vinblastine, ABI compounds can effectively circumvent several clinically relevant multidrug resistant mechanisms, including drug resistance mediated by P-glycoprotein (Pgp), multidrug resistance-associated proteins (MRPs), and breast cancer resistant proteins (BCRP). In vivo study indicated that they significantly inhibited melanoma B16-F10 cell lung metastasis in mice (Wang Z, Chen J, Wang J, et al. "Novel tubulin polymerization inhibitors overcome multidrug resistance and reduce melanoma metastasis to the lung". *Pharm. Res.* (2012) 29: 3040-3052).

With the rapidly rising incidence of cancer, and especially melanoma, and the high resistance to current therapeutic agents, identifying more efficacious drug combinations targeting alternative pathways to overcome BRAFi-resistance in melanoma will significantly benefit patients. In addition, because BRAF mutations are also common in many other types of cancers including ovarian, colorectal, and papillary thyroid cancers. Developing novel combination strategies may have a broader impact for these types of cancers where the use of existing BRAFi+MEKi combinations show little clinical activity, and are urgently needed.

SUMMARY OF THE INVENTION

In one embodiment, this invention is directed to a pharmaceutical composition comprising a tubulin inhibitor in combination with at least one of a BRAF inhibitor or a MEK inhibitor; and a pharmaceutically acceptable carrier.

In one embodiment, this invention is directed to a pharmaceutical composition comprising a compound represented by the structure of formula II:

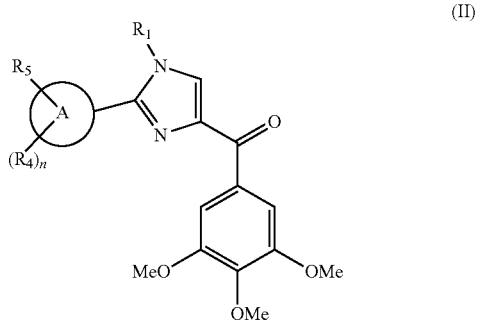

(II)

wherein

A is single or fused aromatic or heteroaromatic ring system;

$R_1$ is H, $C_1$-$C_6$ linear or branched alkyl, aryl, phenyl, benzyl, haloalkyl, aminoalkyl, —$OCH_2Ph$, $SO_2$-aryl, $SO_2$-phenyl, —(C=O)-aryl, —(C=O)-phenyl or OH;

$R_4$ and $R_5$ are each independently hydrogen, $C_1$-$C_6$ linear or branched alkyl, $C_1$-$C_6$ linear or branched haloalkyl, $C_1$-$C_6$ linear or branched alkoxy, $C_1$-$C_6$ linear or branched haloalkoxy, F, Cl, Br, I, $CF_3$, CN, —$CH_2CN$, $NH_2$, OH, —$OC(O)CF_3$, alkylamino, aminoalkyl, —$OCH_2Ph$, —NHCO— alkyl, COOH, —C(O)Ph, C(O)O-alkyl, C(O)H, —$C(O)NH_2$ or $NO_2$; and n is an integer between 1-4;

or its pharmaceutically acceptable salt, N-oxide, hydrate, tautomer or isomer; in combination with at least one of a BRAF inhibitor or a MEK inhibitor; and a pharmaceutically acceptable carrier.

In one embodiment, this invention is directed to a method of treating, suppressing, reducing the severity, reducing the risk, or inhibiting (i) BRAF mutant cancer, (ii) a BRAF inhibitor resistant cancer, (iii) melanoma, (iv) a drug resistant melanoma, (v) cancer metastasis in a subject; or (vi) delaying or preventing BRAF inhibitor resistant cancer in a subject; comprising administering a composition comprising at least one of a BRAF inhibitor or a MEK inhibitor; in combination with a compound represented by the structure of formula II:

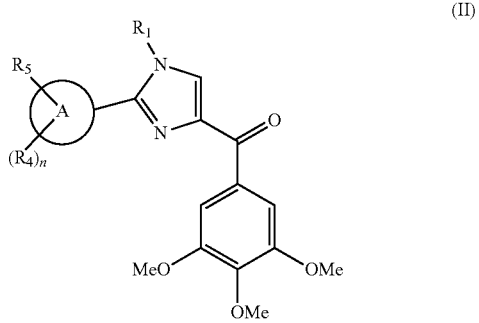

(II)

wherein

A is single or fused aromatic or heteroaromatic ring system;

$R_1$ is H, $C_1$-$C_6$ linear or branched alkyl, aryl, phenyl, benzyl, haloalkyl, aminoalkyl, —$OCH_2Ph$, $SO_2$-aryl, $SO_2$-phenyl, —(C=O)-aryl, —(C=O)-phenyl or OH;

$R_4$ and $R_5$ are each independently hydrogen, $C_1$-$C_6$ linear or branched alkyl, $C_1$-$C_6$ linear or branched haloalkyl, $C_1$-$C_6$ linear or branched alkoxy, $C_1$-$C_6$ linear or branched haloalkoxy, F, Cl, Br, I, $CF_3$, CN, —$CH_2CN$, $NH_2$, OH, —$OC(O)CF_3$, alkylamino, aminoalkyl, —$OCH_2Ph$, —NHCO— alkyl, COOH, —C(O)Ph, C(O)O-alkyl, C(O)H, —$C(O)NH_2$ or $NO_2$; and n is an integer between 1-4;

or its pharmaceutically acceptable salt, N-oxide, hydrate, tautomer or isomer;

to a subject suffering from BRAF mutant cancer under conditions effective to treat said cancer.

In one embodiment, this invention is directed to a method of treating, suppressing, reducing, inhibiting, eliminating, delaying or preventing secondary cancer resistance to taxane drugs in a subject suffering from cancer previously treated with taxane drugs, comprising administering to said subject a composition comprising at least one of a BRAF inhibitor or a MEK inhibitor; in combination with a compound represented by the structure of formula II:

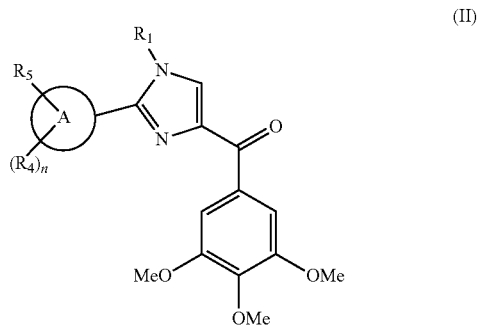

(II)

wherein

A is single or fused aromatic or heteroaromatic ring system;

$R_1$ is H, $C_1$-$C_6$ linear or branched alkyl, aryl, phenyl, benzyl, haloalkyl, aminoalkyl, —$OCH_2Ph$, $SO_2$-aryl, $SO_2$-phenyl, —(C=O)-aryl, —(C=O)-phenyl or OH;

$R_4$ and $R_5$ are each independently hydrogen, $C_1$-$C_6$ linear or branched alkyl, $C_1$-$C_6$ linear or branched haloalkyl, $C_1$-$C_6$ linear or branched alkoxy, $C_1$-$C_6$ linear or branched haloalkoxy, F, Cl, Br, I, $CF_3$, CN, —$CH_2CN$, $NH_2$, OH, —$OC(O)CF_3$, alkylamino, aminoalkyl, —$OCH_2Ph$, —NHCO— alkyl, COOH, —C(O)Ph, C(O)O-alkyl, C(O)H, —$C(O)NH_2$ or $NO_2$; and n is an integer between 1-4;

or its pharmaceutically acceptable salt, N-oxide, hydrate, tautomer or isomer.

In one embodiment, this invention is directed to a method of: (i) treating, suppressing, reducing the severity, reducing the risk, or inhibiting a drug resistant cancer; (ii) suppressing acquired BRAF-inhibitor resistance; (iii) delaying or preventing the development of BRAF-inhibitor resistance; or (iv) treating, suppressing, inhibiting, eliminating, reducing, delaying or preventing cancer metastasis; comprising administering a composition comprising at least one of a BRAF inhibitor and a MEK inhibitor; in combination with a tubulin inhibitor, to a subject suffering from drug resistant cancer under conditions effective to treat said cancer.

In another embodiment, the compound of this invention is compound 12da. In another embodiment, the compound of this invention is compound 17ya.

In one embodiment, this invention is directed to a pharmaceutical composition comprising a tubulin inhibitor, a BRAF inhibitor, and a pharmaceutically acceptable carrier. In another embodiment, the BRAF inhibitor is vemurafenib. In another embodiment, the tubulin inhibitor is docetaxel. In another embodiment, the tubulin inhibitor is a compound of this invention.

In one embodiment, this invention is directed to a pharmaceutical composition comprising a compound represented by the following structure:

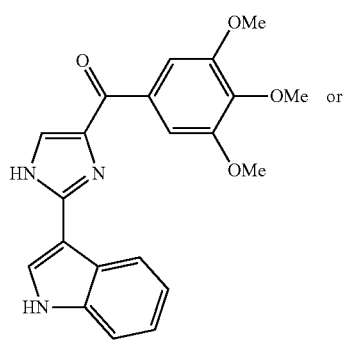

17ya

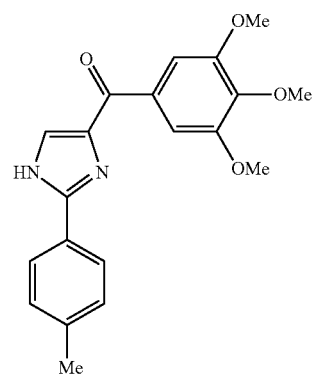

12da in combination with a BRAF inhibitor, and a pharmaceutically acceptable carrier. In another embodiment, the BRAF inhibitor is vemurafenib.

In one embodiment, this invention is directed to a pharmaceutical composition comprising a compound represented by the following structure:

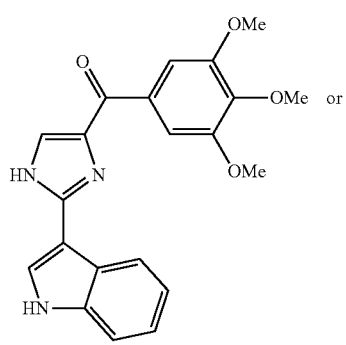

17ya

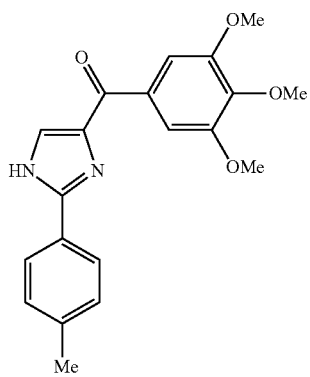

12da in combination with a MEK inhibitor, and a pharmaceutically acceptable carrier. In another embodiment, the MEK inhibitor is RO5068760.

In one embodiment this invention is directed to a method of: (a) treating, suppressing, reducing the severity, reducing the risk, or inhibiting BRAF mutant cancer in a subject; (b) treating, suppressing, reducing the severity, reducing the risk, or inhibiting a BRAF inhibitor resistant cancer; (c) treating, suppressing, reducing the severity, reducing the risk, or inhibiting melanoma; (d) treating, suppressing, reducing the severity, reducing the risk, or inhibiting a drug resistant melanoma; (e) treating, suppressing, reducing the severity, reducing the risk, or inhibiting a drug resistant cancer; (f) overcoming resistance to treatment with BRAF inhibitor in a subject suffering from drug resistant cancer; or (g) preventing, eliminating, reducing or delaying resistance to cancer treatment in a subject suffering from cancer; comprising administering a composition comprising a compound of this invention in combination with at least one of a BRAF inhibitor or a MEK inhibitor. In another embodiment, the BRAF inhibitor is vemurafenib. In another embodiment, the cancer is melanoma, thyroid cancer, colorectal cancer, or ovarian cancer. In another embodiment, the cancer is melanoma. In another embodiment, the melanoma is V600E positive melanoma. In another embodiment, the cancer is drug resistant cancer. In another embodiment, the melanoma is drug resistant melanoma. In another embodiment, the compound of this invention is compound 12da. In another embodiment, the compound of this invention is compound 17ya.

In one embodiment, this invention is directed to a method of treating, suppressing, reducing the severity, reducing the risk, or inhibiting a drug resistant cancer comprising administering a composition comprising a tubulin inhibitor in combination with at least one of a BRAF inhibitor or a MEK inhibitor, to a subject suffering from drug resistant cancer under conditions effective to treat said cancer. In another embodiment, the BRAF inhibitor is vemurafenib. In another embodiment, the tubulin inhibitor is docetaxel, colchicine, vinblastine, taxol or any combination thereof. In another embodiment, the cancer is melanoma, thyroid cancer, colorectal cancer, or ovarian cancer. In another embodiment, the cancer is melanoma.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 18A depicts representative pictures of control and each tested compound (12cb, 12da, and 12fb) at 100 nM. The diameter of each well was 35 mm. FIG. 18B depicts a quantified representation of assay results for each tested compound (12cb, 12da, and 12fb). P value was calculated comparing with control using Student's t test by GraphPad Prism software. Columns, means of three replicates; bars, SD.

FIG. 19A depicts the in vivo activity of 12cb against B16-F1 melanoma tumors in C57/BL mice. FIG. 19B depicts the in vivo activity of 12fb against B16-F1 melanoma in C57BL/6 mice and SHO nude mice. Results showed that 12fb inhibited melanoma tumor growth in a dose-dependent manner. C57BL/6 mice bearing B16-F1 melanoma allograft (n=5 per group). Each mouse received $0.5 \times 10^6$ cells by s.c. injection into the flank. 30 μL i.p. daily treatments were started when tumor size reached ~100 mm$^3$. FIG. 19C depicts the in vivo activity of 12fb against an A375 human melanoma xenograft. SHO nude mice bearing an A375 human melanoma xenograft (n=5 per group). Each mouse received $2.5 \times 10^6$ cells by s.c. injection into the flank. 30 μL i.p. daily treatments were started when the tumor size reached ~150 mm$^3$. Control, vehicle solution only; points, means; bars, SD. DTIC, (5-(3,3,-dimethyl-1-triazenyl)-imidazole-4-carboxamide, dacarbazine.

FIG. 20A, competitive mass binding. Tubulin (1 mg/mL) and colchicine (1.2 μM) were incubated with various concentrations of podophylltoxin, vinblastine, compounds 17ya, and 55. N=3; mean±SD. Podophylltoxin and vinblastine were used as positive and negative controls, respectively. FIG. 20B, effect on tubulin polymerization. Tubulin (0.4 mg) was exposed to test compounds (5 μM). Colchicine was used as positive control. FIGS. 20C and 20D, ability of 17ya and 55 to enhance cytoplasmic DNA-Histone complex formation (apoptosis) at 24 h in PC-3 (C) and PC-3/TxR (D) cells (N=3); mean±SD. Docetaxel was used as positive control.

FIG. 21A, Nude mice bearing PC-3 tumors were treated with docetaxel (i.v., 10 or 20 mg/kg) on day 1 and 9. (N=5-6). Bars, SE. FIG. 21B, Nude mice bearing PC-3/TxR tumors were treated with docetaxel (i.v., 10 or 20 mg/kg) on day 1 and 9, compound 17ya treatments (p.o., 6.7 mg/kg) once daily, five days a week. (N=4-5). Bars, SE. FIG. 21C, Nude mice bearing PC-3/TxR tumors were treated with compound 17ya (PO, 3.3 mg/kg) twice a day for four days in the first week, and then dosed once a day, five days a week for weeks 2-4 (N=7), with compound 55 treatments (p.o., 10 or 30 mg/kg) twice a day, five days a week for four weeks (N=7). Bars, SE. FIG. 21D, Nude mice bearing PC-3/TxR tumors were treated with compound 17ya (PO, 10 mg/kg) three times a week for four weeks (N=5). Bars, SE.

FIGS. 24A to 24C are the data from A375 cells and FIGS. 24D to 24F are the data from A375RF21 cells.

Figure 1:
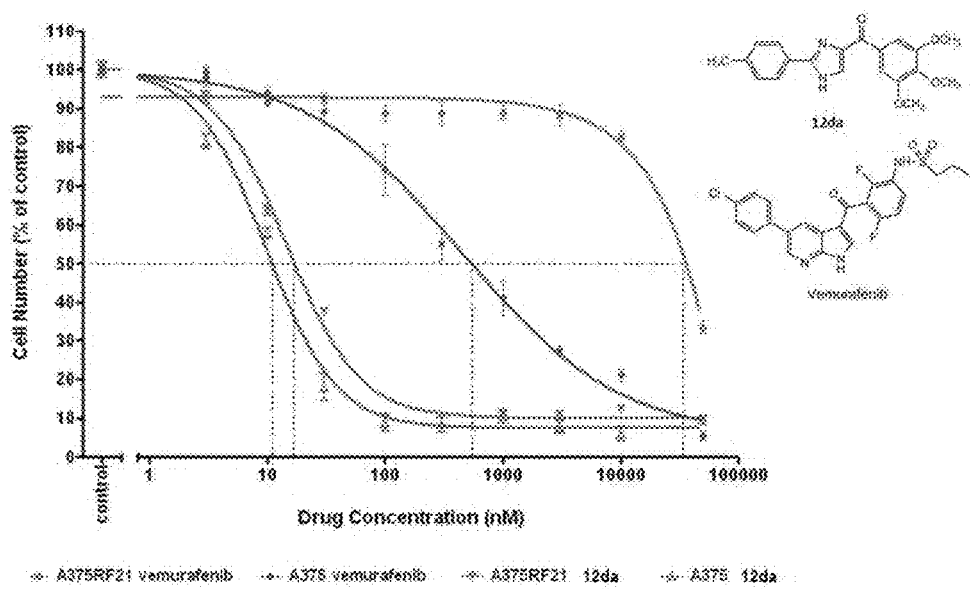
FIG. 1 depicts an establishment of a vemurafenib-resistant A375 melanoma cell line (A375RF21) from its parental A375 cell line using chronic selection over 3 months with increasing concentrations of vemurafenib. MTS assay showed the $IC_{50}$ value for proliferation inhibition in the parental A375 melanoma (0.57±0.03 µM) increased over 50-fold when tested in vemurafenib-resistant A375RF21 cells (28.9±0.6 µM). In contrast, $IC_{50}$ values of compound 12da were not significantly affected (10.7±1.5 nM in A375 parental cell lines and 13.6±4.4 nM in A375RF21, respectively). Structures of compound 12da and vemurafenib are shown in the figure.

It will be appreciated that for simplicity and clarity of illustration, elements shown in the figures have not necessarily been drawn to scale. For example, the dimensions of some of the elements may be exaggerated relative to other elements for clarity. Further, where considered appropriate,

DETAILED DESCRIPTION OF THE INVENTION

In one embodiment, this invention is directed to a compound represented by the structure of formula I:

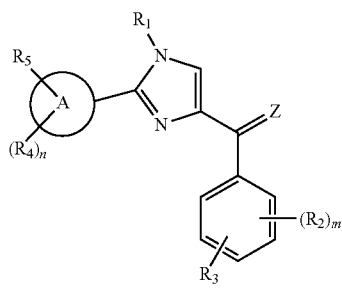

(I)

wherein

A is single or fused aromatic or heteroaromatic ring system;

Z is O or S;

$R_1$ is H, $C_1$-$C_6$ linear or branched alkyl, aryl, phenyl, benzyl, haloalkyl, aminoalkyl, —$OCH_2Ph$, $SO_2$-aryl, $SO_2$-phenyl, —(C=O)-aryl, —(C=O)-phenyl or OH;

$R_2$, $R_3$, $R_4$ and $R_5$ are each independently hydrogen, $C_1$-$C_6$ linear or branched alkyl, $C_1$-$C_6$ linear or branched haloalkyl, $C_1$-$C_6$ linear or branched alkoxy, $C_1$-$C_6$ linear or branched haloalkoxy, F, Cl, Br, I, $CF_3$, CN, —$CH_2CN$, $NH_2$, OH, —$OC(O)CF_3$, alkylamino, aminoalkyl, —$OCH_2Ph$, —NHCO-alkyl, COOH, —C(O)Ph, C(O)O-alkyl, C(O)H, —$C(O)NH_2$ or $NO_2$; and m and n is each independently an integer between 0-4; or its pharmaceutically acceptable salt, N-oxide, hydrate, tautomer or isomer.

In one embodiment, A is an aryl. In another embodiment, A is a phenyl. In another embodiment, A is an indolyl. In another embodiment, A is 3-indolyl. In another embodiment, Z is O.

In one embodiment, $R_2$ is OMe. In another embodiment, $R_3$ is H. In another embodiment, m is 3. In another embodiment, $R_2$ is OMe, $R_3$ is H and m is 3.

In one embodiment, $R_4$ is $C_1$-$C_6$ linear or branched alkyl. In another embodiment, $R_4$ is Me. In another embodiment, $R_4$ is H. In another embodiment, $R_5$ is H. In another embodiment, n is 1. In another embodiment, $R_4$ is Me, $R_5$ is H and n is 1. In another embodiment, $R_4$ is H, $R_5$ is H and n is 1.

In another embodiment, $R_1$ is H. In another embodiment, $R_1$ is $C_1$-$C_6$ linear or branched alkyl. In another embodiment, $R_1$ is Me.

In one embodiment, this invention is directed to a compound represented by the structure of formula II:

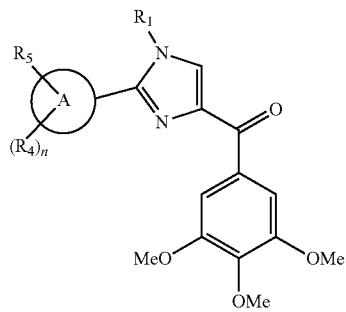

(II)

wherein

A is single or fused aromatic or heteroaromatic ring system;

$R_1$ is H, $C_1$-$C_6$ linear or branched alkyl, aryl, phenyl, benzyl, haloalkyl, aminoalkyl, —$OCH_2Ph$, $SO_2$-aryl, $SO_2$-phenyl, —(C=O)-aryl, —(C=O)-phenyl or OH;

$R_4$ and $R_5$ are each independently hydrogen, $C_1$-$C_6$ linear or branched alkyl, $C_1$-$C_6$ linear or branched haloalkyl, $C_1$-$C_6$ linear or branched alkoxy, $C_1$-$C_6$ linear or branched haloalkoxy, F, Cl, Br, I, $CF_3$, CN, —$CH_2CN$, $NH_2$, OH, —$OC(O)CF_3$, alkylamino, aminoalkyl, —$OCH_2Ph$, —NHCO— alkyl, COOH, —C(O)Ph, C(O)O-alkyl, C(O)H, —$C(O)NH_2$ or $NO_2$; and n is an integer between 1-4;

or its pharmaceutically acceptable salt, N-oxide, hydrate, tautomer or isomer.

In one embodiment, A is an aryl. In another embodiment, A is a phenyl. In another embodiment, A is an indolyl. In another embodiment, A is 3-indolyl.

In one embodiment, $R_4$ is $C_1$-$C_6$ linear or branched alkyl. In another embodiment, $R_4$ is Me. In another embodiment, $R_4$ is H. In another embodiment, $R_5$ is H. In another embodiment, n is 1. In another embodiment, $R_4$ is Me, $R_5$ is H and n is 1. In another embodiment, $R_4$ is H, $R_5$ is H and n is 1.

In another embodiment, $R_1$ is H. In another embodiment, $R_1$ is $C_1$-$C_6$ linear or branched alkyl. In another embodiment, $R_1$ is Me.

In one embodiment, this invention is directed to a compound represented by the structure of formula III:

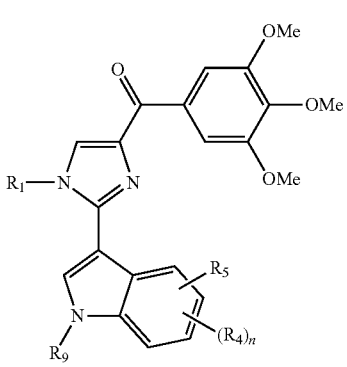

III wherein $R_1$ and $R_9$ are each independently H, $C_1$-$C_6$ linear or branched alkyl, aryl, phenyl, benzyl, haloalkyl, aminoalkyl, —$OCH_2Ph$, $SO_2$-aryl, $SO_2$-phenyl, —(C=O)-aryl, —(C=O)-phenyl or OH;

$R_4$ and $R_5$ are independently hydrogen, $C_1$-$C_6$ linear or branched alkyl, $C_1$-$C_6$ linear or branched haloalkyl, $C_1$-$C_6$ linear or branched alkoxy, $C_1$-$C_6$ linear or branched haloalkoxy, F, Cl, Br, I, $CF_3$, CN, —$CH_2CN$, $NH_2$, OH, —$OC(O)CF_3$, alkylamino, aminoalkyl, —$OCH_2Ph$, —NHCO— alkyl, COOH, —C(O)Ph, C(O)O-alkyl, C(O)H, —$C(O)NH_2$ or $NO_2$; and n is an integer between 1-4;

or its pharmaceutically acceptable salt, N-oxide, hydrate, tautomer or isomer.

In one embodiment, $R_4$ is H. In another embodiment, $R_5$ is H. In another embodiment, n is 1. In another embodiment, $R_4$ is H, $R_5$ is H and n is 1. In another embodiment, $R_9$ is H. In another embodiment, $R_9$ is Me.

In another embodiment, $R_1$ is H. In another embodiment, $R_1$ is $C_1$-$C_6$ linear or branched alkyl. In another embodiment, $R_1$ is Me.

In another embodiment, a compound of formula III is represented by the structure of compound 17ya:

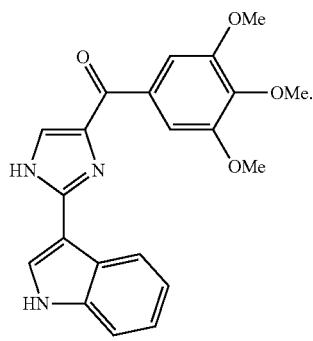

(17ya)

In one embodiment, this invention is directed to a compound represented by the structure of formula IV:

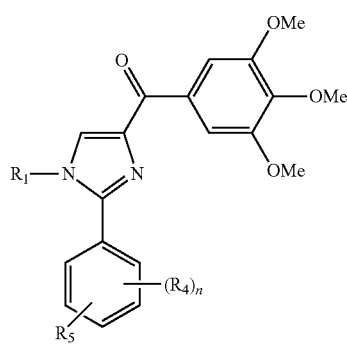

IV wherein $R_1$ is H, $C_1$-$C_6$ linear or branched alkyl, aryl, phenyl, benzyl, haloalkyl, aminoalkyl, —$OCH_2Ph$, $SO_2$-aryl, $SO_2$-phenyl, —(C=O)-aryl, —(C=O)-phenyl or OH;

$R_4$ and $R_5$ are each independently hydrogen, $C_1$-$C_6$ linear or branched alkyl, $C_1$-$C_6$ linear or branched haloalkyl, $C_1$-$C_6$ linear or branched alkoxy, $C_1$-$C_6$ linear or branched haloalkoxy, F, Cl, Br, I, $CF_3$, CN, —$CH_2CN$, $NH_2$, OH, —$OC(O)CF_3$, alkylamino, aminoalkyl, —$OCH_2Ph$, —NHCO— alkyl, COOH, —C(O)Ph, C(O)O-alkyl, C(O)H, —$C(O)NH_2$ or $NO_2$; and n is an integer between 1-4;

or its pharmaceutically acceptable salt, N-oxide, hydrate, tautomer or isomer.

In one embodiment, $R_4$ is $C_1$-$C_6$ linear or branched alkyl. In another embodiment, $R_4$ is Me. In another embodiment, $R_4$ is H. In another embodiment, $R_5$ is H. In another embodiment, n is 1. In another embodiment, $R_4$ is Me, $R_5$ is H and n is 1.

In another embodiment, $R_1$ is H. In another embodiment, $R_1$ is $C_1$-$C_6$ linear or branched alkyl. In another embodiment, $R_1$ is Me.

In another embodiment, a compound of formula IV is represented by the structure of compound 12da:

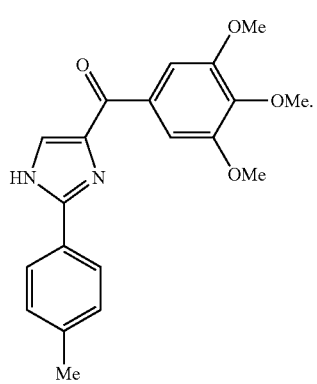

(12da)

In one embodiment, A of compound of Formula I and II is Ph. In another embodiment, A of compound of Formula I and II is indolyl. In another embodiment, A of compound of Formula I and II is 2-indolyl. In another embodiment, A of compound of Formula I and II is 3-indolyl. In another embodiment, A of compound of Formula I and II is 4-indolyl. In another embodiment, A of compound of Formula I and II is 5-indolyl. In another embodiment, A of compound of Formula I and II is 6-indolyl. In another embodiment, A of compound of Formula I and II is 7-indolyl.

In another embodiment, $R_5$ is in the para position. In another embodiment, $R_5$ is in the meta position. In another embodiment, $R_5$ is in the ortho position. In another embodiment, $R_5$ is 4-Me. In another embodiment, $R_5$ is H. In another embodiment, $R_5$ is 4-F.

In another embodiment, $R_4$ is H.

In another embodiment, n is 1.

In one embodiment the A group of formula I and II is furanyl, benzofuranyl, benzothiophenyl, indolyl, pyridinyl, phenyl, biphenyl, triphenyl, diphenylmethane, adamantane-yl, fluorene-yl, and other heterocyclic analogs such as, e.g., pyrrolyl, pyrazolyl, imidazolyl, pyridinyl, pyrimidinyl, pyrazinyl, pyridazinyl, triazinyl, tetrazinyl, pyrrolizinyl, indolyl, isoquinolinyl, quinolinyl, isoquinolinyl, benzimidazolyl, indazolyl, quinolizinyl, cinnolinyl, quinalolinyl, phthalazinyl, naphthyridinyl, quinoxalinyl, oxiranyl, oxetanyl, tetrahydrofuranyl, tetrahydropyranyl, dioxanyl, furanyl, pyrylium, benzodioxolyl, thiranyl, thietanyl, tetrahydrothiophene-yl, dithiolanyl, tetrahydrothiopyranyl, thiophene-yl, thiepinyl, thianaphthenyl, oxathiolanyl, morpholinyl, thioxanyl, thiazolyl, isothiazolyl, thiadiazolyl, oxazolyl, isoxazolyl, oxadiaziolyl.

In one embodiment, A is phenyl. In another embodiment, A is indolyl group; most preferably, 3-indolyl and 5-indolyl.

In one embodiment, Z of formula I is O. in another embodiment, Z is S.

In one embodiment, $R_1$ of formula I, II, III and IV is hydrogen. In another embodiment, $R_1$ is $C_1$-$C_6$ linear or branched alkyl. In another embodiment, $R_1$ is Me. In another embodiment, $R_1$ is $C_1$-$C_6$ linear or branched haloalkyl. In another embodiment, $R_1$ is $CF_3$. In another embodiment, $R_1$ is phenyl. In another embodiment, $R_1$ is benzyl. In another embodiment, $R_1$ is $SO_2$-aryl. In another embodiment, $R_1$ is (C=O)-aryl.

In one embodiment, $R_3$ of formula I is in the para position. In another embodiment, $R_3$ is in the meta position. In another embodiment, $R_3$ is in the ortho position.

In one embodiment, $R_2$ and $R_3$ of formula I are independently hydrogen. In another embodiment, $R_2$ and $R_3$ are independently $C_1$-$C_6$ linear or branched alkoxy. In another embodiment, $R_2$ and $R_3$ are independently $OCH_3$. In another embodiment, $R_2$ and $R_3$ are independently F. In another embodiment, $R_2$ and $R_3$ are independently 4-F. In another embodiment, $R_2$ and $R_3$ are independently Cl. In another embodiment, $R_2$ and $R_3$ are independently Br. In another embodiment, $R_2$ and $R_3$ are independently I. In another embodiment, $R_2$ and $R_3$ are independently $C_1$-$C_6$ linear or branched haloalkyl. In another embodiment, $R_2$ and $R_3$ are independently $CF_3$. In another embodiment, $R_2$ and $R_3$ are independently CN. In another embodiment, $R_2$ and $R_3$ are independently $NH_2$. In another embodiment, $R_2$ and $R_3$ are independently OH. In another embodiment, $R_2$ and $R_3$ are independently $C_1$-$C_6$ linear or branched alkyl. In another embodiment, $R_2$ and $R_3$ are independently $CH_3$. In another embodiment, $R_2$ and $R_3$ are independently $NO_2$. In another embodiment, $R_2$ and $R_3$ are independently alkylamino. In another embodiment, $R_2$ and $R_3$ are independently 4-N(Me)$_2$.

In one embodiment, m of formula I is 0. In another embodiment, m is 1. In another embodiment, m is 2. In another embodiment, m is 3. In another embodiment, m is 4.

In one embodiment, $R_5$ of formula I, II, III and IV is in the para position. In another embodiment, $R_5$ is in the meta position. In another embodiment, $R_5$ is in the ortho position.

In one embodiment, $R_4$ and $R_5$ of formula I, II, III and IV are independently hydrogen. In another embodiment, $R_4$ and $R_5$ are independently $C_1$-$C_6$ linear or branched alkoxy. In another embodiment, $R_4$ and $R_5$ are independently OMe. In another embodiment, $R_4$ and $R_5$ are independently F. In another embodiment, $R_4$ and $R_5$ are independently Cl. In another embodiment, $R_4$ and $R_5$ are independently Br. In another embodiment, $R_4$ and $R_5$ are independently I. In another embodiment, $R_4$ and $R_5$ are independently $C_1$-$C_6$ linear or branched haloalkyl. In another embodiment, $R_4$ and $R_5$ are independently $CF_3$. In another embodiment, $R_4$ and $R_5$ are independently CN. In another embodiment, $R_4$ and $R_5$ are independently $NH_2$. In another embodiment, $R_4$ and $R_5$ are independently OH. In another embodiment, $R_4$ and $R_5$ are independently $C_1$-$C_6$ linear or branched alkyl. In another embodiment, $R_4$ and $R_5$ are independently $NO_2$. In another embodiment, $R_4$ and $R_5$ are independently alkylamino.

In one embodiment, n of formula I, II, III and IV is 0. In another embodiment, n is 1. In another embodiment, n is 2. In another embodiment, n is 3. In another embodiment, n is 4.

It is understood that for heterocyclic rings, n is limited to the number of available positions for substitution, i.e. to the number of CH groups minus one. Accordingly, if A ring is, for example, furanyl, thiophenyl or pyrrolyl, n is between 0 and 2; and if A ring is, for example, oxazolyl, imidazolyl or thiazolyl, n is either 0 or 1; and if A ring is, for example, oxadiazolyl or thiadiazolyl, n is 0.

In one embodiment, $R_9$ of formula III is hydrogen. In another embodiment, $R_9$ is $C_1$-$C_6$ linear or branched alkyl. In another embodiment, $R_9$ is $CH_3$. In another embodiment, $R_9$ is $C_1$-$C_6$ linear or branched haloalkyl. In another embodiment, $R_9$ is $CF_3$. In another embodiment, $R_9$ is phenyl. In another embodiment, $R_9$ is —$CH_2$Ph. In another embodiment, $R_9$ is $SO_2$-aryl. In another embodiment, $R_9$ is (C=O)-aryl. In another embodiment, $R_9$ is ($SO_2$)Ph. In another embodiment, $R_9$ is ($SO_2$)-Ph-$OCH_3$.

As used herein, "single or fused aromatic or heteroaromatic ring system" can be any such ring, including but not limited to phenyl, indolyl, 1H-indole, isoindolyl, pyridinyl, pyrimidinyl, pyridazinyl, pyrazinyl, triazinyl, tetrazinyl, thiazolyl, isothiazolyl, oxazolyl, isoxazolyl, imidazolyl, pyrazolyl, pyrrolyl, furanyl, thiophene-yl, isoquinolinyl, naphthyl, anthracenyl, benzimidazolyl, indazolyl, 2H-indazole, 4,5,6,7-tetrahydro-2H-indazole, 3H-indol-3-one, purinyl, benzoxazolyl, 1,3-benzoxazolyl, benzisoxazolyl, benzothiazolyl, 1,3-benzothiazole, 4,5,6,7-tetrahydro-1,3-benzothiazole, quinazolinyl, quinoxalinyl, cinnolinyl, phthalazinyl, quinolinyl, isoquinolinyl, acridinyl, benzofuranyl, 1-benzofuran, isobenzofuranyl, benzothiophenyl, benzo[c]thiophenyl, benzodioxolyl, thiadiazolyl, [1,3]oxazolo[4,5-b]pyridine, oxadiaziolyl, imidazo[2,1-b][1,3]thiazole, 4H,5H,6H-cyclopenta[d][1,3]thiazole, 5H,6H,7H,8H-imidazo[1,2-a]pyridine, 7-oxo-6H,7H-[1,3]thiazolo[4,5-d]pyrimidine, [1,3]thiazolo[5,4-b]pyridine, 2H,3H-imidazo[2,1-b][1,3]thiazole, thieno[3,2-d]pyrimidin-4(3H)-one, 4-oxo-4H-thieno[3,2-d][1,3]thiazin, imidazo[1,2-a]pyridine, pyrazolo[1,5-a]pyridine, imidazo[1,2-a]pyrazine, imidazo[1,2-a]pyrimidine, 1H-pyrrolo[2,3-b]pyridine, pyrido[2,3-b]pyrazin, pyrido[2,3-b]pyrazin-3(4H)-one, 4H-thieno[3,2-b]pyrrole, quinoxalin-2(1H)-one, 1H-pyrrolo[3,2-b]pyridine, 7H-pyrrolo[2,3-d]pyrimidine, oxazolo[5,4-b]pyridine, thiazolo[5,4-b]pyridine, etc.

As used herein, "heterocyclic ring systems" refer to saturated or unsaturated N-heterocycles, including but not limited to aza- and diaza-cycloalkyls such as aziridinyl, azetidinyl, diazatidinyl, pyrrolidinyl, piperidinyl, piperazinyl, and azocanyl, pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzimidazolyl, indazolyl, quinolizinyl, cinnolinyl, quinololinyl, phthalazinyl, naphthyridinyl, quinoxalinyl, etc; saturated or unsaturated O-heterocycles including but not limited to oxiranyl, oxetanyl, tetrahydrofuranyl, tetrahydropyranyl, dioxanyl, furanyl, pyrylium, benzofuranyl, benzodioxolyl, etc; saturated or unsaturated S-heterocycles, including but not limited to thiranyl, thietanyl, tetrahydrothiophene-yl, dithiolanyl, tetrahydrothiopyranyl, thiophene-yl, benzothiophenyl, thiepinyl, thianaphthenyl, etc; saturated or unsaturated mixed heterocycles which can be any heterocycle containing two or more S-, N-, or O-heteroatoms, including but not limited to oxathiolanyl, morpholinyl, thioxanyl, thiazolyl, isothiazolyl, thiadiazolyl, oxazolyl, isoxazolyl, oxadiaziolyl, etc.

As used herein, the term "alkyl" can be any straight- or branched-chain alkyl group containing up to about 30 carbons unless otherwise specified. In another embodiment, an alkyl includes $C_1$-$C_6$ carbons. In another embodiment, an alkyl includes $C_1$-$C_8$ carbons. In another embodiment, an alkyl includes $C_1$-$C_{10}$ carbons. In another embodiment, an alkyl is a $C_1$-$C_{12}$ carbons. In another embodiment, an alkyl is a $C_1$-$C_{20}$ carbons. In another embodiment, cyclic alkyl group has 3-8 carbons. In another embodiment, branched alkyl is an alkyl substituted by alkyl side chains of 1 to 5 carbons. In one embodiment, the alkyl group may be unsubstituted. In another embodiment, the alkyl group may be substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl.

The alkyl group can be a sole substituent or it can be a component of a larger substituent, such as in an alkoxy, haloalkyl, arylalkyl, alkylamino, dialkylamino, alkylamido, alkylurea, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, etc.

As used herein, the term "aryl" refers to any aromatic ring that is directly bonded to another group. The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkoxy, $C_1$-$C_5$ linear or branched haloalkoxy, $CF_3$, CN, $NO_2$, —$CH_2CN$, $NH_2$, NH-alkyl, N(alkyl)$_2$, hydroxyl, —OC(O)$CF_3$, —$OCH_2Ph$, —NHCO-alkyl, COOH, —C(O)Ph, C(O)O-alkyl, C(O)H, or —C(O)$NH_2$.

As used herein, the term "alkoxy" refers to an ether group substituted by an alkyl group as defined above. Alkoxy refers both to linear and to branched alkoxy groups. Non-limiting examples of alkoxy groups are methoxy, ethoxy, propoxy, iso-propoxy, tert-butoxy.

As used herein, the term "aminoalkyl" refers to an amine group substituted by an alkyl group as defined above. Aminoalkyl refers to monoalkylamine, dialkylamine or trialkylamine. Nonlimiting examples of aminoalkyl groups are —N(Me)$_2$, —NHMe, —$NH_3$.

A "haloalkyl" group refers, in another embodiment, to an alkyl group as defined above, which is substituted by one or more halogen atoms, e.g. by F, Cl, Br or I. Nonlimiting examples of haloalkyl groups are $CF_3$, $CF_2CF_3$, $CH_2CF_3$.

An "alkoxyalkyl" group refers, in another embodiment, to an alkyl group as defined above, which is substituted by alkoxy group as defined above, e.g. by methoxy, ethoxy, propoxy, i-propoxy, t-butoxy etc. Nonlimiting examples of alkoxyalkyl groups are —$CH_2$—O—$CH_3$, —$CH_2$—O—CH($CH_3$)$_2$, —$CH_2$—O—C($CH_3$)$_3$, —$CH_2$—$CH_2$—O—$CH_3$, —$CH_2$—$CH_2$—O—CH($CH_3$)$_2$, —$CH_2$—$CH_2$—O—C($CH_3$)$_3$.

A "cycloalkyl" or "carbocyclic" group refers, in one embodiment, to a ring structure comprising carbon atoms as ring atoms, which may be either saturated or unsaturated, substituted or unsubstituted. In another embodiment the cycloalkyl is a 3-12 membered ring. In another embodiment the cycloalkyl is a 6 membered ring. In another embodiment the cycloalkyl is a 5-7 membered ring. In another embodiment, the cycloalkyl is a 3-8 membered ring. In another embodiment, the cycloalkyl group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the cycloalkyl ring may be fused to another saturated or unsaturated cycloalkyl or heterocyclic 3-8 membered ring. In another embodiment, the cycloalkyl ring is a saturated ring. In another embodiment, the cycloalkyl ring is an unsaturated ring. Non limiting examples of a cycloalkyl group comprise cyclohexyl, cyclohexenyl, cyclopropyl, cyclopropenyl, cyclopentyl, cyclopentenyl, cyclobutyl, cyclobutenyl, cycloctyl, cycloctadienyl (COD), cycloctaene (COE) etc.

A "heterocycle" or "heterocyclic" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 3-8 membered ring. In another embodiment, the heterocycle group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. Non limiting examples of a heterocyclic rings comprise pyridine, piperidine, morpholine, piperazine, thiophene, pyrrole, benzodioxole, or indole.

In one embodiment, this invention provides a compound of this invention or its isomer, metabolite, pharmaceutically acceptable salt, pharmaceutical product, tautomer, hydrate, N-oxide, polymorph, or crystal or combinations thereof. In one embodiment, this invention provides an isomer of the compound of this invention. In another embodiment, this invention provides a metabolite of the compound of this invention. In another embodiment, this invention provides a pharmaceutically acceptable salt of the compound of this invention. In another embodiment, this invention provides a pharmaceutical product of the compound of this invention. In another embodiment, this invention provides a tautomer of the compound of this invention. In another embodiment, this invention provides a hydrate of the compound of this invention. In another embodiment, this invention provides an N-oxide of the compound of this invention. In another embodiment, this invention provides a polymorph of the compound of this invention. In another embodiment, this invention provides a crystal of the compound of this invention. In another embodiment, this invention provides composition comprising a compound of this invention, as described herein, or, in another embodiment, a combination of an isomer, metabolite, pharmaceutically acceptable salt, pharmaceutical product, tautomer, hydrate, N-oxide, polymorph, or crystal of the compound of this invention.

In one embodiment, the term "isomer" includes, but is not limited to, optical isomers and analogs, structural isomers and analogs, conformational isomers and analogs, and the like. In another embodiment, the isomer is an optical isomer.

In one embodiment, the compounds of this invention are the pure (E)-isomers. In another embodiment, the compounds of this invention are the pure (Z)-isomers. In another embodiment, the compounds of this invention are a mixture of the (E) and the (Z) isomers. In one embodiment, the compounds of this invention are the pure (R)-isomers. In another embodiment, the compounds of this invention are the pure (S)-isomers. In another embodiment, the compounds of this invention are a mixture of the (R) and the (S) isomers.

The compounds of the present invention can also be present in the form of a racemic mixture, containing substantially equivalent amounts of stereoisomers. In another embodiment, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 95% pure, more preferably at least about 98% pure, most preferably at least about 99% pure.

Compounds of the present invention can also be in the form of a hydrate, which means that the compound further includes a stoichiometric or non-stoichiometric amount of water bound by non-covalent intermolecular forces.

Compounds of the present invention may exist in the form of one or more of the possible tautomers and depending on the particular conditions it may be possible to separate some or all of the tautomers into individual and distinct entities. It is to be understood that all of the possible tautomers, including all additional enol and keto tautomers and/or isomers are hereby covered. For example the following tautomers, but not limited to these, are included.

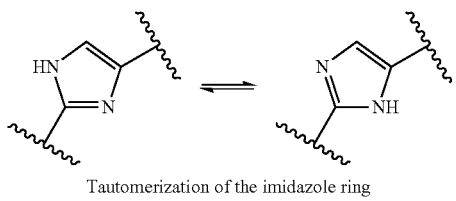 [SMILES: *c1c[nH]c(*)n1 ; *c1cnc(*)[nH]1]

Tautomerization of the imidazole ring

The tautomers of this invention are freely interconverting tautomers, not unresolved mixtures. The imidazoles and other ring systems of this invention are tautomerizable. All tautomers are considered as part of the invention.

It is well understood that in structures presented in this invention wherein the nitrogen atom has less than 3 bonds, H atoms are present to complete the valence of the nitrogen.

The invention includes "pharmaceutically acceptable salts" of the compounds of this invention, which may be produced, by reaction of a compound of this invention with an acid or base. Certain compounds, particularly those possessing acid or basic groups, can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically-acceptable salts of amines of compounds the compounds of this invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

Pharmaceutical Composition

Another aspect of the present invention relates to a pharmaceutical composition including a pharmaceutically acceptable carrier and at least one compound according to the aspects of the present invention. The pharmaceutical composition can contain one or more of the above-identified compounds of the present invention. Typically, the pharmaceutical composition of the present invention will include a compound of the present invention such as a compound of formula I, II, III or IV, or 17ya or 12da or its pharmaceutically acceptable salt, in combination with at least one of a BRAF inhibitor or a MEK inhibitor; and a pharmaceutically acceptable carrier. The pharmaceutical composition of the present invention may also include a tubulin inhibitor in combination with at least one of a BRAF inhibitor or a MEK inhibitor; and a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions. In some embodiments, the pharmaceutical composition includes a combination of a compound of the present invention such as a compound of formula I, II, III or IV, or 17ya or 12da, or its pharmaceutically acceptable salt, with a BRAF inhibitor, and a pharmaceutically acceptable carrier. In some embodiments, the pharmaceutical composition includes a combination of a compound of the present invention such as a compound of formula I, II, III or IV, or 17ya or 12da, or its pharmaceutically acceptable salt, with a MEK inhibitor, and a pharmaceutically acceptable carrier. In some embodiments, the pharmaceutical composition includes a combination of a compound of the present invention such as a compound of formula I, II, III or IV, or 17ya or 12da, or its pharmaceutically acceptable salt, with a BRAF inhibitor and a MEK inhibitor and a pharmaceutically acceptable carrier. In some embodiments, the pharmaceutical composition includes a combination of a tubulin inhibitor, with a BRAF inhibitor, and a pharmaceutically acceptable carrier. In some embodiments, the pharmaceutical composition includes a combination of a tubulin inhibitor, with a MEK inhibitor, and a pharmaceutically acceptable carrier. In some embodiments, the pharmaceutical composition includes a combination of a tubulin inhibitor, with a BRAF inhibitor, a MEK inhibitor and a pharmaceutically acceptable carrier.

As herein described, the term "BRAF" refers to a human gene that makes a protein called B-Raf. The B-Raf protein is involved in sending signals inside cells, which are involved in directing cell growth. In 2002, it was shown to be mutated in human cancers. Drugs that treat cancers driven by BRAF have been developed. Vemurafenib, is one BRAF inhibitor drug that was approved by FDA for treatment of late-stage melanoma. Other specific inhibitors of mutated B-raf protein for anticancer use (as used herein "BRAF inhibitors") are being developed. These include: GDC-0879, PLX-4720, sorafenib tosylate, dabrafenib, and LGX818.

As herein described, the term "MEK" refers to the mitogen-activated protein kinase kinase enzymes MEK1 and/or MEK2. MEK is a kinase enzyme which phosphorylates mitogen-activated protein kinase. MEK is a member of the MAPK signaling cascade that is activated in melanoma. When MEK is inhibited, cell proliferation is blocked and apoptosis (controlled cell death) is induced.

The term "MEK inhibitor" refers to a chemical or drug that inhibits the mitogen-activated protein kinase kinase enzymes MEK1 and/or MEK2. They can be used to affect the MAPK/ERK pathway which is often overactive in some cancers. Hence MEK inhibitors have potential for treatment of some cancers, especially BRAF-mutated melanoma, and KRAS/BRAF mutated colorectal cancer. MEK inhibitors include, but are not limited to: trametinib (GSK1120212), selumetinib, RO5068760, MEK162, PD-325901, cobimetinib or XL518 and CI-1040 or PD035901.

In one embodiment, this invention is directed to a pharmaceutical composition comprising a therapeutically effective amount of two compounds having anti-cancerous activity and a pharmaceutically acceptable carrier. In another embodiment, the composition comprises a BRAF inhibitor and a compound according to this invention such as a compound of formula I, II, III or IV, or 17ya or 12da. In another embodiment, the composition comprises a MEK inhibitor and a compound according to this invention such as a compound of formula I, II, III or IV, or 17ya or 12da. In one embodiment, this invention is directed to a pharmaceutical composition comprising a therapeutically effective amount of three compounds having anti-cancerous activity and a pharmaceutically acceptable carrier. In another embodiment, the composition comprises a BRAF inhibitor, a MEK inhibitor and a compound according to this invention such as a compound of formula I, II, III or IV, or 17ya or 12da. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib (GSK1120212), selumetinib, RO5068760, MEK162, PD-325901, cobimetinib or XL518, CI-1040 or PD035901, or any combination thereof. In another embodiment, the MEK inhibitor is trametinib. In another embodiment, the MEK inhibitor is RO5068760. In another embodiment, the compound of this invention is a compound of formula I, II, III or IV. In another embodiment, the compound of this invention is compound 17ya. In another embodiment, the compound of this invention is compound 12da. In another embodiment, the compound is in the form of its pharmaceutically acceptable salt, N-oxide, hydrate, tautomer or isomer.

In one embodiment, this invention is directed to a pharmaceutical composition comprising a therapeutically effective amount of a tubulin inhibitor in combination with at least one of a BRAF inhibitor or a MEK inhibitor; and a pharmaceutically acceptable carrier. In one embodiment, this invention is directed to a pharmaceutical composition comprising a combination of a therapeutically effective amount of a BRAF inhibitor, and a tubulin inhibitor, and a pharmaceutically acceptable carrier. In one embodiment, this invention is directed to a pharmaceutical composition comprising a combination of a therapeutically effective amount of a MEK inhibitor, and a tubulin inhibitor, and a pharmaceutically acceptable carrier. In one embodiment, this invention is directed to a pharmaceutical composition comprising a combination of a therapeutically effective amount of a BRAF inhibitor, a MEK inhibitor, a tubulin inhibitor, and a pharmaceutically acceptable carrier. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib (GSK1120212), selumetinib, RO5068760, MEK162, PD-325901, cobimetinib or XL518, CI-1040 or PD035901, or any combination thereof. In another embodiment, the MEK inhibitor is trametinib or RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel.

Typically, the composition will contain from about 0.01 to 99 percent, preferably from about 20 to 75 percent of the active compounds, together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

In one embodiment, the methods of this invention may comprise administration of a compound of formula I-IV of this invention at various dosages. In one embodiment, compound of formula I-IV is administered at a dosage of 0.1-200 mg per kg. In one embodiment, the compound of formula I-IV is administered at a dosage of 0.01-1 mg per kg. In one embodiment, compound of formula I-IV is administered at a dose of 0.1-10 mg per kg, or in another embodiment, 0.1-25 mg per kg, or in another embodiment, 10-50 mg per kg, or in another embodiment, 10-25 mg per kg, or in another embodiment, 0.3-30 mg per kg, or in another embodiment, 0.5-25 mg per kg, or in another embodiment, 0.5-50 mg per kg, or in another embodiment, 0.75-15 mg per kg, or in another embodiment, 0.75-60 mg per kg, or in another embodiment, 1-5 mg per kg, or in another embodiment, 1-20 mg per kg, or in another embodiment, 3-15 mg per kg, or in another embodiment, 30-50 mg per kg, or in another embodiment, 30-75 mg per kg, or in another embodiment, 100-2000 mg per kg. In another embodiment, the compound of formula I-IV is administered at a dosage of 5 mg/kg, 10 mg/kg, 15 mg/kg, 20 mg/kg, 25 mg/kg, 30 mg/kg or 35 mg/kg. In another embodiment, the compound of formula I-IV is administered at a dosage of 10 mg/kg. In another embodiment, the compound of formula I-IV is administered at a dosage of 15 mg/kg. In another embodiment, the compound of formula I-IV is administered at a dosage of 25 mg/kg.

In one embodiment, compound of formula I-IV is administered at a dosage of 10 mg. In one embodiment, compound of formula I-IV is administered at a dosage of 15 mg. In one embodiment, compound of formula I-IV is administered at a dosage of 25 mg. In another embodiment the compound of formula I-IV is administered at a dosage of 0.01 mg, 0.03 mg, 0.1 mg, 0.3 mg, 0.75 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg.

In one embodiment, the methods of this invention may comprise administration of a BRAF inhibitor according to this invention at various dosages. In one embodiment, the BRAF inhibitor is administered at a dosage of 0.1-200 mg per kg. In one embodiment, the BRAF inhibitor is administered at a dosage of 0.01-1 mg per kg. In one embodiment, the BRAF inhibitor is administered at a dose of 0.1-10 mg per kg, or in another embodiment, 0.1-25 mg per kg, or in another embodiment, 10-50 mg per kg, or in another embodiment, 10-25 mg per kg, or in another embodiment, 0.3-30 mg per kg, or in another embodiment, 0.5-25 mg per kg, or in another embodiment, 0.5-50 mg per kg, or in another embodiment, 0.75-15 mg per kg, or in another embodiment, 0.75-60 mg per kg, or in another embodiment, 1-5 mg per kg, or in another embodiment, 1-20 mg per kg, or in another embodiment, 3-15 mg per kg, or in another embodiment, 30-50 mg per kg, or in another embodiment, 30-75 mg per kg, or in another embodiment, 100-2000 mg per kg. In another embodiment, the BRAF inhibitor is administered at a dosage of 5 mg/kg, 10 mg/kg, 15 mg/kg, 20 mg/kg, 25 mg/kg, 30 mg/kg, 35 mg/kg, 40 mg/kg, 45 mg/kg or 50 mg/kg. In another embodiment, the BRAF inhibitor is administered at a dosage of 10 mg/kg. In another embodiment, the BRAF inhibitor is administered at a dosage of 20 mg/kg. In another embodiment, the BRAF inhibitor is administered at a dosage of 30 mg/kg. In another embodiment, the BRAF inhibitor is administered at a dosage of 40 mg/kg. In another embodiment, the BRAF inhibitor is administered at a dosage of 45 mg/kg. In another embodiment, the BRAF inhibitor is vemurafenib. In another embodiment, the BRAF inhibitor is dabrafenib.

In one embodiment, the BRAF inhibitor is administered at a dosage of 10 mg. In one embodiment, the BRAF inhibitor is administered at a dosage of 15 mg. In one embodiment, the BRAF inhibitor is administered at a dosage of 25 mg. In one embodiment, the BRAF inhibitor is administered at a dosage of 45 mg. In another embodiment the BRAF inhibitor is administered at a dosage of 5 mg, 10 mg, 15 mg, 20 mg, 25 mg, 30 mg, 35 mg, 40 mg, 45 mg, or 50 mg.

In one embodiment, the methods of this invention may comprise administration of a MEK inhibitor according to this invention at various dosages. In one embodiment, the MEK inhibitor is administered at a dosage of 0.1-200 mg per kg. In one embodiment, the MEK inhibitor is administered at a dosage of 0.01-1 mg per kg. In one embodiment, the MEK inhibitor is administered at a dose of 0.1-1 mg per kg, or in another embodiment, 0.1-25 mg per kg, or in another embodiment, 10-50 mg per kg, or in another embodiment, 10-25 mg per kg, or in another embodiment, 0.3-0.5 mg per kg, or in another embodiment, 0.5-25 mg per kg, or in another embodiment, 0.5-50 mg per kg, or in another embodiment, 0.75-15 mg per kg, or in another embodiment, 0.75-60 mg per kg, or in another embodiment, 1-5 mg per kg, or in another embodiment, 1-20 mg per kg, or in another embodiment, 3-15 mg per kg, or in another embodiment, 30-50 mg per kg, or in another embodiment, 30-75 mg per kg, or in another embodiment, 100-2000 mg per kg. In another embodiment, the MEK inhibitor is administered at a dosage of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg or 1 mg/kg. In another embodiment, the MEK inhibitor is administered at a dosage of 0.1 mg/kg. In another embodiment, the MEK inhibitor is administered at a dosage of 0.3 mg/kg. In another embodiment, the MEK inhibitor is administered at a dosage of 0.5 mg/kg. In another embodiment, the MEK inhibitor is administered at a dosage of 0.7 mg/kg. In another embodiment, the MEK inhibitor is administered at a dosage of 1 mg/kg. In another embodiment, the MEK inhibitor is trametinib or RO5068760.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In one embodiment, this invention provides a pharmaceutical composition, which comprises compound of formula I-IV as herein described and/or its isomer, pharmaceutically acceptable salt, pharmaceutical product, hydrate, N-oxide or any combination thereof, alone or in combination with another therapeutic agent, such as for example, anti-cancer agent including but not limited to: tubulin inhibitors, BRAF inhibitors, MEK inhibitors or other agents suitable for the applications as herein described. In one embodiment, the pharmaceutical composition of compound of formula I-IV as herein described, comprises a compound of this invention in combination with a BRAF inhibitor. In another embodiment, the pharmaceutical composition comprises a compound of this invention in combination with a MEK inhibitor. In another embodiment, the pharmaceutical composition comprises a compound of this invention in combination with a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib (GSK1120212), selumetinib, RO5068760, MEK162, PD-325901, cobimetinib or XL518, CI-1040 or PD035901, or any combination thereof. In another embodiment, the MEK inhibitor is trametinib or RO5068760.

In one embodiment, this invention is directed to a pharmaceutical composition comprising a tubulin inhibitor in combination with at least one of a BRAF inhibitor or a MEK inhibitor; and a pharmaceutically acceptable carrier. In one embodiment, this invention is directed to a pharmaceutical composition comprising a tubulin inhibitor in combination with a BRAF inhibitor, and a pharmaceutically acceptable carrier. In one embodiment, this invention is directed to a pharmaceutical composition comprising a tubulin inhibitor in combination with a MEK inhibitor, and a pharmaceutically acceptable carrier. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib (GSK1120212), selumetinib, RO5068760, MEK162, PD-325901, cobimetinib or XL518, CI-1040 or PD035901, or any combination thereof. In another embodiment, the MEK inhibitor is trametinib or RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel.

In one embodiment, the compounds of this invention are administered in combination with an anti-cancer agent. In one embodiment, the anti-cancer agent is a BRAF inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In one embodiment, the anti-cancer agent is a MEK inhibitor. In another embodiment, the MEK inhibitor is trametinib (GSK1120212), selumetinib, RO5068760, MEK162, PD-325901, cobimetinib or XL518, CI-1040 or PD035901, or any combination thereof. In another embodiment, the MEK inhibitor is trametinib or RO5068760.

In one embodiment, this invention is directed to a pharmaceutical composition comprising a compound represented by the structure of formula II:

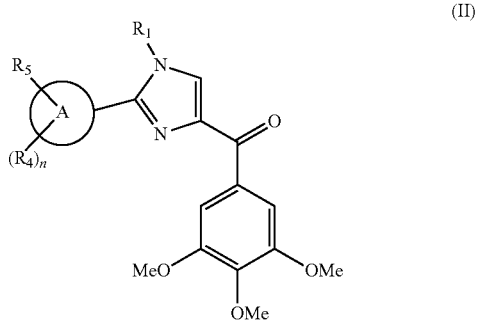

wherein

A is single or fused aromatic or heteroaromatic ring system;

$R_1$ is H, $C_1$-$C_6$ linear or branched alkyl, aryl, phenyl, benzyl, haloalkyl, aminoalkyl, —OCH$_2$Ph, SO$_2$-aryl, SO$_2$-phenyl, —(C=O)-aryl, —(C=O)-phenyl or OH;

$R_4$ and $R_5$ are each independently hydrogen, $C_1$-$C_6$ linear or branched alkyl, $C_1$-$C_6$ linear or branched haloalkyl, $C_1$-$C_6$ linear or branched alkoxy, $C_1$-$C_6$ linear or branched haloalkoxy, F, Cl, Br, I, CF$_3$, CN, —CH$_2$CN, NH$_2$, OH, —OC(O)CF$_3$, alkylamino, aminoalkyl, —OCH$_2$Ph, —NHCO— alkyl, COOH, —C(O)Ph, C(O)O-alkyl, C(O)H, —C(O)NH$_2$ or NO$_2$; and n is an integer between 1-4;

or its pharmaceutically acceptable salt, N-oxide, hydrate, tautomer or isomer; in combination with at least one of a BRAF inhibitor or a MEK inhibitor; and a pharmaceutically acceptable carrier. In another embodiment, the compound of this invention is compound 17ya. In another embodiment, the compound of this invention is compound 12da.

Yet another aspect of the present invention relates to a method of treating cancer that includes selecting a subject in need of treatment for cancer, and administering to the subject a pharmaceutical composition comprising a therapeutically effective amounts of a compound of formula I, II, III or IV, in combination with at least one of a BRAF inhibitor or a MEK inhibitor; and a pharmaceutically acceptable carrier under conditions effective to treat cancer. In another embodiment, the cancer is a drug resistant cancer. In another embodiment, the cancer is melanoma. In another embodiment, the cancer is a BRAF mutant melanoma. In another embodiment, the cancer is a vemurafenib resistant cancer. In another embodiment, the compound of this invention is compound 17ya. In another embodiment, the compound of this invention is compound 12da.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

In some embodiments, any of the compositions of this invention comprise a compound of formula I-IV or a tubulin inhibitor, in combination with at least one of a BRAF inhibitor or a MEK inhibitor, in any form or embodiment as described herein. In some embodiments, any of the compositions of this invention will consist of a compound of formula I-IV or a tubulin inhibitor, in combination with at least one of a BRAF inhibitor or a MEK inhibitor, in any form or embodiment as described herein. In some embodiments, any of the compositions of this invention will consist essentially of a compound of formula I-IV or a tubulin inhibitor, in combination with at least one of a BRAF inhibitor or a MEK inhibitor, in any form or embodiment as described herein. In some embodiments, the term "comprise" refers to the inclusion of the indicated active agent, such as the compound of formula I-IV or a tubulin inhibitor, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient(s), however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient(s). In some embodiments, the term "consisting" refers to a composition, which contains the active ingredient(s) and a pharmaceutically acceptable carrier or excipient.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, alone or as part of the combined therapy or using the compositions of this invention represent additional embodiments of this invention.

Biological Activity

In one embodiment, the invention provides compounds and compositions, including any embodiment described herein, for use in any of the methods of this invention. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In one embodiment, this invention is directed to a method of treating, suppressing, reducing the severity, reducing the risk of developing or inhibiting cancer comprising administering a compound of this invention to a subject suffering from cancer under conditions effective to treat the cancer. In another embodiment, the compound is administered in combination with a BRAF inhibitor. In another embodiment, the compound is administered in combination with a MEK inhibitor. In another embodiment, the compound is administered in combination with a BRAF inhibitor and a MEK inhibitor. In another embodiment, the BRAF inhibitor is vemurafenib. In another embodiment, the BRAF inhibitor is dabrafenib. In another embodiment, the MEK inhibitor is trametinib. In another embodiment, the MEK inhibitor is RO5068760. In another embodiment, the cancer is melanoma, thyroid cancer, colorectal cancer, or ovarian cancer.

In one embodiment, this invention provides methods for: a) treating, suppressing, reducing the severity, reducing the risk, or inhibiting drug resistant tumors; b) treating, suppressing, reducing the severity, reducing the risk, or inhibiting metastatic cancer; c) treating, suppressing, reducing the severity, reducing the risk, or inhibiting drug resistant cancer; d) treating, suppressing, reducing the severity, reducing the risk, or inhibiting melanoma; e) treating, suppressing, reducing the severity, reducing the risk, or inhibiting a drug resistant cancer wherein the cancer is melanoma, thyroid cancer, biliary tract cancer, non-small cell lung cancer (NSCLC), colorectal cancer or ovarian cancer; f) a method of treating, suppressing, reducing the severity, reducing the risk, or inhibiting metastatic melanoma; g) a method of treating, suppressing, reducing the severity, reducing the risk, or inhibiting a BRAF mutant cancer; h) a method of treating, suppressing, reducing the severity, reducing the risk, or inhibiting a BRAF inhibitor resistant cancer; i) a method of treating, suppressing, reducing the severity, reducing the risk, inhibiting, eliminating, delaying or preventing a BRAF inhibitor resistant cancer; j) a method of treating, suppressing, reducing the severity, reducing the risk, or inhibiting a BRAF inhibitor resistant melanoma; k) treating, suppressing, reducing the severity, reducing the risk, or inhibiting cancer in a subject, wherein the subject has been previously treated with chemotherapy, radiotherapy, or biological therapy; l) a method of overcoming resistance to treatment with BRAF inhibitor in a subject; m) treating, suppressing, reducing the severity, reducing the risk, or inhibiting thyroid cancer; n) treating, suppressing, reducing the severity, reducing the risk, or inhibiting colorectal cancer; o) treating, suppressing, reducing the severity, reducing the risk, or inhibiting ovarian cancer; p) treating, suppressing, reducing, inhibiting, eliminating, delaying or preventing cancer metastasis in a subject suffering from cancer; or q) treating, suppressing, reducing, inhibiting, eliminating, delaying or preventing secondary cancer resistance to a taxane drug in a subject suffering from cancer previously treated with a taxane drug, comprising the step of administering to said subject a compound of this invention and/or an isomer, metabolite, pharmaceutically acceptable salt, pharmaceutical product, tautomer, hydrate, N-oxide, polymorph, or crystal of said compound, or any combination thereof, in combination with at least one of a BRAF inhibitor or a MEK inhibitor; or a composition comprising the same. In another embodiment, the methods comprise administering a compound of this invention and/or an isomer, metabolite, pharmaceutically acceptable salt, pharmaceutical product, tautomer, hydrate, N-oxide, polymorph, or crystal of said compound, or any combination thereof, in combination with a BRAF inhibitor or a composition comprising the same. In another embodiment, the methods comprise administering a compound of this invention and/or an isomer, metabolite, pharmaceutically acceptable salt, pharmaceutical product, tautomer, hydrate, N-oxide, polymorph, or crystal of said compound, or any combination thereof, in combination with a MEK inhibitor or a composition comprising the same. In another embodiment, the methods comprise administering a compound of this invention and/or an isomer, metabolite, pharmaceutically acceptable salt, pharmaceutical product, tautomer, hydrate, N-oxide, polymorph, or crystal of said compound, or any combination thereof, in combination with a BRAF inhibitor and a MEK inhibitor; or compositions comprising the same. In another embodiment, the methods comprise administering a tubulin inhibitor in combination with at least one of a BRAF inhibitor or MEK inhibitor; or a composition comprising the same. In another embodiment, the methods comprise administering a tubulin inhibitor in combination with a BRAF inhibitor or a composition comprising the same. In another embodiment, the methods comprise administering a tubulin inhibitor in combination with a MEK inhibitor or a composition comprising the same. In another embodiment, the methods comprise administering a tubulin inhibitor in combination with a BRAF inhibitor and a MEK inhibitor or a composition comprising the same.

In one embodiment, this invention is directed to a method of treating, suppressing, reducing the severity, reducing the risk, or inhibiting BRAF mutant cancer in a subject, comprising administering a composition comprising a BRAF inhibitor, a MEK inhibitor or combination thereof in combination with a compound of this invention or its pharmaceutically acceptable salt, N-oxide, hydrate, tautomer or isomer, to a subject suffering from BRAF mutant cancer, under conditions effective to treat the cancer. In another embodiment, the combination consists essentially of the compound of this invention and a BRAF inhibitor. In another embodiment, the combination consists essentially of the compound of this invention and a MEK inhibitor. In another embodiment, the combination consists essentially of the compound of this invention and a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the cancer is melanoma, thyroid cancer, colorectal cancer or ovarian cancer. In another embodiment, the cancer is melanoma. In another embodiment, the melanoma is V600E positive melanoma. In another embodiment, the cancer is metastatic cancer. In another embodiment, the cancer is drug resistant cancer. In another embodiment, the cancer is resistant to BRAF inhibitors. In another embodiment, the cancer is resistant to taxanes. In another embodiment, the cancer is resistant to docetaxel. In another embodiment, the compound of this invention is a compound of formula I-IV. In another embodiment, the compound of this invention is compound 17ya. In another embodiment, the compound of this invention is compound 12da.

In one embodiment, this invention is directed to a method of treating, suppressing, reducing the severity, reducing the risk, or inhibiting BRAF inhibitor resistant cancer in a subject, comprising administering a composition comprising at least one of a BRAF inhibitor or a MEK inhibitor; in combination with a compound of this invention or its pharmaceutically acceptable salt, N-oxide, hydrate, tautomer or isomer, to a subject suffering from BRAF inhibitor resistant cancer, under conditions effective to treat the cancer. In another embodiment, the combination consists essentially of the compound of this invention and a BRAF inhibitor. In another embodiment, the combination consists essentially of the compound of this invention and a MEK inhibitor. In another embodiment, the combination consists essentially of the compound, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the cancer is melanoma, thyroid cancer, biliary tract cancer, non-small cell lung cancer (NSCLC), colorectal cancer or ovarian cancer. In another embodiment, the cancer is melanoma. In another embodiment, the melanoma is V600E positive melanoma. In another embodiment, the cancer is metastatic cancer. In another embodiment, the compound of this invention is a compound of formula I-IV. In another embodiment, the compound of this invention is compound 17ya. In another embodiment, the compound of this invention is compound 12da.

In one embodiment, this invention is directed to a method of treating, suppressing, reducing the severity, reducing the risk, or inhibiting vemurafenib resistant cancer in a subject, comprising administering a composition comprising at least one of a BRAF inhibitor or a MEK inhibitor; in combination with a compound of this invention or its pharmaceutically acceptable salt, N-oxide, hydrate, tautomer or isomer, to a subject suffering from vemurafenib resistant cancer, under conditions effective to treat the cancer. In another embodiment, the combination consists essentially of the compound of this invention and a BRAF inhibitor. In another embodiment, the combination consists essentially of the compound of this invention and a MEK inhibitor. In another embodiment, the combination consists essentially of the compound of this invention, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the cancer is melanoma, thyroid cancer, biliary tract cancer, non-small cell lung cancer (NSCLC), colorectal cancer or ovarian cancer. In another embodiment, the cancer is melanoma. In another embodiment, the melanoma is V600E positive melanoma. In another embodiment, the cancer has a secondary resistance to taxanes. In another embodiment, the cancer is metastatic cancer. In another embodiment, the compound is a compound of formula I-IV. In another embodiment, the compound of this invention is compound 17ya. In another embodiment, the compound of this invention is compound 12da.

In one embodiment, this invention is directed to a method of treating, suppressing, reducing the severity, reducing the risk, or inhibiting melanoma in a subject, comprising administering a composition comprising at least one of a BRAF inhibitor or a MEK inhibitor, in combination with a compound of this invention or its pharmaceutically acceptable salt, N-oxide, hydrate, tautomer or isomer, to a subject suffering from melanoma, under conditions effective to treat the melanoma. In another embodiment, the combination consists essentially of the compound of this invention and a BRAF inhibitor. In another embodiment, the combination consists essentially of the compound of this invention and a MEK inhibitor. In another embodiment, the combination consists essentially of the compound of this invention, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the melanoma is drug resistant. In another embodiment, the melanoma is V600E positive melanoma. In another embodiment, the melanoma is metastatic melanoma. In another embodiment, the compound is a compound of formula I-IV. In another embodiment, the compound of this invention is compound 17ya. In another embodiment, the compound of this invention is compound 12da.

In one embodiment, this invention is directed to a method of treating, suppressing, reducing the severity, reducing the risk, or inhibiting thyroid cancer in a subject, comprising administering a composition comprising at least one of a BRAF inhibitor or a MEK inhibitor, in combination with a compound of this invention or its pharmaceutically acceptable salt, N-oxide, hydrate, tautomer or isomer, to a subject suffering from thyroid cancer, under conditions effective to treat the thyroid cancer. In another embodiment, the combination consists essentially of the compound of this invention and a BRAF inhibitor. In another embodiment, the combination consists essentially of the compound of this invention and a MEK inhibitor. In another embodiment, the combination consists essentially of the compound of this invention, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the thyroid cancer is drug resistant. In another embodiment, the thyroid cancer is metastatic cancer. In another embodiment, the compound of this invention is a compound of formula I-IV. In another embodiment, the compound of this invention is compound 17ya. In another embodiment, the compound of this invention is compound 12da.

In one embodiment, this invention is directed to a method of treating, suppressing, reducing the severity, reducing the risk, or inhibiting ovarian cancer in a subject, comprising administering a composition comprising at least one of a BRAF inhibitor or a MEK inhibitor, in combination with a compound of this invention or its pharmaceutically acceptable salt, N-oxide, hydrate, tautomer or isomer, to a subject suffering from ovarian cancer, under conditions effective to treat the ovarian cancer. In another embodiment, the combination consists essentially of the compound of this invention and a BRAF inhibitor. In another embodiment, the combination consists essentially of the compound of this invention and a MEK inhibitor. In another embodiment, the combination consists essentially of the compound of this invention, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the ovarian cancer is drug resistant. In another embodiment, the ovarian cancer is metastatic cancer. In another embodiment, the compound of this invention is a compound of formula I-IV. In another embodiment, the compound of this invention is compound 17ya. In another embodiment, the compound of this invention is compound 12da.

In one embodiment, this invention is directed to a method of treating, suppressing, reducing the severity, reducing the risk, or inhibiting colorectal cancer in a subject, comprising administering a composition comprising at least one of a BRAF inhibitor or a MEK inhibitor, in combination with a compound of this invention or its pharmaceutically acceptable salt, N-oxide, hydrate, tautomer or isomer, to a subject suffering from colorectal cancer, under conditions effective to treat the colorectal cancer. In another embodiment, the combination consists essentially of the compound of this invention and a BRAF inhibitor. In another embodiment, the combination consists essentially of the compound of this invention and a MEK inhibitor. In another embodiment, the combination consists essentially of the compound of this invention, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the colorectal cancer is drug resistant. In another embodiment, the colorectal cancer is metastatic cancer. In another embodiment, the compound of this invention is a compound of formula I-IV. In another embodiment, the compound of this invention is compound 17ya. In another embodiment, the compound of this invention is compound 12da.

In one embodiment, this invention is directed to a method of treating, suppressing, reducing the severity, reducing the risk, or inhibiting drug resistant melanoma in a subject, comprising administering a composition comprising at least one of a BRAF inhibitor or a MEK inhibitor, in combination with a compound of this invention or its pharmaceutically acceptable salt, N-oxide, hydrate, tautomer or isomer, to a subject suffering from drug resistant melanoma, under conditions effective to treat the melanoma. In another embodiment, the combination consists essentially of the compound of this invention and a BRAF inhibitor. In another embodiment, the combination consists essentially of the compound of this invention and a MEK inhibitor. In another embodiment, the combination consists essentially of the compound of this invention, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the melanoma is V600E positive melanoma. In another embodiment, the melanoma is metastatic melanoma. In another embodiment, the compound is a compound of formula I-IV. In another embodiment, the compound of this invention is compound 17ya. In another embodiment, the compound of this invention is compound 12da.

In one embodiment, this invention is directed to a method of treating, suppressing, reducing the severity, reducing the risk, or inhibiting drug resistant cancer in a subject, comprising administering a composition comprising at least one of a BRAF inhibitor or a MEK inhibitor, in combination with a compound of this invention or its pharmaceutically acceptable salt, N-oxide, hydrate, tautomer or isomer, to a subject suffering from drug resistant cancer, under conditions effective to treat the cancer. In another embodiment, the combination consists essentially of the compound of this invention and a BRAF inhibitor. In another embodiment, the combination consists essentially of the compound of this invention and a MEK inhibitor. In another embodiment, the combination consists essentially of the compound of this invention, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the cancer is melanoma, thyroid cancer, biliary tract cancer, non-small cell lung cancer (NSCLC), colorectal cancer or ovarian cancer. In another embodiment, the cancer is metastatic cancer. In another embodiment, the cancer is melanoma. In another embodiment, the cancer is V600E positive melanoma. In another embodiment, the compound is a compound of formula I-IV. In another embodiment, the compound of this invention is compound 17ya. In another embodiment, the compound of this invention is compound 12da.

In one embodiment, this invention is directed to a method of overcoming resistance to treatment with BRAF inhibitor in a subject suffering from drug resistant cancer, comprising administering a composition comprising at least one of a BRAF inhibitor or a MEK inhibitor, in combination with a compound of this invention or its pharmaceutically acceptable salt, N-oxide, hydrate, tautomer or isomer, to a subject suffering from drug resistant cancer. In another embodiment, the combination consists essentially of the compound of this invention and a BRAF inhibitor. In another embodiment, the combination consists essentially of the compound of this invention and a MEK inhibitor. In another embodiment, the combination consists essentially of the compound of this invention, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the cancer is melanoma, thyroid cancer, biliary tract cancer, non-small cell lung cancer (NSCLC), colorectal cancer or ovarian cancer. In another embodiment, the cancer is metastatic cancer. In another embodiment, the cancer is melanoma. In another embodiment, the cancer is V600E positive melanoma. In another embodiment, the compound is a compound of formula I-IV. In another embodiment, the compound of this invention is compound 17ya. In another embodiment, the compound of this invention is compound 12da.

In one embodiment, this invention is directed to a method of preventing, eliminating, reducing or delaying resistance to cancer treatment in a subject suffering from cancer, comprising administering a composition comprising at least one of a BRAF inhibitor or a MEK inhibitor, in combination with a compound of this invention or its pharmaceutically acceptable salt, N-oxide, hydrate, tautomer or isomer, to a subject suffering from drug resistant cancer. In another embodiment, the combination consists essentially of the compound of this invention and a BRAF inhibitor. In another embodiment, the combination consists essentially of the compound of this invention and a MEK inhibitor. In another embodiment, the combination consists essentially of the compound of this invention, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the cancer is melanoma, thyroid cancer, biliary tract cancer, non-small cell lung cancer (NSCLC), colorectal cancer or ovarian cancer. In another embodiment, the cancer is metastatic. In another embodiment, the cancer is melanoma. In another embodiment, the cancer is V600E positive melanoma. In another embodiment, the compound is a compound of formula I-IV. In another embodiment, the compound of this invention is compound 17ya. In another embodiment, the compound of this invention is compound 12da.

In one embodiment, this invention is directed to a method of treating, suppressing, reducing the severity, reducing the risk, or inhibiting BRAF mutant cancer in a subject, comprising administering a composition comprising a tubulin inhibitor in combination with at least one of a BRAF inhibitor or a MEK inhibitor, to a subject suffering from BRAF mutant cancer, under conditions effective to treat the cancer. In another embodiment, the combination consists essentially of the tubulin inhibitor and a BRAF inhibitor. In another embodiment, the combination consists essentially of the tubulin inhibitor and a MEK inhibitor. In another embodiment, the combination consists essentially of the tubulin inhibitor, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel, colchicine, vinblastine, taxol or any combination thereof. In another embodiment, the tubulin inhibitor is docetaxel. In another embodiment, the cancer is melanoma, thyroid cancer, biliary tract cancer, non-small cell lung cancer (NSCLC), colorectal cancer or ovarian cancer. In another embodiment, the cancer is melanoma. In another embodiment, the melanoma is V600E positive melanoma. In another embodiment, the cancer is drug resistant cancer. In another embodiment, the cancer is metastatic cancer. In another embodiment, the cancer is resistant to BRAF inhibitors.

In one embodiment, this invention is directed to a method of treating, suppressing, reducing the severity, reducing the risk, or inhibiting BRAF inhibitor resistant cancer in a subject, comprising administering a composition comprising a tubulin inhibitor in combination with at least one of a BRAF inhibitor or a MEK inhibitor, to a subject suffering from BRAF inhibitor resistant cancer, under conditions effective to treat the cancer. In another embodiment, the combination consists essentially of the tubulin inhibitor and a BRAF inhibitor. In another embodiment, the combination consists essentially of the tubulin inhibitor and a MEK inhibitor. In another embodiment, the combination consists essentially of the tubulin inhibitor, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel, colchicine, vinblastine, taxol or any combination thereof. In another embodiment, the tubulin inhibitor is docetaxel. In another embodiment, the cancer is melanoma, thyroid cancer, biliary tract cancer, non-small cell lung cancer (NSCLC), colorectal cancer or ovarian cancer. In another embodiment, the cancer is metastatic cancer. In another embodiment, the cancer is melanoma. In another embodiment, the melanoma is V600E positive melanoma.

In one embodiment, this invention is directed to a method of treating, suppressing, reducing the severity, reducing the risk, or inhibiting vemurafenib resistant cancer in a subject, comprising administering a composition comprising a tubulin inhibitor in combination with at least one of a BRAF inhibitor or a MEK inhibitor; to a subject suffering from vemurafenib resistant cancer, under conditions effective to treat the cancer. In another embodiment, the combination consists essentially of the tubulin inhibitor and a BRAF inhibitor. In another embodiment, the combination consists essentially of the tubulin inhibitor and a MEK inhibitor. In another embodiment, the combination consists essentially of the tubulin inhibitor, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel, colchicine, vinblastine, taxol or any combination thereof. In another embodiment, the tubulin inhibitor is docetaxel. In another embodiment, the cancer is melanoma, thyroid cancer, biliary tract cancer, non-small cell lung cancer (NSCLC), colorectal cancer or ovarian cancer. In another embodiment, the cancer is metastatic cancer. In another embodiment, the cancer is melanoma. In another embodiment, the melanoma is V600E positive melanoma.

In one embodiment, this invention is directed to a method of treating, suppressing, reducing the severity, reducing the risk, or inhibiting melanoma in a subject, comprising administering a composition comprising a tubulin inhibitor in combination with at least one of a BRAF inhibitor or a MEK inhibitor, to a subject suffering from melanoma, under conditions effective to treat the melanoma. In another embodiment, the combination consists essentially of the tubulin inhibitor and a BRAF inhibitor. In another embodiment, the combination consists essentially of the tubulin inhibitor and a MEK inhibitor. In another embodiment, the combination consists essentially of the tubulin inhibitor, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel, colchicine, vinblastine, taxol or any combination thereof. In another embodiment, the tubulin inhibitor is docetaxel. In another embodiment, the melanoma is drug resistant. In another embodiment, the melanoma is metastatic melanoma. In another embodiment, the melanoma is V600E positive melanoma.

In one embodiment, this invention is directed to a method of treating, suppressing, reducing the severity, reducing the risk, or inhibiting thyroid cancer in a subject, comprising administering a composition comprising a tubulin inhibitor in combination with at least one of a BRAF inhibitor or a MEK inhibitor, to a subject suffering from thyroid cancer, under conditions effective to treat the thyroid cancer. In another embodiment, the combination consists essentially of the tubulin inhibitor and a BRAF inhibitor. In another embodiment, the combination consists essentially of the tubulin inhibitor and a MEK inhibitor. In another embodiment, the combination consists essentially of the tubulin inhibitor, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel, colchicine, vinblastine, taxol or any combination thereof. In another embodiment, the tubulin inhibitor is docetaxel. In another embodiment, the thyroid cancer is drug resistant. In another embodiment, the thyroid cancer is metastatic.

In one embodiment, this invention is directed to a method of treating, suppressing, reducing the severity, reducing the risk, or inhibiting colorectal cancer in a subject, comprising administering a composition comprising a tubulin inhibitor in combination with at least one of a BRAF inhibitor or a MEK inhibitor, to a subject suffering from colorectal cancer, under conditions effective to treat the colorectal cancer. In another embodiment, the combination consists essentially of the tubulin inhibitor and a BRAF inhibitor. In another embodiment, the combination consists essentially of the tubulin inhibitor and a MEK inhibitor. In another embodiment, the combination consists essentially of the tubulin inhibitor, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel, colchicine, vinblastine, taxol or any combination thereof. In another embodiment, the tubulin inhibitor is docetaxel. In another embodiment, the colorectal cancer is drug resistant. In another embodiment, the colorectal cancer is metastatic.

In one embodiment, this invention is directed to a method of treating, suppressing, reducing the severity, reducing the risk, or inhibiting ovarian cancer in a subject, comprising administering a composition comprising a tubulin inhibitor in combination with at least one of a BRAF inhibitor or a MEK inhibitor, to a subject suffering from ovarian cancer, under conditions effective to treat the ovarian cancer. In another embodiment, the combination consists essentially of the tubulin inhibitor and a BRAF inhibitor. In another embodiment, the combination consists essentially of the tubulin inhibitor and a MEK inhibitor. In another embodiment, the combination consists essentially of the tubulin inhibitor, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel, colchicine, vinblastine, taxol or any combination thereof. In another embodiment, the tubulin inhibitor is docetaxel. In another embodiment, the ovarian cancer is drug resistant. In another embodiment, the ovarian cancer is metastatic cancer.

In one embodiment, this invention is directed to a method of treating, suppressing, reducing the severity, reducing the risk, or inhibiting drug resistant melanoma in a subject, comprising administering a composition comprising a tubulin inhibitor in combination with at least one of a BRAF inhibitor or a MEK inhibitor, to a subject suffering from drug resistant melanoma, under conditions effective to treat the melanoma. In another embodiment, the combination consists essentially of the tubulin inhibitor and a BRAF inhibitor. In another embodiment, the combination consists essentially of the tubulin inhibitor and a MEK inhibitor. In another embodiment, the combination consists essentially of the tubulin inhibitor, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel, colchicine, vinblastine, taxol or any combination thereof. In another embodiment, the tubulin inhibitor is docetaxel. In another embodiment, the melanoma is V600E positive melanoma. In another embodiment, the melanoma is metastatic.

In one embodiment, this invention is directed to a method of treating, suppressing, reducing the severity, reducing the risk, or inhibiting drug resistant cancer in a subject, comprising administering a composition comprising a tubulin inhibitor in combination with at least one of a BRAF inhibitor or a MEK inhibitor, to a subject suffering from drug resistant cancer, under conditions effective to treat the cancer. In another embodiment, the combination consists essentially of the tubulin inhibitor and a BRAF inhibitor. In another embodiment, the combination consists essentially of the tubulin inhibitor and a MEK inhibitor. In another embodiment, the combination consists essentially of the tubulin inhibitor, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel, colchicine, vinblastine, taxol or any combination thereof. In another embodiment, the tubulin inhibitor is docetaxel. In another embodiment, the cancer is melanoma, thyroid cancer, biliary tract cancer, non-small cell lung cancer (NSCLC), colorectal cancer or ovarian cancer. In another embodiment, the cancer is metastatic cancer. In another embodiment, the cancer is melanoma. In another embodiment, the cancer is V600E positive melanoma.

In one embodiment, this invention is directed to a method of overcoming resistance to treatment with BRAF inhibitor in a subject, comprising administering a composition comprising a tubulin inhibitor in combination with at least one of a BRAF inhibitor or a MEK inhibitor to a subject suffering from drug resistant cancer. In another embodiment, the combination consists essentially of the tubulin inhibitor and a BRAF inhibitor. In another embodiment, the combination consists essentially of the tubulin inhibitor and a MEK inhibitor. In another embodiment, the combination consists essentially of the tubulin inhibitor, a BRAF inhibitor and a MEK inhibitor. In another embodiment, the BRAF inhibitor is vemurafenib, dabrafenib, GDC-0879, PLX-4720, sorafenib tosylate, LGX818 or any combination thereof. In another embodiment, the BRAF inhibitor is vemurafenib. In another embodiment, the BRAF inhibitor is dabrafenib. In another embodiment, the MEK inhibitor is trametinib, selumetinib, RO5068760, MEK162, PD-325901, cobimetinib, CI-1040 or any combination thereof. In another embodiment, the MEK inhibitor is trametinib. In another embodiment, the MEK inhibitor is RO5068760. In another embodiment, the tubulin inhibitor is paclitaxel, epothilone, docetaxel, discodermolide, colchicine, combrestatin, 2-methoxyestradiol, methoxy benzenesulfonamides (E7010), vinblastine, vincristine, vinorelbine, vinfluine, dolastatins, halichondrins, hemiasterlins, cryptophysin 52, taxol or any combination thereof. In another embodiment, the tubulin inhibitor is docetaxel, colchicine, vinblastine, taxol or any combination thereof. In another embodiment, the tubulin inhibitor is docetaxel. In another embodiment, the cancer is melanoma, thyroid cancer, biliary tract cancer, non-small cell lung cancer (NSCLC), colorectal cancer or ovarian cancer. In another embodiment, the cancer is metastatic cancer. In another embodiment, the cancer is melanoma. In another embodiment, the cancer is V600E positive melanoma.

The compounds of the present invention are useful in the treatment, reducing the severity, reducing the risk, or inhibition of cancer, metastatic cancer, drug resistant tumors, drug resistant cancer and various forms of cancer. In a preferred embodiment the cancer is skin cancer (e.g. melanoma), thyroid cancer, colorectal cancer, ovarian cancer, prostate cancer, breast cancer, lung cancer, colon cancer, biliary tract cancer, non-small cell lung cancer (NSCLC), leukemia, lymphoma, head and neck, pancreatic, esophageal, renal cancer or CNS cancer (e.g., glioma, glioblastoma). Treatment of these different cancers is supported by the Examples herein. Moreover, based upon their believed mode of action as tubulin inhibitors, it is believed that other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, in combination with at least one of a BRAF inhibitor or a MEK inhibitor; for treating, suppressing, reducing the severity, reducing the risk, or inhibiting cancer in a subject. In another embodiment, the cancer is skin cancer (e.g. melanoma), thyroid cancer, colorectal cancer, ovarian cancer, adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, urethral cancer, uterine cancer, sarcoma, unusual cancer of childhood, vaginal cancer, vulvar cancer, Wilms' tumor, or any combination thereof. In another embodiment the subject has been previously treated with chemotherapy, radiotherapy or biological therapy.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, in combination with at least one of a BRAF inhibitor or a MEK inhibitor; for treating, suppressing, reducing the severity, reducing the risk, or inhibiting a metastatic cancer in a subject. In another embodiment, the cancer is skin cancer (e.g. melanoma), thyroid cancer, colorectal cancer, ovarian cancer, adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, melanoma, small intestine cancer, soft tissue sarcoma, soft tissue sarcoma, testicular cancer, thymoma, malignant, urethral cancer, uterine cancer, sarcoma, unusual cancer of childhood, vaginal cancer, vulvar cancer, Wilms' tumor, or any combination thereof.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, in combination with at least one of a BRAF inhibitor or a MEK inhibitor; for treating, suppressing, reducing the severity, reducing the risk, or inhibiting a drug-resistant cancer or resistant cancer in a subject. In another embodiment, the cancer is skin cancer (e.g. melanoma), thyroid cancer, colorectal cancer, ovarian cancer, adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycoides fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, Kaposi's sarcoma, skin cancer, melanoma, small intestine cancer, soft tissue sarcoma, soft tissue sarcoma, testicular cancer, thymoma, malignant, urethral cancer, uterine cancer, sarcoma, unusual cancer of childhood, vaginal cancer, vulvar cancer, Wilms' tumor, or any combination thereof.

In one embodiment "metastatic cancer" refers to a cancer that spread (metastasized) from its original site to another area of the body. Virtually all cancers have the potential to spread. Whether metastases develop depends on the complex interaction of many tumor cell factors, including the type of cancer, the degree of maturity (differentiation) of the tumor cells, the location and how long the cancer has been present, as well as other incompletely understood factors. Metastases spread in three ways—by local extension from the tumor to the surrounding tissues, through the bloodstream to distant sites or through the lymphatic system to neighboring or distant lymph nodes. Each kind of cancer may have a typical route of spread. The tumor is called by the primary site (ex. breast cancer that has spread to the brain is called metastatic breast cancer to the brain).

In one embodiment "drug-resistant cancer" refers to cancer cells that acquire resistance to chemotherapy. Cancer cells can acquire resistance to chemotherapy by a range of mechanisms, including the mutation or overexpression of the drug target, inactivation of the drug, or elimination of the drug from the cell. Tumors that recur after an initial response to chemotherapy may be resistant to multiple drugs (they are multidrug resistant). In the conventional view of drug resistance, one or several cells in the tumor population acquire genetic changes that confer drug resistance. Accordingly, the reasons for drug resistance, inter alia, are: a) some of the cells that are not killed by the chemotherapy mutate (change) and become resistant to the drug. Once they multiply, there may be more resistant cells than cells that are sensitive to the chemotherapy; b) Gene amplification. A cancer cell may produce hundreds of copies of a particular gene. This gene triggers an overproduction of protein that renders the anticancer drug ineffective; c) cancer cells may pump the drug out of the cell as fast as it is going in using a molecule called p-glycoprotein; d) cancer cells may stop taking in the drugs because the protein that transports the drug across the cell wall stops working; e) the cancer cells may learn how to repair the DNA breaks caused by some anti-cancer drugs; f) cancer cells may develop a mechanism that inactivates the drug. One major contributor to multidrug resistance is overexpression of P-glycoprotein (P-gp) or other drug efflux pumps (OAT, OCT, BCRP, etc.). This protein is a clinically important transporter protein belonging to the ATP-binding cassette family of cell membrane transporters. It can pump substrates including anticancer drugs out of tumor cells through an ATP-dependent mechanism. Thus, the resistance to anticancer agents used in chemotherapy is the main cause of treatment failure in malignant disorders, provoking tumors to become resistant. Drug resistance is the major cause of cancer chemotherapy failure.

In one embodiment "resistant cancer" refers to drug-resistant cancer as described herein above. In another embodiment "resistant cancer" refers to cancer cells that acquire resistance to any treatment such as chemotherapy, radiotherapy or biological therapy.

In one embodiment, this invention is directed to treating, suppressing, reducing the severity, reducing the risk, or inhibiting cancer in a subject, wherein the subject has been previously treated with chemotherapy, radiotherapy or biological therapy.

In one embodiment "Chemotherapy" refers to chemical treatment for cancer such as drugs that kill cancer cells directly. Such drugs are referred as "anti-cancer" drugs or "antineoplastics." Today's therapy uses more than 100 drugs to treat cancer. To cure a specific cancer. Chemotherapy is used to control tumor growth when cure is not possible; to shrink tumors before surgery or radiation therapy; to relieve symptoms (such as pain); and to destroy microscopic cancer cells that may be present after the known tumor is removed by surgery (called adjuvant therapy). Adjuvant therapy is given to prevent a possible cancer reoccurrence.

In one embodiment, "Radiotherapy" refers to high energy x-rays and similar rays (such as electrons) to treat disease. Many people with cancer will have radiotherapy as part of their treatment. This can be given either as external radiotherapy from outside the body using x-rays or from within the body as internal radiotherapy. Radiotherapy works by destroying the cancer cells in the treated area. Although normal cells can also be damaged by the radiotherapy, they can usually repair themselves. Radiotherapy treatment can cure some cancers and can also reduce the chance of a cancer coming back after surgery. It may be used to reduce cancer symptoms.

In one embodiment "Biological therapy" refers to substances that occur naturally in the body to destroy cancer cells. There are several types of treatment including: monoclonal antibodies, cancer growth inhibitors, vaccines and gene therapy. Biological therapy is also known as immunotherapy.

A still further aspect of the present invention relates to a method of treating or preventing a cancerous condition that includes: providing a composition comprising a compound of the present invention such as a compound of formula I, II, III or IV, or 17ya or 12da, and at least one of a BRAF inhibitor or a MEK inhibitor; and then administering an effective amount of the composition to a patient in a manner effective to treat or prevent a cancerous condition.

According to one embodiment, the patient to be treated is characterized by the presence of a precancerous condition, and the administering of the composition is effective to prevent development of the precancerous condition into the cancerous condition. This can occur by destroying the precancerous cell prior to or concurrent with its further development into a cancerous state.

According to another embodiment, the patient to be treated is characterized by the presence of a cancerous condition, and the administering of the composition is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

As used herein, subject or patient refers to any mammalian patient, including without limitation, humans and other primates, dogs, cats, horses, cows, sheep, pigs, rats, mice, and other rodents. In one embodiment, the subject is male. In another embodiment, the subject is female. In some embodiments, the methods as described herein may be useful for treating both males and females.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

When the compounds or pharmaceutical compositions of the present invention are administered to treat, suppress, reduce the severity, reduce the risk, or inhibit a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

The following examples are presented in order to more fully illustrate the preferred embodiments of the invention. They should in no way, however, be construed as limiting the broad scope of the invention.

EXAMPLES

The Examples set forth below are for illustrative purposes only and are not intended to limit, in any way, the scope of the present invention.

Example 1

Combination of Compound 12da or 17ya and Vemurafenib for Treatment of BRAF Mutant Melanoma and Vemurafenib Resistant Cancer Vemurafenib is a novel anti-melanoma drug which is approved for V600E mutants but develops resistance over the course of ~9 months. Several tubulin inhibitors including compounds 12da and 17ya were screened to evaluate their anti-proliferation combination effects with vemurafenib on parental A375 and MDA-MB-435 cells which were both BRAF V600E mutant cell lines. These combinations may help overcome resistance.

A hypothesis of synergistic cell cycle arrest by the combinations of vemurafenib with 12da or docetaxel was tested in a panel of $BRAF^{V600E}$ mutant parental melanoma cell lines and chronically selected vemurafenib-resistant A375RF21 subline (Su F, Bradley W D, Wang Q, et al. "Resistance to selective BRAF inhibition can be mediated by modest upstream pathway activation." *Cancer Res.* (2012) 72: 969-978). The established vemurafenib-resistant A375RF21 cells were used in vitro and in vivo as the disease relapse model to test whether the proposed synergistic drug combination would be of potential therapy benefit in associated clinical vemurafenib resistance.

Materials and Methods

Reagents and Cell Lines

Vemurafenib (also known as PLX4032, RG7204 or RO5185426), trametinib, sunitinib (malate salt) and docetaxel was purchased from LC Laboratories (Woburn, Mass.). Compound 12da was synthesized in house as described infra. Compounds were dissolved in dimethyl sulfoxide (DMSO, Sigma-Aldrich, St. Louis, Mo.) to make stock solution of 10 mM. Human melanoma A375 cell line was acquired from ATCC (Manassas, Va.). WM164 and MDA-MB-435 cells were obtained from Dr. Meenhard Herlyn (Wistar Institute, Philadelphia, Pa.), and Dr. Robert Clarke (Georgetown University, Washington, D.C.), respectively. All cell lines were authenticated prior to use for this study. Cells were cultured in DMEM medium (Mediatech, Inc., Manassas, Va.), supplemented by 10% fetal bovine serum (FBS, Atlanta Biologicals, Lawrenceville, Ga.), 1% antibiotic/antimycotic mixture (Sigma-Aldrich, St. Louis, Mo.) and 5 μg/mL bovine insulin (Sigma-Aldrich, St. Louis, Mo.).

In Vitro Acquired Vemurafenib Resistance

A melanoma cell line with acquired resistance to vemurafenib was chronically selected by culturing parental A375 cells in increasing concentrations of vemurafenib, following a reported method (Su F, Bradley W D, Wang Q, et al. "Resistance to selective BRAF inhibition can be mediated by modest upstream pathway activation." *Cancer Res.* (2012) 72: 969-978), for at least three months. The isolated resistant A375RF21 cell line steadily increased $IC_{50}$ for vemurafenib over 50 fold (28.9±0.6 μM on A375RF21 cell compared to 0.57±0.03 μM in the parental A375 cell line determined by MTS assay, FIG. 1). The resistant A375RF21 cell line was maintained in full growth medium containing 2.5 μM vemurafenib.

Cell Proliferation and In Vitro Combination Assay

Cell proliferation viability was investigated using MTS or SRB assay as described previously. An in vitro study of the combination of vemurafenib and the tubulin inhibitors was designed and conducted using CalcuSyn software (Biosoft, Ferguson, Mo.) with five duplicates of each set of treatment. Drug concentrations were selected based on the $IC_{50}$ value of each drug tested from a pilot study. Synergism, additive activity or antagonism was determined through Chou-Talalay method (Chou T C. "Drug combination studies and their synergy quantification using the Chou-Talalay method." *Cancer Res.* (2010) 70: 440-446), showing a combination index (CI) as calculated in the software output.

Cell Cycle Analysis

Figure 23:
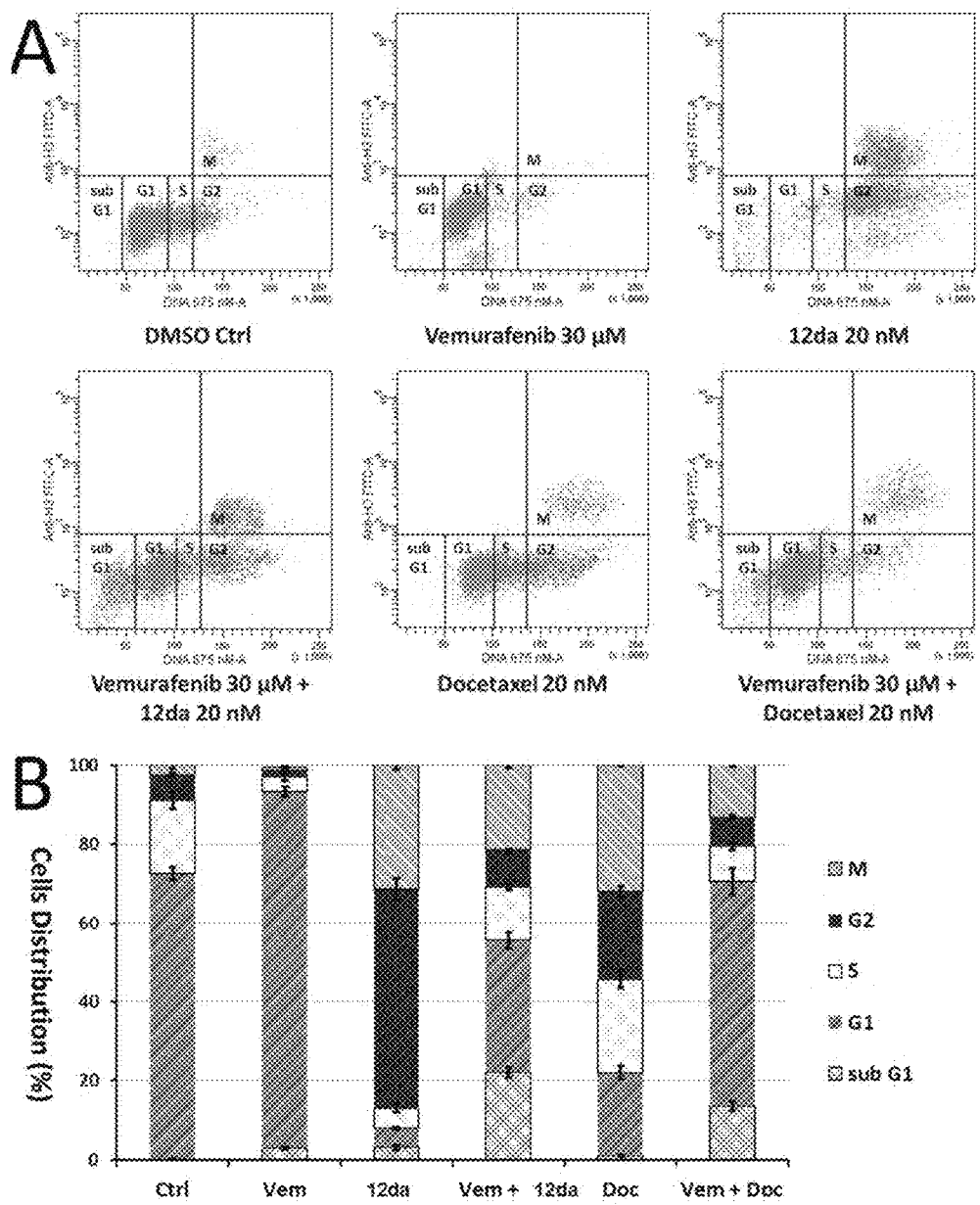
FIG. 23 depicts an anti-phospho-histone H3 and PI (propidium iodide) bivariate staining cell cycle analysis on vemurafenib-resistant cells. A375RF21 cells (biological replicates n=4) were treated with cell culture medium containing either 5‰ DMSO (vehicle control), single agent or the indicated combinations for 24 h before staining with anti-phospho-histone H3-AlexaFluor® 488 antibody and PI then analyzed with flow cytometry. A, representative diagrams illustrated the cell distribution. The red lines were defined manually to show how the cell cycle phases distribution had been calculated accordingly. B, quantification data (mean±SD) for cell cycle phases distribution. Ctrl: 5‰ DMSO; Vem: vemurafenib 30 μM; ABI: compound 12da 20 nM; Vem+ABI: vemurafenib 30 μM+compound 12da 20 nM; Doc: docetaxel 20 nM; Vem+Doc: vemurafenib 30 μM+docetaxel 20 nM.

Flow cytometry analysis was performed as described before (Wang Z, Chen J, Wang J, et al. "Novel tubulin polymerization inhibitors overcome multidrug resistance and reduce melanoma lung metastasis." *Pharm. Res.* (2012) 29: 3040-3052). To determine cell cycle distributions in the $G_2$ and M phases (FIG. 23), cells were harvested with trypsin, stained using antiphospho-histone H3-AlexaFluor® 488 antibody on ice for one hour in the dark, followed by stained using PI/RNase solution for 30 minutes at room temperature in the dark per the manufacturer's instructions (#FCCH025103, EMD Millipore Corporation, Ballerica, Mass.). Data were further processed and graphs were prepared using the Modfit 2.0 program (Verity Software House, Topsham, Me.).

Tubulin Polymerization Assay

HTS-tubulin polymerization assay was performed as described previously using a commercial kit following the manufacturer's instructions (#BK004P, Cytoskeleton, Inc., Denver, Colo.). Bovine brain tubulin (0.4 mg) was mixed with 5 μM 12da, 20 μM vemurafenib or the combination of two agents and incubated in 110 μL of general tubulin buffer (80 mM PIPES, 2.0 mM $MgCl_2$, 0.5 mM EDTA, and 1 mM GTP) at pH 6.9. The absorbance at 340 nm was kinetically recorded every 1 min for 45 min at 37° C. by the SYNERGY HT micro-plate reader (Bio-Tek Instruments, Winooski, Vt.). The data from either single or combination treatments was compared to that from the positive control group, 10 μM colchicine.

Western Blot Analysis

At the indicated time treatment, human melanoma A375RF21, MDA-MB-435 or WM164 cells were collected to investigate relevant cascade protein or apoptosis markers by western blots. Total protein was extracted by lysing cells with RIPA buffer (Sigma-Aldrich, St. Louis, Mo.) containing phosphatase-proteinase inhibitor cocktail (Sigma-Aldrich, St. Louis, Mo.). General protein concentration was then determined by BCA method using kit (Sigma-Aldrich, St. Louis, Mo.). The cell lysates were diluted to equal general protein concentration using Laemmli loading buffer (Bio-Rad, Hercules, Calif.) and boiled for 5 min to denature the protein. Then group samples containing 10 μg general proteins were loaded to each well of 4-15% Tris-HCl pre-cast polyacrylamide gel (Bio-Rad, Hercules, Calif.) for electrophoresis and subsequently transferred to 0.2 μm nitrocellulose membrane (Bio-Rad, Hercules, Calif.). After blocking with 5% bovine serum albumin in 1×TBST for one hour at room temperature, the membranes were further incubated separately with the primary rabbit antibodies (Cell Signaling Technology, Inc., Danvers, Mass.): anti-phospho-ERK1/2 (Thr202/Tyr204; #9101), anti-p44/42 MAPK (ERK1/2; #9102), anti-phospho-AKT (Ser473; #9271), anti-AKT (#9272), anti-cyclin D1 (92G2; #2978); anti-cleaved PARP (Asp214; #9185), anti-cleaved caspase-3 (Asp 175; #9664), anti-RAS (#3339), anti-ARAF (#4432), anti-BRAF (#9433), anti-CRAF (#9422), phosphor-PI3 kinase p85 (Tyr458)/p55 (Tyr199) (#4228), anti-PTEN (#9188), anti-PDGF receptor β (#3169), or anti-GAPDH (#3683) overnight at 4° C. Membrane then was incubated with anti-rabbit IgG HRP-conjugated secondary antibody (Cell Signaling, #7071) for 1 h at room temperature. Target proteins were detected by incubating with 1×LumiGLO® reagent (Cell Signaling, #7003) for one minute and exposed to x-ray film. The films were scanned with grey scale and lane intensities were quantified with the ImageJ software (NIH, Bethesda, Md., USA).

Apoptosis Detection

A375RF21 cells were seeded in 6-well plates ($1\times10^6$ per well) and treated with growth medium containing 5‰ DMSO, vemurafenib, 12da, docetaxel or the indicated combinations. After 48 hours incubation, apoptosis analysis was performed using the Annexin V-FITC Apoptosis Detection Kit (Abcam, Cambridge, Mass.) as per manufacturer's instructions and analyzed by a BD LSR-II cytometer (BD Biosciences, San Jose, Calif.).

Tumor Xenograft and Treatment

Seven to eight week old male nude mice were purchased from Charles River Laboratories International, Inc. (Wilmington, Mass.). A375RF21 cells were suspended in ice-cold phenol red-free and FBS-free DMEM medium without FBS and mixed with high concentration Matrigel (BD Biosciences, San Joes, Calif.) at ratio of 1:1 right before use. 100 μL of this mixture containing $3\times10^6$ cells were injected subcutaneously (s.c.) to the left-side dorsal flank of each mouse. One week after the inoculation, the mice were randomized into four groups (n=7 for the initial low dose and n=5 for subsequent high dose drug combination) and the treatments started. Compound 12da or vemurafenib was diluted in PEG300 (Sigma-Aldrich, St. Louis, Mo.) and administered through intraperitoneal (i.p.) injection once per day, 5 days per week for three continuous weeks. Vehicle control group was i.p. injected with same volume (100 μL)

of PEG300 at the same dosing frequency. At the end of the experiments, mice were euthanized and tumor tissue were isolated, weighted and then fixed in 10% buffered formalin phosphate solution.

Tumor volume and body weight of each mouse were evaluated three times a week. The tumor volume was calculated using formula $a \times b^2 \times 0.5$, where a and b represented the larger and smaller tumor diameters. Data was showed as mean±SD for each group and plotted as a function of time. Tumor growth inhibition (TGI) was calculated as $100-100 \times [(T-T_0)/(C-C_0)]$, and tumor regression was calculated as $(T-T_0)/T_0 \times 100$, where T, $T_0$, C and $C_0$ are the mean tumor volume for the specific group on the last day of treatment, mean tumor volume of the same group on the first day of treatment, mean tumor volume for the vehicle control group on the last day of treatment and mean tumor volume for the vehicle control group on the first day of treatment, respectively.

Pathology and Immunohistochemistry Analysis

Tumor tissues fixed in formalin buffer for over one week were stained with hematoxylin and eosin. For immunohistochemistry (IHC) analysis, the following primary antibodies were used: rabbit anti-Ki67, anti-phospho-AKT (Ser473) and anti-phospho-ERK1/2 (Thr202/Tyr204) (#9027; #4060; #4376; Cell Signaling Technology, Inc., Danvers, Mass.). Anti-S100 primary antibody was purchased from Abcam (#ab868, Abcam Inc., Cambridge, Mass.). Analyses were performed following manufacturer's protocols.

Statistical Analysis

Data were analyzed using Prism Software 5.0 (GraphPad Software, Inc., San Diego, Calif.). The statistical significance (P<0.05) was evaluated by Mann-Whitney Rank Test, nonparametric t-test and one-way ANOVA for in vitro apoptosis detection and xenograft study. Treated groups were compared with the vehicle group and combination treatment groups were compared with the groups that received single agent treatment, accordingly.

Results

Combination of Vemurafenib with Tubulin Inhibitors 17ya and 12da Showed Strong Synergies in Both Parental and Vemurafenib-Resistant Melanoma Cell Lines.

Figure 24:
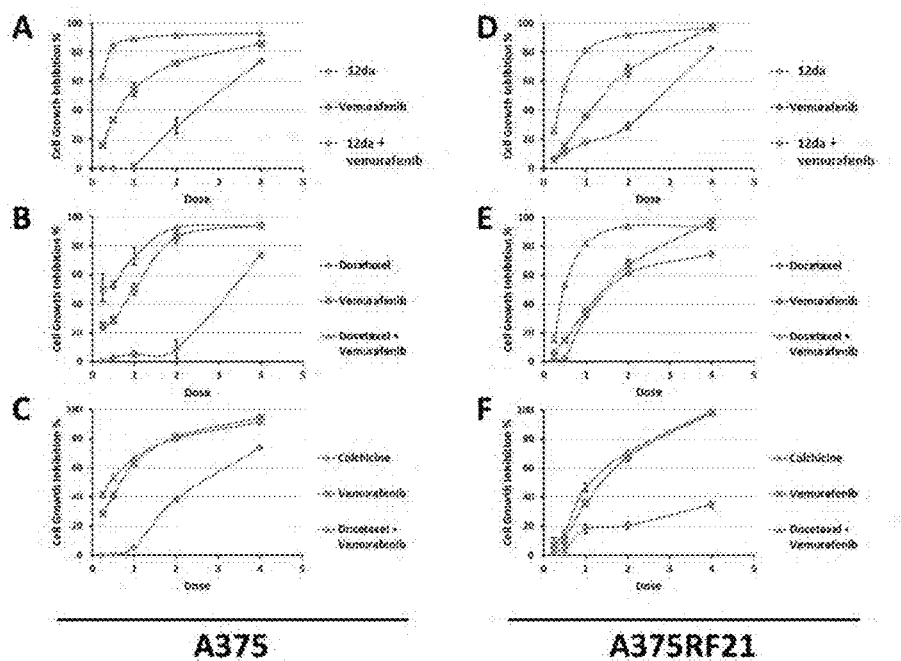
FIG. 24 depicts the in vitro dose-response curves (n=5) of each combination in A375 and A375RF21 cells. X-axis of each plot is the dose density regarding $IC_{50}$ concentrations of drug A or B on A375 or A375RF21 cells in an A+B combination treatment.

Several tubulin inhibitors including compounds 12da and 17ya were screened to evaluate their anti-proliferation combination effects with vemurafenib on parental A375 and MDA-MB-435 cells which were both $BRAF^{V600E}$ mutant cell lines. Both docetaxel and colchicine, two well-known tubulin inhibitors, were included for comparison (Table 1 and FIG. 24). It was found that calculated CI values for combination of 12da and vemurafenib was as low as 0.32 (in A375 cell line) and 0.10 (in MDA-MB-435 cell line) at their $ED_{50}$. Further it was shown that a MEKi (trametinib) and a general receptor tyrosine kinase inhibitor (RTKi; sunitinib) demonstrated only addition CI values (Table 1).

Based on the results below, these combinations may help overcome resistance seen in vemurafenib treated patients.

Both 17ya and 12da demonstrated synergistic activity when combined with vemurafenib or docetaxel. The work was initiated with 17ya but was migrated toward 12da for in vivo studies. The concept of combination index (CI) is introduced. Essentially, CI values <1.0 indicate synergistic activity, a value of 1.0 indicates additive activity, and values >1.0 indicate less than additive or antagonistic activity.

TABLE 1

Combination of vemurafenib with tubulin inhibitors showed synergistic effects in the parental and vemurafenib-resistant melanoma cell lines. Combinations of vemurafenib with tubulin inhibitors maintain strong synergy (CI <0.9) in this resistant line, but Vem + MEKi or Vem + RTKi are only additive. The combination index (CI) values were calculated based on the results from cell viability MTS assay (n = 5). CI <0.9 indicates synergism; $0.9 \leq CI \leq 1.1$ indicates additive effect; CI >1.1 indicates antagonism between the two tested drugs. Establishing a stable, highly vemurafenib-resistant A375RF21 subline ($IC_{50}$ = 28.9 μM) from parental A375 cells ($IC_{50}$ = 0.57 μM).

| Treatment + Vemurafenib | A375 CI $ED_{50}$ | MDA-MB-435 CI $ED_{50}$ | WM164 CI $ED_{50}$ | A375RF21 CI $ED_{50}$ | A375RF21 CI $ED_{75}$ | A375RF21 CI $ED_{90}$ |
|---|---|---|---|---|---|---|
| 12da | 0.32 | 0.10 | 0.61 | 0.53 | 0.59 | 0.70 |
| Docetaxel | 0.50 | 0.55 | 0.54 | 0.63 | 0.80 | 0.90 |
| Colchicine | 0.47 | 0.78 | 1.28 | 0.84 | 0.94 | 1.36 |
| Trametinib (MEKi) | ND | ND | ND | 0.93 | 0.90 | 0.90 |
| Sunitinib (RTKi) | ND | ND | ND | 0.91 | 0.91 | 0.93 |

ND—not determimed

Figure 25:
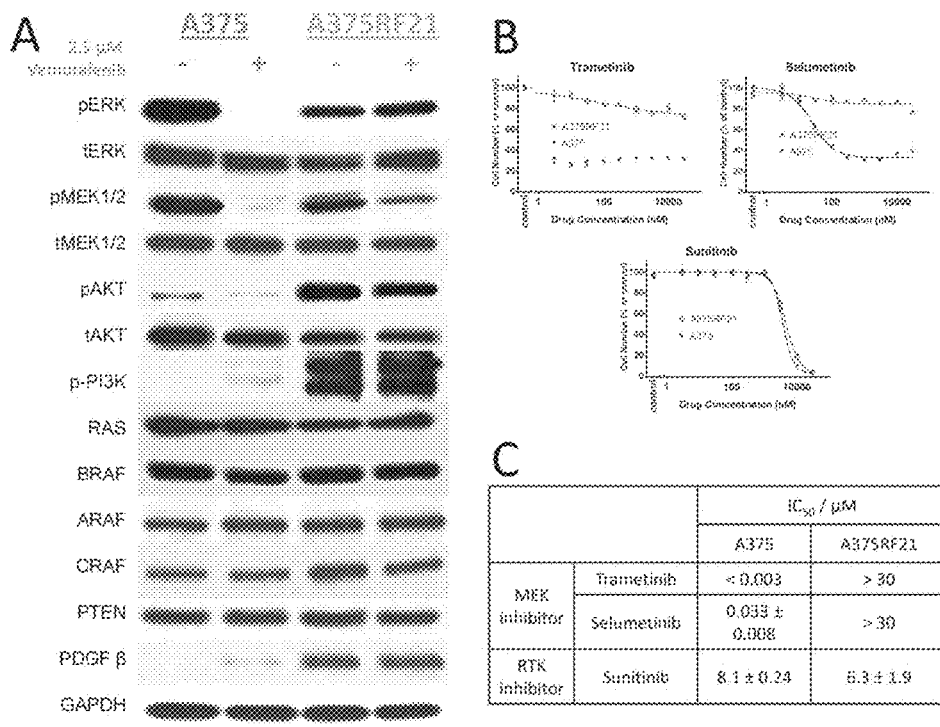
FIG. 25 depicts that the major vemurafenib resistance mechanisms in A375RF21 cells are the over-expression of PDGFβ and the activations of the PI3K-AKT pathway. Both resistant mechanisms have been well established from clinical tumors, indicating that the resistant mechanisms of A375RF21 cells can represent clinically relevant drug resistant mechanisms. Panel A: western blot analyses to compare the differential protein levels in the sensitive parental A375 and the vemurafenib-resistant A375RF21 cells, in the presence or absence of 2.5 μM vemurafenib (A375RF21 cell culture maintenance concentration). Cells were incubated with control vehicle or 2.5 μM vemurafenib for 24 h. Phospho-PI3K level was determined after 30 minutes stimulation with 30 μM hydrogen peroxide. Graph showed representative results of three independent experiments. Panel B: growth inhibition efficacy of kinase inhibitors determined in MTS assay (n=4) on A375 and A375RF21 cells. Trametinib and selumenitib are MEK inhibitors while sunitinib (malate salt) is an RTK inhibitor. Panel C: comparison of calculated $IC_{50}$ values (showed as mean±SD).

Clinically melanoma tumors inevitably relapse only 3 to 6 months after receiving vemurafenib chemotherapy, and therefore it was desired to determine whether the observed synergy will remain effective in vemurafenib-resistant cells. Towards this goal, the vemurafenib-resistant A375RF21 subline was established from the parental A375 human melanoma cells by chronic selection following literature reported procedures (Su F, Bradley W D, Wang Q, et al. "Resistance to selective BRAF inhibition can be mediated by modest upstream pathway activation." Cancer Res. (2012) 72: 969-978). Western blot analyses were performed using both A375 and A375RF21 cells to determine differential protein activations known to result in vemurafenib resistance. As shown in FIG. 25A, the pERK level in A375RF21 in the presence of 2.5 μM vemurafenib (maintenance concentration of its culture medium) did not change, confirming the development of acquired vemurafenib resistance. The pMEK expression also remains active in A375RF21 cells, indicating their potential cross-resistance to MEK1/2 inhibitors. This cross-resistance was confirmed by incubating cells with two known MEK inhibitors (trametinib and selumetinib, FIGS. 25B and 25C). The PI3K/AKT pathway was over-activated in A375RF21 cells while no significant changes of RAS, BRAF, ARAF, CRAF levels were observed. These results are consistent with the report of Fei Su et al. Interestingly, it was found that the level of PDGF receptor β also increased significantly in A375RF21 cells in the presence or absence of the 2.5 μM vemurafenib maintenance medium. Both resistance mechanisms (pAKT and PDGF 13) that confer drug resistance in A375RF21 cells are well known to exist in vemurafenib-resistant patient tumors.

As shown in Table 1, the drug combination study when repeated using A375RF21 cells produced calculated CI values for compound 12da in combination with vemurafenib that were all less than 0.9 (range: 0.53-0.70), indicating a strong synergy in all concentrations tested. At $ED_{50}$, all three tubulin inhibitors acted in a synergistic manner with vemurafenib. With an increase in drug concentration, the CI values for docetaxel or colchicine groups increased relatively quickly. At the dose of $ED_{90}$, the combination of docetaxel with vemurafenib was almost additive (CI value as 0.90) while the combination effect of colchicine with vemurafenib has reversed to antagonism (CI value as 1.36). Compared with the other two tubulin inhibitors, compound 12da showed greater synergy when combined with vemurafenib in the resistant A375RF21 cells.

Surprisingly, calculated CI values for combination of 12da and vemurafenib was found to be as low as 0.1 and 0.3 at $EC_{50}$. Since the clinical tumor regression widely developed only 3 to 6 months after receiving vemurafenib chemotherapy, this study on whether the primarily observed synergy effect for the combination treatments could be consistent on vemurafenib resistant A375RF21 cell line, was continued.

Across the panel of chemotherapeutics tested, the B-RAF mutant inhibitor vemurafenib demonstrated particularly synergistic cytotoxicities in the MDA-MB-435 cells, which originally were believed to be breast cancer cells but now known to be melanoma cells (Table 2), showing a CI value of 0.10 for vemurafenib+17ya, and also showing strong but lesser syngery at $EC_{75}$ and $EC_{90}$ (Table 5). This activity can be rationalized as the B-RAF inhibitor and anti-tubulin agent (17ya) arresting cells in different portions of the cell cycle, $G_1$ and $G_2/M$ (as discussed herein), respectively. Accordingly, the dual targeting of mitosis should more completely target mitotic cells for cell death. Synergistic CI results are also shown in Table 3 with A375 melanoma cells for not just 17ya, but also other anti-tubulin agents such as colchicine, vinblastine and taxol. Limited synergy was seen with an AKT inhibitor and no synergy with a MEK inhibitor (Table 4).

TABLE 2

CI values at $EC_{50}$ for 17ya in combination with various drugs.

|  | A375 | MDA-MB-435 | MDA-MB-435/ LCC6MDR1 |
|---|---|---|---|
|  |  | +17ya |  |
| Doxorubicin | 1.16 | 0.72 | 0.96 |
| Vemurafenib | 0.22 | 0.10 | 0.61 |
| Taxol | 1.00 | 1.16 | 0.93 |
| Vinblastine | 0.96 | 1.22 | 1.03 |

CI: Combination Index
Additive effect: CI = 1
Synergism: CI < 1
Antagonism: CI > 1

TABLE 3

CI values on A375 cell line.

|  | $EC_{50}$ | $EC_{75}$ | $EC_{90}$ |
|---|---|---|---|
|  |  | +Vemurafenib |  |
| 17ya | 0.22 | 0.18 | 0.11 |
| Colchicine | 0.47 | 0.55 | 1.11 |
| Vinblastine | 0.38 | 0.78 | 0.88 |
| Taxol | 0.50 | 0.23 | 0.11 |
| Doxorubicin | 0.44 | 11.6 | 545.6 |

TABLE 4

CI values on A375 cell line.

|  | $EC_{50}$ | $EC_{75}$ | $EC_{90}$ |
|---|---|---|---|
|  |  | +Vemurafenib |  |
| MK2206 (AKT inhibitor) | 0.38 | 0.67 | 0.53 |

TABLE 4-continued

CI values on A375 cell line.

|  | $EC_{50}$ | $EC_{75}$ | $EC_{90}$ |
|---|---|---|---|
|  |  | +Vemurafenib |  |
| RO5068760 (MEK inhibitor) | 0.52 |  |  |

GSK1120212: MEK inhibitor, CI value of vemurafenib with GSK2126458 (PI3K inhibitor) at $IC_{50}$ was 0.45 ± 0.13.
MK2206: AKT inhibitor, CI value of vemurafenib with PLX4032 at $EC_{90}$ was 0.384.

TABLE 5

CI values on MDA-MB-435 cell line.

|  | $EC_{50}$ | $EC_{75}$ | $EC_{90}$ |
|---|---|---|---|
|  |  | +Vemurafenib |  |
| 17ya | 0.10 | 0.23 | 0.60 |
| Vinblastine | 0.44 |  |  |
| Taxol | 0.20 |  |  |

Combination of 12da and Vemurafenib Produced Synergistic Cell Cycle Arrest in A375RF21 Cells (Table 1)

Figure 2:
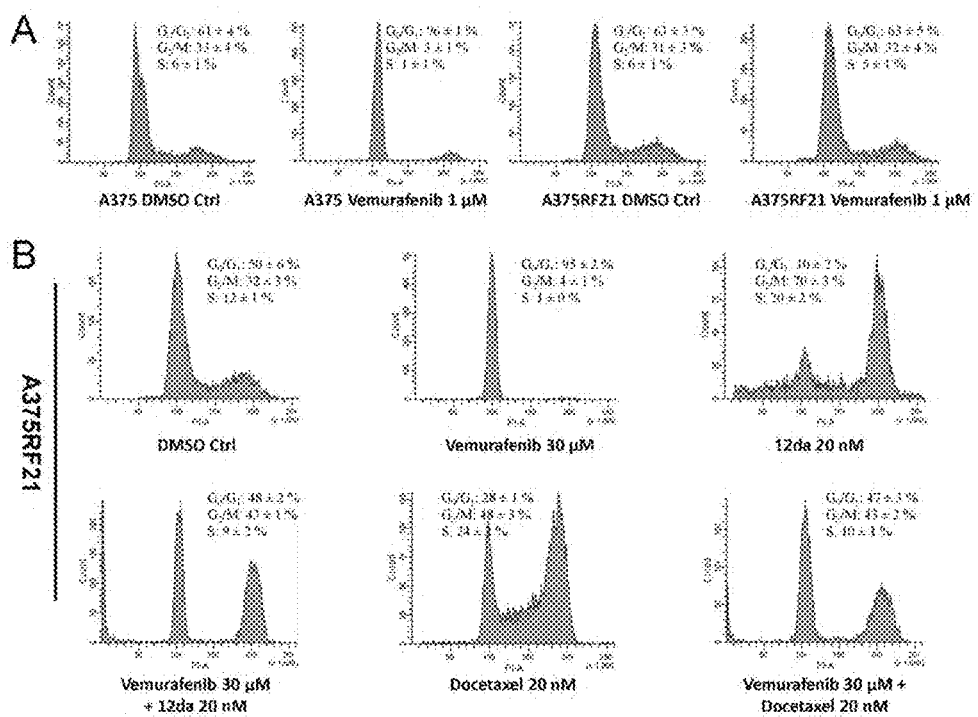
FIG. 2 depicts cell cycle analysis (n=4). A, A375 or A375RF21 cells treated with 1 µM vemurafenib for 24 h and compared with the DMSO control group. Vemurafenib at 1 µM effectively arrested A375 cells at $G_0/G_1$ phases but could not arrest resistant A375RF21 cells. B, A375RF21 cells treated with DMSO, 30 µM vemurafenib, 20 nM compound 12da, 20 nM docetaxel and the combinations for 24 h. Compound 12da and docetaxel induced $G_2/M$ arrest in A375RF21 cells and their combinations with vemurafenib arrested cells in $G_1/G_2/M$ phases.

As a tubulin inhibitor binding to the colchicine site, compound 12da effectively blocks the $G_2/M$ phase in the parent A375 cell line in a dose-dependent manner. To determine whether a combination of compound 12da and vemurafenib will arrest vemurafenib-resistant cells at different replication phases, a cell cycle analysis was carried out in A375RF21 cells. After 24 h exposure to a compound solution at the indicated concentrations, data in FIG. 2B clearly indicated synergistic cell cycle arrests. For DMSO controls, 50% of A375RF21 cells were distributed in $G_0/G_1$ phase and percentage of cell in S or $G_2/M$ phase was 12% or 32%, correspondingly. For compound 12da single treated group at a concentration of 20 nM, the percentage of cells distributed in $G_2/M$ phase had accumulated up to 70%. Using vemurafenib as a single agent, to produce similar $G_0/G_1$ cell cycle arrest in the resistant A375RF21 cell line, the concentration of vemurafenib had to be increased to 30 μM or higher, compared with less than 1 μM in the parental A375 parental cells. As anticipated, the combination of vemurafenib and compound 12da strongly arrested A375RF21 cells in both $G_0/G_1$ (48%) and $G_2/M$ (43%) phase. In addition, the combination treatment generated much more cell debris, which indicated an increase in cancer cell apoptosis. Treatment with the combination of vemurafenib and docetaxel produced similar synergistic effects.

Combination Treatment Induced Significantly Increased Apoptotic Cell Death in Vemurafenib-Resistant Cells To understand more clearly the possible cell apoptosis induction effect of the combination treatment, Annexin V and propidium iodide co-staining flow cytometry was utilized to differentiate live and apoptosis cells in A375RF21. As expected, single agent treatment produced only moderate effects on inducing cell apoptosis at tested concentrations; in contrast, the combination treatment groups significantly enhanced the apoptosis (FIG. 3A). As shown in FIG. 3B, which quantifies the percentage sum of cell distributed in Q1 (early apoptosis), Q2 (apoptosis) and Q4 (dead cells), the combination of compound 12da and vemurafenib resulted in 50±7.6% of counted cell apoptosis or death, which is much higher than the simple sum of apoptotic percentages in two single agent treatment groups (11.8±3.0% for compound 12da and 11.9±3.5% for vemurafenib). A similar synergy effect of apoptosis induction was also observed in the combination treatment group containing docetaxel (6.4±3.0% for docetaxel group, 38.1±2.6% for combination).
Combination Mitigates Acquired Vemurafenib Resistance Through Down-Regulating pAKT or Total AKT and Activating Apoptosis Cascades.

Figure 4:
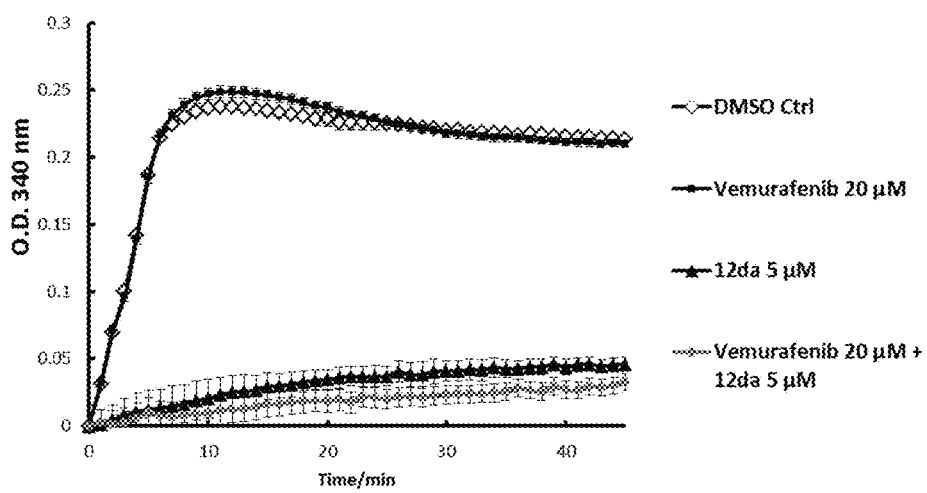
FIG. 4 depicts the effect of single agent and combination treatment on purified-protein based tubulin polymerization assay (n=3). Vemurafenib at 20 µM did not significantly influence tubulin polymerization compared with DMSO control group. The tubulin polymerization inhibition effect in the combination treated group was solely contributed by compound 12da.
Figure 5:
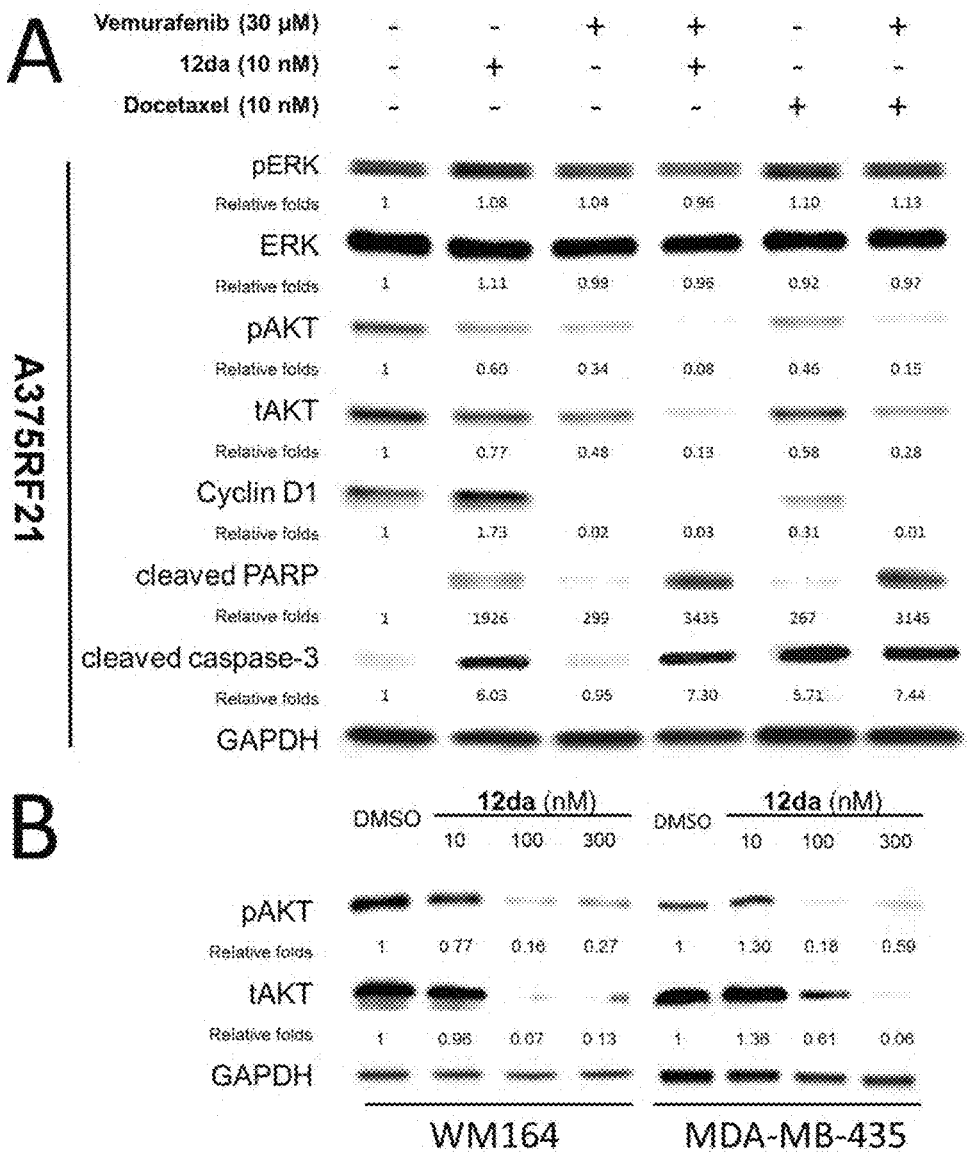
FIG. 5 depicts western blot analysis with indicated antibodies on lysate of A375RF21 (A), MDA-MB-435 and WM164 cells (B) after 48 h treatment. GAPDH was used as a loading control. A, while the indicated combination treatments only caused moderately decreased p-ERK levels, they largely inhibited the AKT phosphorylation and increased the level of apoptotic markers including cleaved PARP and cleaved caspase-3. B, compound 12da also displayed AKT knock-out effects in other two $BRAF^{V600E}$ mutant human melanoma cell lines, MDA-MB-435 and WM164.
Figure 26:
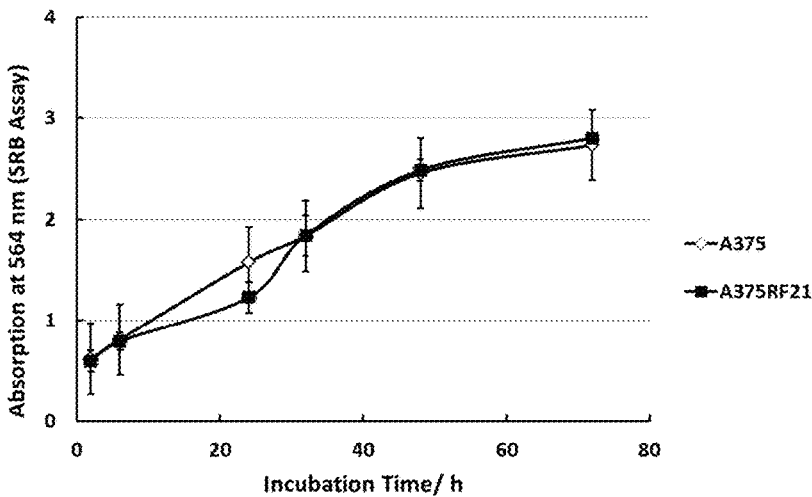
FIG. 26 depicts the in vitro growth curve for A375 and vemurafenib-resistant subline A375RF21 cells. 2000 cells in 100 μl cell growing medium were seeded to each well (n=6) in 96-well plates and incubated at 37° C., 5% $CO_2$. The total protein amount was determined by SRB assay at each indicated time point, accordingly. Then the absorption values at 564 nm were plotted versus growth time.

It has been established that compound 12da targets tubulin polymerization (Chen J, Li C M, Wang J, et al. "Synthesis and antiproliferative activity of novel 2-aryl-4-benzoyl-imidazole derivatives targeting tubulin polymerization." *Bioorg. Med. Chem.* (2011) 19: 4782-4795; Chen J, Wang Z, Li C M, et al, "Discovery of novel 2-aryl-4-benzoyl-imidazoles targeting the colchicines binding site in tubulin as potential anticancer agents." *J. Med. Chem.* (2010) 53: 7414-7427) and vemurafenib targets $BRAF^{V600E}$. As the first approach to understand responsible molecular mechanisms leading to this strong synergistic combination, it was investigated whether the synergy is mediated through potentiation of the direct target of compound 12da or vemurafenib. As shown in FIG. 4 vemurafenib by itself did not have any effect on tubulin polymerization, even at a high concentration of 20 µM. The addition of vemurafenib to compound 12da at most marginally increased the inhibition of tubulin polymerization compared with the single agent compound 12da. The inhibition of tubulin polymerization in the combination treatment was exclusively contributed by compound 12da, suggesting the synergistic combination was not mediated through potentiation of the direct target inhibition for compound 12da. Next it was determined whether the combination has any effects on pERK, the hallmark of $BRAF^{V600E}$ inhibition by vemurafenib, using western blotting. FIG. 5A revealed that either compound 12da or the combination treatments had no obvious effect on pERK or total ERK level after 48 h incubation with A375RF21 resistant cells. Replacing compound 12da with another tubulin inhibitor, docetaxel, produced similar results (FIG. 5A). Therefore, the synergistic combination was unlikely through potentiation of the inhibition of $BRAF^{V600E}$.
Combination Mitigates Acquired Vemurafenib Resistance Through Down-Regulating pAKT or Total AKT and Activating Apoptosis Cascades Recently, Fei Su et al. reported that pAKT levels were increased in A375 vemurafenib-resistant clones compared with their parental vemurafenib-sensitive cells (Su F, Bradley W D, Wang Q, et al. "Resistance to selective BRAF inhibition can be mediated by modest upstream pathway activation." *Cancer Res.* (2012) 72: 969-978). Since A375RF21 cells also have strong pAKT activation (FIG. 25A), it was hypothesized that the combination treatment may produce its strong synergy through down-regulating activities in the AKT pathway in vemurafenib-resistant A375RF21 cells. As shown in FIG. 5A, both pAKT and total AKT (tAKT) were greatly reduced in single-agent compound 12da or its combination treatment group after 48 h incubation, suggesting that the synergistic antiproliferation might be mediated by simultaneously targeting both ERK and AKT phosphorylation. Docetaxel also reduced the pAKT and tAKT expression and had similar effects in its combined treatment with vemurafenib. For example, in addition to the obvious reduction of tAKT levels, the combination of compound 12da and vemurafenib reduced the level of pAKT to 61% relative to tAKT (calculated from the quantified relative folds of lane density: 0.08/0.13×100%) while the single-agent treatment only reduced the levels of pAKT to 77% (12da, 0.6/0.77×10%) and 70% (vemurafenib, 0.34/0.48×100%) relative to the corresponding levels of tAKT, respectively. The strong dose-dependent pAKT/tAKT inhibition effects of compound 12da were further confirmed in two other $BRAF^{V600E}$ mutant cell lines, WM164 and MDA-MB-435 (FIG. 5B). In the vemurafenib-resistant cells (FIG. 5A), decreased cyclin D1 levels in vemurafenib and the combination treatment groups indicated inhibitions on $G_0/G_1$ cell-cycle progression. Apoptosis markers, cleaved PARP and caspase-3, were highly induced by tubulin inhibitors while vemurafenib slightly increased their expression. This result is consistent with the observation in the apoptosis detection experiment.
Combination of Vemurafenib and Compound 12da Synergistically Suppresses Vemurafenib-Resistant Tumor Growth In Vivo To evaluate whether the strong synergy observed against A375RF21 cells in vitro could be transferred to vemurafenib-resistant tumors in vivo, the effect of combination efficacy on tumor growth was compared with that of single agent treatments. It was previously established that compound 12da is effective in suppressing parental A375 melanoma tumor growth in vivo at a dose of 25 mg/kg (Wang Z, Chen J, Wang J, et al. "Novel tubulin polymerization inhibitors overcome multidrug resistance and reduce melanoma lung metastasis". *Pharm. Res.* 29(11): 3040-3052). A pilot study showed that vemurafenib-resistant A375RF21 cells had similar growth kinetics (FIG. 26) to their parental A375 cells in the absence of drug treatment. In order to avoid any potentially unexpected toxicity due to its combination with vemurafenib, the dose of compound 12da was reduced to 10 mg/kg.

TABLE 6

Tumor growth inhibition (TGI) and tumor weight comparison for in vivo combination of vemurafenib and compound 12da in the resistant A375RF21 xenograft model (n = 7). The combination of compound 12da at 10 mg/kg and vemurafenib at 20 mg/kg achieved greater antitumor activity (TGI) compared with the simple sum of TGI in two single agent treatment groups (*P < 0.05). The synergistic tumor inhibition sustained after additional one week without further treatment (*P < 0.05).

| Treatment group | | TGI (%) | Tumor weight (gram) |
|---|---|---|---|
| Vehicle | | — | 2.48 ± 0.27 |
| 12da 10 mg/kg | | 38.12 ± 6.14 | 1.77 ± 0.11 |
| Vemurafenib 20 mg/kg | | 22.65 ± 8.31 | 2.05 ± 0.14 |
| Vemurafenib 20 mg/kg + 12da 10 mg/kg | After 3 weeks of treatment | 88.56 ± 3.57* | 0.77 ± 0.17 |
| | Additional 7 days without treatment | 81.27 ± 5.52* | 0.90 ± 0.11 |

Figure 6:
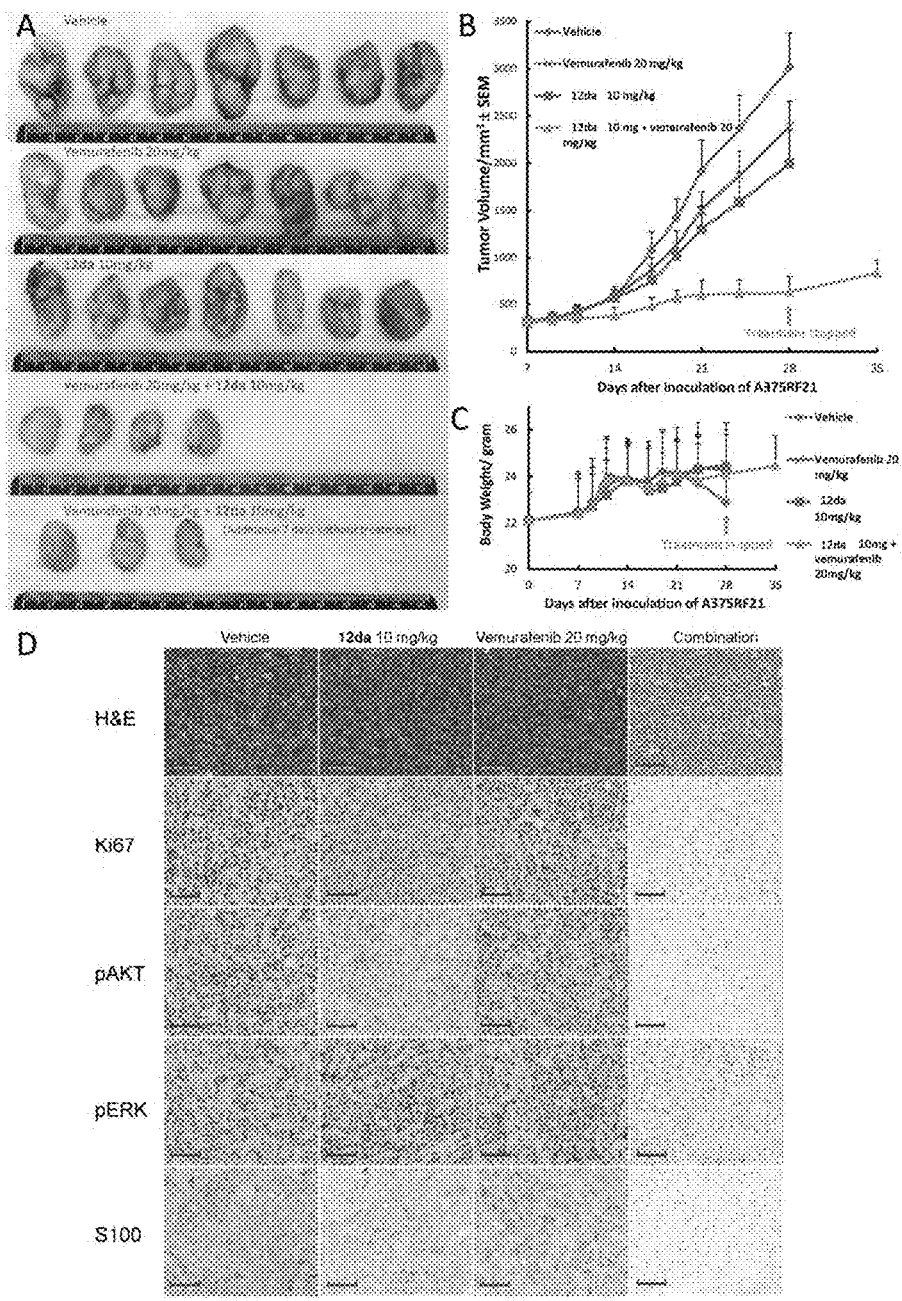
FIG. 6 depicts the in vivo combination of vemurafenib and compound 12da in the resistant A375RF21 xenograft model (n=7). A, pictures of isolated tumor tissue. B, tumor volume growth curve. C, mice body weight versus time plot. D, representative immunohistochemistry images for H&E, Ki67, pAKT, pERK and S100 staining of tumor tissue sections after three weeks of single agent or combination treatment. The blue scale bar in each image represents 100 µm.

As shown in FIG. 6 and Table 6, vemurafenib (20 mg/kg) mono-therapy only achieved minimal (22.65%) TGI and compound 12da (10 mg/kg) by itself resulted in slightly better TGI at 38.12% in this vemurafenib-resistant tumor model; in contrast, their combination treatment significantly enhanced the tumor inhibition to 88.56% after 3-week treatment (FIGS. 6A, 6B and 6D Table 6). Three out of the seven mice that received combination therapy were kept for additional 7 days without further treatment, and showed no significant (P=0.2857) tumor relapse and maintained 81.27% tumor suppression. During the entire experiment, no mice in the four groups lost body weight by more than 10% (FIG. 6C), indicating the absence of gross toxicity for these treatments. When mice were euthanized, major organs including brain, heart, kidneys, liver, spleen, and lungs were isolated and were submitted for pathological analysis. No abnormalities were observed on these organs. Collectively, these results strongly indicated that this combination treatment effectively helped overcoming the acquired resistance to vemurafenib in A375RF21 melanoma model and further confirmed the synergistic anti-proliferation effects observed in vitro.

To determine whether the down-regulation of AKT signaling by combination treatment observed in vitro also functions in vivo, immunohistochemistry analysis was performed on tumor sections from all the experimental groups. The activity in the ERK pathway was also determined, and the proliferation level indicated by cell marker Ki-67 in tumor sections was assessed. As evidenced in FIG. 6D, the improved pathway and proliferation inhibition in the combination treatment group corresponded well with overall tumor response TGI results. ERK and AKT phosphorylation together with Ki67 expression levels in either nucleus or cytoplasm were largely reduced in the combination treatment group. Furthermore, wide area of background pink colored from Matrigel in H&E staining for tumor sections in the combination treatment group indicated that very few tumor cells, if any, remained after combination treatment. The significant reduction of melanoma cells in the combination treatment group was further confirmed by the reduced density in S100 immunostains (FIG. 6D)

Figure 7:
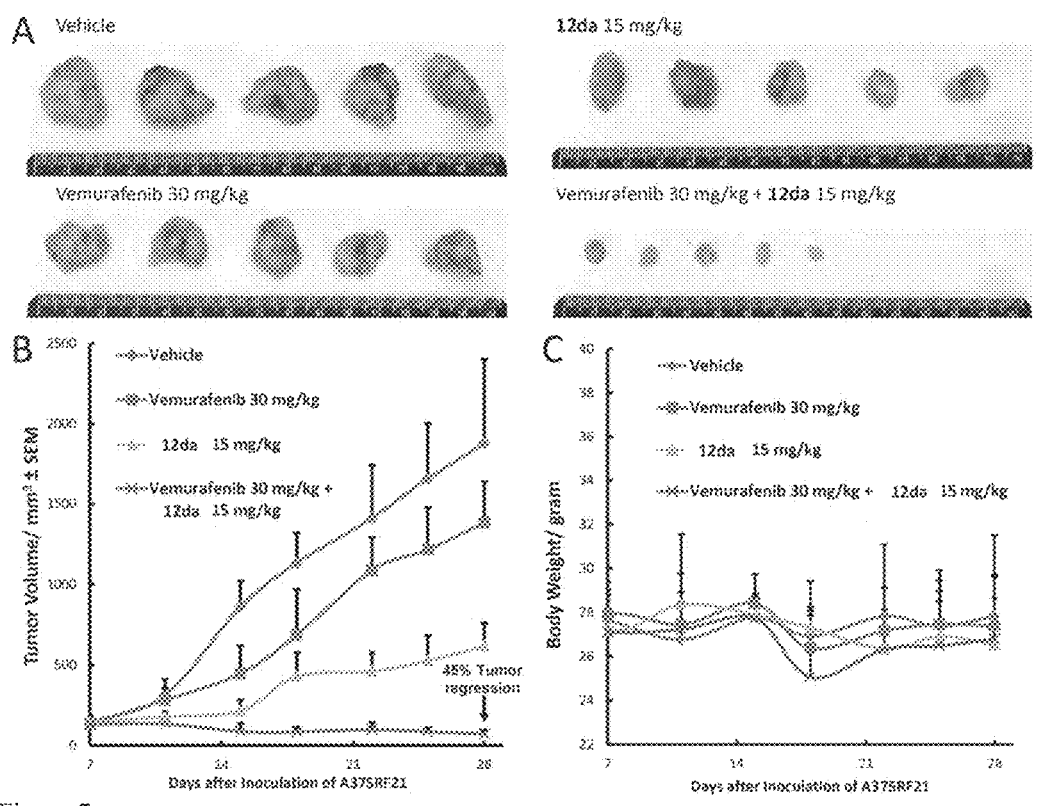
FIG. 7 depicts in vivo combination of high dose vemurafenib (30 mg/kg) and compound 12da (15 mg/kg) in A375RF21 xenograft model (n=5). A, pictures of isolated tumor tissue. B, tumor volume growth curve. C, mice body weight versus time plot. Combination of compound 12da and vemurafenib at this dose achieved 44.9% of tumor regression.

Higher Dose Combination of Vemurafenib with Compound 12da Resulted in Significant Vemurafenib Resistant Tumor Regression without Observable Toxicity Since the results presented in FIG. 6 and Table 6 were promising but did not seem to result in tumor regression, the experiment was repeated by increasing the dose by 50% for both compound 12da and vemurafenib. The results are shown in FIG. 7 and Table 7.

TABLE 7

Tumor growth inhibition (TGI) and tumor weight comparison for in vivo combination of vemurafenib (30 mg/kg) and compound 12da (15 mg/kg) in the resistant A375RF21 xenograft model (n = 5).

| Treatment group | TGI (%) | Tumor weight (gram) |
|---|---|---|
| Vehicle | — | 1.60 ± 0.22 |
| Vemurafenib 30 mg/kg | 28.10 ± 4.81 | 1.05 ± 0.21 |
| 12da 15 mg/kg | 72.72 ± 8.29 | 0.51 ± 0.12 |
| Vemurafenib 30 mg/kg + 12da 15 mg/kg | 103.38 ± 1.42 | 0.08 ± 0.03 |

There is a slight increase of efficacy for vemurafenib (TGI of 22.65% at 20 mg/kg vs. 28.10% at 30 mg/kg), and there is substantial increase of efficacy for compound 12da (TGI of 38.12% at 10 mg/kg vs. 72.72% at 15 mg/kg). Moderate tumor regression (44.9%) on the combination treatment group with the increased drug dose was apparent as shown in FIG. 7B, whereas regression was not seen at lower doses. Collectively, these data provided the first convincing evidence that the combination of novel tubulin inhibitors such as compound 12da with vemurafenib are likely to overcome the acquired resistance to vemurafenib for melanoma patients having $BRAF^{V600E}$ mutation.

In summary these studies strongly suggested that the combination of BRAF inhibitor (e.g. vemurafenib) and novel tubulin inhibitors (e.g. compound 12da) effectively overcome the acquired BRAF inhibitor resistance in BRAF mutated melanomas, with several possible mechanisms including synergistic cell cycle arrest, enhanced apoptosis, and strong inhibition of the AKT pathway. At least in vitro, such a combination seems to be more efficacious than the combinations of vemurafenib with MEK or AKT inhibitors, or existing tubulin inhibitors. With the lack of sustained efficacy of BRAFi+MEKi combination for melanoma, developing this combination strategy targeting alternative pathways could have high impact in this field.

Discussion

Although vemurafenib, the first drug approved for melanoma patients harboring $BRAF^{V600E}$ mutation, showed remarkable responses in initial therapy, almost all patients taking this drug developed resistance to vemurafenib within a few months (Bollag G, Tsai J, Zhang J, et al. "Vemurafenib: the first drug approved for BRAF-mutant cancer." *Nat. Rev. Drug Discov.* (2012) 11: 873-886). Understanding the underlying mechanisms of either primary or acquired resistance and developing suitable combination strategies could provide more effective ways to overcome such resistance. There is a rich literature in both preclinical studies and clinical trials to search for effective combination of vemurafenib with other agents in order to eliminate or reduce melanoma tumor resistances to BRAF or MEK1/2 inhibitors (Greger J G, Eastman S D, Zhang V, et al. "Combinations of BRAF, MEK, and PI3K/mTOR inhibitors overcome acquired resistance to the BRAF inhibitor GSK2118436 dabrafenib, mediated by NRAS or MEK mutations." *Mol. Cancer Ther.* (2012) 11: 909-920; Patel S P, Lazar A J, Papadopoulos N E, et al. "Clinical responses to selumetinib (AZD6244; ARRY-142886)-based combination therapy stratified by gene mutations in patients with metastatic melanoma." *Cancer* (2013) 119(4): 799-805; Flaherty K T, Infante J R, Daud A, et al. "Combined BRAF and MEK inhibition in melanoma with BRAF V600 mutations." *N. Engl. J. Med.* (2012) 367: 1694-1703; Niehr F, von Euw E, Attar N, et al. "Combination therapy with vemurafenib (PLX4032/RG7204) and metformin in melanoma cell lines with distinct driver mutations." *J. Transl. Med.* (2011) 9: 76; Paraiso K H, Haarberg H E, Wood E, et al. "The HSP90 inhibitor XL888 overcomes BRAF inhibitor resistance mediated through diverse mechanisms." *Clin. Cancer Res.* (2012) 18: 2502-2514; Koya R C, Mok S, Otte N, et al. "BRAF inhibitor vemurafenib improves the antitumor activity of adoptive cell immunotherapy." *Cancer Res.* (2012) 72: 3928-3937). Inhibitors to the RAF/MEK/ERK pathway mainly produce $G_1$ cell-cycle arrest rather than melanoma tumor cell death. Thus a combination of agents targeting different components in the same pathway (e.g. combination of vemurafenib and MEK1/2 inhibitors), while effective initially (Little A S, Smith P D, Cook S J. "Mechanisms of acquired resistance to ERK1/2 pathway inhibitors." *Oncogene* (2012) 32(10): 1207-1215), may not maintain long-lasting synergy against resistant cells that can escape from these $G_1$ cell-cycle arrests. Since one of the major hallmarks for tubulin inhibitors is their ability to strongly arrest cells in the $G_2/M$ phase, the combination of vemurafenib and a tubulin inhibitor was thought to synergistically arrest melanoma cells, leading to enhanced apoptosis, and overcome acquired resistance. In this study a novel tubulin inhibitor, compound 12da, was selected to investigate its combination with vemurafenib against melanoma tumors. Vemurafenib-resistant human melanoma cell line A375RF21 was developed, and it was shown that the combination of compound 12da and vemurafenib had strong synergy in vitro. It was confirmed that the synergy is unlikely through enhanced inhibition of tubulin polymerization or diminished of p-ERK activation. Instead, experimental results revealed that this combined treatment overcomes the acquired vemurafenib-resistance through enhanced apoptosis induction produced by synergistic $G_1$ and $G_2/M$ cell-cycle arrest and substantially impaired the survival signaling pathway related to AKT phosphorylation. It was shown that the strong synergy observed in vitro clearly translated to significant efficacy in vivo when tested in a vemurafenib-resistant xenograft model. Further immunohistochemistry analyses on tissue sections confirmed the strong inhibition of tumor proliferation and the diminished activity of pAKT. Activation of the PI3K/AKT/mTOR signaling pathway has been shown to contribute to the diminished sensitivity to ERK1/2 inhibition in human melanoma cell lines (Bartholomeusz C, Gonzalez-Angulo A M. "Targeting the PI3K signaling pathway in cancer therapy." *Expert Opin. Ther. Targets* (2012) 16: 121-130), and several recent studies have clearly demonstrated the synergistic combination of an inhibitor targeting PI3K/AKT/mTOR pathway and a BRAF inhibitor or a MEK inhibitor (Liu R, Liu D, Xing M. "The Akt inhibitor MK2206 synergizes, but perifosine antagonizes, the BRAF (V600E) inhibitor PLX4032 and the MEK1/2 inhibitor AZD6244 in the inhibition of thyroid cancer cells." *J. Clin. Endocrinol. Metab.* (2012) 97: E173-182). Recently several novel classes of compounds were reported as inhibitors of tubulin polymerization and also showed strong inhibition of the AKT pathway (Krishnegowda G, Prakasha Gowda A S, et al. "Synthesis and biological evaluation of a novel class of isatin analogs as dual inhibitors of tubulin polymerization and Akt pathway." *Bioorg. Med. Chem.* (2011) 19: 6006-6014; Viola G, Bortolozzi R, Hamel E, et al. "MG-2477, a new tubulin inhibitor, induces autophagy through inhibition of the Akt/mTOR pathway and delayed apoptosis in A549 cells." *Biochem. Pharmacol.* (2012) 83: 16-26; Zhang C, Yang N, Yang C H, et al. "S9, a novel anticancer agent, exerts its anti-proliferative activity by interfering with both PI3K-Akt-mTOR signaling and microtubule cytoskeleton." *PLoS One* (2009) 4: e4881). In addition, constitutively active PI3K/AKT pathway has been shown to lead to multidrug resistances to microtubule-targeted tubulin-polymerizing agents (MTPA) and inhibition of PI3K/AKT mediated signaling pathway has been shown to sensitize cancer cells to MTPA-induced apoptosis (Bhalla K N. "Microtubule-targeted anticancer agents and apoptosis." *Oncogene* (2003) 22: 9075-9086). These studies indicate a close interplay between tubulin polymerization inhibitors and AKT down regulation in cancer cells. In addition, it has been recently reported that MEK inhibitor AZD6244 induced growth arrest in melanoma cells and tumor regression when combined with docetaxel (Haass N K, Sproesser K, Nguyen T K, et al. "The mitogen activated protein/extracellular signal-regulated kinase kinase inhibitor AZD6244 (ARRY-142886) induces growth arrest in melanoma cells and tumor regression when combined with docetaxel." *Clin. Cancer Res.* (2008) 14: 230-239). Interestingly, the current results are consistent with these studies. The in vivo studies presented in this invention show an effective combination treatment in tumor cells that are already vemurafenib-resistant by using A375RF21 xenograft models. It is conceivable that if the combination is used before tumor cells became resistant to vemurafenib, tumor regression may be more enhanced and the development of resistant tumor cells can be significantly delayed or even prevented. This could translate into at least a substantially longer progression-free time in patients, and/or enhanced disease regression. Collectively, this study offers the first direct evidence and a rationale for combining a potent tubulin inhibitor with an inhibitor targeting the RAF/MEK/ERK pathway for greatly improved therapy for melanoma patients.

Example 2

Synthesis of Selected Aryl-Benzoyl-Imidazole Compounds

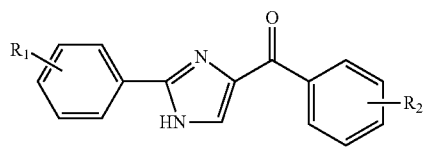

Figure 8:
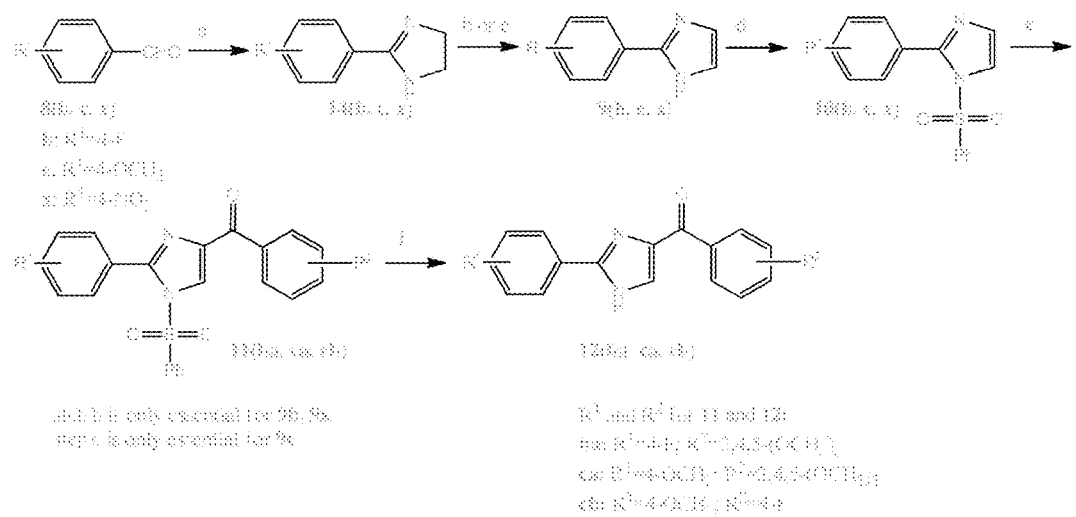
FIG. 8 depicts a synthetic scheme for the preparation of Aryl-Benzoyl-Imidazole (ABI) compounds of this invention. Reagents and conditions: (a) t-BuOH, $I_2$, ethylenediamine, $K_2CO_3$, reflux; (b) PhI (OAc)$_2$, $K_2CO_3$, DMSO; (c) DBU, CBrCl$_3$, DMF; (d) NaH, PhSO$_2$Cl, THF, 0° C. —RT; (e) t-BuLi, substituted benzoyl chloride, THF, −78° C.; (f) Bu$_4$NF, THF, RT.

Preparation of 2-aryl-4,5-dihydro-1H-imidazoles 14b, 14c, 14x (FIG. 8)

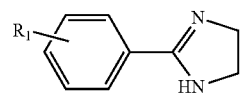

To a solution of appropriate benzaldehyde 8(b, c, x) (60 mmol) in t-BuOH (300 mL) was added ethylenediamine (66 mmol) and stirred for 30 min at RT. Potassium carbonate (75 mmol) and iodine (180 mmol) were added to the reaction mixture sequentially followed by stirring at 70° C. for 3 h. Sodium sulfite (Na$_2$SO$_3$) was added and the mixture was extracted by chloroform. The organic layer was dried over magnesium sulfate and concentrated. The residue was purified by flash column chromatography (chloroform: methanol 20:1) to give a white solid. Yield: 50-60%.

Figure 9:
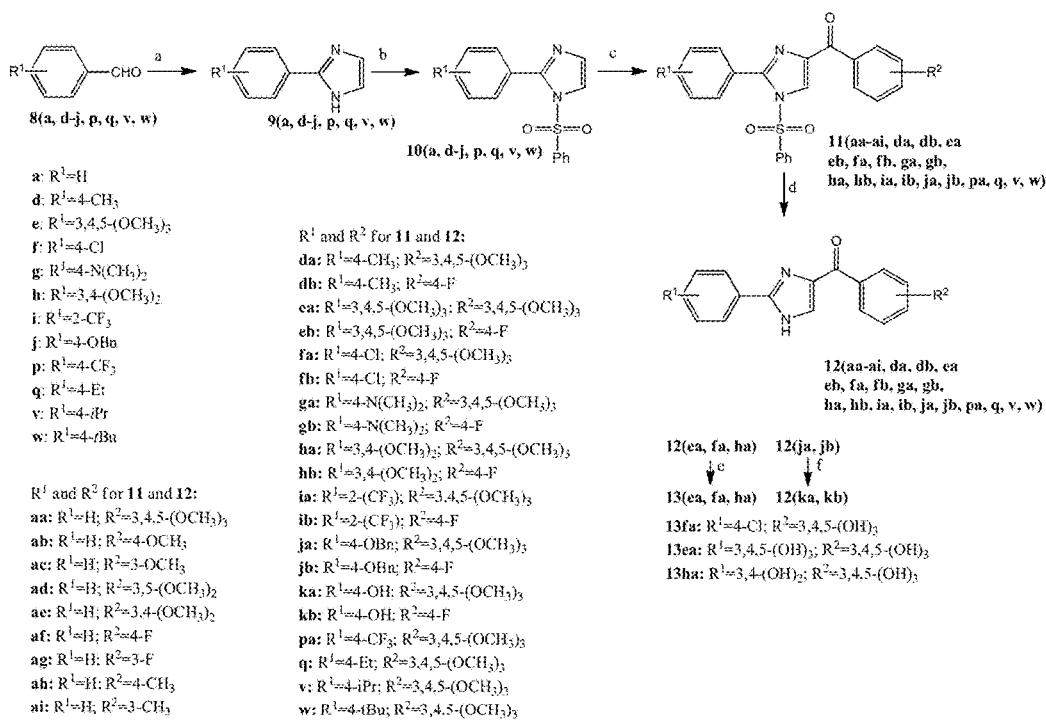
FIG. 9 depicts a synthetic scheme for the preparation of Aryl-Benzoyl-Imidazole (ABI) compounds of this invention. Reagents and conditions: (a) NH$_4$OH, oxalaldehyde, ethanol, RT; (b) NaH, PhSO$_2$Cl, THF, 0° C.—RT; (c) t-BuLi, substituted benzoyl chloride, THF, −78° C.; (d) Bu$_4$NF, THF, RT; (e) BBr$_3$, CH$_2$Cl$_2$; (f) c-HCl, AcOH, reflux.

Preparation of 2-aryl-1H-imidazoles (9a-j, p, x; FIGS. 8 and 9)

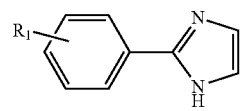

Method A (essential for only 9b, 9x, FIG. 8): To a solution of 2-aryl-4,5-dihydro-1H-imidazole 14b, x (35 mmol) in DMSO (100 mL) was added potassium carbonate (38.5 mmol) and diacetoxyiodobenzene (38.5 mmol). The reaction mixture was stirred overnight in darkness. Water was added followed by extraction with dichloromethane. The organic layer was dried over magnesium sulfate and concentrated. The residue was subjected to flash column chromatography (hexane:ethyl acetate 3:2) to give a white solid. Yield: 30%-50%.

Method B (essential for only 9c; FIG. 8): To a solution of 2-aryl-4,5-dihydro-1H-imidazole 14c (50 mmol) in DMF (70 mL) was added DBU (55 mmol) and CBrCl$_3$ (55 mmol). The reaction mixture was stirred overnight and a saturated NaHCO$_3$ (aqueous) solution was added followed by extraction with dichloromethane. The organic layer was dried over magnesium sulfate and concentrated. The residue was subjected to flash column chromatography (chloroform: methanol 50:1) to yield a white solid. Yield: 7%.

Method C (essential for 9a, 9d-j, 9p; FIG. 9): To a solution of appropriate benzaldehyde (8a, 8d-j, 8p) (100 mmol) in ethanol (350 mL) at 0° C. was added a solution of 40% oxalaldehyde in water (12.8 mL, 110 mmol) and a solution of 29% ammonium hydroxide in water (1000 mmol, 140 mL). After stirring for 2-3 days at RT, the reaction mixture was concentrated and the residue was subjected to flash column chromatography with dichloromethane as eluent to yield the titled compound as a yellow powder. Yield: 20%-40%.

Preparation of
2-aryl-1-(phenylsulfonyl)-1H-imidazoles (10a-j, p, x; FIGS. 8 and 9)

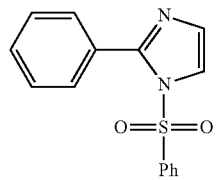

To a solution of 2-aryl-1H-imidazole 9a-j, p, x (20 mmol) in anhydrous THF (200 mL) at 0° C. was added sodium hydride (60% dispersion in mineral oil, 1.2 g, 30 mmol) and stirred for 30 min. Benzenesulfonyl chloride (2.82 mL, 22 mmol) was added and the reaction mixture was stirred overnight. After dilution by 100 mL of saturated $NaHCO_3$ solution (aqueous), the reaction mixture was extracted by ethyl acetate (500 mL). The organic layer was dried over magnesium sulfate and concentrated. The residue was purified by flash column chromatography (hexane:ethyl acetate 2:1) to give a pale solid. Yield: 50%-70%.

Preparation of aryl (2-aryl-1-(phenylsulfonyl)-1H-imidazol-4-yl)methanones (11aa-ai, ba, ca, cb, da, db, ea, eb, fa, fb, ga, gb, ha, hb, ia, ib, ja, jb, pa; FIGS. 8 and 9)

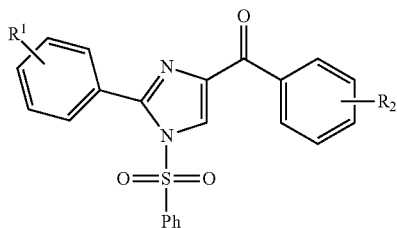

To a solution of 2-aryl-1-(phenylsulfonyl)-1H-imidazole (6.0 mmol) 10a-j, p, x in anhydrous THF (30 mL) at −78° C. was added 1.7M tert-butyllithium in pentane (5.3 mL, 9.0 mmol) and stirred for 10 min. Appropriate substituted benzoyl chloride (7.2 mmol) was added at −78° C. and stirred for overnight. The reaction mixture was diluted with 100 mL of saturated $NaHCO_3$ solution (aqueous) and extracted by ethyl acetate (200 mL). The organic layer was dried over magnesium sulfate and concentrated. The residue was purified by flash column chromatography (hexane:ethyl acetate 4:1) to give a white solid. Yield: 15%-40%.

General Procedure for the Preparation of aryl (2-aryl-1H-imidazol-4-yl)methanones (12aa-ai, ba, ca, cb, da, db, ea, eb, fa, fb, ga, gb, ha, hb, ia, ib, ja, jb, pa; FIGS. 8 and 9)

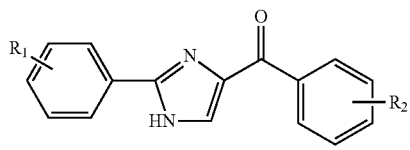

To a solution of aryl (2-aryl-1-(phenylsulfonyl)-1H-imidazol-4-yl)methanones (2.0 mmol) 11aa-ai, ba, ca, cb, da, db, ea, eb, fa, fb, ga, gb, ha, hb, ia, ib, ja, jb, pa in THF (20.0 mL) was added 1.0 M tetrabutyl ammonium fluoride (4.0 mmol) and stirred overnight. The reaction mixture was diluted by 50 mL of saturated $NaHCO_3$ solution (aqueous) and extracted by ethyl acetate (100 mL). The organic layer was dried over magnesium sulfate and concentrated. The residue was purified by flash column chromatography (hexane:ethyl acetate 3:1) or recrystallized from water and methanol to give a white solid. Yield: 80-95%.

Preparation of (2-(4-hydroxyphenyl)-1H-imidazol-4-yl) (aryl)methanones (12ka, 12kb; FIG. 9)

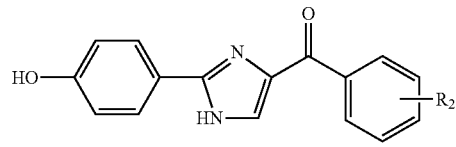

To a solution of (2-(4-(benzyloxy)phenyl)-1H-imidazol-4-yl)(aryl)methanone 12ja or 12jb, (1 mmol) in AcOH (20 mL) was added concentrated HCl (2 mL) and refluxed overnight. After removing the solvent, the residue was recrystallized from dichloromethane to give the titled compound as a yellow solid. Yield: 70-85%.

Preparation of (2-aryl-1H-imidazol-4-yl) (3,4,5-trihydroxyphenyl)methanones 13ea, 13fa, 13ha (FIG. 9)

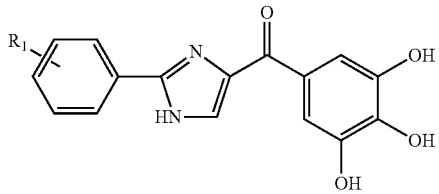

To a solution of aryl (2-aryl-1H-imidazol-4-yl)methanone 12ea, 12fa or 12ha (0.5 mmol) in $CH_2Cl_2$ (6.0 mL) was added 1.0 M of $BBr_3$ (2 mmol) in $CH_2Cl_2$ and stirred for 1 h at RT. Water was added to destroy excess $BBr_3$. The precipitated solid was filtered and recrystallized from MeOH to afford a yellow solid. Yield: 60-80%.

Preparation of aryl (2-aryl-1H-imidazol-4-yl)methanone-HCl salt (12db-HCl)

To a solution of 12db (0.5 mmol) in methanol (20 mL) was added 2 M solution of hydrogen chloride (5 mmol) in ethyl ether and stirred overnight at RT. The reaction mixture was concentrated and the residue was washed by $CH_2Cl_2$ to yield the titled compound. Yield: 95%.

Figure 10:
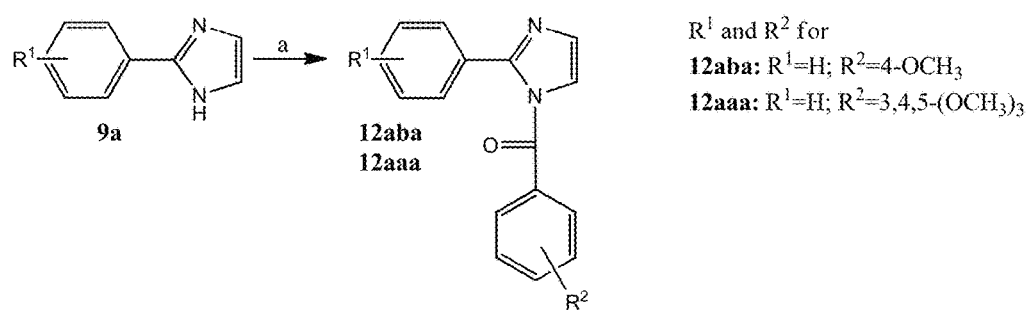
FIG. 10 depicts a synthetic scheme for the preparation of Aryl-Benzoyl-Imidazole (ABI) compounds of this invention. Reagents and conditions: (a) N$_a$H, substituted benzoyl chloride, THF.

Preparation of aryl (2-phenyl-1H-imidazol-1-yl)methanone (12aba, 12aaa; FIG. 10)

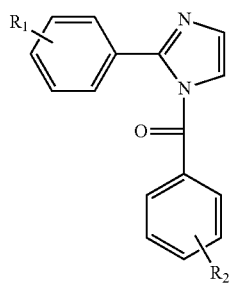

To a solution of 2-phenyl-1H-imidazole 9a (10 mmol) in THF (20 mL) was added NaH (15 mmol) and substituted benzoyl chloride (12 mmol) at 0° C. The reaction mixture was stirred overnight and diluted by saturated $NaHCO_3$ solution followed by extraction with ethyl acetate. The organic layer was dried over magnesium sulfate and concentrated. The residue was purified by flash column chromatography (chloroform) to give a white solid. Yield: 12-16%.

Figure 11:
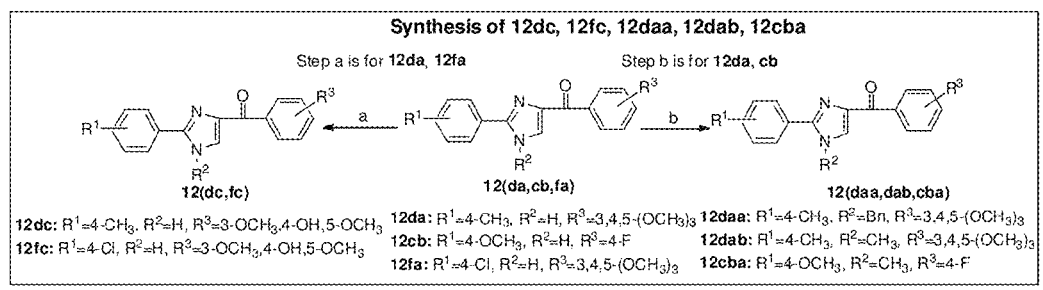
FIG. 11 depicts the synthetic scheme of compounds 12dc, 12fc, 12daa, 12dab, 12cba. (a) AlCl$_3$, THF, reflux; (b) NaH, CH$_3$I for 12dab and 12cba and BnBr for 12daa, THF, reflux.
Figure 12:
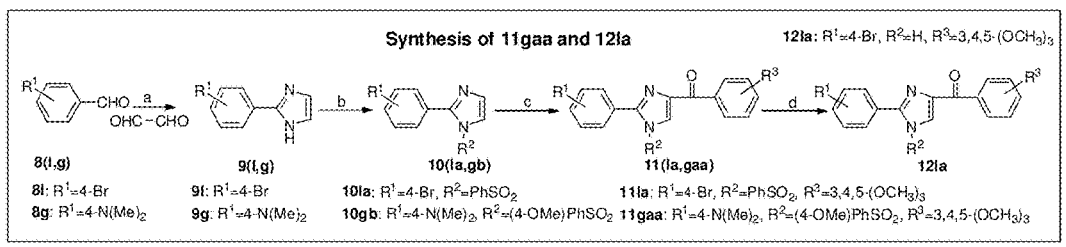
FIG. 12 depicts the synthetic scheme of compounds 11gaa, 12la. (a) NH$_4$OH, ethanol, glyoxal, RT; (b) NaH, substituted PhSO$_2$Cl, THF, 0° C.—RT; (c) t-BuLi (1.7 M in pentane), substituted benzoyl chloride, THF, −78° C.; (d) Bu$_4$NF, RT.

Preparation of 1-substituted-(2-phenyl-1H-imidazol-1-yl)-aryl-methanone (12dc, 12fc, 12daa, 12 dab, 12 cba, 11gaa, 12la; FIGS. 11-12)

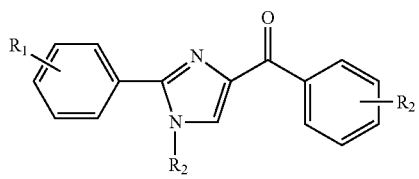

The synthesis of 12dc, 12fc and 12daa, 12dab and 12cba is summarized in FIG. 11. Compounds 12da, 12cb and 12fa were synthesized according to the synthesis described above and in FIGS. 8 and 9. Treatment of 12da and 12fa with aluminum chloride provided the para-demethylated 12dc, 12fc with the 3,5-dimethoxy being intact. Compound 12daa was prepared by benzylation of the N−1 position of 12da. While methylation of the N−1 position of 12da and 12cb afforded compounds 12dab and 12cba, respectively.

Synthesis of 12dc, 12fc, 12daa, 12dab, 12cba: Method D. (for 12dc and 12fc) [FIG. 11]:

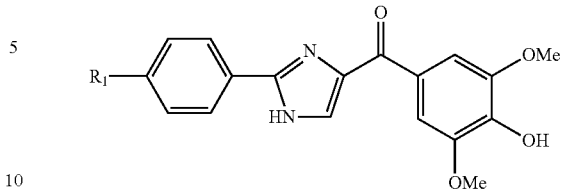

$R_1=CH_3$ (12dc)
$R_1=Cl$ (12fc)

To a solution of 12da and 12fa (200 mg) in THF (20 mL) was added aluminum chloride (10 equiv). The reaction mixture was stirred overnight. Water was added followed by extraction with ethyl acetate. The organic layer was dried over magnesium sulfate and concentrated. The residue was subjected to flash column chromatography (hexane:ethyl acetate 1:1) to give a white-yellowish solid. Yield: 60%-80%.

Synthesis of 12daa, 12dab, 12cba, Method E: [FIG. 11]:

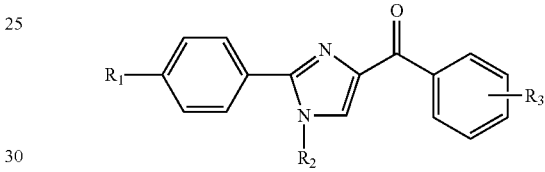

$R_1$=Me; $R_2$=Bn; $R_3$=3,4,5-$(OMe)_3$(12daa)
$R_1$=Me; $R_2$=$CH_3$; $R_3$=3,4,5-$(OMe)_3$(12dab)
$R_1$=OMe; $R_2$=$CH_3$; $R_3$=F (12cba)

To a solution of 12da and 12cb (100 mg) in THF (10 mL) in an ice-bath was added sodium hydride (1.2 equiv) followed by the addition of methyl iodide (for 12dab, 12cba) or benzyl bromide (for 12daa) (2 equiv). The resulted reaction mixture was stirred for 5 h under reflux condition. After dilution by 50 mL of saturated $NaHCO_3$ solution (aqueous), the reaction mixture was extracted by ethyl acetate (100 mL). The organic layer was dried over magnesium sulfate and concentrated. The residue was purified by flash column chromatography (hexane: ethyl acetate 2:1) to give a white solid. Yield: 50%-98%. 12daa: Yield: 92.8%; mp 135-137° C. $^1$H NMR ($CDCl_3$, 500 MHz) δ 7.81 (s, 1H), 7.80 (d, J=6.5 Hz, 2H), 7.58 (d, J=8.0 Hz, 2H), 7.41-7.45 (m, 3H), 7.31-7.33 (m, 2H), 7.20 (d, J=7.0 Hz, 2H), 5.33 (s, 2H), 3.99 (s, 3H), 3.98 (s, 6H), 2.47 (s, 3H). MS (ESI) calcd for $C_{27}H_{26}N_2O_4$ 442.2. found 443.1 $[M+H]^+$. HPLC1: $t_R$ 4.28 min, purity >99%.

Synthesis of 11gaa and 12la (FIG. 12):

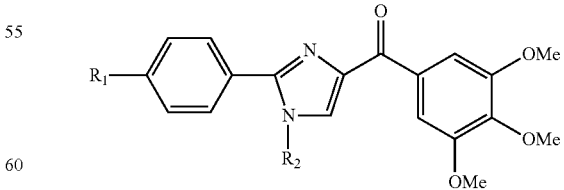

$R_1$=$N(Me)_2$; $R_2$=(4-OMe)$PhSO_2$ (11gaa)
$R_1$=Br; $R_2$=H (12la)

The substituted benzaldehyde compounds 8(l, g) were converted to compounds 9(l, g) in the presence of ammonium hydroxide and glyoxal to construct the imidazole scaffold. The imidazole rings of compounds 9(l, g) were protected by an appropriate phenylsulfonyl group followed by coupling with 3,4,5-trimethoxybenzoyl chloride to achieve compound 11(la,gaa). Treatment of 11la with tert-butylammoniumfluoride to remove the protecting group afforded 12la.

Synthesis of (2-(4-bromophenyl)-1H-imidazol-4-yl)(3,4,5-trimethoxyphenyl)methanone (12la) (FIG. 12

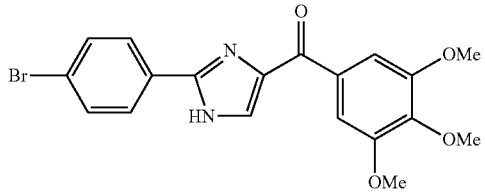

Synthesis of 9l, 9g:

To a solution of appropriate benzaldehyde (8l, and 8g, 100 mmol) in ethanol (400 mL) at 0° C. was added a solution of 40% oxalaldehyde (glyoxal) in water (1.1 equiv) and a solution of 29% ammonium hydroxide in water (10 equiv). After stirring for 2-3 days at RT, the reaction mixture was concentrated and the residue was subjected to flash column chromatography with dichloromethane as eluent to yield the titled compound as a yellow powder. Yield: 10%-30%.

Synthesis of 10la, 10gb:

To a solution of imidazoles (9l, 9g) (10 mmol) in anhydrous THF (200 mL) at 0° C. was added sodium hydride (60% dispersion in mineral oil, 1.2 equiv) and stirred for 20 min. 4-Methoxybenzenesulfonyl chloride (for 10gb) or benzenesulfonyl chloride (for others)(1.2 equiv) was added and the reaction mixture was stirred overnight. After dilution by 200 mL of saturated NaHCO₃ solution (aqueous), the reaction mixture was extracted by ethyl acetate (600 mL). The organic layer was dried over magnesium sulfate and concentrated. The residue was purified by flash column chromatography (hexane:ethyl acetate 2:1) to give a pale solid. Yield: 40%-95%.

Synthesis of 11la, 11gaa:

To a solution of 2-aryl-1-(phenylsulfonyl)-1H-imidazole (10la, 10gb) (5.0 mmol) in anhydrous THF (30 mL) at −78° C. was added 1.7 M tert-butyllithium in pentane (1.2 equiv) and stirred for 10 min. 3,4,5-Trimethoxybenzoyl chloride (1.2 equiv) was added at −78° C. and stirred overnight. The reaction mixture was diluted with 100 mL of saturated NaHCO₃ solution (aqueous) and extracted by ethyl acetate (300 mL). The organic layer was dried over magnesium sulfate and concentrated. The residue was purified by flash column chromatography (hexane:ethyl acetate 3:1) to give a white solid. Yield: 5%-45%.

Synthesis of 12la:

To a solution of aryl (2-aryl-1-(phenylsulfonyl)-1H-imidazol-4-yl)methanone (11la), 2.0 mmol) in THF (25.0 mL) was added 1.0 M tetrabutyl ammonium fluoride (2 equiv) and stirred overnight. The reaction mixture was diluted by 60 mL of saturated NaHCO₃ solution (aqueous) and extracted by ethyl acetate (150 mL). The organic layer was dried over magnesium sulfate and concentrated. The residue was purified by flash column chromatography (hexane:ethyl acetate 4:1) or recrystallized from water and methanol to give a white solid. Yield: 80-98%.

Synthesis of (4-Fluorophenyl)(2-(4-methoxyphenyl)-1H-imidazol-4-yl)methanone (12cb) (FIG. 8)

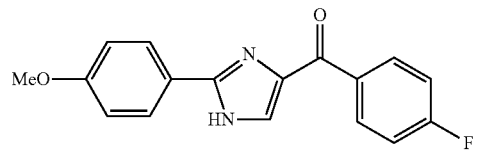

To a solution of (4-fluorophenyl)(2-(4-methoxyphenyl)-1-(phenylsulfonyl)-1H-imidazol-4-yl)methanone (11cb, 872 mg, 2.0 mmol) in THF (20.0 mL) was added 1.0 M tetrabutyl ammonium fluoride (4.0 mL, 4.0 mmol) and stirred overnight. The reaction mixture was diluted by 50 mL of saturated NaHCO₃ solution (aqueous) and extracted by ethyl acetate (100 mL). The organic layer was dried over magnesium sulfate and concentrated. The residue was recrystallized from water and methanol to give a white solid. Yield: 90%; mp 245-247° C.

Synthesis of (2-(p-Tolyl)-1H-imidazol-4-yl)(3,4,5-trimethoxyphenyl)methanone (12da) (FIG. 9)

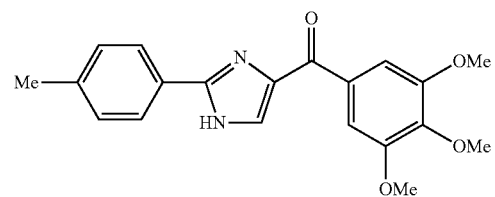 [SMILES: COc1cc(C(=O)c2c[nH]c(-c3ccc(Br)cc3)n2)cc(OC)c1OC]

To a solution of (1-(phenylsulfonyl)-2-(p-tolyl)-1H-imidazol-4-yl)(3,4,5-trimethoxyphenyl)methanone (11da, 492 mg, 1.0 mmol) in THF (15.0 mL) was added 1.0 M tetrabutyl ammonium fluoride (2.0 mL, 2.0 mmol) and stirred overnight. The reaction mixture was diluted by 30 mL of saturated NaHCO₃ solution (aqueous) and extracted by ethyl acetate (80 mL). The organic layer was dried over magnesium sulfate and concentrated. The residue was recrystallized from water and methanol to give a white solid. Yield: 88.5%.

Figure 13:
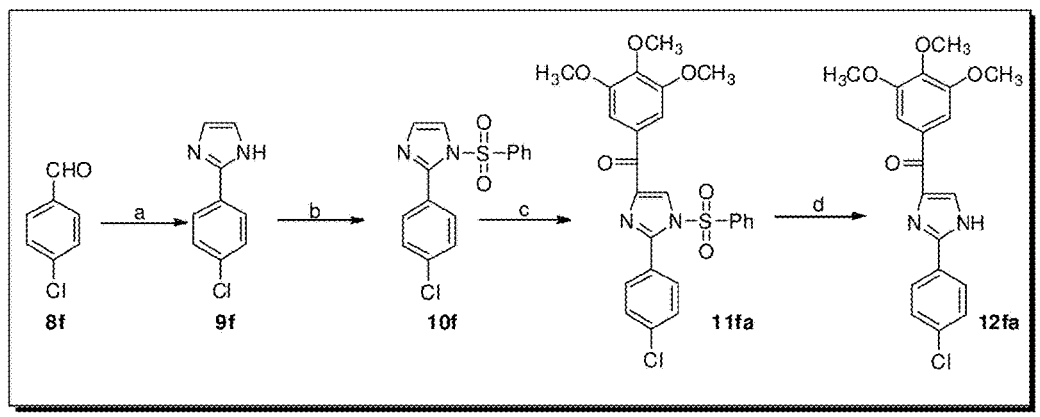
FIG. 13 depicts synthetic scheme of 12fa. (a) NH$_4$OH, oxalaldehyde, ethanol, RT; (b) NaH, PhSO$_2$Cl, THF, 0° C.—RT; (c) t-BuLi, 3,4,5-trimethoxybenzoyl chloride, THF, −78° C.; (d) Bu$_4$NF, THF, RT.

Synthesis of (2-(4-Chlorophenyl)-1H-imidazol-4-yl)(3,4,5-trimethoxyphenyl)methanone (12fa) (FIGS. 9 and 13)

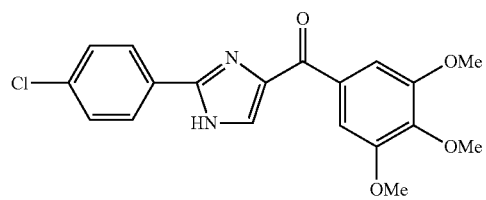 [SMILES: COc1cc(C(=O)c2c[nH]c(-c3ccc(Cl)cc3)n2)cc(OC)c1OC]

2-(4-Chlorophenyl)-1H-imidazole (9f)

To a solution of 4-chlorobenzaldehyde (8f) (100 mmol) in ethanol (350 mL) at 0° C. was added a solution of 40% oxalaldehyde in water (12.8 mL, 110 mmol) and a solution of 29% ammonium hydroxide in water (1000 mmol, 140 mL). After stirring for 2-3 days at RT, the reaction mixture was concentrated and the residue was subjected to flash column chromatography with dichloromethane as eluent to yield the titled compound as a yellow powder. Yield: 19.8%. $^1$H NMR (500 MHz, DMSO-$d_6$) δ 13.60 (br, 1H), 7.94 (d, J=8.5 Hz, 2H), 7.51 (d, J=8.0 Hz, 2H), 7.27 (s, 1H), 7.03 (s, 1H). MS (ESI): calculated for $C_9H_7ClN_2$, 178.0. found 178.9 [M+H]$^+$.

2-(4-Chlorophenyl)-1-(phenylsulfonyl)-1H-imidazole (10f)

To a solution of 2-(4-chlorophenyl)-1H-imidazole (9f) (20 mmol) in anhydrous THF (200 mL) at 0° C. was added sodium hydride (60% dispersion in mineral oil, 1.2 g, 30 mmol) and stirred for 30 min. Benzenesulfonyl chloride (2.82 mL, 22 mmol) was added and the reaction mixture was stirred overnight. After dilution by 100 mL of saturated NaHCO$_3$ solution (aqueous), the reaction mixture was extracted by ethyl acetate (500 mL). The organic layer was dried over magnesium sulfate and concentrated. The residue was purified by flash column chromatography (hexane:ethyl acetate 2:1) to give a pale solid. Yield: 54.9%. $^1$H NMR (500 MHz, CDCl$_3$) δ 7.65 (d, J=2.0 Hz, 1H), 7.58 (t, J=7.5 Hz, 1H), 7.43 (d, J=8.5 Hz, 2H), 7.38 (t, J=8.0 Hz, 2H), 7.34-7.36 (m, 4H), 7.12 (d, J=1.5 Hz, 1H). MS (ESI): calculated for $C_{15}H_{11}ClN_2O_2S$, 318.0. found 341.0 [M+Na]$^+$.

(2-(4-Chlorophenyl)-1-(phenylsulfonyl)-1H-imidazol-4-yl)(3,4,5-trimethoxyphenyl)methanone (11fa)

To a solution of 2-(4-chlorophenyl)-1-(phenylsulfonyl)-1H-imidazole (10f) (6.0 mmol) in anhydrous THF (30 mL) at −78° C. was added 1.7 M tert-butyllithium in pentane (5.3 mL, 9.0 mmol) and stirred for 10 min. 3,4,5-Trimethoxybenzoyl chloride (7.2 mmol) was added at −78° C. and stirred for overnight. The reaction mixture was diluted with 100 mL of saturated NaHCO$_3$ solution (aqueous) and extracted by ethyl acetate (200 mL). The organic layer was dried over magnesium sulfate and concentrated. The residue was purified by flash column chromatography (hexane:ethyl acetate 4:1) to give a white solid. Yield: 36.8%; $^1$H NMR (500 MHz, CDCl$_3$) δ 8.05 (d, J=7.5 Hz, 2H), 7.77 (t, J=7.5 Hz, 1H), 7.62 (t, J=8.0 Hz, 2H), 7.48 (s, 1H), 7.44 (d, J=9.0 Hz, 2H), 7.39 (d, J=8.5 Hz, 2H), 7.37 (s, 2H). MS (ESI): calculated for $C_{25}H_{21}ClN_2O_6S$, 512.1. found 513.1 [M+H]$^+$.

(2-(4-Chlorophenyl)-1H-imidazol-4-yl)(3,4,5-trimethoxyphenyl)methanone (12fa)

To a solution of (2-(4-chlorophenyl)-1-(phenylsulfonyl)-1H-imidazol-4-yl)(3,4,5-trimethoxyphenyl)methanone (11fa) (2.0 mmol) in THF (20.0 mL) was added 1.0 M tetrabutyl ammonium fluoride (4.0 mmol) and stirred overnight. The reaction mixture was diluted by 50 mL of saturated NaHCO$_3$ solution (aqueous) and extracted by ethyl acetate (100 mL). The organic layer was dried over magnesium sulfate and concentrated. The residue was purified by flash column chromatography (hexane:ethyl acetate 3:1) or recrystallized from water and methanol to give a white solid. Yield: 80-95%. Yield: 36.9%; mp 193-195° C. $^1$H NMR (500 MHz, CDCl$_3$) δ 10.75 (br, 1H), 7.96 (d, J=8.5 Hz, 2H), 7.83 (s, 1H), 7.47 (d, J=9.0 Hz, 2H), 7.23 (s, 2H), 3.97 (s, 3H), 3.94 (s, 6H), 2.43 (s, 3H). MS (ESI): calculated for $C_{19}H_{17}ClN_2O_4$, 372.1. found 395.1 [M+Na]$^+$, 370.9 [M−H]$^−$. HPLC Gradient: Solvent A (water) and Solvent B (methanol): 0-15 min 40-100% B (linear gradient), 15-25 min 100% B: $t_R$ 16.36 min, purity >99%.

Synthesis of (2-(4-Chlorophenyl)-1H-imidazol-4-yl)(4-fluorophenyl)methanone (12fb) (FIG. 9)

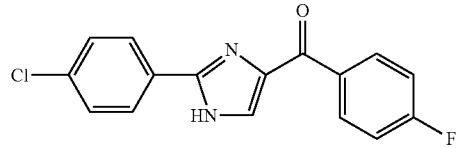 [SMILES: O=C(c1ccc(F)cc1)c1c[nH]c(-c2ccc(Cl)cc2)n1]

To a solution of (2-(4-chlorophenyl)-1-(phenylsulfonyl)-1H-imidazol-4-yl)(4-fluorophenyl)methanone (11fb, 440 mg, 1.0 mmol) in THF (12.0 mL) was added 1.0 M tetrabutyl ammonium fluoride (2.0 mL, 2.0 mmol) and stirred overnight. The reaction mixture was diluted by 20 mL of saturated NaHCO$_3$ solution (aqueous) and extracted by ethyl acetate (60 mL). The organic layer was dried over magnesium sulfate and concentrated. The residue was recrystallized from water and methanol to give a white solid. Yield: 83.7%.

Physicochemical Characterization of Aryl-Benzoyl-Imidazole Compounds and Intermediates

| Compound | Physicochemical Cheracterization |
| --- | --- |
| 2-phenyl-1H-imidazole (9a) | Yield: 36.8%. $^1$H NMR (500 MHz, DMSO-$d_6$) δ 12.52 (br, 1 H), 7.95 (d, J = 7.0 Hz, 2 H), 7.44 (t, J = 7.5 Hz, 2 H), 7.34 (t, J = 7.0 Hz, 1H), 7.25-7.27 (m, 1 H), 7.04-7.07 ☐m, 1 H). MS (ESI): calculated for $C_9H_8N_2$, 144.1, found 167.1 [M + Na]$^+$. |
| 2-(4-fluorophenyl)-1H-imidazole (9b) | Yield: 56.5%. $^1$H NMR (300 MHz, DMSO-$d_6$) δ 12.46 (br, 1 H), 7.94-7.99 (m, 2 H), 7.24-7.30 (m, 2 H), 7.00-7.03 (m, 2 H). MS (ESI): calculated for $C_9H_7FN_2$, 162.1, found 163 [M + H]$^+$, 160.6 [M − H]$^−$. |
| 2-(4-methoxyphenyl)-1H-imidazole (9c) | Yield: 22.2%. $^1$H NMR (500 MHz, CDCl$_3$) δ 7.80 (d, J = 10.0 Hz, 2 H), 7.15 (s, 2 H), 3.86 (s, 3 H). MS (ESI): calculated for $C_{10}H_{10}N_2O$, 174.1, found 175 [M + H]$^+$, 172.8 [M − H]$^−$. |
| 2-(p-tolyl)-1H-imidazole (9d) | Yield: 36.1%. $^1$H NMR (500 MHz, CDCl$_3$) δ 7.64 (d, J = 7.5 Hz, 2 H), 7.16 (d, J = 7.5 Hz, 2 H), 7.12 (s, 1 H), 7.02 (s, 1 H). MS (ESI): |

-continued

| Compound | Physicochemical Characterization |
|---|---|
| | calculated for $C_{10}H_{10}N_2$, 158.1, found 159.0 $[M + H]^+$, 156.8 $[M - H]^-$. |
| 2-(3,4,5-trimethoxyphenyl)-1H-imidazole (9e) | Yield: 26.0%. $^1$H NMR (500 MHz, CDCl$_3$) δ 7.26 (s, 2 H), 7.08 (d, J = 1.5 Hz, 2 H), 3.86 (s, 3 H), 3.82 (s, 6 H). MS (ESI): calculated for $C_{12}H_{14}N_2O_3$, 234.1, found 234.9 $[M + H]^+$. |
| 2-(4-chlorophenyl)-1H-imidazole (9f) | Yield: 19.8%. $^1$H NMR (500 MHz, DMSO-d$_6$) δ 13.60 (br, 1 H), 7.94 (d, J = 8.5 Hz, 2 H), 7.51 (d, J = 8.0 Hz, 2 H), 7.27 (s, 1 H), 7.03 (s, 1 H). MS (ESI): calculated for $C_9H_7ClN_2$, 178.0, found 178.9 $[M + H]^+$. |
| 4-(1H-imidazol-2-yl)-N,N-dimethylaniline (9g) | Yield: 16.5%. $^1$H NMR (300 MHz, CDCl$_3$) δ 7.70 (dd, J = 7.0 Hz, 2.0 Hz, 2 H), 7.10 (s, 2 H), 6.75 (dd, J = 9.0 Hz, 2.0 Hz, 2 H), 3.02 (s, 6 H). MS (ESI): calculated for $C_{11}H_{13}N_3$, 187.1, found 187.9 $[M + H]^+$, 185.8 $[M - H]^-$. |
| 2-(3,4-dimethoxyphenyl)-1H-imidazole (9h) | Yield: 22.0%. $^1$H NMR (500 MHz, CDCl$_3$) δ 7.52 (d, J = 1.5 Hz, 1 H), 7.27-7.28 (m, 1 H), 7.14 (s, 2 H), 6.88 (d, J = 8.0 Hz, 1 H), 3.91 (s, 3 H), 3.87 (s, 3 H). MS (ESI): calculated for $C_{11}H_{12}N_2O_2$, 204.1, found 205.1 $[M + H]^+$, 202.8 $[M - H]^-$. |
| 2-(2-(trifluoromethyl)phenyl)-1H-imidazole (9i) | Yield: 25.5%. $^1$H NMR (500 MHz, DMSO-d$_6$) δ 12.31 (br, 1 H), 7.84 (d, J = 8.0 Hz, 1 H), 7.76 (t, J = 8.0 Hz, 1 H), 7.65 (t, J = 7.5 Hz, 1 H), 7.16 (br, 2 H). MS (ESI): calculated for $C_{10}H_7F_3N_2$, 212.1, found 212.9 $[M + H]^+$, 210.7 $[M - H]^-$. |
| 2-(4-(benzyloxy)phenyl)-1H-imidazole (9j) | Yield: 12.1%. $^1$H NMR (500 MHz, CDCl$_3$) δ 7.77 (d, J = 8.5 Hz, 2 H), 7.36-7.47 (m, 5 H), 7.10-7.18 (m, 2 H), 7.06 (d, J = 9.0 Hz, 2 H), 5.13 (s, 2 H). MS (ESI): calculated for $C_{16}H_{14}N_2O$, 250.1, found 251.1 $[M + H]^+$, 248.8 $[M - H]^-$. |
| 2-(4-Bromophenyl)-1H-imidazole (9l) | Yield: 19.5%. $^1$H NMR (300 MHz, CDCl$_3$) δ 12.59 (s, 1 H), 7.87 (d, J = 8.1 Hz, 2 H), 7.64 (d, J = 8.1 Hz, 1 H), 7.27 (s, 1 H), 7.04 (s, 1 H). MS (ESI) calcd for $C_9H_7BrN_2$ 222.0, found 222.8 $[M + H]^+$. |
| 2-(4-(Trifluoromethyl)phenyl)-1H-imidazole (9p) | Yield: 26.2%; $^1$H NMR (500 MHz, CDCl$_3$) δ 8.03 (d, J = 8.0 Hz, 2 H), 7.66 (d, J = 8.0 Hz, 2 H), 7.25 (s, 2 H). MS (ESI) calcd for $C_{10}H_7F_3N_2$ 212.1, found 213.1 $[M + H]^+$ |
| 2-(4-nitrophenyl)-1H-imidazole (9x) | Yield: 53.7%. $^1$H NMR (500 MHz, DMSO-d$_6$) δ 12.97 (br, 1 H), 8.32 (d, J = 9.0 Hz, 2 H), 8.17 (d, J = 9.0 Hz, 2 H), 7.42 (s, 1 H), 7.17 (s, 1H). MS (ESI): calculated for $C_9H_7N_3O_2$, 189.1, found 189.9 $[M + H]^+$, 187.8 $[M - H]^-$. |
| 2-phenyl-1-(phenylsulfonyl)-1H-imidazole (10a) | Yield: 50.3%. $^1$H NMR (500 MHz, CDCl$_3$) δ 7.64-7.67 (m, 1 H), 7.56 (t, J = 9.0 Hz, 1 H), 7.32-7.48 (m, 9 H), 7.12-7.16 (m, 1 H). MS (ESI): calculated for $C_{15}H_{12}N_2O_2S$, 284.1, found 307.1 $[M + Na]^+$. |
| 2-(4-fluorophenyl)-1-(phenylsulfonyl)-1H-imidazole (10b) | Yield: 56.9%. $^1$H NMR (500 MHz, CDCl$_3$) δ 7.66 (d, J = 2.0 Hz, 1 H), 7.58 (t, J = 10.0 Hz, 1 H), 7.36-7.42 (m, 6 H), 7.12 (d, J = 2.0 Hz, 1 H), 7.06 (t, J = 10.0 Hz, 2 H). MS (ESI): calculated for $C_{15}H_{11}FN_2O_2S$, 302.1, found 300.8 $[M - H]^-$. |
| 2-(4-methoxyphenyl)-1-(phenylsulfonyl)-1H-imidazole (10c) | Yield: 40.9%. $^1$H NMR (500 MHz, CDCl$_3$) δ 7.62 (d, J = 5.0 Hz, 1 H), 7.56 (tt, J = 15.0 Hz, 5.0 Hz, 1 H), 7.32-7.43 (m, 6 H), 7.10 (d, J = 5.0 Hz, 1 H), 6.88 (dt, J = 16.0 Hz, 6.0 Hz, 2 H), 3.87 (s, 3 H). MS (ESI): calculated for $C_{16}H_{14}N_2O_3S$, 314.1, found 337.1 $[M + Na]^+$, 312.9 $[M - H]^-$. |
| 1-(phenylsulfonyl)-2-(p-tolyl)-1H-imidazole (10d) | Yield: 46.6%. $^1$H NMR (500 MHz, CDCl$_3$) δ 7.63 (d, J = 1.0 Hz, 1 H), 7.55 (t, J = 8.0 Hz, 1 H), 7.42 (d, J = 8.0 Hz, 2 H), 7.35 (t, J = 7.5 Hz, 2 H), 7.27-7.29 (m, 2 H), 7.16 (d, J = 7.5 Hz, 2 H), 7.10 (s, 1 H), 2.41 (s, 3 H). MS (ESI): calculated for $C_{16}H_{14}N_2O_2S$, 298.1, found 321.1 $[M + Na]^+$. |
| 1-(phenylsulfonyl)-2-(3,4,5-trimethoxyphenyl)-1H-imidazole (10e) | Yield: 55.7%. $^1$H NMR (500 MHz, CDCl$_3$) δ 7.68 (d, J = 1.5 Hz, 1 H), 7.55 (t, J = 7.0 Hz, 1 H), 7.42 (d, J = 7.5 Hz, 2 H), 7.35 (t, J = 8.5 Hz, 2 H), 7.11 (d, J = 1.5 Hz, 2 H), 6.60 (s, 1 H), |

| Compound | Physicochemical Cheracterization |
| --- | --- |
| 2-(4-chlorophenyl)-1-(phenylsulfonyl)-1H-imidazole (10f) | 3.90 (s, 3 H), 3.79 (s, 6 H). MS (ESI): calculated for $C_{18}H_{18}N_2O_5S$, 374.1, found 397.1 [M + Na]$^+$. Yield: 54.9%. $^1$H NMR (500 MHz, CDCl$_3$) δ 7.65 (d, J = 2.0 Hz, 1 H), 7.58 (t, J = 7.5 Hz, 1 H), 7.43 (d, J = 8.5 Hz, 2 H), 7.38 (t, J = 8.0 Hz, 2 H), 7.34-7.36 (m, 4 H), 7.12 (d, J = 1.5 Hz, 1 H). MS (ESI): calculated for $C_{15}H_{11}ClN_2O_2S$, 318.0, found 341.0 [M + Na]$^+$. |
| N,N-dimethyl-4-(1-(phenylsulfonyl)-1H-imidazol-2-yl) aniline (10g) | Yield: 48.3%. $^1$H NMR (300 MHz, CDCl$_3$) δ 7.59 (d, J = 2.0 Hz, 1 H), 7.55 (t, J = 8.0 Hz, 1 H), 7.45 (d, J = 7.5 Hz, 2 H), 7.28-7.38 (m, 4 H), 7.07 (d, J = 2.0 Hz, 1 H), 6.68 (d, J = 8.5 Hz, 2 H), 3.04 (s, 3 H). MS (ESI): calculated for $C_{17}H_{17}N_3O_2S$, 327.10, found 350.0 [M + Na]$^+$, 325.9 [M − H]$^−$. |
| 4-(1-((4-Methoxyphenyl)sulfonyl)-1H-imidazol-2-yl)-N,N-dimethylaniline (10gb) | Yield: 61.5%. $^1$H NMR (500 MHz, CDCl$_3$) δ 7.58 (d, J = 1.5 Hz, 1 H), 7.36 (t, J = 8.43 Hz, 4 H), 7.03-7.09 (m, 1 H), 6.80 (d, J = 9.0 Hz, 2 H), 6.69 (d, J = 8.8 Hz, 2 H), 3.84 (s, 3 H), 3.05 (s, 6 H). MS (ESI): calculated for $C_{17}H_{17}N_3O_2S$, 327.1, found 358.2 [M + Na]$^+$. |
| 2-(3,4-dimethoxyphenyl)-1-(phenylsulfonyl)-1H-imidazole (10h) | Yield: 60.3%. $^1$H NMR (500 MHz, CDCl$_3$) δ 7.64 (d, J = 7.0 Hz, 1 H), 7.55 (t, J = 7.5 Hz, 1 H), 7.40 (dd, J = 8.5 Hz, 1.5 Hz, 2 H), 7.35 (t, J = 8.0 Hz, 2H), 7.09 (d, J = 2.0 Hz, 1 H), 7.02 (dd, J = 8.0 Hz, 2.0 Hz, 1 H), 6.89 (d, J = 1.5 Hz, 1 H), 6.86 (d, J = 8.0 Hz, 1 H), 3.95 (s, 3 H), 3.81 (s, 3 H). MS (ESI): calculated for $C_{17}H_{16}N_2O_4S$, 344.10, found 367.0 [M + Na]$^+$. |
| 1-(phenylsulfonyl)-2-(2-(trifluoromethyl)phenyl)-1H-imidazole (10i) | Yield: 58.6%. $^1$H NMR (500 MHz, CDCl$_3$) δ 7.64-7.67 (m, 2 H), 7.61-7.63 (m, 3 H), 7.40-7.46 (m, 5 H), 7.16 (d, J = 1.5 Hz, 1 H). MS (ESI): calculated for $C_{16}H_{11}F_3N_2O_2S$, 352.10, found 353.1 [M + H]$^+$. |
| 2-(4-(benzyloxy)phenyl)-1-(phenylsulfonyl)-1H-imidazole (10j) | Yield: 62.0%; mp 102-104° C. $^1$H NMR (500 MHz, CDCl$_3$) δ 7.56 (d, J = 1.0 Hz, 1 H), 7.46 (t, J = 8.0 Hz, 1 H), 7.20-7.40 (m, 11 H), 7.03 (d, J = 1.0 Hz, 1H), 6.89 (t, J = 8.0 Hz, 2 H), 5.08 (s, 2 H). MS (ESI): calculated for $C_{22}H_{18}N_2O_3S$, 390.10, found 413.1 [M + Na]$^+$. HPLC2: $t_R$ 18.22 min, purity 95.9%. |
| 2-(4-Bromophenyl)-1-(phenylsulfonyl)-1H-imidazole (10la) | Yield: 61.2%. $^1$H NMR (500 MHz, CDCl$_3$) δ 7.71 (d, J = 2.0 Hz, 1 H), 7.64 (t, J = 7.0 Hz, 1 H), 7.57 (d, J = 9.0 Hz, 2 H), 7.49 (d, J = 7.0 Hz, 2 H), 7.45 (t, J = 9.0 Hz, 2 H), 7.34 (d, J = 8.5 Hz, 2 H), 7.18 (d, J = 1.5 Hz, 1 H). MS (ESI) calcd for $C_{15}H_{11}BrN_2O_2S$ 362.0, found 363.0 [M + H]$^+$. |
| 1-(Phenylsulfonyl)-2-(4-(trifluoromethyl)phenyl)-1H-imidazole (10p) | Yield: 36.7%; $^1$H NMR (500 MHz, CDCl$_3$) δ 7.75 (d, J = 2.0 Hz, 1 H), 7.69 (d, J = 8.0 Hz, 2 H), 7.65 (t, J = 8.0 Hz, 1 H), 7.60 (d, J = 8.0 Hz, 2 H), 7.48 (d, J = 7.5 Hz, 2 H), 7.43 (t, J = 8.0 Hz, 2 H), 7.22 (d, J = 2.0 Hz, 1 H). MS (ESI) calcd for $C_{16}H_{11}F_3N_2O_2S$ 352.1, found 553.1 [M + H]$^+$ |
| 2-(4-nitrophenyl)-1-(phenylsulfonyl)-1H-imidazole (10x) | Yield: 50%; mp 145-147° C. $^1$H NMR (500 MHz, DMSO-d$_6$) δ 8.28 (d, J = 8.5 Hz, 2 H), 8.03 (d, J = 1.5 Hz, 1 H), 7.78 (t, J = 7.5 Hz, 1 H), 7.64-7.68 (m, 4H), 7.60 (t, J = 8.0 Hz, 2 H), 7.30 (d, J = 1.5 Hz, 1 H). MS (ESI): calculated for $C_{15}H_{11}N_3O_4S$, 329.10, found 352.0 [M + Na]$^+$, 327.9 [M − H]$^−$. HPLC2: $t_R$ 14.87 min, purity 98.8%. |
| (4-methoxyphenyl)(2-phenyl-1-(phenylsulfonyl)-1H-imidazol-4-yl)methanone (11ab) | Yield: 26.3%; mp 118-120° C. $^1$H NMR (500 MHz, DMSO-d$_6$) δ 8.37 (d, J = 1.0 Hz, 1 H), 8.15-8.18 (m, 2 H), 8.12 (d, J = 9.0 Hz, 2 H), 7.56-7.64 (m, 5 H), 7.46-7.50 (m, 3 H), 7.16 (d, J = 8.0 Hz, 2 H), 3.90 (s, 3 H). MS (ESI): calculated for $C_{23}H_{18}N_2O_4S$, 418.10, found 419.1 [M + H]$^+$. HPLC2: $t_R$ 17.72 min, purity 95.7%. |
| (3-methoxyphenyl)(2-phenyl-1-(phenylsulfonyl)-1H-imidazol-4-yl)methanone (11ac) | Yield: 31.2%; mp 136-138° C. $^1$H NMR (500 MHz, CDCl$_3$) δ 8.35 (s, 1 H), 7.86 (d, J = 8.0 Hz, 1 H), 7.72 (s, 1 H), 7.60 (t, J = 7.5 Hz, 1 H), 7.51 (t, J = 7.5 Hz, 1 H), 7.35-7.42 (m, 9H), 7.14 (dd, J = 8.0 Hz, 2.0 Hz, 1 H), 3.88 (s, 3 H). |

| Compound | Physicochemical Cherecterization |
| --- | --- |
| (2-phenyl-1-(phenylsulfonyl)-1H-imidazol-4-yl)(p-tolyl)methanone (11ah) | MS (ESI): calculated for $C_{23}H_{18}N_2O_4S$, 418.10, found 419.1 $[M + H]^+$. HPLC2: $t_R$ 17.72 min, purity 95.7%. Yield: 28.9%; mp 108-110° C. $^1$H NMR (500 MHz, CDCl$_3$) δ 8.00 (d, J = 7.5 Hz, 2 H), 7.98 (q, J = 8.0 Hz, 1.5 Hz, 2 H), 7.91 (d, J = 8.0 Hz, 1 H), 7.81 (s, 1 H), 7.44-7.48 (m, 3 H), 7.35-7.40 (m, 2 H), 7.30 (t, J = 8.0 Hz, 2 H), 7.20 (s, 2 H), 2.42 (s, 3 H). MS (ESI): calculated for $C_{23}H_{18}N_2O_3S$, 402.10, found 403.1 $[M + H]^+$. HPLC2: $t_R$ 16.06 min, purity 96.2%. |
| (4-fluorophenyl)(2-phenyl-1-(phenylsulfonyl)-1H-imidazol-4-yl)methanone(11af) | Yield: 25.4%; mp 114-116° C. $^1$H NMR (500 MHz, CDCl$_3$) δ 8.10 (q, J = 3.5 Hz, 5.5 Hz, 2 H), 7.88 (d, J = 7.5 Hz, 2 H), 7.67 (t, J = 7.5 Hz, 1 H), 7.48-7.54 (m, 3 H), 7.38-7.41 (m, 5 H), 7.24 (t, J = 8.5 Hz, 2 H). MS (ESI): calculated for $C_{22}H_{15}FN_2O_3S$, 406.10, found 429.1 $[M + Na]^+$. HPLC2: $t_R$ 15.43 min, purity 96.1%. |
| (3-fluorophenyl)(2-phenyl-1-(phenylsulfonyl)-1H-imidazol-4-yl)methanone(11ag) | Yield: 18.3%; mp 102-104° C. $^1$H NMR (500 MHz, CDCl$_3$) δ 8.14 (d, J = 7.5 Hz, 1 H), 7.76-7.87 (m, 3 H), 7.74 (d, J = 9.0 Hz, 1 H), 7.37-7.57 (m, 10 H), 7.38-7.41 (m, 5 H), 7.24 (t, J = 8.5 Hz, 2 H). MS (ESI): calculated for $C_{22}H_{15}FN_2O_3S$, 406.10, found 429.1 $[M + Na]^+$. HPLC2: $t_R$ 15.75 min, purity 96.5%. |
| (4-fluorophenyl)(2-(4-methoxyphenyl)-1-(phenylsulfonyl)-1H-imidazol-4-yl)methanone (11cb) | Yield: 23.5%; mp 135-137° C. $^1$H NMR (500 MHz, CDCl$_3$) δ 8.00 (d, J = 5.5 Hz, 2 H), 7.74-7.76 (m, 2 H), 7.54-7.58 (m, 1 H), 7.40 (d, J = 7.0 Hz, 2 H), 7.28-7.30 (m, 3 H), 7.14-7.16 (m, 2 H), 6.80-6.82 (m, 2 H), 3.80 (s, 3 H). MS (ESI): calculated for $C_{23}H_{17}FN_2O_4S$, 436.10, found 459.0 $[M + Na]^+$, 434.9 $[M - H]^-$. HPLC2: $t_R$ 16.53 min, Purity 96.1%. |
| (1-(phenylsulfonyl)-2-(p-tolyl)-1H-imidazol-4-yl)(3,4,5-trimethoxyphenyl)methanone (11da) | Yield: 33.8%; $^1$H NMR (500 MHz, CDCl$_3$) δ 8.00 (d, J = 8.0 Hz, 2 H), 7.70 (t, J = 7.5 Hz, 1 H), 7.55 (t, J = 8.0 Hz, 2 H), 7.44 (s, 2 H), 7.34 (s, 2H), 7.31 (d, J = 8.0 Hz, 2 H), 7.21 (d, J = 8.0 Hz, 2 H), 4.00 (s, 3 H), 3.98 (s, 6 H). MS (ESI): calculated for $C_{26}H_{24}N_2O_6S$, 492.14, found 515.2 $[M + Na]^+$. |
| (4-fluorophenyl)(1-(phenylsulfonyl)-2-(p-tolyl)-1H-imidazol-4-yl)methanone (11db) | Yield: 18.6%; mp 142-144° C. $^1$H NMR (500 MHz, CDCl$_3$) δ 8.07 (q, J = 8.5 Hz, 5.5 Hz, 2 H), 7.88 (d, J = 7.5 Hz, 2 H), 7.64 (t, J = 8.0 Hz, 1 H), 7.49 (d, J = 8.0 Hz, 2 H), 7.38 (s, 1H), 7.30 (d, J = 8.0 Hz, 2 H), 7.18-7.24 (m, 4 H), 2.43 (s, 3 H). MS (ESI): calculated for $C_{23}H_{17}FN_2O_3S$, 420.10, found 443.0 $[M + Na]^+$, 418.9 $[M - H]^-$. HPLC2: $t_R$ 17.28 min, purity 97.3%. |
| (1-(phenylsulfonyl)-2-(3,4,5-trimethoxyphenyl)-1H-imidazol-4-yl)(3,4,5-trimethoxyphenyl)methanone (11ea) | Yield: 21.1%; mp 135-137° C. $^1$H NMR (500 MHz, CDCl$_3$) δ 7.91 (d, J = 8.0 Hz, 2 H), 7.65 (t, J = 7.5 Hz, 1 H), 7.51 (t, J = 8.0 Hz, 2 H), 7.44 (s, 1 H), 7.34 (s, 2 H), 6.60 (s, 2 H), 3.98 (s, 3 H), 3.96 (s, 6 H), 3.91 (s, 3 H), 3.73 (s, 6 H). MS (ESI): calculated for $C_{28}H_{28}N_2O_9S$, 568.2, found 569.2 $[M + H]^+$. HPLC1: $t_R$ 17.86 min, purity 98.9%. |
| (4-fluorophenyl)(1-(phenylsulfonyl)-2-(3,4,5-trimethoxyphenyl)-1H-imidazol-4-yl)methanone (11eb) | Yield: 18.8%; mp 135-137° C. $^1$H NMR (500 MHz, CDCl$_3$) δ 8.11 (q, J = 5.5 Hz, 3.0 Hz, 1 H), 8.00-8.03 (m, 1 H), 7.82 (d, J = 7.5 Hz, 1 H), 7.78 (s, 1 H), 7.64 (t, J = 7.0 Hz, 1 H), 7.48 (t, J = 8.0 Hz, 1 H), 7.42 (s, 1 H), 7.21-7.26 (m, 4 H), 6.62 (s, 1 H), 3.98 (s, 3 H), 3.96 (s, 6 H), 3.93 (s, 3 H). MS (ESI): calculated for $C_{25}H_{21}FN_2O_6S$, 496.10, found 497.1 $[M + H]^+$. HPLC2: $t_R$ 15.26 min, purity 98%. |
| (2-(4-chlorophenyl)-1-(phenylsulfonyl)-1H-imidazol-4-yl)(4-fluorophenyl)methanone (11fb) | Yield: 36.8%; mp 153-155° C. $^1$H NMR (500 MHz, CDCl$_3$) δ 8.06 (q, J = 5.5 Hz, 3.0 Hz, 2 H), 7.89 (d, J = 7.5 Hz, 2 H), 7.68 (t, J = 8.0 Hz, 1 H), 7.52 (t, J = 8.0 Hz, 2 H), 7.34-7.38 (m, 5H), 7.23 (t, J = 8.5 Hz, 2 H). MS (ESI): calculated for $C_{22}H_{14}ClFN_2O_3S$, 440.0, found 463.0 $[M + Na]^+$. HPLC2: $t_R$ 17.72 min, purity 97.38%. |
| (2-(4-(dimethylamino)phenyl)-1-(phenylsulfonyl)-1H-imidazol-4-yl)(3,4,5-trimethoxyphenyl)methanone (11ga) | Yield: 32.2%; mp 157-159° C. $^1$H NMR (500 MHz, CDCl$_3$) δ 7.89 (d, J = 8.0 Hz, 2 H), 7.62 (t, J = 7.5 Hz, 1 H), 7.48 (t, J = 8.0 Hz, 2 H), 7.43 (s, 1 H), 7.32 (d, J = 8.5 Hz, 2 H), 7.30 (s, 2H), |

-continued

| Compound | Physicochemical Cheracterization |
|---|---|
| | 6.62 (d, J = 9.0 Hz, 2 H), 3.97 (s, 3 H), 3.95 (s, 6 H), 3.05 (s, 6 H). MS (ESI): calculated for $C_{27}H_{27}N_3O_6S$, 521.2, found 544.1 [M + Na]$^+$, 519.8 [M − H]$^−$. HPLC2: $t_R$ 16.00 min, purity 97.9%. |
| (2-(4-(dimethylamino)phenyl)-1-(phenylsulfonyl)-1H-imidazol-4-yl)(4-fluorophenyl)methanone (11gb) | Yield: 38.5%; mp 125-127° C. $^1$H NMR (500 MHz, CDCl$_3$) δ 8.04 (q, J = 5.5 Hz, 3.5 Hz, 2 H), 7.80 (d, J = 7.5 Hz, 2 H), 7.61 (t, J = 8.0 Hz, 1 H), 7.45 (t, J = 8.0 Hz, 2 H), 7.39 (s, 1 H), 7.35 (d, J = 9.0 Hz, 2 H), 7.21 (t, J = 8.5 Hz, 2 H), 6.62 (d, J = 9.0 Hz, 2 H), 3.05 (s, 6 H). MS (ESI): calculated for $C_{24}H_{20}FN_3O_3S$, 449.10, found 472.1 [M + Na]$^+$, 447.9 [M − H]$^−$. HPLC2: $t_R$ 16.85 min, purity 96.5%. |
| (2-(3,4-dimethoxyphenyl)-1-(phenylsulfonyl)-1H-imidazol-4-yl)(3,4,5-trimethoxyphenyl)methanone (11ha) | Yield: 28.6%; mp 136-138° C. $^1$H NMR (300 MHz, CDCl$_3$) δ 7.92 (dd, J = 8.5 Hz, 1.5 Hz, 2 H), 7.66 (t, J = 7.5 Hz, 2 H), 7.51 (t, J = 7.5 Hz, 2 H), 7.43 (s, 1 H), 7.33 (s, 2 H), 7.02 (dd, J = 8.0 Hz, 2.0 Hz, 1 H), 6.91 (d, J = 2.0 Hz, 1 H), 6.86 (d, J = 8.5 Hz, 1 H), 3.98 (s, 3 H), 3.96 (s, 9 H), 3.77 (s, 3 H). MS (ESI): calculated for $C_{27}H_{26}N_2O_8S$, 538.10, found 561.1 [M + Na]$^+$, 536.8 [M − H]$^−$. HPLC2: $t_R$ 14.67 min, purity 98.2%. |
| (2-(3,4-dimethoxyphenyl)-1-(phenylsulfonyl)-1H-imidazol-4-yl)(4-fluorophenyl)methanone (11hb) | Yield: 31.9%; mp 144-145° C. $^1$H NMR (300 MHz, CDCl$_3$) δ 8.09 (q, J = 5.5 Hz, 3.5 Hz, 2 H), 7.81 (d, J = 8.0 Hz, 2 H), 7.62 (t, J = 7.5 Hz, 2 H), 7.48 (t, J = 7.5 Hz, 2 H), 7.40 (s, 1 H), 7.21-7.25 (m, 2 H), 7.04 (dd, J = 8.0 Hz, 2.0 Hz, 1 H), 6.92 (d, J = 2.0 Hz, 1 H), 6.86 (d, J = 8.5 Hz, 1 H), 3.96 (s, 3 H), 3.79 (s, 6 H). MS (ESI): calculated for $C_{24}H_{19}FN_2O_5S$, 466.10, found 489.1 [M + Na]$^+$, 464.8 [M − H]$^−$. HPLC2: $t_R$ 15.52 min, purity 97.4%. |
| (1-(phenylsulfonyl)-2-(2-(trifluoromethyl)phenyl)-1H-imidazol-4-yl)(3,4,5-trimethoxyphenyl)methanone (11ia) | Yield: 25.0%; mp 155-157° C. $^1$H NMR (500 MHz, DMSO-d$_6$) δ 7.91 (d, J = 8.0 Hz, 1 H), 7.84 (q, J = 7.5 Hz, 5.0 Hz, 2 H), 7.77-7.80 (m, 2 H), 7.75 (s, 2 H), 7.66 (t, J = 8.0 Hz, 2 H), 7.56 (d, J = 7.5 Hz, 1 H), 7.18 (s, 2 H), 3.87 (s, 6 H), 3.81 (s, 3 H). MS (ESI): calculated for $C_{26}H_{21}F_3N_2O_6S$, 546.10, found 569.0 [M + Na]$^+$. HPLC2: $t_R$ 16.16 min, purity 98.9%. |
| (1-(phenylsulfonyl)-2-(2-(trifluoromethyl)phenyl)-1H-imidazol-4-yl)(4-fluorophenyl)methanone (11ib) | Yield: 25.0%; mp 151-153° C. $^1$H NMR (500 MHz, CDCl$_3$) δ 8.03 (q, J = 5.5 Hz, 3.0 Hz, 2 H), 7.90 (d, J = 8.0 Hz, 2 H), 7.80 (d, J = 8.0 Hz, 1 H), 7.69 (q, J = 7.0 Hz, 6.5 Hz, 2 H), 7.61 (t, J = 8.0 Hz, 1 H), 7.52 (t, J = 8.0 Hz, 2 H), 7.34-7.36 (m, 2 H), 7.23 (t, J = 8.5 Hz, 2 H). MS (ESI): calculated for $C_{23}H_{14}F_4N_2O_3S$, 474.10, found 497.0 [M + Na]$^+$. HPLC2: $t_R$ 16.80 min, purity 98.2%. |
| (2-(4-(benzyloxy)phenyl)-11-(phenylsulfonyl)-1H-imidazol-4-yl)(4-fluorophenyl)methanone (11jb) | Yield: 22.3.0%; mp 149-151° C. $^1$H NMR (500 MHz, CDCl$_3$) δ 8.09 (q, J = 5.5 Hz, 3.5 Hz, 2 H), 7.82 (d, J = 7.5 Hz, 2 H), 7.63 (t, 7.5 Hz, 1 H), 7.36-7.50(m, 10 H), 7.25 (t, J = 8.5 Hz, 2 H), 6.98 (d, J = 8.0 Hz, 2 H), 5.17 (s, 2 H). MS (ESI): calculated for $C_{29}H_{21}FN_2O_4S$, 512.10, found 535.0 [M + Na]$^+$. HPLC2: $t_R$ 18.35 min, purity 95.1%. |
| (2-(4-bromophenyl)-1-(phenylsulfonyl)-1H-imidazol-4-yl)(3,4,5-trimethoxyphenyl)methanone (11la) | Yield: 32.6% $^1$H NMR (500 MHz, CDCl$_3$) δ 8.06 (d, J = 8.0 Hz, 2 H), 7.88 (d, J = 8.5 Hz, 1 H), 7.77 (t, J = 7.0 Hz, 1 H), 7.54-7.63 (m, 4 H), 7.31-7.36 (m, 4 H), 4.04 (s, 3 H), 4.01 (s, 6 H). MS (ESI) calcd for $C_{25}H_{21}BrN_2O_6S$ 556.0, found 557.0 [M + H]$^+$. |
| (1-(phenylsulfonyl)-2-(4-(trifluoromethyl)phenyl)-1H-imidazol-4-yl)(3,4,5-trimethoxyphenyl)methanone (11pa) | Yield: 36.7%; $^1$H NMR (500 MHz, CDCl$_3$) δ 8.06 (d, J = 7.5 Hz, 2 H), 7.78 (t, J = 8.0 Hz, 1 H), 7.72 (d, J = 8.0 Hz, 2 H), 7.62 (d, J = 8.0 Hz, 2 H), 7.59 (d, J = 8.0 Hz, 2 H), 7.50 (s, 1 H), 7.37 (s, 2 H), 4.04 (s, 3 H), 4.02 (s, 6 H). MS (ESI) calcd for $C_{26}H_{21}F_3N_2O_6S$ 546.1, found 547.1 [M + H]$^+$ |
| (2-(4-(dimethylamino)phenyl)-1-((4-methoxyphenyl)sulfonyl)-1H-imidazol-4-yl)(3,4,5-trimethoxyphenyl)methanone (11gaa) | Yield: 34.1%; mp 147-149° C. $^1$H NMR (500 MHz, CDCl$_3$) δ 8.07 (q, J = 8.5 Hz, 5.5 Hz, 2 H), 7.78 (d, J = 9.0 Hz, 2 H), 7.41 (d, J = 8.5 Hz, 2 H), 7.39 (s, 1 H), 7.23 (t, J = 8.5 Hz, 2 H), 6.91 (d, J = 9.0 Hz, 2 H), 6.68 (d, J = 9.0 |

| Compound | Physicochemical Cheracterization |
|---|---|
| | Hz, 2 H), 3.89 (s, 3 H), 3.08 (s, 3 H). MS (ESI) calcd for $C_{28}H_{29}N_3O_7S$ 551.2, found 573.1 $[M + Na]^+$. HPLC2: $t_R$ 18.6 min, purity 96.9%. |
| (2-phenyl-1H-imidazol-4-yl)(3,4,5-trimethoxyphenyl)methanone (12aa) | Yield: 10.1%; mp 227-229° C. $^1$H NMR (500 MHz, CDCl$_3$) δ 8.0-8.03 (m, 2 H), 7.83 (s, 1 H), 7.34-7.38 (m, 3 H), 7.21 (s, 2 H), 3.90 (s, 3 H), 3.84 (s, 6 H). MS (ESI): calculated for $C_{19}H_{18}N_2O$, 338.1, found 337.1 $[M - H]^-$. HPLC2: $t_R$14.19 min, purity 96.3%. |
| (4-methoxyphenyl)(2-phenyl-1H-imidazol-4-yl)methanone (12ab) | Yield: 16.6%; mp 179-181° C. $^1$H NMR (500 MHz, CDCl$_3$) δ 11.1 (br, 1 H), 8.07-8.10 (m, 2 H), 8.04 (d, J = 8.5 Hz, 2 H), 7.84 (d, J = 1.0 Hz, 1 H), 7.49-7.51 (m, 3 H), 7.07 (d, J = 9.0 Hz, 2 H), 3.95 (s, 3 H). MS (ESI): calculated for $C_{17}H_{14}N_2O_2$, 278.10, found 279.0 $[M + H]^+$. HPLC1: $t_R$ 15.14 min, purity >99%. |
| (3-methoxyphenyl)(2-phenyl-1H-imidazol-4-yl)methanone (12ac) | Yield: 22.5%; mp 160-162° C. $^1$H NMR (500 MHz, CDCl$_3$) δ 11.2 (br, 1 H), 8.10-8.12 (m, 2 H), 7.87 (d, J = 1.0 Hz, 1 H), 7.61 (d, J = 7.5 Hz, 1 H), 7.48-7.52 (m, 5 H), 7.21 (dd, J = 2.5 Hz, 8.5 Hz, 1 H), 3.91 (s, 3 H). MS (ESI): calculated for $C_{17}H_{14}N_2O_2$, 278.10, found 279.0 $[M + H]^+$. HPLC2: $t_R$ 15.07 min, purity >99%. |
| (3,5-dimethoxyphenyl)(2-phenyl-1H-imidazol-4-yl)methanone (12ad) | Yield: 26.2%; mp 168-170° C. $^1$H NMR (500 MHz, CDCl$_3$) δ 8.04-8.06 (m, 2 H), 7.88 (s, 1 H), 7.50-7.52 (m, 3 H), 7.15 (d, J = 2.0 Hz, 2 H), 6.75 (t, J = 1.0 Hz, 1 H), 3.89 (s, 6 H). MS (ESI): calculated for $C_{18}H_{16}N_2O_3$, 308.10, found 331.1 $[M + Na]^+$, 306.9 $[M - H]^-$. HPLC2: $t_R$ 15.59 min, purity >99%. |
| (3,4-dimethoxyphenyl)(2-phenyl-1H-imidazol-4-yl)methanone (12ae) | Yield: 18.6%; mp 162-164° C. $^1$H NMR (500 MHz, CDCl$_3$) δ 10.9 (br, 1 H), 8.05 (dd, J = 1.5 Hz, 8.0 Hz, 2 H), 7.86 (d, J = 1.5 Hz, 1 H), 7.74 (dd, J = 2.0 Hz, 8.5 Hz, 1 H), 7.56 (d, J = 2.0 Hz, 1 H), 7.50-7.52 (m, 3 H), 7.04 (d, J = 8.5 Hz, 1 H), 4.03 (s, 3 H), 3.99 (s, 3 H). MS (ESI): calculated for $C_{18}H_{16}N_2O_3$, 308.10, found 331.1 $[M + Na]^+$, 306.9 $[M - H]^-$. HPLC2: $t_R$ 13.54 min, purity >99%. |
| (4-fluorophenyl)(2-phenyl-1H-imidazol-4-yl)methanone (12af) | Yield: 30.2%; mp 231-233° C. $^1$H NMR (500 MHz, CDCl$_3$) δ 10.6 (br, 1 H), 8.02-8.05 (m, 4 H), 7.81 (d, J = 1.0 Hz, 1 H), 7.51-7.54 (m, 3 H), 7.27 (t, J = 8.5 Hz, 2 H). MS (ESI): calculated for $C_{16}H_{11}FN_2O$, 266.10, found 267.0 $[M + H]^+$, 264.8 $[M - H]^-$. HPLC1: $t_R$ 15.37 min, purity 98.9%. |
| (3-fluorophenyl)(2-phenyl-1H-imidazol-4-yl)methanone (12ag) | Yield: 23.4%; mp 212-214° C. $^1$H NMR (500 MHz, CDCl$_3$) δ 8.05 (dd, J = 1.5 Hz, 7.5 Hz, 2 H), 7.86 (s, 1 H), 7.84 (d, J = 7.0 Hz, 1 H), 7.74 (d, J = 8.5 Hz, 1 H), 7.52-7.58 (m, 4 H), 7.37 (dt, J = 2.0 Hz, 6.0 Hz, 1 H). MS (ESI): calculated for $C_{16}H_{11}FN_2O$, 266.10, found 267.0 $[M + H]^+$, 264.8 $[M - H]^-$. HPLC1: $t_R$ 15.29 min, purity >99%. |
| (2-phenyl-1H-imidazol-4-yl)(p-tolyl)methanone (12ah) | Yield: 15.6%; mp 225-227° C. $^1$H NMR (500 MHz, CDCl$_3$) δ 11.1 (br, 1 H), 8.08 (d, J = 7.5 Hz, 2 H), 7.93 (d, J = 9.0 Hz, 2 H), 7.84 (s, 1 H), 7.48-7.52 (m, 3 H), 7.38 (d, J = 10.0 Hz, 2 H), 2.50 (s, 3 H). MS (ESI): calculated for $C_{17}H_{14}N_2O$, 262.10, found 263.0 $[M + H]^+$, 260.8 $[M - H]^-$. HPLC2: $t_R$ 15.86 min, purity 98.7%. |
| (2-phenyl-1H-imidazol-4-yl)(m-tolyl)methanone (12ai) | Yield: 20.5%; mp 168-169° C. $^1$H NMR (500 MHz, CDCl$_3$) δ 11.0 (br, 1 H), 8.09-8.11 (m, 2 H), 7.84 (d, J = 1.5 Hz, 1 H), 7.81-7.82 (m, 2 H), 7.47-7.52 (m, 5 H), 2.50 (s, 3 H). MS (ESI): calculated for $C_{17}H_{14}N_2O$, 262.10, found 285.0 $[M + Na]^+$, 260.8 $[M - H]^-$. HPLC2: $t_R$ 15.89 min, purity >99%. |
| (2-(4-fluorophenyl)-1H-imidazol-4-yl)(3,4,5-trimethoxyphenyl)methanone (12ba) | Yield: 12.2%. mp 176-178° C. $^1$H NMR (500 MHz, CDCl$_3$) δ 10.72 (br, 1 H), 8.02 (q, J = 5.0 Hz, 2 H), 7.84 (s, 1 H), 7.19 (t, J = 10.0 Hz, 2 H), 4.00 (s, 6 H), 3.97 (s, 3 H). MS (ESI): calculated for $C_{19}H_{17}FN_2O_4$, 356.10, found 379.1 $[M + Na]^+$, 354.9 $[M - H]^-$. HPLC1: $t_R$ 17.23 min, purity >99% |

| Compound | Physicochemical Cheracterization |
| --- | --- |
| (2-(4-methoxyphenyl)-1H-imidazol-4-yl)(3,4,5-trimethoxyphenyl)methanone (12ca) | Yield: 10.2%; mp 220-222° C. $^1$H NMR (300 MHz, CDCl$_3$) δ 10.24 (br, 1 H), 7.93 (d, J = 14.5 Hz, 2 H), 7.81 (s, 1 H), 7.24 (s, 2 H), 7.03 (d, J = 14.5 Hz, 2 H), 3.97 (s, 3 H), 3.95 (s, 6 H), 3.90 (s, 3 H). MS (ESI): calculated for C$_{20}$H$_{20}$N$_2$O$_5$, 368.10, found 391.0 [M + Na]$^+$, 367.0 [M − H]$^-$. HPLC2: t$_R$ 14.46 min, purity 98.4%. |
| (4-fluorophenyl)(2-(4-methoxyphenyl)-1H-imidazol-4-yl)methanone (12cb) | Yield: 15.2%; mp 245-247° C. $^1$H NMR (500 MHz, CDCl$_3$) δ 10.20 (br, 1 H), 7.93-7.96 (m, 2 H), 7.85 (d, J = 5.0 Hz, 2 H), 7.68 (s, 1 H), 7.15-7.17 (m, 2 H), 6.95 (d, J = 6.0 Hz, 2 H), 3.82 (s, 3 H). MS (ESI): calculated for C$_{17}$H$_{13}$FN$_2$O$_2$, 296.10, found 319.1 [M + Na]$^+$, 294.9 [M − H]$^-$. HPLC2: t$_R$ 15.40 min, purity 98.8%. |
| (2-(p-tolyl)-1H-imidazol-4-yl)(3,4,5-trimethoxyphenyl)methanone (12da) | Yield: 48.5%; mp 201-203° C. $^1$H NMR (500 MHz, CDCl$_3$) δ 10.40 (br, 1 H), 7.88 (d, J = 8.0 Hz, 2 H), 7.82 (s, 1 H), 7.31 (d, J = 8.0 Hz, 2 H), 7.24 (s, 2 H), 3.96 (s, 3 H), 3.94 (s, 6 H), 2.43 (s, 3 H). MS (ESI): calculated for C$_{20}$H$_{20}$N$_2$O$_4$, 352.10, found 375.2 [M + Na]$^+$. HPLC2: t$_R$ 15.45 min, purity 97.4%. |
| (4-fluorophenyl)(2-(p-tolyl)-1H-imidazol-4-yl)methanone (12db) | Yield: 56.3%; mp 229-231° C. $^1$H NMR (500 MHz, CDCl$_3$) δ 10.50 (br, 1 H), 7.99-8.02 (m, 2 H), 7.88 (d, J = 8.0 Hz, 2 H), 7.60 (d, J = 1.0 Hz, 1 H), 7.30 (d, J = 8.0 Hz, 2 H), 7.23 (t, J = 9.0 Hz, 2 H), 2.43 (s, 3 H). MS (ESI): calculated for C$_{17}$H$_{13}$FN$_2$O, 280.10, found 281.0 [M + H]$^+$, 278.9 [M − H]$^-$. HPLC2: t$_R$ 16.31 min, purity >99%. |
| (4-hydroxy-3,5-dimethoxyphenyl)(2-(p-tolyl)-1H-imidazol-4-yl)methanone (12dc) | Yield: 56.8%; mp 220-222° C. $^1$H NMR (500 MHz, CDCl$_3$) δ 8.02 (d, J = 8.0 Hz, 2H), 7.91(s, 1H), 7.39 (s, 2H), 7.28 (d, J = 7.5 Hz, 2H), 4.00 (s, 6H), 2.44 (s, 3H). MS (ESI) calcd for C$_{19}$H$_{18}$ FN$_2$O$_4$ 338.1, found 339.1 [M + H]$^+$. HPLC1: t$_R$ 3.91 min, purity >99%. |
| (3,4,5-trimethoxyphenyl)(2-(3,4,5-trimethoxyphenyl)-1H-imidazol-4-yl)methanone (12ea) | Yield: 86.8%; mp 196-198° C. $^1$H NMR (500 MHz, DMSO-d$_6$) δ 13.3 (br, 0.47 H), 13.50 (br, 0.52 H), 8.19 (s, 0.49 H), 7.90 (s, 1 H), 7.83 (s, 0.5 H), 7.59 (s, 1 H), 7.40 (s, 1 H), 7.18 (s, 1 H), 3.89 (s, 6 H), 3.86 (s, 6 H), 3.77 (s, 3 H), 3.72 (s, 3 H). MS (ESI): calculated for C$_{22}$H$_{24}$N$_2$O$_7$, 428.2, found 451.1[M + Na]$^+$, 426.9 [M − H]$^-$. HPLC2: t$_R$ 14.49 min, purity >99%. |
| (4-fluorophenyl)(2-(3,4,5-trimethoxyphenyl)-1H-imidazol-4-yl)methanone (12eb) | Yield: 90.2%; mp 153-155° C. $^1$H NMR (500 MHz, CDCl$_3$) δ 10.42 (br, 1 H), 8.00 (q, J = 5.5 Hz, 3.0 Hz, 2 H), 7.76 (s, 1 H), 7.23 (t, J = 8.5 Hz, 2 H), 7.19 (s, 2 H), 3.94 (s, 3 H), 3.92 (s, 3 H). MS (ESI): calculated for C$_{19}$H$_{17}$FN$_2$O$_4$, 356.1, found 379.0 [M + Na]$^+$, 354.9 [M − H]$^-$. HPLC2: t$_R$ 15.31 min, purity >99%. |
| (2-(4-chlorophenyl)-1H-imidazol-4-yl)(3,4,5-trimethoxyphenyl)methanone (12fa) | Yield: 36.9%; mp 193-195° C. $^1$H NMR (500 MHz, CDCl$_3$) δ 10.75 (br, 1 H), 7.96 (d, J = 8.5 Hz, 2 H), 7.83 (s, 1 H), 7.47 (d, J = 9.0 Hz, 2 H), 7.23 (s, 2 H), 3.97 (s, 3 H), 3.94 (s, 6 H), 2.43 (s, 3 H). MS (ESI): calculated for C$_{19}$H$_{17}$ClN$_2$O$_4$, 372.1, found 395.1 [M + Na]$^+$, 370.9 [M − H]$^-$. HPLC2: t$_R$ 16.36 min, purity >99%. |
| (2-(4-chlorophenyl)-1H-imidazol-4-yl)(4-fluorophenyl)methanone (12fb) | Yield: 83.7%; mp 232-234° C. $^1$H NMR (500 MHz, CDCl$_3$) δ 10.78 (br, 1 H), 8.00 (q, J = 5.5 Hz, 3.0 Hz, 2 H), 7.96 (d, J = 9.0 Hz, 2 H), 7.78 (s, 1 H), 7.47 (d, J = 8.0 Hz, 2 H), 7.24 (t, J = 8.5 Hz, 2 H). MS (ESI): calculated for C$_{16}$H$_{10}$ClFN$_2$O, 300.1, found 323.0 [M + Na]$^+$, 298.8 [M − H]$^-$. HPLC2: t$_R$ 17.08 min, purity >99%. |
| (2-(4-chlorophenyl)-1H-imidazol-4-yl)(4-hydroxy-3,5-dimethoxyphenyl)methanone (12fc) | Yield: 80.2%; mp 216-218° C. $^1$H NMR (500 MHz, CD$_3$OD) δ 8.06 (d, J = 8.5 Hz, 2 H), 7.99 (s, 1 H), 7.61 (d, J = 8.0 Hz, 2 H), 7.52 (s, 2 H), 4.01 (s, 6 H). MS (ESI) calcd for C$_{18}$H$_{15}$ClN$_2$O$_4$ 358.1, found 359.1 [M + H]$^+$. HPLC2: t$_R$ 4.12 min, purity >99%. |
| (2-(4-(dimethylamino)phenyl)-1H-imidazol-4-yl)(3,4,5-trimethoxyphenyl)methanone (12ga) | Yield: 91.2%; mp 195-197° C. $^1$H NMR (500 MHz, CDCl$_3$) δ 10.39 (br, 1 H), 7.87 (d, J = 8.5 Hz, 2 H), 7.80 (s, 1 H), 7.23 (s, 2 H), 6.75(d, J = 9.0 Hz, 2 H), 3.95 (s, 3 H), 3.94 (s, 6 H), 3.05 (s, |

| Compound | Physicochemical Cheracterization |
| --- | --- |
| | 6 H). MS (ESI): calculated for $C_{21}H_{23}N_3O_4$, 381.2, found 404.2 [M + Na]$^+$, 380.0 [M − H]$^−$. HPLC2: $t_R$ 15.20 min, purity 95.8%. |
| (2-(4-(dimethylamino)phenyl)-1H-imidazol-4-yl)(4-fluorophenyl)methanone (12gb) | Yield: 86.7%; mp 278-280° C. $^1$H NMR (500 MHz, CDCl$_3$) δ 10.21 (br, 1 H), 7.98 (q, J = 5.0 Hz, 3.5 Hz, 2 H), 7.84 (d, J = 8.5 Hz, 2 H), 7.72 (s, 1 H), 7.20 (t, J = 8.5 Hz, 2 H), 6.76 (t, J = 9.0 Hz, 2 H), 3.06 (s, 6 H). MS (ESI): calculated for $C_{18}H_{16}FN_3O$, 309.1, found 332.1 [M + Na]$^+$, 307.9 [M − H]$^−$. HPLC2: $t_R$ 16.06 min, purity 95.6%. |
| (2-(3,4-dimethoxyphenyl)-1H-imidazol-4-yl)(3,4,5-trimethoxyphenyl)methanone (12ha) | Yield: 85.0%; mp 100-102° C. $^1$H NMR (500 MHz, CDCl$_3$) δ 10.19 (br, 1 H), 7.81 (s, 1 H), 7.58 (d, J = 1.5 Hz, 1 H), 7.48 (d, J = 8.0 Hz, 1 H), 7.25 (s, 2 H), 6.97 (d, J = 8.5 Hz, 1 H), 4.00 (s, 3 H), 3.96 (s, 6 H), 3.95 (s, 6 H). MS (ESI): calculated for $C_{21}H_{22}N_2O_6$, 398.2, found 399.1 [M + H]$^+$, 397.0 [M − H]$^−$. HPLC2: $t_R$ 13.73 min, purity >99%. |
| (2-(3,4-dimethoxyphenyl)-1H-imidazol-4-yl)(4-fluorophenyl)methanone (12hb) | Yield: 78.3%; mp 174-176° C. $^1$H NMR (500 MHz, CDCl$_3$) δ 8.02 (t, J = 9.0 Hz, 2 H), 7.75 (s, 1 H), 7.57 (s, 1 H), 7.48 (d, J = 8.5 Hz, 1 H), 7.23 (t, J = 8.5 Hz, 2 H), 6.95 (d, J = 8.5 Hz, 1 H), 3.99 (s, 3 H), 3.96 (s, 3 H). MS (ESI): calculated for $C_{18}H_{15}FN_2O_3$, 326.1, found 349.0 [M + Na]$^+$, 324.9 [M − H]$^−$. HPLC2: $t_R$ 14.65 min, purity >99%. |
| (2-(2-(trifluoromethyl)phenyl)-1H-imidazol-4-yl)(3,4,5-trimethoxyphenyl)methanone (12ia) | Yield: 83.8%; mp 75-77° C. $^1$H NMR (500 MHz, CDCl$_3$) δ 10.37 (br, 1 H), 8.00-8.02 (m, 1 H), 7.87 (s, 1 H), 7.82-7.85 (m, 1 H), 7.69-7.74 (m, 1 H), 7.62-7.66 (m, 1 H), 7.25 (s, 2 H), 3.99 (s, 3 H), 3.98 (s, 6 H). MS (ESI): calculated for $C_{20}H_{17}F_3N_2O_4$, 406.1, found 429.1 [M + Na]$^+$, 405.0 [M − H]$^−$. HPLC2: $t_R$ 13.98 min, purity >99%. |
| (4-fluorophenyl)(2-(2-(trifluoromethyl)phenyl)-1H-imidazol-4-yl)methanone (12ib) | Yield: 91.1%; mp 152-154° C. $^1$H NMR (500 MHz, CDCl$_3$) δ 8.12-8.14 (m, 2 H), 7.97 (d, J = 7.5 Hz, 1 H), 7.82-7.85 (m, 2 H), 7.69 (t, J = 7.5 Hz, 1 H), 7.61 (t, J = 8.0 Hz, 1 H), 7.22 (t, J = 9.0 Hz, 2 H). MS (ESI): calculated for $C_{17}H_{10}F_4N_2O$, 334.1, found 357.1 [M + Na]$^+$, 332.9 [M − H]$^−$. HPLC2: $t_R$ 15.10 min, purity >99%. |
| (2-(4-(benzyloxy)phenyl)-1H-imidazol-4-yl)(3,4,5-trimethoxyphenyl)methanone (12ja) | Yield: 16.5%; mp 191-193° C. $^1$H NMR (500 MHz, CDCl$_3$) δ 10.22 (br, 1 H), 7.93 (d, J = 9.0 Hz, 2 H), 7.81 (s, 1 H), 7.37-7.47 (m, 5 H), 7.24 (s, 2 H), 7.11 (d, J = 8.5 Hz, 2 H), 5.16 (s, 2 H), 3.97 (s, 3 H), 3.95 (s, 6 H). MS (ESI): calculated for $C_{26}H_{24}N_2O_5$, 444.2, found 467.1 [M + Na]$^+$, 442.9 [M − H]$^−$. HPLC2: $t_R$ 17.36 min, purity 95.5%. |
| (2-(4-(benzyloxy)phenyl)-1H-imidazol-4-yl)(4-fluorophenyl)methanone (12jb) | Yield: 84.7%; mp 212-214° C. $^1$H NMR (300 MHz, CDCl$_3$) δ 10.28 (br, 1 H), 799-8.04 (m, 2 H), 7.92-7.95 (m, 2 H), 7.76 (d, J = 1.5 Hz, 1 H), 7.38-7.48 (m, 5 H), 7.20-7.25 (m, 2 H), 7.09-7.12 (m, 2 H), 5.16 (s, 2 H). MS (ESI): calculated for $C_{23}H_{17}FN_2O_2$, 372.1, found 395.1 [M + Na]$^+$. HPLC2: $t_R$ 17.97 min, purity 97.8%. |
| (2-(4-hydroxyphenyl)-1H-imidazol-4-yl)(3,4,5-trimethoxyphenyl)methanone (12ka) | Yield: 72.3%. mp 191-193° C. $^1$H NMR (500 MHz, CD$_3$OD) δ 8.31 (s, 1 H), 7.90 (d, J = 8.5 Hz, 2 H), 7.31 (s, 2 H), 7.05 (s, 2 H), 3.95 (s, 6 H), 3.88 (s, 3 H). MS (ESI): calculated for $C_{19}H_{18}N_2O_5$, 354.1, found 355.1 [M + H]$^+$, 352.9 [M − H]$^−$. HPLC2: $t_R$ 12.25 min, purity 98.7%. |
| (2-(4-(hydroxyphenyl)-1H-imidazol-4-yl)(4-fluorophenyl)methanone (12kb) | Yield: 89.0%; mp 276-278° C. $^1$H NMR (500 MHz, CDCl$_3$) δ 8.31 (s, 1 H), 8.13 (q, J = 5.5 Hz, 3.0 Hz, 2 H), 7.93 (d, J = 8.5 Hz, 2 H), 7.38 (t, J = 8.5 Hz, 2 H), 7.07 (d, J = 8.5 Hz, 2 H). MS (ESI): calculated for $C_{16}H_{11}FN_2O_2$, 282.1, found 283.0 [M + H]$^+$, 280.9 [M − H]$^−$. HPLC2: $t_R$ 13.46 min, purity 97.65%. |
| (2-(4-bromophenyl)-1H-imidazol-4-yl)(3,4,5-trimethoxyphenyl)methanone (12la) | Yield: 25.6%; mp 190-192° C. $^1$H NMR (500 MHz, CDCl$_3$) δ 7.99 (d, J = 8.5 Hz, 2 H), 7.92 (s, 1 H), 7.70 (d, J = 8.5 Hz, 2 H), 7.32 (s, 2 H), 4.03 (s, 3 H), 4.00 (s, 6 H). MS (ESI) calcd for $C_{19}H_{17}BrN_2O_4$ 416.0, found 417.0 [M + H]$^+$. |

-continued

| Compound | Physicochemical Cheracterization |
|---|---|
| (2-(4-(trifluoromethyl)phenyl)-1H-imidazol-4-yl)(3,4,5-trimethoxyphenyl)methanone (12pa) | HPLC2: $t_R$ 4.24 min, purity 98.8%. Yield: 85.3%; mp 195-196° C. $^1$H NMR (500 MHz, CDCl$_3$) δ 8.22 (d, J = 8.5 Hz, 2 H), 7.96 (s, 1 H), 7.83 (d, J = 8.5 Hz, 2 H), 7.34 (s, 2 H), 4.04 (s, 3 H), 4.00 (s, 6 H). MS (ESI) calcd for C$_{20}$H$_{17}$F$_3$N$_2$O$_4$ 406.1, found 407.1 [M + H]$^+$, HPLC2: $t_R$ 18.00 min, purity >99%. |
| (2-phenyl-1H-imidazol-1-yl)(3,4,5-trimethoxyphenyl)methanone (12aaa) | Yield: 39.8%; mp 113-115° C. $^1$H NMR (500 MHz, CDCl$_3$) δ 7.53 (q, J = 5.0 Hz, 3.0 Hz, 2 H), 7.41 (d, J = 1.0 Hz, 1 H), 7.33-7.35 (m, 3 H), 7.23 (d, J = 1.0 Hz, 1 H), 7.03 (s, 2 H), 3.93 (s, 3 H), 3.85 (s, 6 H). MS (ESI): calculated for C$_{19}$H$_{18}$N$_2$O$_4$, 338.1, found 339.1 [M + H]$^+$. HPLC2: $t_R$ 13.8 min, purity 95.6%. |
| (4-methoxyphenyl)(2-phenyl-1H-imidazol-1-yl)methanone (12aba) | Yield: 56.3%; mp 68-70° C. $^1$H NMR (500 MHz, CDCl$_3$) δ 7.78 (d, J = 9.0 Hz, 2 H), 7.54-7.56 (m, 2 H), 7.32-7.34 (m, 4 H), 7.21 (d, J = 1.0 Hz, 1 H), 6.93 (d, J = 8.5 Hz, 2 H), 3.90 (s, 3 H). MS (ESI): calculated for C$_{17}$H$_{14}$N$_2$O$_2$, 278.1, found 301.0 [M + Na]$^+$, 276.8 [M − H]$^-$. HPLC2: $t_R$ 14.72 min, purity 95.7%. |
| (4-fluorophenyl)(2-(p-tolyl)-1H-imidazol-4-yl)methanone HCl salt (12db-HCl) | Yield: 95%; mp 115-117° C. $^1$H NMR (500 MHz, DMSO-d$_6$) δ 8.20-8.23 (m, 2 H), 8.18 (s, 1 H), 8.04 (d, J = 6.5 Hz, 2 H), 7.42 (t, J = 8.0 Hz, 2 H), 7.37 (d, J = 7.0 Hz, 2 H), 2.38 (s, 3 H). MS (ESI): calculated for C$_{17}$H$_{14}$FClN$_2$O, 316.1, found 281.0 [M − HCl + H]$^+$. HPLC2: $t_R$ 17.16 min, purity >99%. |
| (4-fluorophenyl)(2-(4-methoxyphenyl)-1-methyl-1H-imidazol-4-yl)methanone (12cba) | Yield: 90.2%; mp 148-150° C. $^1$H NMR (500 MHz, CDCl$_3$) δ 8.45 (q, J = 8.5 Hz, 5.5 Hz, 2 H), 7.79 (s, 1 H), 7.63 (d, J = 8.5 Hz, 2 H), 7.16 (t, J = 8.5 Hz, 2 H), 7.03 (d, J = 9.0 Hz, 2 H), 3.89 (s, 3 H), 3.82 (s, 3 H). MS (ESI) calcd for C$_{18}$H$_{15}$FN$_2$O$_2$ 310.1, found 311.0 [M + H]$^+$. HPLC2: $t_R$ 4.01 min, purity 97.6%. |
| (1-benzyl-2-(p-tolyl)-1H-imidazol-4-yl)(3,4,5-trimethoxyphenyl)methanone (12daa) | Yield: 92.8%; mp 135-137° C. $^1$H NMR (500 MHz, CDCl$_3$) δ 7.81 (s, 1 H), 7.80(d, J = 6.5 Hz, 2 H), 7.58 (d, J = 8.0 Hz, 2 H), 7.41-7.45 (m, 3 H), 7.31-7.33 (m, 2 H), 7.20 (d, J = 7.0 Hz, 2 H), 5.33 (s, 2 H), 3.99 (s, 3 H), 3.98 (s, 6 H), 2.47 (s, 3 H). MS (ESI) calcd for C$_{27}$H$_{26}$N$_2$O$_4$ 442.2, found 443.1 [M + Na]$^+$. HPLC1: $t_R$ 4.28 min, purity >99%. |
| (1-methyl-2-(p-tolyl)-1H-imidazol-4-yl)(3,4,5-trimethoxyphenyl)methanone (12dab) | Yield: 87.4%; mp 110-112° C. $^1$H NMR (500 MHz, CDCl$_3$) δ 7.87 (s, 2 H), 7.86 (d, J = 8.0 Hz, 1 H), 7.65 (d, J = 10 Hz, 2 H), 7.37 (d, J = 10 Hz, 2 H), 4.01 (s, 6 H), 4.00 (s, 3 H), 3.90 (s, 3 H). MS (ESI) calcd for C$_{21}$H$_{22}$N$_2$O$_4$ 366.2, found 367.2 [M + H]$^+$. HPLC1: $t_R$ 4.23 min, purity >99%. |
| (2-(4-(dimethylamino)phenyl)-1-((4-methoxyphenyl)sulfonyl)-1H-imidazol-4-yl)(4-fluorophenyl)methanone (12gba) | Yield: 34.1%; mp 147-149° C. $^1$H NMR (CDCl$_3$, 500 MHz) δ 8.07 (q, J = 8.5 Hz, 5.5 Hz, 2 H), 7.78 (d, J = 9.0 Hz, 2 H), 7.41 (d, J = 8.5 Hz, 2 H), 7.39 (s, 1 H), 7.23 (t, J = 8.5 Hz, 2 H), 6.91 (d, J = 9.0 Hz, 2 H), 6.68 (d, J = 9.0 Hz, 2 H), 3.89 (s, 3 H), 3.08 (s, 3 H). MS (ESI) calcd for C$_{25}$H$_{22}$FN$_3$O$_4$S 479.1, found 502.1 [M + Na]$^+$. HPLC2: $t_R$ 18.6 min, purity 96.9%. |
| (3,4,5-trihydroxyphenyl)(2-(3,4,5-trihydroxyphenyl)-1H-imidazol-4-yl)methanone (13ea) | Yield: 66.1%. mp 294-296° C. $^1$H NMR (500 MHz, CD$_3$OD) δ 8.07 (s, 1 H), 7.07 (s, 2 H), 7.02 (s, 2 H). MS (ESI): calculated for C$_{16}$H$_{12}$N$_2$O$_7$, 344.1, found 345.0[M + H]$^+$, 342.9 [M − H]$^-$. HPLC2: $t_R$ 3.62 min, purity 97.9%. |
| (2-(4-chlorophenyl)-1H-imidazol-4-yl)(3,4,5-trihydroxyphenyl)methanone (13fa) | Yield: 79.3%; mp >300° C. $^1$H NMR (500 MHz, CD$_3$OD) δ 8.02 (d, J = 8.5 Hz, 2 H), 7.77 (s, 1 H), 7.54 (d, J = 8.5 Hz, 2 H), 7.14 (s, 2 H). MS (ESI): calculated for C$_{16}$H$_{11}$ClN$_2$O$_4$, 330.0, found 331.1 [M + Na]$^+$, 328.9 [M − H]$^-$. HPLC2: $t_R$ 11.9 min, purity 95.6%. |
| (2-(3,4-dihydroxyphenyl)-1H-imidazol-4-yl)(3,4,5-trihydroxyphenyl)methanone (13ha) | Yield: 62.2%; mp >300° C. $^1$H NMR (500 MHz, CD$_3$OD) δ 8.11 (s, 1 H), 7.46 (d, J = 2.0 Hz, 1 H), 7.42 (dd, J = 8.5 Hz, 2.0 Hz, 1 H), 7.10 (s, 2 H), 7.02 (d, J = 8.5 Hz, 1 H). MS (ESI): calculated for C$_{16}$H$_{12}$N$_2$O$_6$, 328.1, found 329.0 [M + H]$^+$, 326.9 [M − H]$^-$. HPLC2: $t_R$ 3.64 min, purity 97.9%. |

| Compound | Physicochemical Cheracterization |
|---|---|
| 2-(4-nitrophenyl)-4,5-dihydro-1H-imidazole (14x) | Yield: 70.3%. $^1$H NMR (500 MHz, CDCl$_3$) δ 8.30 (d, J = 9.0 Hz, 2 H), 7.98 (d, J = 8.5 Hz, 2 H), 3.88-3.95 (m, 4 H). MS (ESI): calculated for C$_9$H$_9$N$_3$O$_2$, 191.10, found 191.9 [M + H]$^+$, 189.7 [M − H]$^−$. |
| 2-(4-fluorophenyl)-4,5-dihydro-1H-imidazole (14b) | Yield: 60.2%. $^1$H NMR (500 MHz, CDCl$_3$) δ 7.80 (q, J = 7.0 Hz, 2 H), 7.11 (d, J = 10.0 Hz, 2 H), 3.82 (br, 4 H). MS (ESI): calculated for C$_9$H$_9$FN$_2$, 164.10, found 165 [M + H]$^+$. |
| 2-(4-methoxyphenyl)-4,5-dihydro-1H-imidazole (14c) | Yield: 56.9%. $^1$H NMR (500 MHz, CDCl$_3$) δ 7.84 (d, J = 8.5 Hz, 2 H), 6.94 (d, J = 9.0 Hz, 2 H), 3.87 (s, 3 H), 3.85 (br, 4 H). MS (ESI): calculated for C$_{10}$H$_{12}$N$_2$O, 176.10, found 177.0 [M + H]$^+$. |

Example 3

Figure 14:
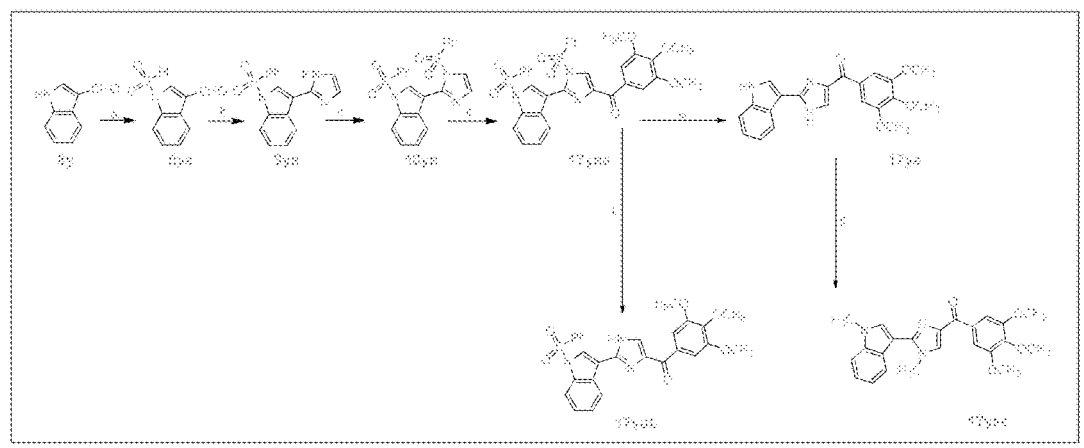
FIG. 14 depicts synthetic scheme of 17ya, 17yab and 17yac. (a) 1. KOH, ethanol, 2. PhSO$_2$Cl, acetone, RT; (b) NH$_4$OH, glyoxal, ethanol, RT; (c) NaH, PhSO$_2$Cl, THF, 0° C.—RT; (d) t-BuLi (1.7 M in pentane), 3,4,5-trimethoxybenzoyl chloride, THF, −78° C.; (e) NaOH, ethanol, H$_2$O, reflux; (f) TBAF, THF, RT; (g) NaH, CH$_3$I, THF.

Synthesis of (indolyl)-1H-imidazol-4-yl)(3,4,5-trimethoxyphenyl)methanones (17ya), (17yab) and (17yac) (FIG. 14)

Synthesis of (2-(1H-indol-3-yl)-1H-imidazol-4-yl) (3,4,5-trimethoxyphenyl)methanone (17ya)

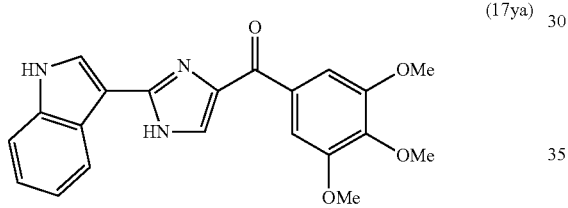

(17ya)

Synthesis of 1-(phenylsulfonyl)-1H-indole-3-carboxaldehyde (8ya)

To a solution of indole 3-carboxaldehyde (8y) (100 mmol) in ethanol (500 mL) at RT was added potassium hydroxide (1.1 equiv). The mixture was stirred until total solubilization. The ethanol was completely removed in vacuum and the residual was dissolved in acetone (250 mL) followed by adding benzenesulfonyl chloride (1.1 equiv, 110 mmol). The reaction mixture was stirred for half hour. The precipitate was filtered off and the filtrate was concentrated and recrystallized from methanol to give a white solid. Yield: 33%. $^1$H NMR (500 MHz, CDCl$_3$) δ 10.17 (s, 1H), 8.25-8.39 (m, 2H), 7.97-8.09 (m, 3H), 7.69 (t, J=7.33 Hz, 1H), 7.59 (t, J=7.5 Hz, 2H), 7.39-7.54 (m, 2H). MS (ESI) calcd for C$_{15}$H$_{11}$NO$_3$S 285.1. found 286.0 [M+H]$^+$.

Synthesis of 3-(1H-imidazol-2-yl)-1-(phenylsulfonyl)-1H-indole (9ya)

To a solution of 1-(phenylsulfonyl)-1H-indole-3-carboxaldehyde (8ya) (100 mmol) in ethanol (400 mL) at 0° C. was added a solution of 40% oxalaldehyde (glyoxal) in water (1.1 equiv, 110 mmol) and a solution of 29% ammonium hydroxide in water (10 equiv, 1000 mmol). After stirring for 2-3 days at RT, the reaction mixture was quenched by water and extracted by dichloromethane. The organic layer was removed by vacuum and the residue was subjected to flash column chromatography with hexane/ethyl acetate (4:1-2:1) as eluent to yield the titled compound as a yellow powder. Yield: 12%. $^1$H NMR (500 MHz, DMSO-d$_6$) δ 8.33 (d, J=2.9 Hz, 2H), 8.13 (d, J=7.8 Hz, 2H), 7.98-8.04 (m, 1H), 7.62-7.67 (m, 1H), 7.55 (d, J=7.82 Hz, 2H), 7.22-7.34 (m, 4H). MS (ESI) calcd for C$_{17}$H$_{13}$N$_3$O$_2$S 323.1. found 324.0 [M+H]$^+$.

Synthesis of 1-(phenylsulfonyl)-3-(1-(phenylsulfonyl)-1H-imidazol-2-yl)-1H-indole (10ya)

To a solution of 3-(1H-imidazol-2-yl)-1-(phenylsulfonyl)-1H-indole (9ya) (20 mmol) in anhydrous THF (300 mL) at 0° C. was added sodium hydride (60% dispersion in mineral oil, 1.2 equiv, 24 mmol) and stirred for 20 min. Benzenesulfonyl chloride (1.2 equiv, 24 mmol) was added and the reaction mixture was stirred overnight. After dilution by 200 mL of saturated NaHCO$_3$ solution (aqueous), the reaction mixture was extracted by ethyl acetate (600 mL). The organic layer was dried over magnesium sulfate and concentrated. The residue was purified by flash column chromatography (hexane:ethyl acetate 5:1) to give a white solid. Yield: 40%. $^1$H NMR (CDCl$_3$, 300 MHz) δ 8.02-8.08 (m, 4H), 7.72 (d, J=1.5 Hz, 1H), 7.35-7.60 (m, 8H), 7.23 (d, J=1.5 Hz, 1H), 7.10-7.16 (m, 3H). MS (ESI) calcd for C$_{23}$H$_{17}$N$_3$O$_4$S$_2$ 463.1. found 486.0 [M+Na]$^+$.

Synthesis of (1-(phenylsulfonyl)-2-(1-(phenylsulfonyl)-1H-indol-3-yl)-1H-imidazol-4-yl)(3,4,5-trimethoxyphenyl)methanone (17yaa)

To a solution of 1-(phenylsulfonyl)-3-(1-(phenylsulfonyl)-1H-imidazol-2-yl)-1H-indole (10ya) (5.0 mmol) in anhydrous THF (100 mL) at −78° C. was added 1.7 M tert-butyllithium in pentane (1.2 equiv, 6.0 mmol) and stirred for 10 min. A solution of 3,4,5-trimethoxybenzoyl chloride (1.2 equiv, 6.0 mmol) in THF was added at −78° C. and stirred overnight. The reaction mixture was quenched with 100 mL of saturated NaHCO$_3$ solution (aqueous) and extracted by ethyl acetate (300 mL). The organic layer was dried over magnesium sulfate and concentrated. The residue was purified by flash column chromatography (hexane:ethyl acetate 3:1) to give a white solid. Yield: 30%. $^1$H NMR (500 MHz, CDCl$_3$) δ 8.09 (d, J=10 Hz, 1H), 8.04 (d, J=10 Hz, 2H), 7.91 (s, 1H), 7.76 (d, J=5 Hz, 2H), 7.65 (t, J=10 Hz, 1H), 7.55-7.58 (m, 5H), 7.40 (s, 2H), 7.33-7.36 (m, 3H), 7.25 (t, J=10 Hz, 1H), 4.05 (s, 3H), 4.03 (s, 6H). MS (ESI) calcd for C$_{33}$H$_{27}$N$_3$O$_8$ 657.0. found 680.1 [M+Na]$^+$.

Synthesis of (2-(1H-indol-3-yl)-1H-imidazol-4-yl)(3,4,5-trimethoxyphenyl)methanone (17ya)

To a solution of (1-(phenylsulfonyl)-2-(1-(phenylsulfonyl)-1H-indol-3-yl)-1H-imidazol-4-yl)(3,4,5-trimethoxyphenyl)methanone (17yaa) (1 mmol) in ethanol (40 mL) and water (4 mL) was added sodium hydroxide (10 equiv, 10 mmol) and stirred overnight under refluxing condition in darkness. The reaction mixture was diluted by 50 mL of water and extracted by ethyl acetate (200 mL). The organic layer was dried over magnesium sulfate and concentrated. The residue was purified by flash column chromatography (hexane:ethyl acetate 1:1) to give a yellow solid. Yield: 60%. $^1$H NMR (500 MHz, CD$_3$OD) δ 8.31 (d, J=6.5 Hz, 1H), 7.99 (s, 1H), 7.90 (s, 1H), 7.48-7.52 (m, 3H), 7.24-7.28 (m, 2H), 4.00 (s, 6H), 3.93 (s, 3H). MS (ESI) calcd for $C_{21}H_{19}N_3O_4$ 377.1. found 400.1 [M+Na]$^+$. Mp 208-210° C.

Synthesis of (2-(1-(Phenylsulfonyl)-1H-indol-3-yl)-1H-imidazol-4-yl)(3,4,5-trimethoxyphenyl)methanone (17yab)

(17yab)

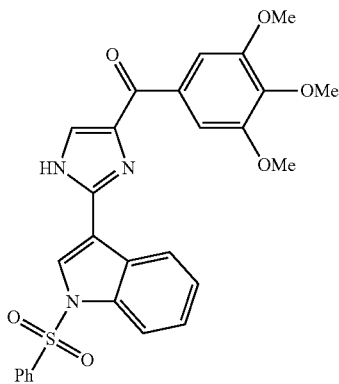

To a solution of compound 17yaa (66 mg) in THF (1.0 ml) was added 1.0 M tetrabutyl ammonium fluoride (0.4 mL, 0.4 mmol) and stirred overnight. The reaction mixture was diluted by 20 ml of saturated NaHCO$_3$ solution (aqueous) and extracted by ethyl acetate (20 ml). The organic layer was dried over magnesium sulfate and concentrated. The residue was purified by flash column chromatography (hexane:ethyl acetate, 2:1) to give a pale white solid. Yield: 45%. Mp 110-112° C. $^1$H NMR (CDCl$_3$, 500 MHz) δ 8.40-8.42 (m, 2H), 8.09 (d, J=8.0 Hz, 1H), 7.93-7.98 (m, 4H), 7.59 (t, J=7.5 Hz, 1H), 7.41-7.49 (m, 5H), 4.01 (s, 3H), 3.97 (s, 6H). MS (ESI) calcd for $C_{27}H_{23}N_3O_6S$ 517.1. found 540.0 [M+Na]$^+$. HPLC: $t_R$ 6.81 min, purity 96.3%.

Synthesis of (1-methyl-2-(1-(methyl)-1H-indol-3-yl)-1H-imidazol-4-yl)(3,4,5-trimethoxyphenyl)methanone (17yac)

(17yac)

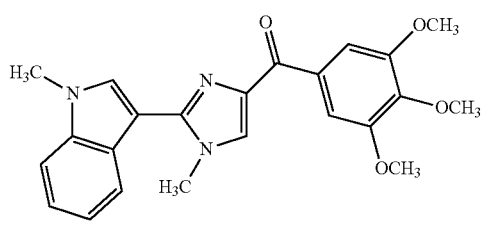

To a solution of 17ya (75 mg, 0.2 mmol) in anhydrous THF (20 ml) at 0° C. was added sodium hydride (60% dispersion in mineral oil, 20 mg, 0.5 mmol) and stirred for 20 min. Methyl iodide (70 mg, 0.5 mmol) was added, and the reaction mixture was stirred 1 h. After dilution by 20 ml of saturated NaHCO$_3$ solution (aqueous), the reaction mixture was extracted by ethyl acetate (60 ml). The organic layer was dried over magnesium sulfate and concentrated. The residue was recrystallized from water and methanol to give a white solid. 75% yield. Mp 164-166° C. $^1$H NMR (CDCl$_3$, 500 MHz) δ 8.30 (d, J=7.5 Hz, 1H), 8.01 (s, 1H), 7.87 (s, 1H), 7.41 (t, J=8.5 Hz, 1H), 7.39 (s, 1H), 7.35 (t, J=7.0 Hz, 1H), 7.23 (t, J=7.0 Hz, 1H), 3.98 (s, 6H), 3.95 (s, 3H), 3.91 (s, 3H), 3.89 (s, 3H). MS (ESI) calcd for $C_{23}H_{23}N_3O_4$ 405.2. found 406.4 [M–+H]$^+$. HPLC: $t_R$ 4.80 min, purity >99%.

Example 4

Antiproliferative Activity of Selected ABI Compounds of this Invention

Cell Culture Cytotoxicity Assay

Materials and Methods

The antiproliferative activity of the ABI compounds in three melanoma cell lines (A375 and WM-164, human melanoma cell line; B16-F1, mouse melanoma cell line) and four human prostate cancer cell lines (LNCaP, DU 145, PC-3, and PPC-1) were studied. All these cell lines were purchased from ATCC (American Type Culture Collection, Manassas, Va.) except the PPC-1 cell line. MDA-MB-435 and MDA-MB-435/LCCMDR1 cells were kindly provided by Dr. Robert Clarke at Georgetown University School of Medicine, Washington, D.C. Melanoma cells were cultured in DMEM (Cellgro Mediatech, Inc., Herndon, Va.) and prostate cancer cells were cultured in RPMI 1640 (Cellgro Mediatech, Inc., Herndon, Va.) supplemented with 10% FBS (Cellgro Mediatech). Cultures were maintained at 37° C. in a humidified atmosphere containing 5% CO$_2$. 1000 to 5000 cells were plated into each well of 96-well plates depending on growth rate and exposed to different concentrations of a test compound for 48 h (fast growing melanoma cells) or 96 h (slow growing prostate cancer cells) in three to five replicates. Cell numbers at the end of the drug treatment were measured by the sulforhodamine B (SRB) assay. Briefly, the cells were fixed with 10% trichloroacetic acid and stained with 0.4% SRB, and the absorbances at 540 nm were measured using a plate reader (DYNEX Technologies, Chantilly, Va.). Percentages of cell survival versus drug concentrations were plotted, and the IC$_{50}$ (concentration that inhibited cell growth by 50% of untreated control) values were obtained by nonlinear regression analysis using Graph-Pad Prism (GraphPad Software, San Diego, Calif.).

Results

The results of the in vitro antiproliferative activities of the compounds of this invention using three melanoma cell lines (one murine melanoma cell line, B16-F1, and two human metastatic melanoma cell lines, A375 and WM-164) and four human prostate cancer cell lines (LNCaP, PC-3, Du 145, and PPC-1) are summarized in Tables 8-10.

TABLE 8

In vitro growth inhibitory effects of compounds without A ring substitutions.

| Structure | ID | R | IC$_{50}$ (nM) | | | | | | |
|---|---|---|---|---|---|---|---|---|---|
| | | | A375 | B16-F1 | WM164 | LNCaP | PC-3 | Du 145 | PPC-1 |
| 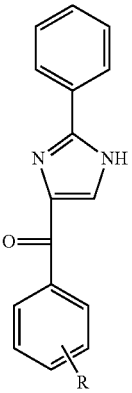 | 12aa | 3,4,5-(OMe)$_3$ | 160 | 120 | 10 | 152 | 288 | 196 | 133 |
| | 12ab | 4-OMe | >10000 | >10000 | >10000 | >10000 | >10000 | >10000 | >10000 |
| | 12ac | 3-OMe | >10000 | >10000 | >10000 | >10000 | >10000 | >10000 | >10000 |
| | 12ad | 3,5-(OMe)$_2$ | 2800 | 5400 | 2100 | 3611 | 3274 | 2590 | 2129 |
| | 12ae | 3,4-(OMe)$_2$ | >10000 | >10000 | >10000 | >10000 | >10000 | >10000 | >10000 |
| | 12af | 4-F | 580 | 930 | 630 | 613 | 2197 | 846 | 575 |
| | 12ag | 3-F | >10000 | >10000 | >10000 | >10000 | >10000 | >10000 | >10000 |
| | 12ah | 4-Me | >10000 | >10000 | >10000 | >10000 | >10000 | >10000 | >10000 |
| | 12ai | 3-Me | >10000 | >10000 | >10000 | >10000 | >10000 | >10000 | >10000 |
| 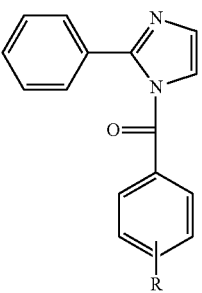 | 12aba | 4-OMe | >10000 | >10000 | >10000 | >10000 | >10000 | >10000 | >10000 |
| | 12aaa | 3,4,5-(OMe)$_3$ | >10000 | >10000 | >10000 | >10000 | >10000 | >10000 | >10000 |
| 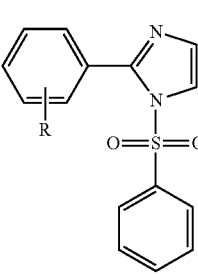 | 10a | H | >10000 | >10000 | >10000 | >10000 | >10000 | >10000 | >10000 |
| | 10x | 4-NO$_2$ | >10000 | >10000 | >10000 | >10000 | >10000 | >10000 | >10000 |
| | 10j | 4-OBn | >10000 | >10000 | >10000 | >10000 | >10000 | >10000 | >10000 |

From Table 8, compounds 12aa-12ai showed moderate activity with IC$_{50}$ values in the μM range (average of all seven cell lines). The most potent compound of this series was 12aa with an average IC$_{50}$ value of 160 nM. The removal of one of the methoxy groups from the 3,4,5-trimethoxy on the C ring (12ad, 12ae) led to a significant loss of activity (IC$_{50}$>10 μM for 12ae and an average IC$_{50}$ of 3.1 μM for 12ad). Compound with 4-fluoro on the C ring (12af) also showed relatively good activity (IC$_{50}$=0.91 μM), a finding that has an important implication, because replacing the trimethoxy moiety with a 4-fluoro group may provide good activity and improved metabolic stability. The position of the fluorine on the C ring was critical for activity because a shift from 4-fluoro to 3-fluoro resulted in a total loss of activity (IC$_{50}$>10 μM for 12ag compared with 0.91 μM for 12af). This result suggested that a potential hydrogen bond donor is present close to the 4-position of this ring.

As clearly indicated in Table 8, the positions of the A and C rings were critical. A simple shift of the C-ring moiety from position 4 to position 1 in the imidazole ring (B ring) resulted in total loss of activity (IC$_{50}$>10 μM for 12aba, 12aaa, 10a, 10x, 10j).

TABLE 9

In vitro growth inhibitory effects of compounds with substitutions on A ring.

| | | | IC$_{50}$ ± SEM (nM) | | | | | | | | |
|---|---|---|---|---|---|---|---|---|---|---|---|
| ID | R$^1$ | R$^2$ | A375 | B16-F1 | WM164 | LNCaP | PC-3 | Du 145 | PPC-1 | OV-CAR-8 | NCI/ADR-RES |
| 12ba | 4-F | 3,4,5-(OMe)$_3$ | 205 ± 19 | 320 ± 41 | 73 ± 8 | 98 ± 2 | 169 ± 12 | 132 ± 24 | 81 ± 1 | | |
| 12ca | 4-OMe | 3,4,5-(OMe)$_3$ | 30 ± 5 | 108 ± 12 | 31 ± 4 | 31 ± 1 | 45 ± 1 | 48 ± 0.5 | 34 ± 0.3 | | |
| 12cb | 4-OMe | 4-F | 31 ± 5 | 63 ± 7 | 28 ± 3 | 28 ± 2 | 31 ± 2 | 41 ± 38 | 29 ± 1 | | |
| 12da | 4-Me | 3,4,5-(OMe)$_3$ | 9 ± 2 | 46 ± 5 | 8 ± 2 | 12 ± 1 | 9 ± 0.4 | 15 ± 0.5 | 11 ± 0.1 | | |
| 12db | 4-Me | 4-F | 143 ± 13 | 222 ± 10 | 156 ± 19 | 45 ± 2 | 56 ± 3 | 78 ± 5 | 54 ± 1 | | |
| 12db-HCl | | | 108 ± 11 | 297 ± 23 | 112 ± 9 | ND | ND | ND | ND | | |
| 12dc | 4-Me | 3,5-(OMe)$_2$-4-OH | 105 | 387 | 123 | 134 | 127 | 174 | 110 | | |
| 12ea | 3,4,5-(OMe)$_3$ | 3,4,5-(OMe)$_3$ | 4800 | >10000 | >10000 | >10000 | >10000 | >10000 | >10000 | | |
| 12eb | 3,4,5-(OMe)$_3$ | 4-F | >10000 | >10000 | >10000 | >10000 | >10000 | >10000 | >10000 | | |
| 12fa | 4-Cl | 3,4,5-(OMe)$_3$ | 43 ± 5 | 168 ± 14 | 26 ± 3 | 24 ± 1 | 35 ± 1 | 36 ± 0.4 | 26 ± 0.2 | 47 | 19 |
| 12fb | 4-Cl | 4-F | 52 ± 4 | 73 ± 6 | 74 ± 9 | 49 ± 2 | 81 ± 2 | 65 ± 1 | 52 ± 1 | | |
| 13fa | 4-Cl | 3,4,5-(OH)$_3$ | 3900 | 1810 | 2100 | 10000 | 10000 | >10000 | | | |
| 12ga | 4-N(Me)$_2$ | 3,4,5-(OMe)$_3$ | 82 ± 9 | 361 ± 29 | 80 ± 11 | 58 ± 2 | 92 ± 4 | 95 ± 1 | 67 ± 0.7 | | |
| 12gb | 4-N(Me)$_2$ | 4-F | 56 ± 7 | 129 ± 11 | 62 ± 8 | 57 ± 6 | 81 ± 3 | 72 ± 0.4 | 45 ± 0.3 | | |
| 12ha | 3,4-(OMe)$_2$ | 3,4,5-(OMe)$_3$ | 113 ± 14 | 1400 ± 200 | 191 ± 18 | 121 ± 10 | 203 ± 7 | 168 ± 15 | 117 ± 1 | | |
| 12hb | 3,4-(OMe)$_2$ | 4-F | 10000 | 4210 | 1400 | 2533 | 10000 | 10000 | 2172 ± 48 | | |
| 12ia | 2-CF$_3$ | 3,4,5-(OMe)$_3$ | >10000 | >10000 | >10000 | >10000 | >10000 | >10000 | >10000 | | |
| 12ib | 2-CF$_3$ | 4-F | >10000 | >10000 | >10000 | >10000 | >10000 | >10000 | >10000 | | |
| 13ea | 3,4,5-(OH)$_3$ | 3,4,5-(OH)$_3$ | >10000 | >10000 | >10000 | >10000 | >10000 | >10000 | >10000 | | |
| 12ja | 4-OBn | 3,4,5-(OMe)$_3$ | 5200 | 10000 | 5500 | 2786 | 10000 | 10000 | 2844 | | |
| 12jb | 4-OBn | 4-F | 93 ± 8 | 117 ± 16 | 90 ± 12 | 44 ± 7 | 79 ± 0.4 | 60 ± 3 | 43 ± 0.2 | | |
| 12ka | 4-OH | 3,4,5-(OMe)$_3$ | 1600 | 2400 | 1800 | ND | ND | ND | ND | | |
| 12kb | 4-OH | 4-F | 10000 | >10000 | >10000 | 10000 | >10000 | >10000 | >10000 | | |
| 12kc | 4-OH | 3-OH, 4,5-(OMe)$_2$ | 10000 | 5600 | 6400 | | | | | | |
| 12la | 4-Br | 3,4,5-(OMe)$_3$ | 32 | 74 | 36 | 34 | 36 | 49 | 33 | | |
| 12pa | 4-CF3 | 3,4,5-(OMe)$_3$ | 163.1 | 468.7 | 175 | 134 | 127 | 174 | 110 | | |
| 13ha | 3,4-(OH)$_2$ | 3,4,5-(OH)$_3$ | >10000 | >10000 | >10000 | ND | ND | ND | ND | | |
| 12q | 4-Et | 3,4,5-(OMe)$_3$ | ND | ND | ND | 9 | 13 (PC3/TXR = 8) | 25 (DU145/TXR = 20) | 15 | | |
| 12v | 4-CH(CH$_3$)$_2$ | 3,4,5-(OMe)$_3$ | ND | ND | ND | 171 | 136 | 482 | 173 | | |
| 12w | 4-C(CH$_3$)$_3$ | 3,4,5-(OMe)$_3$ | ND | ND | ND | 423 | 436 | 1698 | 294 | | |
| Colchicine | | | 20 ± 3 | 29 ± 5 | ND | 16 ± 4 | 11 ± 1 | 10 ± 2 | 20 ± 1 | | |

ND—not determined

From Table 9 compounds with 3,4,5-trimethoxy and 4-fluoro substitutions on the C ring showed good activity with different substitutions on the A ring. These compounds demonstrated excellent antiproliferative activity with IC$_{50}$ values as low as 8.0 nM on WM164 cell line (12da). In general, compounds incorporating a single substituent on the para-position of the A ring were more potent as can be seen from the activities of 12ca, 12cb, 12da, 12db, 12fa, 12fb, 12ga, and 12gb (IC$_{50}$=7.9-110 nM). 12db-HCl salt (IC$_{50}$=172 nM) showed slightly diminished activity compared with the corresponding free base 12db (IC$_{50}$=109 nM). Compound 12fb (IC$_{50}$=63.7 nM), with a single halogen substituent in the para-position of the A and C rings, demonstrated potent and was devoid of a methoxy moiety. Compounds with 3,4,5-trimethoxy substituents on the A ring lost activity completely (IC$_{50}$>10 μM for 12ea, 12eb), suggesting very different binding environments near the A ring and C ring. Removal of the 5-methoxy substituent from the A-ring improved activity significantly (IC$_{50}$=330 nM and >10 μM for 12ha, 12ea respectively). Demethylation of the 3,4,5-trimethoxy decreased activity sharply from 43 nM (12fa) to 3.89 μM (13fa). Similar results were observed for 13ea, 12ka, 12kb, and 13ha due to the demethylation of substituents on either the A or C ring. Electron-donating groups (4-methoxy, 4-dimethylamino, 4-methyl) and electron-withdrawing groups (4-chloro, 2-trifluoromethyl) on the A ring did not show substantial differences in activity. The introduction of a trifluoromethyl group at the ortho position of the A ring caused complete loss of activity (IC$_{50}$>10 μM for 12ia, 12ib). The presence of a benzyloxy group at the para position of A ring (IC$_{50}$=75 nM for 12jb) resulted in a 440-fold increase in activity when compared with the para-hydroxy compound 12kb (IC$_{50}$=33 μM). It is worthwhile to note that compound 12jb, with the 4-fluoro in the C ring, has better activity than does its counterpart 12ja, which has a 3,4,5-trimethoxy group in the C ring (IC$_{50}$ is 75 nM for 12jb, and 7.3 μM for 12ja).

TABLE 10

In vitro growth inhibitory effects of compounds with protection on B ring.

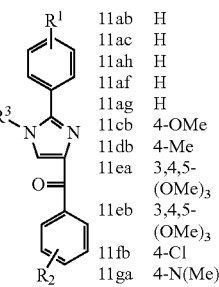

| Structure | ID | R¹ | R² | R³ | A375 | B16-F1 | WM164 | LNCaP | PC-3 | Du 145 | PPC-1 |
|---|---|---|---|---|---|---|---|---|---|---|---|
| 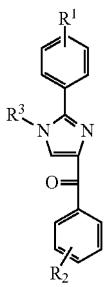 | 11ab | H | 4-OMe | $SO_2Ph$ | >10000 | >10000 | >10000 | >10000 | >10000 | >10000 | >10000 |
| | 11ac | H | 3-OMe | $SO_2Ph$ | >10000 | >10000 | >10000 | >10000 | >10000 | >10000 | >10000 |
| | 11ah | H | 4-Me | $SO_2Ph$ | >10000 | >10000 | >10000 | >10000 | >10000 | >10000 | >10000 |
| | 11af | H | 4-F | $SO_2Ph$ | 630 ± 72 | 946 ± 86 | 596 ± 61 | 573 | 2233 | 846 | 575 |
| | 11ag | H | 3-F | $SO_2Ph$ | >10000 | >10000 | >10000 | >10000 | >10000 | >10000 | >10000 |
| | 11cb | 4-OMe | 4-F | $SO_2Ph$ | 36 ± 5 | 71 ± 8 | 43 ± 6 | 31 ± 2 | 33 ± 2 | 52 ± 3 | 32 ± 0.7 |
| | 11db | 4-Me | 4-F | $SO_2Ph$ | 113 ± 14 | 287 ± 31 | 107 ± 14 | 55 ± 3 | 80 ± 1 | 80 ± 1 | 57 ± 1 |
| | 11ea | 3,4,5-(OMe)₃ | 3,4,5-(OMe)₃ | $SO_2Ph$ | >10000 | >10000 | >10000 | >10000 | >10000 | >10000 | >10000 |
| | 11eb | 3,4,5-(OMe)₃ | 4-F | $SO_2Ph$ | 3840 | >10000 | >10000 | >10000 | >10000 | >10000 | >10000 |
| | 11fb | 4-Cl | 4-F | $SO_2Ph$ | 88 ± 9 | 107 ± 12 | 70 ± 6 | 48 ± 1 | 76 ± 2 | 64 ± 1 | 54 ± 1 |
| | 11ga | 4-N(Me)₂ | 3,4,5-(OMe)₃ | $SO_2Ph$ | 162 ± 13 | 1200 ± 90 | 308 ± 32 | 62 ± 2 | 93 ± 6 | 99 ± 2 | 72 ± 0.4 |
| | 11gb | 4-N(Me)₂ | 4-F | $SO_2Ph$ | 55 ± 7 | 242 ± 26 | 56 ± 4 | 56 ± 6 | 83 ± 3 | 74 ± 0.5 | 48 ± 0.3 |
| | 11ha | 3,4-(OMe)₂ | 3,4,5-(OMe)₃ | $SO_2Ph$ | 192 ± 15 | 970 ± 68 | 139 ± 15 | 114 ± 6 | 197 ± 9 | 144 ± 29 | 117 ± 2 |
| | 11hb | 3,4-(OMe)₂ | 4-F | $SO_2Ph$ | 960 ± 59 | 2000 ± 400 | 1400 ± 30 | 1915 ± 77 | 10000 | 3312 | 1441 ± 49 |
| | 11ia | 2-CF₃ | 3,4,5-(OMe)₃ | $SO_2Ph$ | >10000 | >10000 | >10000 | >10000 | >10000 | >10000 | >10000 |
| | 11ib | 2-CF₃ | 4-F | $SO_2Ph$ | >10000 | >10000 | >10000 | >10000 | >10000 | >10000 | >10000 |
| | 11jb | 4-OBn | 4-F | $SO_2Ph$ | 64 ± 7 | 110 ± 15 | 48 ± 5 | 35 ± 1 | 75 ± 0.5 | 58 ± 1 | 38 ± 0.2 |
| | 12dab | 4-Me | 3,4,5-(OMe)₃ | Me | 32 | 134 | 40 | 32 | 46 | 36 | 28 |
| | 12cba | 4-OMe | 4-F | Me | >10000 | >10000 | >10000 | >10000 | >10000 | >10000 | >10000 |
| | 12daa | 4-Me | 3,4,5-(OMe)₃ | $CH_2Ph$ | | | | 683.2 | 465.8 | 1501 | 777.9 |
| | 12gba | 4-N(Me)₂ | 4-F | $SO_2PhOMe$ | ~100 | ~100 | ~100 | 73.2 | 44.14 | 129.4 | 63.4 |

TABLE 10A

Reversed aryl benzoyl imidazole (RABI)-inhibitory effects

| Structure | ID | R₄ | R₉ | R₁₂ | LNCaP (nM) | PC3 (nM) | PC3/TXR (nM) | PPC1 (nM) | DU145 (nM) | DU145/TXR (nM) |
|---|---|---|---|---|---|---|---|---|---|---|
| 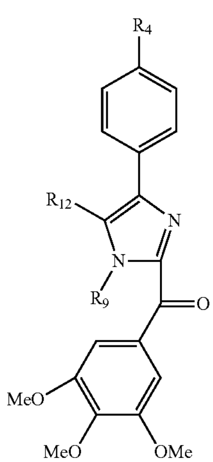 | 70a | —H | —H | —H | 6 | 14 | 4 | 13 | 21.5 | 22.9 |
| | 70b | —F | —H | —H | 114 | 196 | — | 13 | 353 | — |
| | 70c | —Cl | —H | —H | 22 | 64 | 25 | 51 | 125 | 121 |
| | 70d | —Br | —H | —H | 15 | 33 | 17 | 30 | 66 | 63 |
| | 70e | —CF₃ | —H | —H | 47 | 93 | 46 | 75 | 210 | 202 |
| | 70f | —CH₃ | —H | —H | 13 | 19 | 10 | 18 | 30 | 21 |
| | 70g | —OCH₃ | —H | —H | 30 | 61 | 25 | 54 | 210 | 111 |
| | 70h | —N(CH₃)₂ | —H | —H | 96 | 117 | — | 120 | 263 | — |
| | 70i | —OH | —H | —H | 219 | 155 | — | 122 | 518 | — |
| | 70j | —H | —H | —Me | 938 | 1617 | — | 860 | 2001 | — |
| | 70k | —H | —H | —Et | 2029 | 3654 | — | 2078 | 5079 | — |
| | 70l | —H | —H | —n-Pr | 3094 | 12360 | — | 11410 | 16350 | — |
| | 70m | —H | —Me | —H | 10 | 16 | 7.5 | 13 | 26 | 27 |
| | 70n | —H | —Et | —H | 29 | 25 | 20 | 30 | 66 | 66 |
| | 70o | —H | —Bn | —H | 67 | 72 | — | 77 | 160 | — |
| | 70p | —H | -cyclopentyl | —H | 51 | 56 | — | 63 | 167 | — |
| | 70ab | —H | n-Pr | —H | 49.4 | 25.6 | — | 9.8 | 71.6 | |
| | 70ac | —H | —CH(CH₃)₂ | —H | 62.2 | 52.5 | — | 15.0 | 114.1 | |
| | 70ad | —H | (2-pyridyl) | —H | 19.5 | 11.1 | — | 7.8 | 36.3 | |

TABLE 10B

Reversed aryl benzoyl imidazole (RABI)-inhibitory effects

| Structure | ID | $R_1$ | $R_2$ | $R_3$ | $R_4$ | $R_5$ | $R_6$ | LNCaP (nM) | PC3 (nM) | PPC1 (nM) | DU145 (nM) |
|---|---|---|---|---|---|---|---|---|---|---|---|
| 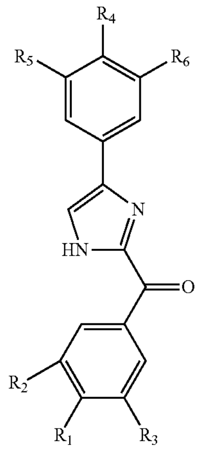 | 70q | OMe | OMe | OMe | OMe | OMe | OMe | >50000 | >50000 | >50000 | >50000 |
| | 70r | F | H | H | F | H | H | >50000 | >50000 | >50000 | >50000 |
| | 70s | Cl | H | H | Cl | H | H | >50000 | >50000 | >50000 | >50000 |
| | 70t | Br | H | H | Br | H | H | 16930 | 18940 | 13210 | 25490 |
| | 70u | $CF_3$ | H | H | $CF_3$ | H | H | >50000 | >50000 | >50000 | >50000 |
| | 70v | $CH_3$ | H | H | $CH_3$ | H | H | 3762 | 5159 | 2405 | 6541 |
| | 70w | OMe | H | H | OMe | H | H | 6410 | 23370 | 38150 | 9389 |
| | 70x | H | H | H | OMe | OMe | OMe | 195.4 | 631.5 | 408.5 | 1301 |
| | 70y | OMe | H | H | OMe | OMe | OMe | 708.5 | 10390 | 5685 | >50000 |
| | 70z | Br | H | H | OMe | OMe | OMe | 131 | 371 | 107 | 430 |
| | 70aa | H | H | H | H | H | H | >50000 | >50000 | >50000 | >50000 |

From Table 10, compounds with a phenylsulfonyl protection group attached to the nitrogen of the imidazole ring (11eb, 11db, 11fb, 11ga, 11gb, 11ha, 11jb) were also very active with $IC_{50}$ in the nM range (Table 10). Generally the activities of these compounds are comparable to their corresponding unprotected counterparts as exemplified by comparing the activities of 11cb (43 nM), 11db (111 nM), 11fb (72 nM), 11ga (285 nM), 110 (87 nM), 11ha (268 nM), and 11jb (61 nM) with their corresponding unprotected counterparts 12cb (36 nM), 12db (109 nM), 12fb (64 nM), 12ga (131 nM), 12gb (72 nM), 12ha (330 nM), and 12jb (75 nM). Other compounds (11ab-11ag, 11ea, 11eb, 11hb, 11ia, and 11ib, 1-50 μM) were generally much less active, also in line with their counterparts (12ab-12ag, 12ea, 12eb, 12hb, 12ia, and 12ib, 1-50 μM).

Figure 15:
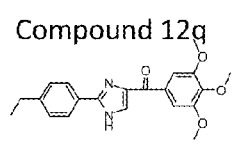
FIG. 15 depicts PC3 cell cycle distribution for 24 hours treatment of compounds of this invention (12q, 70a, 70f and 70m).
Figure 15:
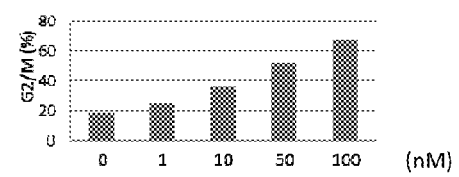
Figure 15:
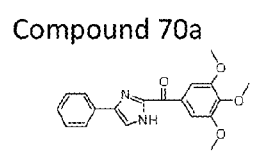
Figure 15:
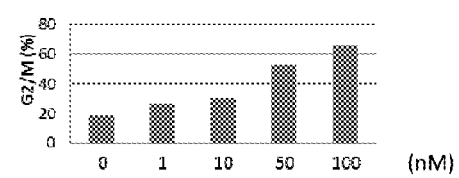
Figure 15:
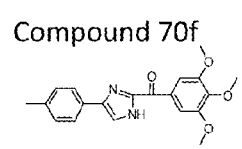
Figure 15:
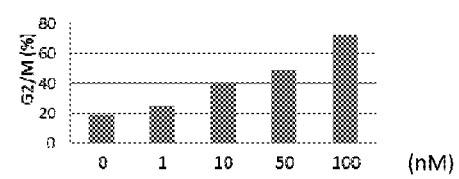
Figure 15:
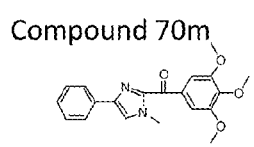
Figure 15:
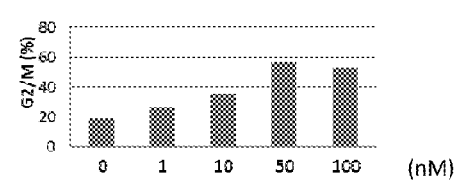

The PC3 cell cycle distributions of compounds of this invention are presented in FIG. 15.

Cell Cycle Analysis.

Cell cycle distribution was determined by propidium iodide (PI) staining. Treated cells were washed with PBS and fixed with 70% ice-cold ethanol overnight. Fixed cells were then stained with 20 μg/mL of PI in the presence of RNase A (300 μg/mL) at 37° C. for 30 min. Cell cycle distribution was analyzed by fluorescence-activated cell sorting (FACS) analysis core services at the University of Tennessee Health Science Center, TN.

Results

Reversed ABIs (RABIs) demonstrated by cell cycle analysis that they arrest cells in the $G_2/M$ phase. Compounds 12q, 70a, 70f, and 70m were treated on PC3 cells for 24 h (FIG. 15) and the distribution of PI stained cells was investigated by FACS analysis. Four different concentrations—1, 10, 50, and 100 nM—of each compound were chosen to examine the dose effect. In the vehicle treated group, about 18% of PC3 cells were distributed in the $G_2/M$ phase. RABIs increased the proportion of cells in $G_2/M$ phase up to 70% approximately in a concentration-dependent manner. The potency of the different concentrations in arresting cells in the $G_2/M$ phase positively correlated with in vitro cell growth inhibitory activity. The anti-proliferation of RABIs are reported in Table 10A and Table 10B. Some of the RABIs exhibited quite potent anti-proliferation (e.g., see 70a).

Example 5

Activity of Aryl-Benzoyl-Imidazole (ABI) Compounds in Drug-Resistant Melanoma Cells P-glycoprotein (Pgp)-mediated drug efflux represents a major mechanism for cancer cells to prevent the build up of effective anticancer intracellular drug concentrations. The activity of the ABI compounds were compared against multidrug-resistant (MDR) melanoma cells (MDA-MB-435/LCCMDR1) and their parental nonresistant cancer cells (MDA-MB-435). Although MDA-MB-435 was originally designated as a breast cancer cell line, it has been shown definitively to originate from the M14 melanoma cell line. Compounds 12da, 12fb, 12cb, 11cb, and 11fb together with other tubulin-targeting agents including colchicine, paclitaxel, and vinblastine were tested on both the MDR melanoma cell line and its parental melanoma cell line (Table 11A). Paclitaxel and vinblastine are clinically used anticancer drugs known to target cell tubulin. Although colchicine is not an FDA-approved drug for cancer treatment, its prodrug, ZD6126, is in clinical trial for solid tumors. Bortezomib is the first therapeutic proteasome inhibitor and was approved in 2003 by the FDA for use in multiple myeloma. ABT-751 is known to target the tubulin colchicine binding site. It is a promising drug candidate in clinical trial for children with relapsed or refractory neuroblastoma. Compounds 12da, 12fb, 12cb, 11cb, 11fb had much better resistance indices (3.0 for 12da, 0.9 for 12fb, 1.3 for 12cb, 0.8 for 11cb, 0.7 for 11fb) than colchicine (65.8), paclitaxel (69.3), and vinblastine (27.5). Although colchicine, paclitaxel, and vinblastine showed excellent activity in nonresistant melanoma cell lines (0.5-10 nM), these compounds were significantly less potent in the MDR melanoma cell line (277-658 nM). In contrast, 12cb, 11cb, 11fb had essentially equivalent potency on both MDR (15 nM, 38 nM, 30 nM, 30 nM, 35 nM for 12da, 12fb, 12cb, 11cb and 11fb respectively) and nonresistant melanoma cell lines (5 nM, 41 nM, 24 nM, 38 nM, 50 nM for 12da, 12fb, 12cb, 11cb and 11fb respectively). Compound 12da was more active than paclitaxel and colchicine on A375 and WM-164 cells.

TABLE 11A

In vitro growth inhibitory effects of the ABI compounds in comparison to other anticancer drugs on multidrug-resistant melanoma cell line (MDR cell) and the matching sensitive parent cell line (Normal Melanoma cell).

| | IC$_{50}$ ± SEM (nM) (n = 3) | | | | | | |
|---|---|---|---|---|---|---|---|
| Compound ID | A375 | B16-F1 | WM-164 | Tubulin binding (μm) | MDA-MB-435 | MDA-MB-435/ LCC6MDR1 | Resistance index* |
| 12da | 9 ± 2 | 46 ± 5 | 8 ± 2 | 0.2 ± 0.1 | 5 ± 1 | 15 ± 2 | 3.0 |
| 12fb | 52 ± 4 | 73 ± 6 | 74 ± 9 | 3.9 ± 2.1 | 41 ± 2 | 38 ± 2 | 0.9 |
| 12cb | 31 ± 5 | 63 ± 7 | 28 ± 3 | 3.4 ± 1.5 | 24 ± 2 | 30 ± 4 | 1.3 |
| 11cb | 36 ± 5 | 71 ± 8 | 43 ± 6 | ND | 38 ± 3 | 30 ± 2 | 0.8 |
| 11fb | 88 ± 9 | 107 ± 12 | 74 ± 8 | ND | 50 ± 6 | 35 ± 3 | 0.7 |
| Paclitaxel | 12 ± 3 | 17 ± 2 | 18 ± 3 | N/A | 4 ± 1 | 277 ± 41 | 69.3 |
| Vinblastine | 1.1 ± 0.2 | 4.7 ± 0.7 | 0.6 ± 0.1 | ND | 0.4 ± 0.1 | 11 ± 1 | 27.5 |
| Colchicine | 20 ± 3 | 29 ± 5 | 10 ± 2 | 1.8 ± 0.5 | 10 ± 1 | 658 ± 50 | 65.8 |
| Bortezomib | 8 ± 1 | 24 ± 2 | 8 ± 1 | ND | ND | ND | ND |
| ABT-751 | 1111 ± 108 | 2127 ± 351 | 661 ± 56 | ND | ND | ND | ND |

*Resistance indexes were calculated by dividing IC$_{50}$ values on multidrug-resistant cell line MDA-MB-435/LCC6MDR1 by IC$_{50}$ values on the matching sensitive parental cell line MDA-MB-435.
Abbreviations:
N/A, value not available;
ND, not determined.

TABLE 11B

Anticancer efficacy and colchicine site binding affinity of ABIs in different cancer and MDR cell lines with different resistance mechanisms. ABIs showed excellent potency against all tested melanoma cell lines including highly metastatic and multidrug resistant cell lines. High binding affinity of ABIs to the colchicine binding site in tubulin confirmed their target inside cells.

| | IC$_{50}$ ± SEM (nmol/L) (n = 3) | | | | | | | |
|---|---|---|---|---|---|---|---|---|
| | 12cb | 12da | 12fb | Paclitaxel | Vinblastine | Colchicine | ABT-751 | SN-38 |
| A375 | 31 ± 5 | 9 ± 2 | 52 ± 4 | 12 ± 3 | 1 ± 0.1 | 20 ± 3 | 685 ± 108 | ND |
| A375MA2 | 44 ± 5 | 8 ± 1 | 55 ± 4 | 8 ± 1 | 1 ± 0.2 | 18 ± 2 | 265 ± 36 | ND |
| B16-F1 | 63 ± 7 | 46 ± 5 | 73 ± 6 | 17 ± 2 | 5 ± 1 | 29 ± 5 | 2127 ± 351 | ND |
| WM-164 | 28 ± 3 | 8 ± 2 | 74 ± 9 | 18 ± 3 | 0.6 ± 0.1 | 10 ± 2 | 661 ± 56 | ND |
| MDR1 | | | | | | | | |
| MDA-MB-435* | 24 ± 2 | 5 ± 1 | 41 ± 2 | 4 ± 1 | 0.4 ± 0.1 | 10 ± 1 | 417 ± 23 | ND |
| MDA-MB-435/LCC6MDR1 | 30 ± 4 (1) | 11 ± 2 (2) | 38 ± 2 (1) | 277 ± 4 (69) | 11 ± 1 (28) | 658 ± 50 (66) | 577 ± 31 (1) | ND |
| OVCAR-8* | 25 ± 2 | 11 ± 1 | 45 ± 2 | 10 ± 0.2 | 2 ± 0.1 | 12 ± 1 | 785 ± 17 | 2 ± 0.2 |
| NCI/ADR-RES | 13 ± 1 (0.5) | 5 ± 0.1 (0.5) | 20 ± 6 (0.4) | 5109 ± 170 (511) | 570 ± 84 (285) | 737 ± 51 (61) | 864 ± 42 (1) | 10 ± 1 (5) |
| MRP | | | | | | | | |
| HEK293-pcDNA3.1* | 12 ± 2 | 9 ± 1 | 54 ± 0.3 | 9 ± 0.3 | 5 ± 0.1 | 3 ± 0.4 | 645 ± 153 | 3 ± 0.4 |
| HEK293-MRP1 | 16 ± 2 (1) | 8 ± 1 (0.9) | 33 ± 7 (0.6) | 30 ± 3 (3) | 24 ± 1 (5) | 5 ± 0.1 (2) | 717 ± 28 (1) | 9 ± 0.04 (3) |
| HEK293-MRP2 | 14 ± 4 (1) | 8 ± 0.3 (0.9) | 39 ± 12 (0.7) | 37 ± 2 (4) | 28 ± 2 (6) | 3 ± 0.3 (1) | 747 ± 7 (1) | 7 ± 0.1 (2) |
| BCRP | | | | | | | | |
| HEK293-482R2 | 17 ± 1 (1) | 8 ± 1 (0.9) | 23 ± 3 (0.4) | 50 ± 1 (6) | 25 ± 1 (5) | 5 ± 0.1 (2) | 653 ± 72 (1) | 123 ± 28 (41) |
| Tubulin binding (μM)+ | 3 ± 1 | 0.2 ± 0.1 | 4 ± 1 | N/A | ND | 2 ± 1 | 3.1++ | ND |

Notes:
*parental cell line to drug resistant cell subline;
MDR1 were overexpressed in MDA-MB-435/LCC6MDR1 and NCI/ADR-RES;
MRP1, MRP2 and BCRP were overexpressed in HEK293-MRP1, HEK293-MRP2, and HEK293-482R2. The resistance indexes (numbers in the parenthesis) were calculated by dividing IC$_{50}$ values on the resistant cell subline by that of the matching parental cell line.
+IC$_{50}$ for tubulin binding was calculated from [$^3$H]colchicine competition-binding scintillation proximity assay.
++binding affinity reported in the literature for ABT-751.
Abbreviations:
N/A, not applicable since they bind to tubulin at different sites.

TABLE 11C

Anti-proliferative activity of methylene linked compounds (aryl-benzyl-imidazoles) in melanoma cells.

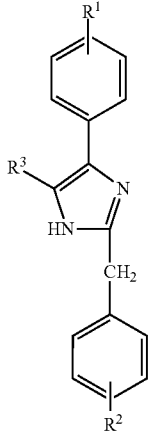

| Structure | ID | $R_1$ | $R_2$ | $R_3$ | A375 | MDA-MB-435 | MDA-MB-435/LCC6MDR1 |
|---|---|---|---|---|---|---|---|
| 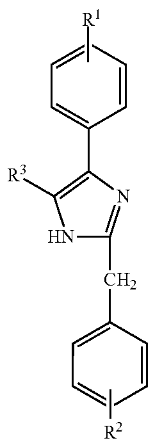 | 102a | H | 3,4,5-OMe)$_3$ | H | 10.204 ± 0.392 | ND | ND |
| | 102b | F | 3,4,5-OMe)$_3$ | Me | >50 | ND | ND |
| | 102c | H | 3,4,5-OMe)$_3$ | Et | ND | >50 | >50 |
| | 102d | H | 3,4,5-OMe)$_3$ | n-Pr | ND | 10.951 ± 0.037 | 15.949 ± 0.012 |
| | 102 e | H | 3,4,5-OMe)$_3$ | Ph | ND | >50 | >50 |
| | Colchicine | N/A | N/A | N/A | 0.024 ± 0.003 | 0.011 ± 0.002 | 0.643 ± 0.009 |

*N/A = not applicable
ND = not determined

TABLE 11D

Anti-proliferative activity of aryl-benzoyl-imidazoles in melanoma cells.

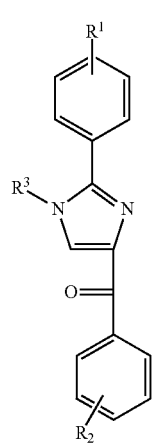

| Structure | ID | $R_1$ | $R_2$ | $R_3$ | A375 | MDA-MB-435 | MDA-MB-435/LCC6MDR1 |
|---|---|---|---|---|---|---|---|
| 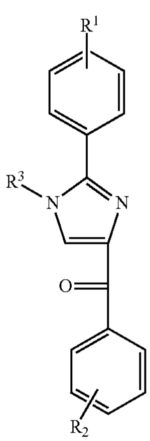 | 12q | 4-Et | 3,4,5-(OMe)$_3$ | H | 0.0014 ± 0.005 | 0.107 ± 0.005 | 0.027 ± 0.003 |
| | 12v | 4-iPr | 3,4,5-(OMe)$_3$ | H | ND | 0.312 ± 0004 | 0.250 ± 0.004 |
| | 12w | 4-tBu | 3,4,5-(OMe)$_3$ | H | ND | 3.691 ± 0.006 | 3.074 ± 0.005 |

TABLE 11D-continued

Anti-proliferative activity of aryl-benzoyl-imidazoles in melanoma cells.

| Structure | ID | R$_1$ | R$_2$ | R$_3$ | A375 | IC$_{50}$ ± SEM (μm) MDA-MB-435 | MDA-MB-435/LCC6MDR1 |
|---|---|---|---|---|---|---|---|
| (structure: aryl-benzoyl-imidazole with R$_1$, R$_2$ substituents) | 70aa | H | H | N/A | ND | >50 | >50 |
| | 70a | H | 3,4,5-(OMe)$_3$ | N/A | ND | 0.079 ± 0.003 | 0.043 ± 0.002 |
| | 70x | 3,4,5-(OMe)$_3$ | H | N/A | ND | 4.605 ± 0.007 | 5.770 ± 0.006 |
| | 70q | 3,4,5-(OMe)$_3$ | 3,4,5-(OMe)$_3$ | N/A | ND | 0.149 ± 0.003 | 0.211 ± 0.005 |

*N/A = not applicable
ND = not determined

Figure 16:
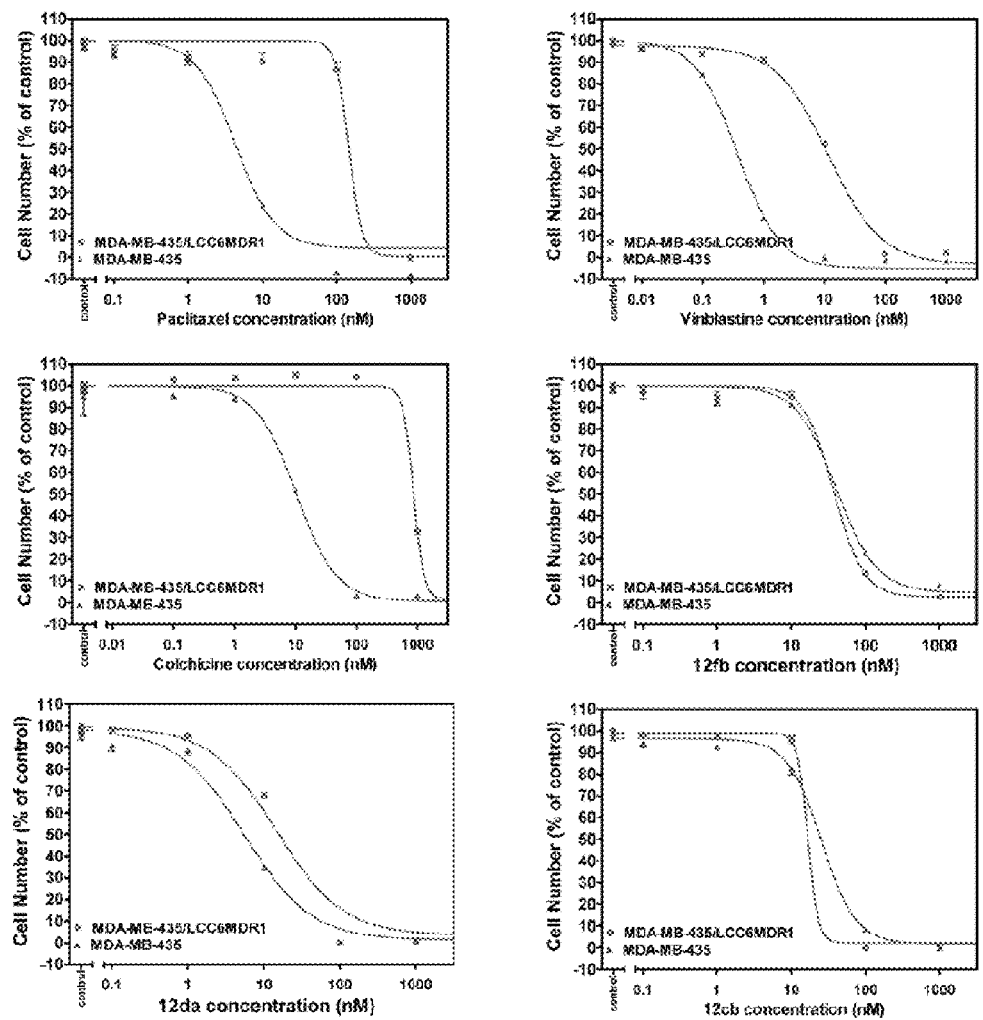
FIG. 16 depicts dose-response curves of 2-aryl-4-benzoyl-imidazole compounds (ABIs) compared with other anticancer drugs and compounds on multidrug resistant melanoma cell line (MDR cell) and the matched sensitive parent cell line (normal melanoma cell). The large distance between the two curves for paclitaxel, vinblastine, and colchicine indicates that they were substrates for P-glycoprotein (P-gp). The overlapping two curves of each ABI compound indicate that the ABI compounds were not substrates for P-gp and overcame multidrug resistance.

The results of Table 11A showed that cell line MDA-MB-435/LCCMDR1 was very resistant to colchicine, paclitaxel, and vinblastine. But the ABIs of this invention showed equal potency to the drug-resistant cell line and the sensitive parent cell line. This result strongly suggests that ABIs are not substrates for P-gp. Thus, they overcame the multidrug resistance found in MDA-MB-435/LCCMDR1 cells. The dose response curves are shown in FIG. 16 for 12fb, 12da, and 12cb. Table 11B explores further the resistance mechanisms for paclitaxel, SN-38, vinblastine, and colchicine as compared to the ABIs 12cb, 12da, and 12fb. MRP and BCRP conferred moderate resistance to paclitaxel (resistance indexes of 4 and 6, respectively), vinblastine (resistance indexes of 6 and 5, respectively), and BCRP conferred significant resistance to SN-38 (resistance index of 41). However, none of the ABIs were susceptible to MRP- or BCRP-mediated resistance (resistance indexes ranged from 0.4 to 1.0). ABT-751, like the ABIs, was not susceptible to MDR1, MRP, or BCRP.

Example 6

In Vitro Microtubule Polymerization Assay

Materials and Methods

Bovine brain tubulin (0.4 mg) (Cytoskeleton, Denver, Colo.) was mixed with 10 μM of the test compound and incubated in 110 μl of general tubulin buffer (80 mM PIPES, 2.0 mM MgCl$_2$, 0.5 mM EGTA, and 1 mM GTP) at pH 6.9. The absorbance at 340 nm was monitored every 1 min for 15 min by the SYNERGY 4 Microplate Reader (Bio-Tek Instruments, Winooski, Vt.). The spectrophotometer was set at 37° C. for tubulin polymerization.

Results

Figure 17:
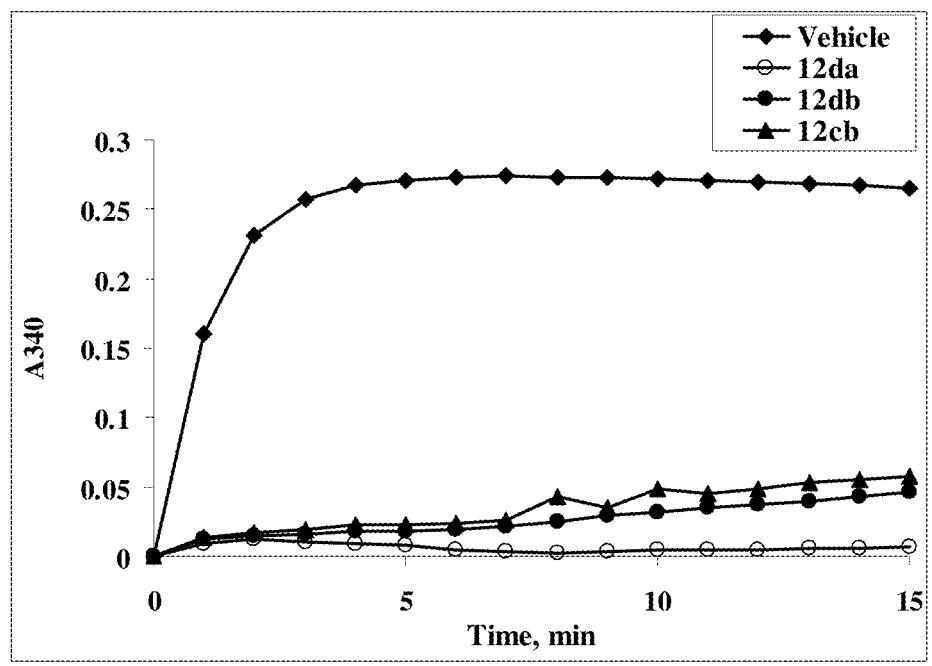
FIG. 17 presents the effect of ABI compounds on tubulin polymerization in vitro. Tubulin (0.4 mg/assay) was exposed to 10 µM ABI compounds (vehicle control, 5% DMSO). Absorbance at 340 nm was monitored at 37° C. every minute for 15 min and demonstrated that ABI compounds 12da, 12db, and 12cb inhibited tubulin polymerization in vitro.

The inhibition of tubulin polymerization by Aryl-Benzoyl-Imidazole (ABI) compounds was examined. Bovine brain tubulin (>97% pure) was incubated with three potent ABI compounds, 12cb, 12da, and 12db at a concentration of 10 μM, to determine the effect of these ABI compounds on tubulin polymerization (FIG. 17). Tubulin polymerization was completely inhibited by compound 12da, while ~80% inhibition was observed during incubation with compounds 12cb and 12db.

This microtubule destabilization effect was similar to that of colchicine and vinblastine but was opposite to that of paclitaxel. The results not only confirmed that ABIs can directly interact with tubulin but also suggested that they may share the same binding site with colchicine (or vinblastine).

Example 7

Melanoma Inhibition In Vitro

Materials and Methods

B16-F1 melanoma cells were plated at a colony-forming density (2000 cells per well on six-well plates) on top of 0.8% base agar. Cells were grown in 0.4% agar together with DMEM medium supplemented with fetal bovine serum and an antibiotic-antimycotic solution at 37° C. in an atmosphere of 95% air and 5% CO$_2$. Cells were treated with compounds 12da, 12cb and 12fb at different concentrations (20, 100, and 500 nM). Compounds were added to the media from 1 mM DMSO stock solutions, and a corresponding dilution of DMSO was used as control. Cells were grown for 14 days. Plates were photographed, and the number of colonies was measured by Artek 880 Automated Colony Counter (Artek Systems Corporation, Farmingdale, N.Y.).

Results

Figure 18:
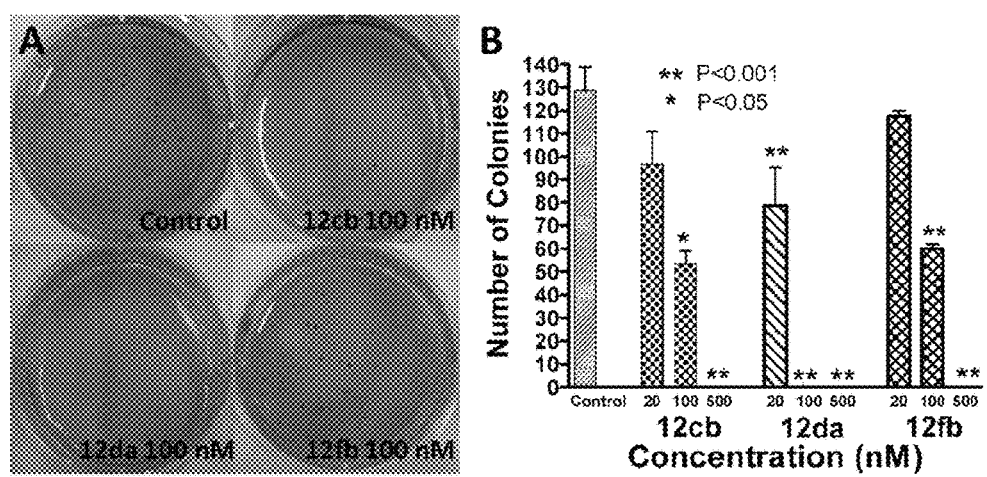
FIG. 18 depicts B16-F1 melanoma colony formation assay in soft agar which showed that ABI compounds inhibited colony formation in a concentration-dependent manner.

Four representative photos are shown in FIG. 18. After 14 days of incubation, about 130 detectable colonies (diameter larger than 100 μm) were formed in controls (no treatment). Compounds 12cb and 12da effectively inhibited B16-F1 melanoma colony formation even at the lowest tested concentration, 20 nM (p<0.05 compared with control). 12fb showed effective inhibition at 100 nM. All three tested compounds showed complete inhibition of colony formation at 0.5 μM, further proving ABIs' antimelanoma efficacy.

Example 8

In Vivo Anti-Tumor Activity

Materials and Methods

Animals:

Female C57/BL mice, age 4-6 weeks, were purchased from Harlan Laboratories (Harlan Laboratories Inc., Indianapolis, Ind.). The animal housing met the Association for Assessment and Accreditation and Laboratory Animal Care specifications. All of the procedures were conducted in accordance with guidelines of our Institutional Animal Care and Use Committee.

In Vivo Evaluation of Efficacy.

Mouse melanoma B16-F1 cells were prepared in FBS-free DMEM medium (Cellgro Mediatech) at a concentration of $5 \times 10^6$ viable cells/mL. The cell suspension (100 µL) was injected subcutaneously in the right dorsal flank of each mouse. When tumor size reached about 100-150 mm³, about 7 days after cell inoculation, all mice bearing tumors were divided into control and treatment groups based on tumor size (n=5 per group). Each group had similar average tumor size. Mice in control groups (negative control) were injected intraperitoneally with 50 µL vehicle solution only or DTIC at 60 mg/kg (positive control) once daily. Tumor volume was measured every 2 days with a traceable electronic digital caliper (Fisher Scientific, Inc., Pittsburgh, Pa.) and calculated using the formula $a \times b^2 \times 0.5$, where a and b represented the larger and smaller diameters, respectively. Tumor volume was expressed in cubic millimeters. Data were expressed as mean±SE for each group and plotted as a function of time. Percentage tumor reduction at the conclusion of the experiment (14 days after starting treatment) was calculated with the formula $100 - 100 \times [(T-T_0)/(C-C_0)]$, where T represents mean tumor volume of a treated group on a specific day, $T_0$ represents mean tumor volume of the same group on the first day of treatment, C represents mean tumor volume of a control on a specific day, and $C_0$ represents mean tumor volume of the same group on the first day of treatment. Animal activity and average body weight of each group were monitored during the entire experiment period to assess compound toxicity. At the end of treatment, all mice were euthanized by $CO_2$ followed by cervical dislocation, and tumors were harvested for further studies.

Results

Figure 19:
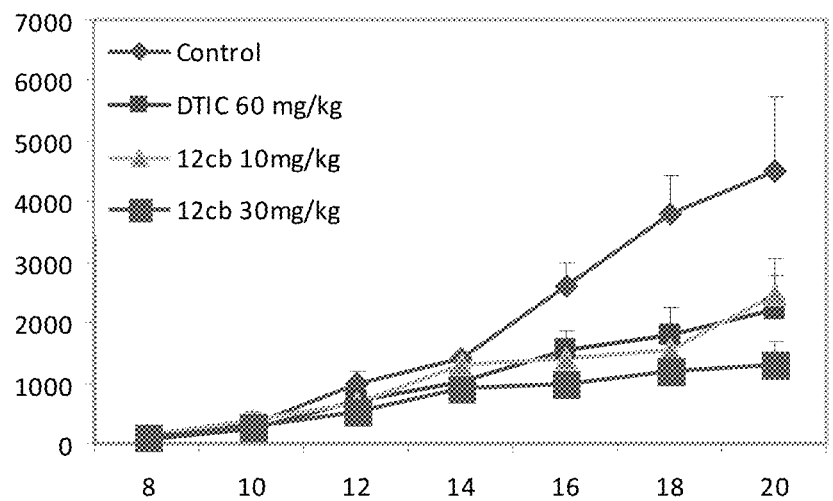
FIG. 19 depicts in vivo study of ABI compounds.
Figure 19:
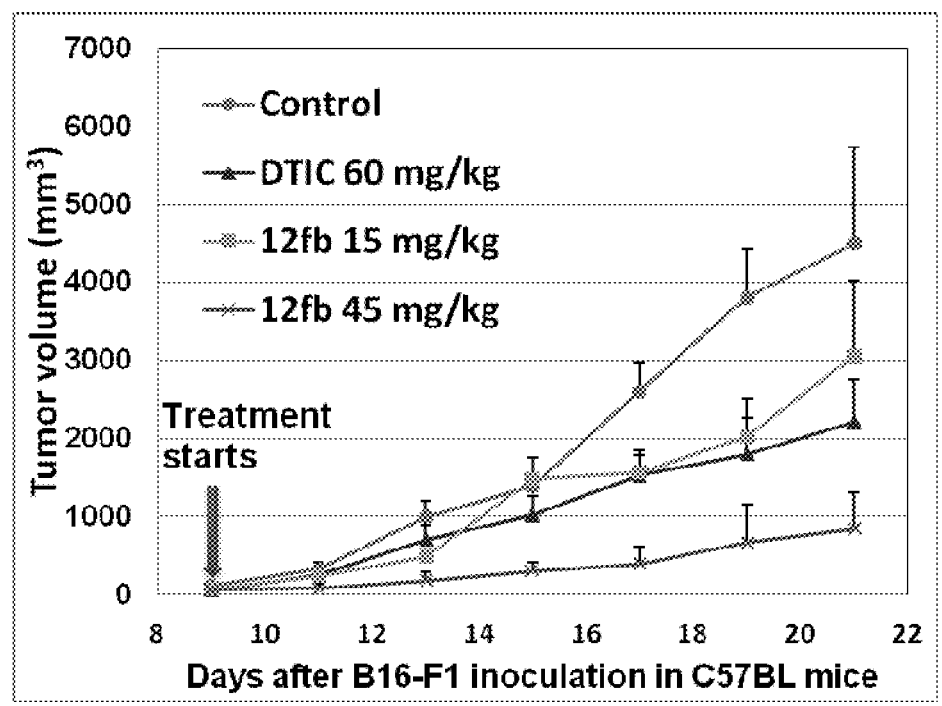
Figure 19:
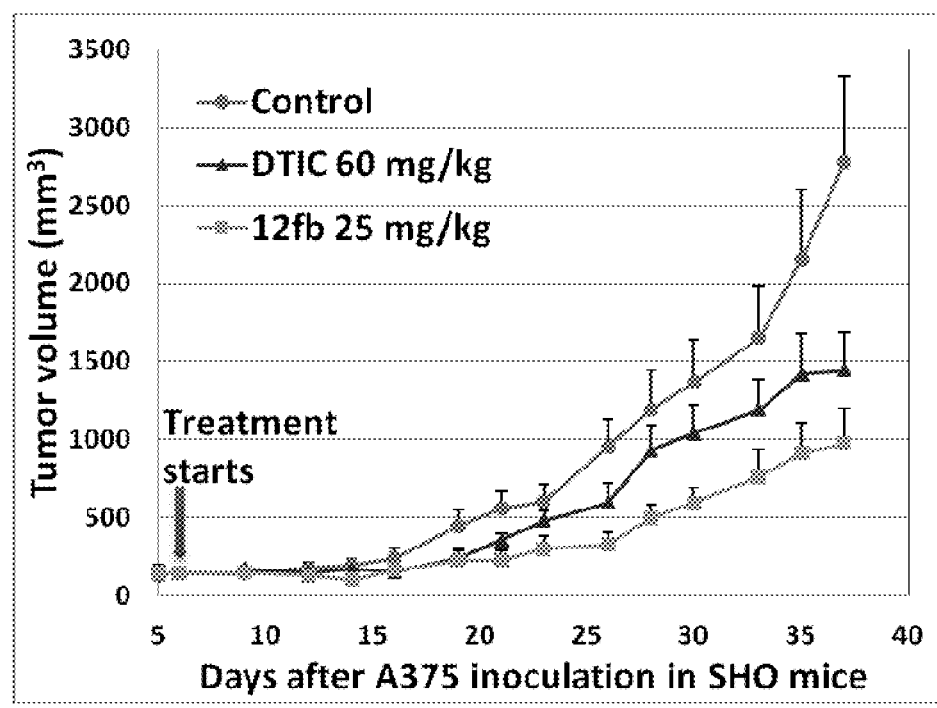

To evaluate efficacy of ABI analogs in vivo, we tested the antitumor activity of compound 12cb on mice melanoma B16-F1 xenograft. Against DTIC, the gold standard in malignant melanoma treatment, was used as a positive control (FIG. 19A). Twenty female C57/BL mice were divided into four groups: a vehicle control group, a DTIC (60 mg/kg) treatment group, a 12cb (10 mg/kg) treatment group, and a 12cb (30 mg/kg) treatment group. Each mouse was injected with 0.5 million B16-F1 melanoma cells subcutaneously. Seven days after tumor inoculation, treatment started with each compound injected intraperitoneally daily (FIG. 19). Tumor volume was significantly (p<0.05) reduced 47%, 51%, and 73% for 12cb (10 mg/kg), DTIC (60 mg/kg), and 12cb (30 mg/kg), respectively, after 14 days of treatment. No significant weight loss was observed in any of the treatment groups during the experiment.

Two dose levels of 12fb, 15 and 45 mg/kg, were chosen. DTIC at 60 mg/kg was used as a positive control. B16-F1 melanoma allograft model on C57BL/6 mice was first chosen for study. After 13 days of treatment (FIG. 19B), compound 12fb inhibited melanoma tumor growth (TGI value) by 32% at 15 mg/kg and 82% at 45 mg/kg. Student's t test p value of 12fb at 45 mg/kg compared with control was less than 0.001, indicating a significant difference. The t test p value of 12fb at 15 mg/kg compared with control was 0.08, suggesting that this dose was not effective. Comparing 12fb at 45 mg/kg with DTIC at 60 mg/kg, which had a TGI of 51%, the t test p value was about 0.001, suggesting that 12fb had substantially better activity than did DTIC. For the control and 12fb 15 mg/kg treatment groups, average body weight increased slightly throughout the experiment period.

To further confirm ABIs' in vivo activity, A375 human melanoma xenograft model on SHO mice was used, and 12fb at 25 mg/kg was tested. DTIC at 60 mg/kg was used as a positive control again. After 31 days of treatment (FIG. 19C), 12fb inhibited melanoma tumor growth (TGI value) by 69%, whereas DTIC inhibited growth by 52%. The t test p value of 12fb treatment versus control was less than 0.001, suggesting that 12fb significantly inhibited melanoma tumor growth at 25 mg/kg. The t test p value of 12fb treatment versus DTIC was less than 0.05, suggesting again that 12fb had better activity than did DTIC. Average body weight of all groups increased slightly throughout the experiment period. Physical activities for the mice also looked normal, suggesting that 25 mg/kg was a well tolerated dose for SHO mice.

Example 9

In Vitro and In Vivo Pharmacology of Compounds 17ya, 12fa, & 55

Materials and Methods

Cell Culture and Cytotoxicity Assay of Prostate Cancer.

All prostate cancer cell lines (LNCaP, PC-3, and DU145, PPC-1) were obtained from ATCC (American Type Culture Collection, Manassas, Va., USA). Human PC-3_TxR, was resistant to paclitaxel and used a MDR model compared with PC-3. Cell culture supplies were purchased from Cellgro Mediatech (Herndon, Va., USA). All cell lines were used to test the antiproliferative activity of compounds 17ya, 12fa, and 55 by sulforhodamine B (SRB) assay. All cancer cell lines were maintained in RPMI 1640 media with 2 mM glutamine and 10% fetal bovine serum (FBS).

In Vitro Microtubule Polymerization Assay.

Porcine brain tubulin (0.4 mg) (Cytoskeleton, Denver, Colo.) was mixed with 1 and 5 µM of the test compound or vehicle (DMSO) and incubated in 100 µL of buffer (80 mM PIPES, 2.0 mM $MgCl_2$, 0.5 mM EGTA, pH 6.9 and 1 mM GTP). The absorbance at 340 nm wavelength was monitored every min for 15 min (SYNERGY 4 Microplate Reader, Bio-Tek Instruments, Winooski, Vt.). The spectrophotometer was maintained at 37° C. for tubulin polymerization.

Metabolic Incubations.

Metabolic stability studies were conducted by incubating 0.5 µM of test compounds in a total reaction volume of 1 mL containing 1 mg/mL microsomal protein in reaction buffer [0.2 M of phosphate buffer solution (pH 7.4), 1.3 mM $NADP^+$, 3.3 mM glucose-6-phosphate, and 0.4 U/mL glucose-6-phosphate dehydrogenase] at 37° C. in a shaking water bath. The NADPH regenerating system (solution A and B) was obtained from BD Biosciences (Bedford, Mass.). For glucuronidation studies, 2 mM UDP-glucuronic acid (Sigma, St. Louis, Mo.) cofactor in deionized water was incubated with 8 mM $MgCl_2$, 25 μg of alamethicin (Sigma, St. Louis, Mo.) in deionized water, and NADPH regenerating solutions (BD Biosciences, Bedford, Mass.) as described previously. The total DMSO concentration in the reaction solution was approximately 0.5% (v/v). Aliquots (100 μL) from the reaction mixtures used to determine metabolic stability were sampled at 5, 10, 20, 30, 60, and 90 min. Acetonitrile (150 μL) containing 200 nM of the internal standard was added to quench the reaction and to precipitate the proteins. Samples were then centrifuged at 4,000 g for 30 min at RT, and the supernatant was analyzed directly by LC-MS/MS.

Analytical Method.

Sample solution (10 μL) was injected into an Agilent series HPLC system (Agilent 1100 Series Agilent 1100 Chemstation, Agilent Technology Co, Ltd). All analytes were separated on a narrow-bore C18 column (Alltech Alltima HP, 2.1×100 mm, 3 μm, Fisher, Fair Lawn, N.J.). Two gradient modes were used. For metabolic stability studies, gradient mode was used to achieve the separation of analytes using mixtures of mobile phase A [$ACN/H_2O$ (5%/95%, v/v) containing 0.1% formic acid] and mobile phase B [$ACN/H_2O$ (95%/5%, v/v) containing 0.1% formic acid] at a flow rate of 300 μL/min. Mobile phase A was used at 10% from 0 to 1 min followed by a linearly programmed gradient to 100% of mobile phase B within 4 min, 100% of mobile phase B was maintained for 0.5 min before a quick ramp to 10% mobile phase A. Mobile phase A was continued for another 10 min towards the end of analysis.

A triple-quadruple mass spectrometer, API Qtrap 4000™ (Applied Biosystems/MDS SCIEX, Concord, Ontario, Canada), operating with a TurboIonSpray source was used. The spraying needle voltage was set at 5 kV for positive mode. Curtain gas was set at 10; Gas 1 and gas 2 were set 50. Collision-Assisted-Dissociation (CAD) gas at medium and the source heater probe temperature at 500° C. Multiple reaction monitoring (MRM) mode, scanning m/z 378→210 (17ya), m/z 373→205 (12fa), m/z 410→242 (55) and m/z 309→171 (internal standard), was used to obtain the most sensitive signals. Data acquisition and quantitative processing were accomplished using Analyst software, Ver. 1.4.1 (Applied Biosystems).

Aqueous Solubility.

The solubility of drugs was determined by Multiscreen Solubility Filter Plate (Millipore Corporate, Billerica, Mass.) coupled with LC-MS/MS. Briefly, 198 μL of phosphate buffered saline (PBS) buffer (pH 7.4) was loaded into 96-well plate, and 2 μL of 10 mM test compounds (in DMSO) was dispensed and mixed with gentle shaking (200-300 rpm) for 1.5 hours at RT (N=3). The plate was centrifuged at 800 g for 10 min, and the filtrate was used to determine its concentration and solubility of test compound by LC-MS/MS as described previously.

Pharmacokinetic Study.

Male ICR mice (n=3 per group) 6 to 8 weeks of age were purchased from Harlan Inc., and used to examine the pharmacokinetics (PK) of 17ya, 12fa, and 55. All compounds (10 mg/kg) were dissolved in DMSO/PEG300 (1/9) and administered by a single intravenously (i.v.) injection (50 μL) into the tail vein. Blood samples were collected at 5, 15, and 30 min, 1, 1.5, 2, 3, 4, 8, 12, and 24 h after i.v. administration. Mice were given (p.o.) by oral gavage at 20 mg/kg (in Tween80/DMSO/$H_2O$, 2/2/6) of each test compound to evaluate their oral bioavailability. Blood samples were collected at 0.5, 1, 1.5, 2, 3, 4, 8, 12, and 24 h after p.o. administration.

Female Sprague-Dawley rats (n=3; 254±4 g) were purchased from Harlan Inc. (Indianapolis, Ind.). Rat thoracic jugular vein catheters were purchased from Braintree Scientific Inc. (Braintree, Mass.). On arrival at the animal facility, the animals were acclimated for 3 days in a temperature-controlled room (20-22° C.) with a 12 h light/dark cycle before any treatment. Compounds 17ya, 12fa, and 55 were administered i.v. into the thoracic jugular vein at a dose of 5 mg/kg (in DMSO/PEG300, 1/9). An equal volume of heparinized saline was injected to replace the removed blood, and blood samples (250 μL) were collected via the jugular vein catheter at 10, 20, 30 min, and 1, 2, 4, 8, 12, 24 h. Rats were given (p.o.) by oral gavage at 10 mg/kg (in Tween80/DMSO/$H_2O$, 2/2/6) of each test compound to evaluate their oral bioavailability. All blood samples (250 μL) after oral administration were collected via the jugular vein catheter at 30, 60, 90 min, 120 min, 150 min, 180 min, 210 min, 240 min, and 8, 12, 24 h. Heparinized syringes and vials were prepared prior to blood collection. Plasma samples were prepared by centrifuging the blood samples at 8,000 g for 5 min. All plasma samples were stored immediately at −80° C. until analyzed.

Analytes were extracted from 100 μL of plasma with 200 μL of acetonitrile containing 200 nM the internal standard. The samples were thoroughly mixed, centrifuged, and the organic extract was transferred to autosampler for LC-MS/MS analysis.

PC-3_TxR Xenograft Studies.

PC-3 TxR cells ($10 \times 10^7$ per mL) were prepared in RPMI1640 growth media containing 10% FBS, and mixed with Matrigel (BD Biosciences, San Jose, Calif.) at 1:1 ratio. Tumors were established by injecting 100 μL of the mixture ($5 \times 10^6$ cells per animal) subcutaneously (s.c.) into the flank of 6-8-week-old male athymic nude mice. Length and width of tumors were measured and the tumor volume ($mm^3$) was calculated by the formula, $\pi/6 \times L \times W^2$, where length (L) and width (W) were determined in mm. When the tumor volumes reached 300 $mm^3$, the animals bearing PC-3_TxR tumors were treated with vehicle [Tween80/DMSO/$H_2O$ (2/2/6)], or 17ya (10 mg/kg) orally. The dosing schedule was 3 times a week for four weeks.

Results

17ya and 55 Exhibit Broad Cytotoxicity in Cells, Including Multidrug-Resistant Cells.

The ability of 17ya and 55 to inhibit the growth of cancer cell lines was evaluated using SRB assay (Table 12). Both compounds inhibited the growth of several human cancer cell lines, including five prostate and one glioma cancer cell lines, with $IC_{50}$ values in the low nanomolar range. 17ya exhibited 1.7-4.3 fold higher potency than 55 in these cell lines. Paclitaxel-resistant PC-3 (PC-3/TxR) cell line that over-expresses P-glycoprotein (P-gp), was used to study the effect of drug resistance on 17ya and 55 and to compare against its parent, PC-3 cell line. The $IC_{50}$ values of docetaxel were 1.2±0.1 nM and 17.7±0.7 nM in PC-3 and PC-3/TxR cells, respectively. 17ya and 55 were both equipotent against parent PC-3 and PC-3/TxR, whereas paclitaxel and docetaxel exhibited relative resistance of 85- and 15-fold, respectively. These data indicate that both 17ya and 55 circumvent P-gp-mediated drug resistance.

TABLE 12

Cytotoxicity data of 17ya and 55.

Cytotoxicity [IC$_{50}$ values, mean ± SD nM]

| Cell line | Type | 17ya | 55 | Paclitaxel |
|---|---|---|---|---|
| PC-3 | Prostate | 5.2 ± 0.2 | 16 ± 1.5 | 0.6 ± 0.05 |
| PC-3/TxR | Prostate | 2.1 ± 0.1 (0.4) | 6.7 ± 0.5 (0.4) | 51 ± 2.3 (85) |
| LNCaP | Prostate | 12 ± 0.1 | 27 ± 0.6 | 1.7 ± 0.2 |
| Du-145 | Prostate | 17 ± 0.2 | 38 ± 0.6 | 5.1 ± 0.1 |
| PPC-1 | Prostate | 21 ± 0.1 | 36 ± 0.4 | 2.3 ± 0.8 |
| U87MG | Glioma | 10 ± 1.6 | 22 ± 3.0 | NR |

IC$_{50}$ values (mean ± SD) were determined after 96 h treatment (N = 3). Paclitaxel was used as a positive control. Data in parentheses indicated resistance factor when compared IC$_{50}$ values in PC-3 and PC-3/TxR. NR, Not Reported.

Figure 20:
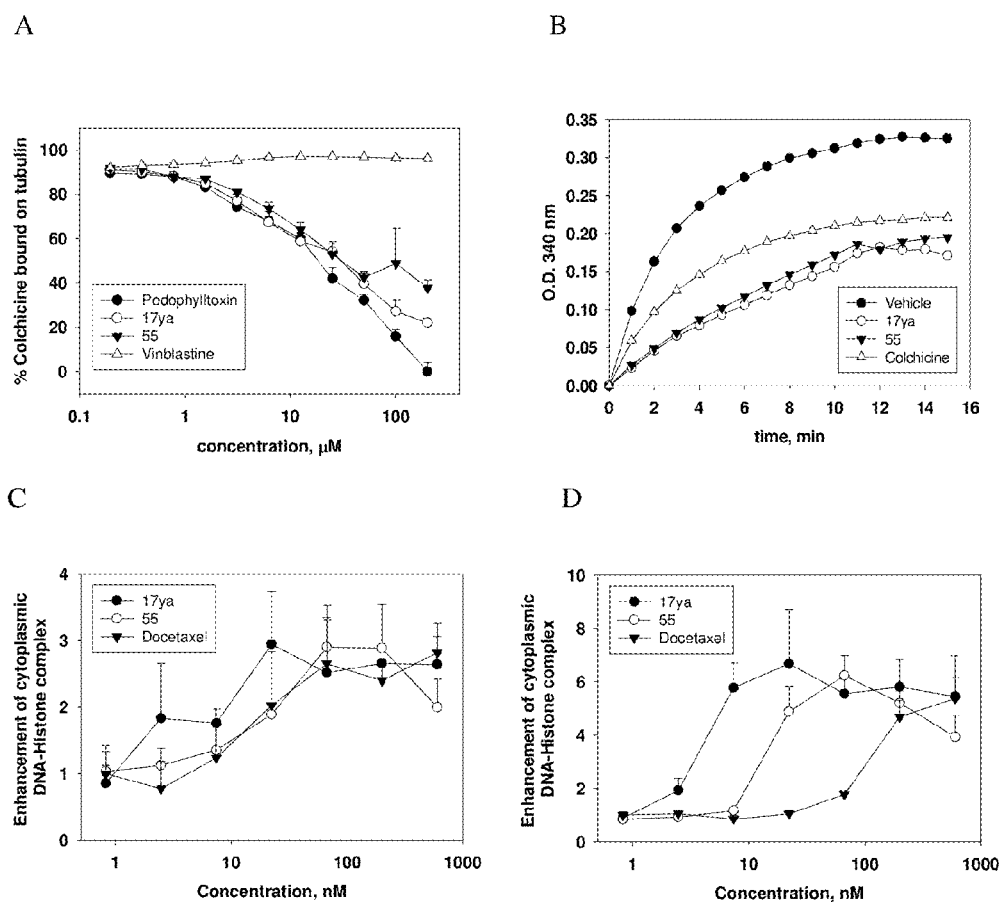
FIG. 20 depicts the effect of 17ya and 55 on tubulin polymerization. Compounds 17ya and 55 bind to colchicine-binding site on tubulin, and inhibit tubulin polymerization.

17ya and 55 Bind to Colchicine-Binding Site on Tubulin, Inhibit Tubulin Polymerization, and Induce Cell Apoptosis (FIG. 20).

A competitive mass binding assay was developed to study the interaction of small molecule inhibitors with tubulin. In this study, varying concentrations of 17ya or 55 were used to compete with colchicine-tubulin binding. Both compounds competed effectively with colchicine for tubulin binding (FIG. 20A); however, their competitive binding curves deviated substantially from zero at higher concentrations when compared to podophylltoxin, a known potent colchicine-site binding ligand. This suggests that both 17ya and 55 exhibited less affinity than podophylltoxin or they partially bind to the colchicine-binding site. Vinblastine, the negative control, did not inhibit the colchicine-tubulin binding, successfully demonstrating the specificity of this competitive mass binding assay Porcine brain tubulin (>97% pure) was incubated with 17ya or 55 (5 µM) to test their effect on tubulin polymerization (FIG. 20B). 17ya and 55 inhibited tubulin polymerization by 47% and 40% at 15 min, respectively. Colchicine at 5 µM was used as a positive control and inhibited tubulin polymerization by 32%. These data suggest that both 17ya and 55 have slightly greater inhibition of tubulin polymerization than colchicine. Therefore, the molecular mechanism of these compounds is binding to the colchicine-binding site, inhibiting tubulin polymerization, and inducing cytotoxicity.

PC-3 and PC-3/TxR cells were exposed to 0.8 to 600 nmol/L of 17ya, 55, or docetaxel for 24 h. The levels of DNA-histone complexes were used to represent cell apoptosis. Both 17ya and 55 were equally potent to induce cell apoptosis in PC-3 (FIG. 20C) and PC-3/TxR (FIG. 20D) in 24 h. Though, docetaxel was highly potent to induce apoptosis of PC-3 cells, it was weaker in PC-3/TxR cells due to over-expression of P-gp.

17ya and 55 Exhibited Favorable Drug-Like Properties.

Drug-like properties, such as metabolic stability, permeability, aqueous solubility, and drug-drug interactions, were examined for 17ya and 55 (Table 13A). 17ya exhibited greater metabolic stability, and aqueous solubility than 55. Both chemicals exhibited more than adequate permeability values, suggesting their potential to be orally used. In addition, both 17ya and 55 showed high IC$_{50}$ values in micromolar range on CYP enzyme inhibition assays, indicating that both compounds may avoid drug-drug interactions through main CYP liver enzymes. Overall, both compounds exhibited favorable drug-like properties.

TABLE 13A

Drug-like properties of compound 17ya and 55. Metabolic stability, permeability, solubility, and potential drug-drug interactions were evaluated. Each value represents the mean from duplicate studies.

| Measurment | Units | 17ya | 55 | positive controls (mean) |
|---|---|---|---|---|
| Metabolic stability | | | | |
| half-life in human liver microsomes | min | >60 | 28 | Verapamil (12) |
| Permeability | | | | |
| P$_{app(A-B)}$ in CaCO-2 assay | 10$^{-8}$ cm/s | 36 | 99 | Propranolol (19) |
| Aqueous solubility | µg/mL | >75 | 19 | 1 h (1.1) |
| Drug-drug interactions | | | | |
| IC$_{50}$ value in Cyp3A4 (substrate: Testosterone) | µM | 20 | 5.5 | Ketoconazole (0.02) |
| IC$_{50}$ value in Cyp2D6 (substrate: Dextromethorphan) | µM | >50 | 34 | Quinindine (0.1) |
| IC$_{50}$ value in Cyp2C19 (substrate: (S)-mephenytoin) | µM | 6.6 | 5.3 | Ticlopidine (0.37) |
| IC$_{50}$ value in Cyp2C9 (substrate: Diclofenac) | µM | 17 | 4.9 | Sulfaphenazole (0.5) |
| IC$_{50}$ value in Cyp1A2 (substrate: Phenacetin) | µM | 9.2 | 8.1 | Furafylline (2.2) |

TABLE 13B

Summary of drug-like and pharmacokinetic properties of 17ya, 12fa, 55, and 1 h.

| | | 17ya | 12fa |
|---|---|---|---|
| Molecular weight | | 377 | 372 |
| $IC_{50}$ in PC3 (nM) | nM | 10 | 35 |
| Half-life in HLM (Phase I) | min | ~80 | 44 |
| Half-life in HLM (Phase I + II) | min | ~90 | NA |
| Solubility | µg/mL | >75 | 12 |
| RatPK_IV5mgk_Cl | mL/min/kg | | 16 |
| RatPK_IV5mgk_V | L/kg | | 1.9 |
| RatPK_PO10mgk_Cmax | ng/mL | | 1109 |
| RatPK_PO10mgk_AUC | min*µg/mL | | 218 |
| RatPK_Bioavailability | % F | | 35 |
| MousePK_IV10mgk_Cl | mL/min/kg | | 61 |
| MousePK_IV10mgk_V | L/kg | | 4 |
| MousePK_PO20mgk_Cmax | ng/mL | | 2592 |
| MousePK_PO20mgk_AUC | min * µg /mL | | 201 |
| MousePK_Bioavailability | % F | | 62 |

| | | 55 | 1h |
|---|---|---|---|
| Molecular weight | | 409 | 355 |
| $IC_{50}$ in PC3 (nM) | nM | 28 | 21 |
| Half-life in HLM (Phase I) | min | 30 | 17 |
| Half-life in HLM (Phase I + II) | min | 43 | 17 |
| Solubility | µg/mL | 19 | 1 |
| RatPK_IV5mgk_Cl | mL/min/kg | | 7.7 (2.5mpk) |
| RatPK_IV5mgk_V | L/kg | | 4.9 (2.5mpk) |
| RatPK_PO10mgk_Cmax | ng/mL | | 212 |
| RatPK_PO10mgk_AUC | min*µg/mL | | 37 |
| RatPK_Bioavailability | % F | | 3.3 |
| MousePK_IV10mgk_Cl | mL/min/kg | | 130 |
| MousePK_IV10mgk_V | L/kg | | 4.9 |
| MousePK_PO20mgk_Cmax | ng/mL | | NA |
| MousePK_PO20mgk_AUC | min * µg /mL | | NA |
| MousePK_Bioavailability | % F | | NA |

As shown in Table 13B, 17ya had a half-life of 80 min by phase I reaction, suggesting that 17ya was stable in phase I metabolic processes. The half-life (90 min) in the presence of UDP-glucuronic acid was similar to that observed in its absence. These data suggested that 17ya is stable in human liver microsomes, and it was hoped that low clearance and long half-life will be obtained in human. On the other hand, 55 exhibited 30 and 43 min as half lives when it was in the presence and absence of UDP-glucuronic acid, respectively. Compound 12fa shows the half-life with 44 in phase I. These data suggested that all three compounds showed acceptable stability in human liver microsomes, and 17ya is more stable than 12fa and 55. When investigating their metabolism, it was found that 12fa and 55 exhibited higher levels of ketone-reduction (data not shown), suggesting that 12fa and 55 are more labile than 17ya.

Compound 17ya Exhibited Great Aqueous Solubility, 12fa and 55 Showed Acceptable Solubility.

Compound 17ya contained an imidazole ring, and this ring improved aqueous solubility, resulting in >75 μg/mL aqueous solubility (Table 13A). Compounds 12fa and 55 exhibited less aqueous solubility, and exhibited 12 and 19 μg/mL, respectively. Overall, 17ya demonstrated a great aqueous solubility, and 12fa and 55 showed acceptable aqueous solubility, and much improved over 1 h. The greater solubility of 12fa translated into much improved oral bioavailability compared to 1 h (35% vs. 3.3% in rat). Similarly for 17ya and 55, aqueous solubility correlated with much improved oral bioavailability as discussed infra (Table 14). Pharmacokinetic Studies of 17ya and 55 in Mice, Rats and Dogs.

The pharmacokinetic parameters of 17ya and 55 given in a single (i.v. or p.o.) dose in ICR mice, Sprague-Dawley rats, and beagle dogs are summarized in Table 14. 17ya exhibited low clearance in mice and rats, suggesting that 17ya exhibited metabolic stability, and minimal first-pass metabolism in these species. In addition, 17ya had moderate volume of distribution in mice and rats, indicating that it may properly distribute into tissues, including tumors. Unlike in mice and rats, surprisingly, the total clearance of 17ya in dogs was high. Two abundant metabolites in dog plasma, a hydroxylated metabolite and an unknown metabolite with +34 m/z of the parent (data not shown), were consistent with those found in dog liver microsomes. In summary, higher clearance and lower oral exposure was obtained for 17ya compared to 55 in dogs, but not in mice and rats. In addition, 17ya exhibited abundant metabolites only in dog liver microsomes, but not in mouse, rat or human liver microsomes (data not shown). 17ya showed acceptable 21%, 36%, and 50% oral bioavailability in rats, mice, and dogs, respectively. Meanwhile, 55 had low clearance in rats, and moderate clearance in mice and dogs. Similar to 17ya, 55 exhibited moderate volume of distribution in these species. 55 had constant oral bioavailability rates among three species (24%-36%). These properties indicate that both 17ya and 55 are potential orally available tubulin inhibitors.

TABLE 14

Pharmacokinetic studies of compounds 17ya and 55 in mice, rats, and dogs.

| | 17ya | | 55 | |
|---|---|---|---|---|
| | IV | PO | IV | PO |
| Mouse PK (N = 3) | | | | |
| Dose, mg/kg | 10 | 20 | 10 | 20 |
| Clearance, mL/min/kg | 19 | NR | 40 | NR |
| Vss, L/kg | 2.9 | NR | 1.3 | NR |
| $t_{1/2}$, min | 101 | 339 | 46 | 126 |
| AUC, min*μg/mL | 540 | 384 | 249 | 171 |
| $C_{max}$, ng/mL | 4800 | 1560 | 7739 | 1253 |
| F, % | | 36% | | 34% |
| Rat PK (n = 3) | | | | |
| Dose, mg/kg | 5 | 10 | 5 | 10 |
| Clearance, mL/min/kg | 9.5 ± 2.3 | NR | 10 ± 1.4 | NR |
| Vss, L/kg | 1.8 ± 0.2 | NR | 1.0 ± 0.1 | NR |
| $t_{1/2}$, min | 139 ± 24 | 206 ± 12 | 73 ± 5.0 | 350 ± 214 |
| AUC, min*μg/mL | 553 ± 143 | 233 ± 134 | 509 ± 73 | 246 ± 163 |

TABLE 14-continued

Pharmacokinetic studies of compounds 17ya and 55 in mice, rats, and dogs.

| | 17ya | | 55 | |
|---|---|---|---|---|
| | IV | PO | IV | PO |
| $C_{max}$, ng/mL | 3672 ± 519 | 999 ± 445 | 4609 ± 55 | 757 ± 520 |
| F, % | | 21% | | 24% |
| Dog PK (N = 4) | | | | |
| Dose, mg/kg | 2 | 5 | 2 | 5 |
| Clearance, mL/min/kg | 109 ± 29 | NR | 15 ± 3.2 | NR |
| Vss, L/kg | 94 ± 95 | NR | 0.9 ± 0.2 | NR |
| $t_{1/2}$, min | 2757 ± 1573 | 1695 ± 439 | 82 ± 15 | 191 ± 8.0 |
| AUC, min*μg/mL | 18.5 ± 4.7 | 23.1 ± 11.3 | 141 ± 30 | 128 ± 154 |
| $C_{max}$, ng/mL | 400 ± 118 | 210 ± 133 | 2552 ± 576 | 862 ± 1010 |
| F, % | | 50% | | 36% |

17ya and 55 Inhibit Paclitaxel Resistant Prostate (PC-3/TxR) Xenografts Growth.

Figure 21:
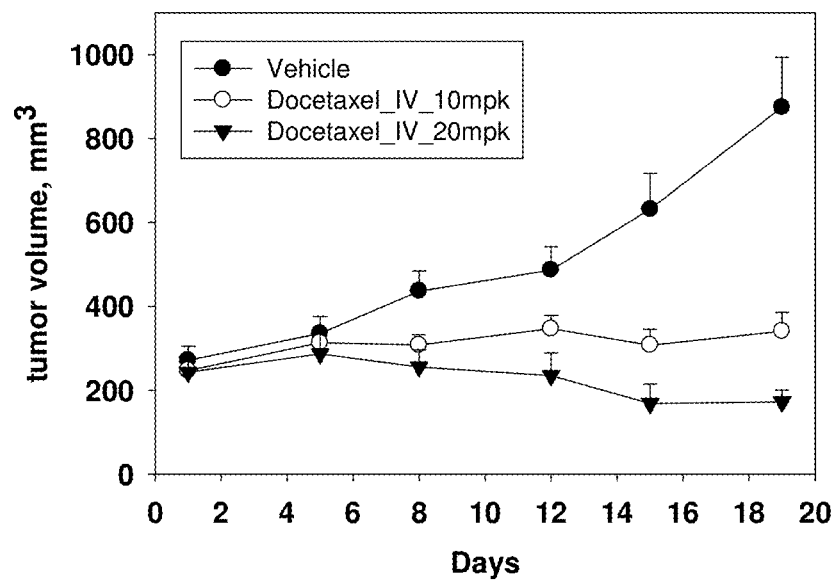
FIG. 21 depicts in vivo anticancer efficacy.
Figure 21:
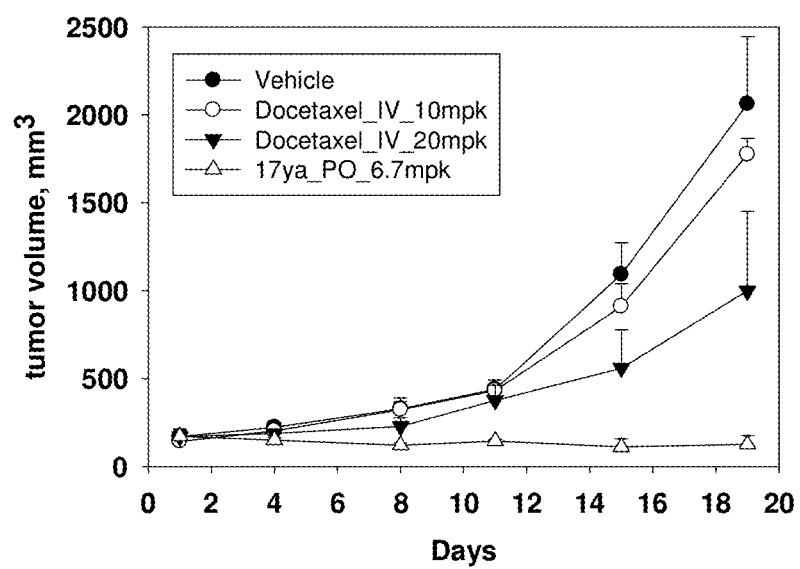
Figure 21:
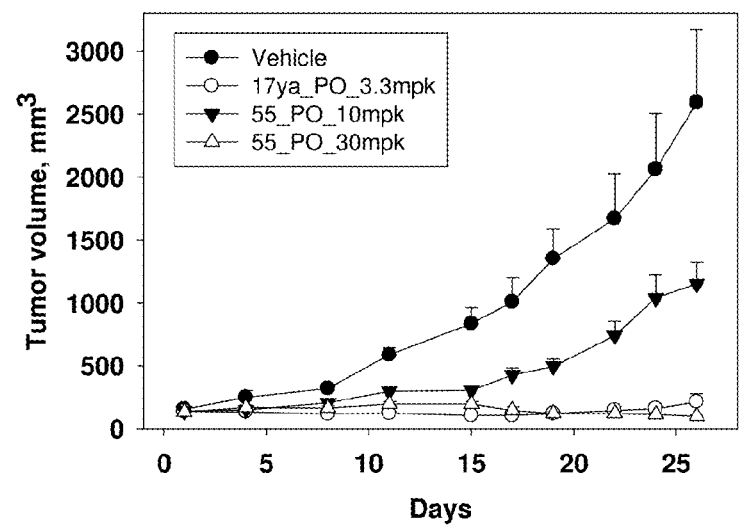
Figure 21:
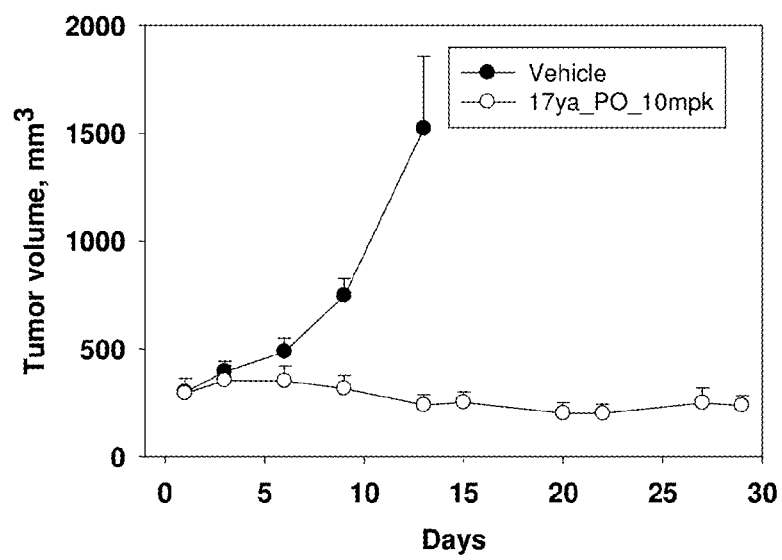

PC-3 (FIG. 21A) and paclitaxel-resistant prostate cancer (PC-3/TxR) (FIG. 21B) cells were inoculated in nude mice and the tumor volumes were allowed to reach about 150-300 mm$^3$. Docetaxel (10 or 20 mg/kg), which is in clinic for prostate cancer, was used to evaluate its effectiveness in models of P-gp-mediated drug resistance in vivo. PC-3/TxR tumor was found to be fast-growing and the volume reached 1500-2500 mm$^3$ at the termination of the study. Though 10 and 20 mg/kg intravenously administered docetaxel exhibited a dose response in both models (FIGS. 21A and 21B), the tumor growth inhibition (TGI) effect decreased from 84% TGI in PC-3 tumors to 14% TGI in PC-3/TxR tumors when intravenously dosed at 10 mg/kg (Table 15). In addition, at the higher dose (20 mg/kg), docetaxel elicited partial regression (>100% TGI) of PC-3 tumors, but barely 56% TGI in PC-3/TxR tumors. The effectiveness of docetaxel in PC-3/TxR tumors was dramatically decreased when compared to that in PC-3 tumors, suggesting that the efficacy was impaired by P-gp-mediated drug resistance, and these results are in very good agreement with our in vitro cytotoxicity or apoptosis data. In contrast to the lack of efficacy of docetaxel in PC-3/TxR tumors, orally administered 17ya (6.7 mg/kg) demonstrated more than 100% TGI without an effect on their body weights (FIG. 21B and Table 15). In addition, 2 out of 4 nude mice bearing PC-3/TxR tumors were tumor free on day 19 (data not shown).

Figure 3:
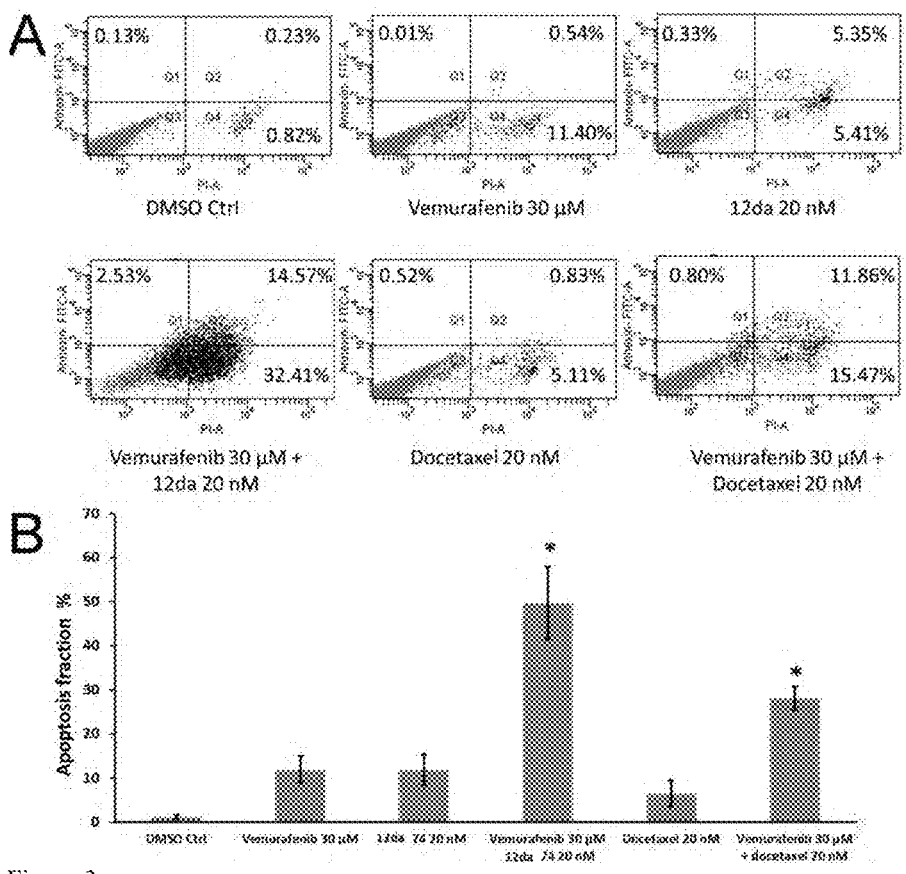
FIG. 3 depicts that combinations of a tubulin inhibitor with vemurafenib synergistically increased proportion of cell apoptosis or death in resistant A375RF21 cells. A, representative quadrant diagrams illustrated the cell distribution in Q1 (early apoptosis), Q2 (apoptosis), Q3 (live), and Q4 (dead). Cell clusters with high-SSC (side scatter)/low-FSC (forward scatter) cyto-morphological profiles were colored in black. There was no back-gating difference between grey and black populations. B, apoptosis fraction was calculated by adding distribution percentage in Q1, Q2 and Q4 together. Drug combination groups induced significantly higher (*P<0.05) portion of apoptosis compared with simple sum of apoptosis fraction in two single agent treatment groups.

The PC-3/TxR xenograft model was further utilized to evaluate efficacies of 17ya (in other dosing schedules) and 55. The maximal tolerated dose (body weight loss >20%) of 17ya was found to be 10 mg/kg, when orally dosed once daily for four days; or at 3.3 mg/kg twice a day (b.i.d.) for five days (data not shown). As shown in FIG. 21C, 3.3 mg/kg of 17ya was dosed b.i.d. for first consecutive four days in the first week, and the schedule was then changed to once daily between weeks 2 and 4. The result shows that partial regression was obtained during day 4-19, and the TGI was 97%, and one of the seven mice was tumor free on day 26. Higher dose (10 mg/kg) with lower dosing frequency (q2d) of 17ya (FIG. 21D) elicited partial regression during days 13 to 29. These data suggest that regimens with optimized doses and dosing schedules will facilitate 17ya to successfully inhibit PC-3/TxR tumors. 55, was orally administered to nude mice with 10 or 30 mg/kg b.i.d., and five times a week between weeks 1 and 4. As shown in FIG.

21C, the inhibition profiles exhibit a dose-response in PC-3/TxR tumor. The TGI value was 59% for the treatment group with a lower dose (10 mg/kg). Moreover, the higher dose (30 mg/kg) started to show partial regression (>100% TGI) from day 19 to the termination of the study (day 26). Some mice in the vehicle group lost body weight at the endpoint, in part, due to cancer cachexia. On the contrary, mice treated with 17ya (3.3 mg/kg) or 55 (30 mg/kg) were gaining weight (Table 15), suggesting that these optimized doses of 17ya or 55 may be well-tolerated and were preventive of cancer cachexia.

Example 10

Figure 22:
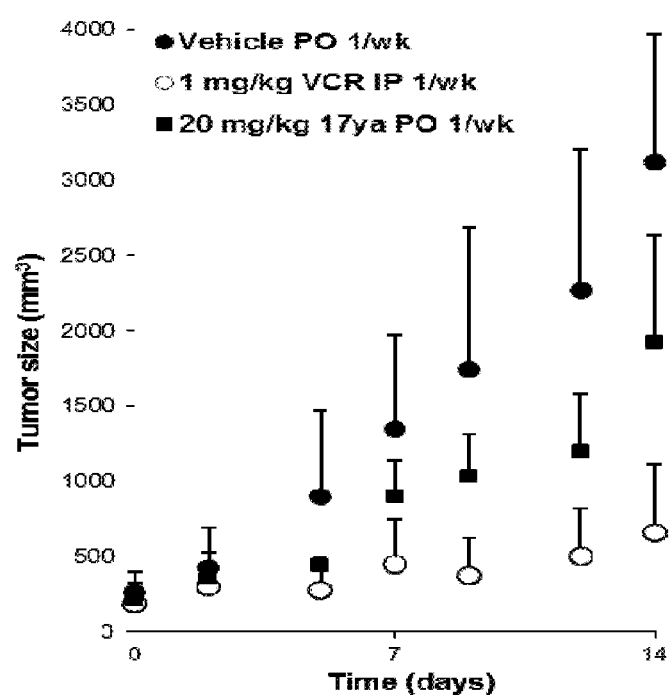
FIG. 22 depicts the in vivo anti-cancer efficacy of 17ya in HL60 leukemia cell xenografts.

In Vivo Efficacy in Leukemia (HL60) Xenograft (FIG. 22)

HL60 cells ($10 \times 10^7$ per mL) were prepared in RPMI1640 growth media containing 10% FBS, and mixed with Matrigel (BD Biosciences, San Jose, Calif.) at 1:1 ratio. Tumors were established by injecting 100 μL of the mixture ($5 \times 10^6$ cells per animal) subcutaneously into the flank of 6-8-week-old male athymic nude mice. Length and width of tumors

TABLE 15

Antitumor activity of compounds 17ya and 55 versus concomitantly evaluated docetaxel in vivo.

| | Dosing Schedule | End point | Number End/Start | Body weight (g) Start | Body weight (g) End | Tumor size (mm²) Start | Tumor size (mm²) End | TGI (%) |
|---|---|---|---|---|---|---|---|---|
| PC-3 xenograft | | | | | | | | |
| Vehicle_IV | day 1 and 9 | day 19 | 6/6 | 30 ± 2 | 32 ± 4 | 271 ± 63 | 878 ± 292 | — |
| Docetaxel_IV_10mpk | day 1 and 9 | day 19 | 5/5 | 29 ± 2 | 24 ± 2 | 247 ± 49 | 341 ± 101 | 84 |
| Docetaxel_IV_20mpk | day 1 and 9 | day 19 | 6/5 | 28 ± 3 | 24 ± 3 | 243 ± 58 | 172 ± 82 | >100 |
| PC-3/TxR xenograft | | | | | | | | |
| Vehicle_IV | day 1 and 9 | day 19 | 5/6 | 33 ± 1 | 25 ± 5 | 171 ± 57 | 2061 ± 858 | — |
| Docetaxel_IV_10mpk | day 1 and 9 | day 19 | 4/4 | 31 ± 2 | 25 ± 2 | 143 ± 20 | 1774 ± 183 | 14 |
| Docetaxel_IV_20mpk | day 1 and 9 | day 19 | 4/4 | 30 ± 1 | 25 ± 4 | 170 ± 80 | 999 ± 905 | 56 |
| 17ya_PO_6.7mpk | qd × 5/w | day 19 | 4/4 | 33 ± 3 | 34 ± 3 | 172 ± 69 | 126 ± 100 | >100 |
| Vehicle_PO | b.i.d × 5/w | day 26 | 6/7 | 30 ± 2 | 25 ± 2 | 156 ± 30 | 2591 ± 1423 | — |
| 55_PO_10mpk | b.i.d × 5/w | day 26 | 7/7 | 29 ± 2 | 26 ± 3 | 143 ± 44 | 1152 ± 433 | 59 |
| 55_PO_30mpk | b.i.d × 5/w | day 26 | 7/7 | 29 ± 3 | 30 ± 2 | 134 ± 34 | 101 ± 19 | >100 |
| 17ya_PO_3.3mpk[a] | qd × 5/w | day 26 | 7/7 | 29 ± 2 | 30 ± 2 | 139 ± 44 | 214 ± 172 | 97 |
| Vehicle_PO | q2d × 3/w | day 29 | 6/5 | 24 ± 2 | 21 ± 1 | 299 ± 40 | 1521 ± 680 | — |
| 17ya_PO_10mpk | q2d × 3/w | day 29 | 5/5 | 24 ± 2 | 26 ± 2 | 294 ± 156 | 237 ± 103 | >100 |

Dosing schedule: qd × 5/w = one administration given on five consecutive days per week; b.i.d. × 5/w = two administrations given on five consecutive days per week; or q2d × 3/w = every other day administration or three times a week.
[a]Dose schedule was two administrations given on four consecutive days of the first week, and dose schedule was changed (because of toxicity) to one administration given on five consecutive days per week for the second to fourth week.

Brain Penetration of 17ya and 55 in Nude Mice.

Whole brain concentrations in nude mice at 1 h and 4 h after oral administration of 20 mg/kg 17ya or 55 were determined (Table 16). The ratios of brain to plasma concentrations were determined and compared to docetaxel in the nude mice. 55 exhibited greater brain penetration than 17ya and docetaxel. 17ya only exhibited slightly greater brain/plasma concentration ratios than docetaxel at both 1 and 4 h. The brain concentrations of 55 reached 14 to 19% of plasma concentrations at 1 h and 4 h, respectively, showing a 3.2-fold higher brain/plasma ratio at both 1 h and 4 h compared to docetaxel. These data suggest that 55 exhibited potentially favorable properties to treat glioma, since it has greater brain penetration and high potency (22 nM, Table 12) in glioma cells.

were measured and the tumor volume (mm³) was calculated by the formula, $\pi/6 \times L \times W^2$, where length (L) and width (W) were determined in mm. When the tumor volumes reached 200 mm³ approximately, the animals bearing HL60 tumors were treated with vehicle [Tween80/DMSO/$H_2O$ (2/2/6)], or 17ya (20 mg/kg) orally. The dosing schedule was once a week for two weeks. Vincristine (1 mg/mL) was administrated via intraperitoneal injection once a week.

Results

Human promyelocytic leukemia cells, HL60 cells were inoculated in nude mice and the tumor volumes were allowed to reach about 200 mm³. Vincristine (1 mg/kg), which is in clinic for hematological cancers including leukemia, was used to evaluate the response of this in vivo model against a positive control drug. The tumor volumes

TABLE 16

Brain-Blood Barrier (BBB) studies of compounds 17ya and 55. Brain and plasma concentrations were determined in nude mice at 1 and 4 h after administration of docetaxel (IP, 10 mpk), 17ya (PO, 20 mpk), and 55 (PO, 20 mpk). Each value represents the mean ± SD from 3 nude mice.

| | Docetaxel | | 17ya | | 55 | |
|---|---|---|---|---|---|---|
| Measurement | 1 hr | 4 hr | 1 hr | 4 hr | 1 hr | 4 hr |
| Brain (ng/mL) | 33 ± 14 | 20 ± 9 | 124 ± 108 | 49 ± 32 | 180 ± 44 | 73 ± 18 |
| Plasma (ng/mL) | 768 ± 92 | 345 ± 94 | 2058 ± 1252 | 570 ± 438 | 1669 ± 867 | 380 ± 32 |
| Brain/plasma (%) | 4.4 ± 2.0 | 6.0 ± 2.9 | 5.4 ± 1.9 | 8.9 ± 1.7 | 14 ± 7.9 | 19 ± 3.1 |

(mm³) were plotted against time and are the means±SD from four to five animals. HL60 tumor was found to be fast-growing and the volume reached 2000-3000 mm³ within two weeks. Though 1 mg/kg intraperitoneal injection of vincristine exhibited very potent tumor growth inhibitory effect (FIG. 22) and the tumor growth inhibition (TGI) was 84%. Orally administered 17ya (20 mg/kg) showed 40% tumor growth inhibition. The size of HL60 tumors was maintained up to 5 days after 17ya treatment without dramatic increase but during the next 2 days tumor sizes increased significantly (60-100%). It suggests that more a frequent dosing schedule could enhance the tumor growth inhibitory effect of 17ya.

Example 11

Figure 27:
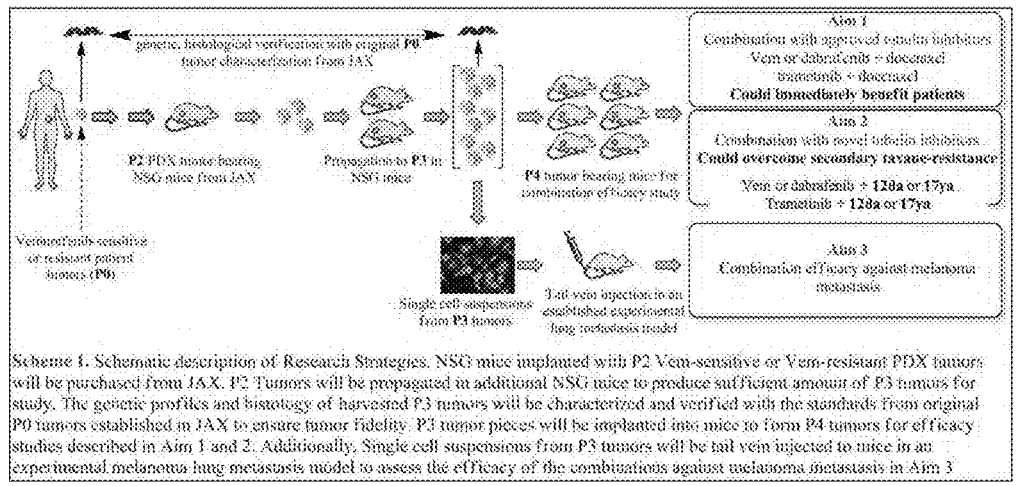
FIG. 27 depicts a schematic description of research strategies. NSG mice implanted with P2 vemurafenib-sensitive or vemurafenib-resistant PDX tumors are purchased from JAX. P2 tumors are propagated in additional NSG mice to produce a sufficient amount of P3 tumors for study. The genetic profiles and histology of harvested P3 tumors are characterized and verified with the standards from original P0 tumors established in JAX to ensure tumor fidelity. P3 tumor pieces are implanted into mice to form P4 tumors for efficacy studies described in Aim 1 and 2 (Example 11). Additionally, single cell suspensions from P3 tumors are tail vein injected to mice in an experimental melanoma lung metastasis model to assess the efficacy of the combinations against melanoma metastasis in Aim 3.

The Combination of a BRAFi and a Tubulin Inhibitor Targeting Alternative Pathways can Delay or Prevent the Development of Vemurafenib-Resistance The therapeutically specific aims of this study are summarized in FIG. 27.
Combination of Docetaxel (an Approved Tubulin Inhibitor) with a BRAFi (Vemurafenib or Dabrafenib) or MEKi (Trametinib) can Suppress Acquired Vemurafenib-Resistance in Melanoma Patient Derived Xenografts (PDX, or "Xenopatient") Tumor Models.

The usefulness of any new treatment strategy ultimately rests on its ability to demonstrate sustained clinical efficacy. Melanoma is well-known to be a heterogeneous tumor displaying a high phenotypic and functional plasticity in response to microenvironment or epigenetic factors. In fact, recent reports have revealed that vemurafenib-resistant tumors can develop multiple resistant mechanisms within one patient or even within the same tumor biopsy taken from a single metastatic site. Unlike melanoma tumors in patients, tumors grown from established cell lines such as A375 have two major limitations: (a) they have lost their original tumor heterogeneity which can significantly affect drug efficacy; and (b) they often develop irreversible genetic changes due to their adaptation to the cell culture conditions that are different from the natural tumor microenvironment. Extensive studies have demonstrated that early passage PDX tumors (≤5 passages) maintain the genetic fidelity to patient tumors, preserve the original tumor morphology and heterogeneity, and have the pattern of response to therapy resembling those observed in the clinic. Therefore, it is imperative to confirm that the observed strong synergy and efficacy in A375RF21 tumors (see FIGS. 6 and 7), remains effective in PDX tumors. It is also critical to assess the potential development of drug resistance using PDX tumors instead of tumors grown from established cell lines for more direct bench-to-bedside translations.

Because approved tubulin inhibitors exist, to facilitate the development of this innovative combination to benefit patients quickly, evaluation of combination efficacy of docetaxel with the three currently approved BRAFi/MEKi is first established to determine the optimal combination. Furthermore, a new combination strategy has higher impact if it is used to treat both groups of melanoma patients with BRAF$^{V600E}$ mutations. The first group is BRAFi-naïve patients who have not taken BRAFi and/or MEKi. Such patients benefit most if the combination can significantly delay or even prevent the potential development of BRAFi-resistance. The second group is BRAFi-resistant patients who have been treated with BRAFi and/or MEKi in clinical reality. These patients benefit if the combination can effectively overcome acquired drug resistance.

The in vivo combination efficacy and potential development of drug resistance in vemurafenib-sensitive PDX tumors is determined, mimicking clinical use (e.g. upfront use of combination treatment before vemurafenib-resistance occurs) to treat BRAFi-naïve melanoma patients. Because the best strategy to overcome acquired drug resistance is to significantly delay or even prevent its development.
Establishment of Early Stage PDX Tumors Based on PDX Tumor Bearing Mice.

Recent efforts in the field have standardized some protocols for establishing successful PDX models. Various PDX models are now available from commercial sources. Purchased NSG mice (typically 1-2 mice) implanted with small passage two (P2) PDX tumors, are used. The tumor is grown to about 1,500 mm³ and is propagated to up to five new NSG mice to provide sufficient P3 tumors. The genetic profile and histology of five randomly picked P3 tumors are characterized and verified with data from original P0 tumors to ensure overall genetic and histological fidelity, before tumor pieces are implanted into a large number of mice for subsequent studies (FIG. 27). Histological analysis is performed to ensure the unambiguity in these verification analyses.

a. Determine the In Vivo Efficacy in Vemurafenib-Sensitive PDX Tumors Treated with the Combination of Docetaxel with Vemurafenib, Dabrafenib, or Trametinib.

The three currently approved BRAFi or MEKi are tested to rank their combination efficacy for future prioritization clinically. While NSG mice are the mice of choice for tumor propagation, they have fur and are more expensive (2~3×) than nude mice. Numerous studies have demonstrated that terminal experimental results using nude mice are equally good compared with using the more expensive and difficult NSG mice in PDX studies. Therefore, nude mice are used in the terminal efficacy studies. The standard combination of dabrafenib+trametinib is included as a reference combination treatment. In addition, all drugs used in this step are approved drugs and their pharmacokinetic properties are known. Thus established doses and administration routes are followed for this study. Specifically, vemurafenib (45 mg/kg), dabrafenib (30 mg/kg), and trametinib (0.3 mg/kg) are given to mice by oral gavage. Docetaxel (10 mg/kg) is intravenously injected through tail vein because it is not orally available.

Seven mice per group are used to assess whether sustained tumor regressions are achieved in three independent vemurafenib-sensitive PDX tumors. Statistical analyses and sample size calculations are performed to ensure statistical significance in these important animal studies.

Briefly, 6-week-old male athymic nude mice are purchased from Charles River. P3 vemurafenib-sensitive PDX melanoma tumors are minced into small pieces (~3 mm³) before they are surgically implanted subcutaneously into the flanks of 63 anesthetized nude mice, following established procedures reported in the literature. When the tumors reach approximately 100-200 mm³ after 2~3 weeks of implantation, mice are randomized into nine groups (n=7), minimizing weight and tumor size differences: a negative control group with vehicle only (Group 1); four single-agent treatment groups (Groups 2 to 5) with continuous daily treatment orally using vemurafenib, dabrafenib, trametinib, or docetaxel (i.v.); and four combination treatment groups (Groups 6-9) with continuous daily treatment using dabrafenib+trametinib (reference combination), docetaxel+vemurafenib, docetaxel+dabrafenib, and docetaxel+trametinib, using the same dose and route of administration as single agents.

Due to the PDX nature, it is impractical to attach any in vivo luminescence probes for tumor monitoring. Thus, tumors are measured every three days with a caliper, and their volumes are calculated using the formula: (width$^2$× length)/2. Based on earlier reports, vemurafenib-sensitive tumors clearly developed acquired resistance to single-agent vemurafenib treatment in mice within 60 days. Thus, tumors are monitored for up to 90 days or until the tumor has completely regressed. Potential development of drug resistance is closely monitored by tumor growth kinetics. In addition, serial tumor biopsies from each tumor are taken bi-weekly with a fine needle following reported procedures. Levels of BRAF and pERK/tERK in these biopsies are determined by western blots to monitor the potential development of drug resistance to BRAFi and MEKi. Mice weight, activities, and appearance are closely monitored for potential toxicity.

At the end of experiments, terminal blood samples (0.8~1 mL/mouse) are collected by cardiac puncture for comprehensive clinical pathology analyses offered by Charles River Laboratories. All animals are sacrificed by $CO_2$ inhalation followed by cervical dislocation immediately after the blood collection and the main organs (brain, heart, lung, liver, spleen, kidney) of each mouse are collected and stored separately in 10% buffered formalin phosphate solution. These organs are carefully examined and analyzed for potential drug toxicity (e.g. hepatic toxicity) and signs of metastasis. Tumors are carefully harvested, weighed, and processed to determine drug effects on key indicators of cell proliferation, anti-angiogenesis, and apoptosis as well as fixed and processed for histopathological examinations. The above experiment is repeated using two additional vemurafenib-sensitive PDX tumor models to ensure the efficacy is not associated with a particular PDX tumor model, thus the total mice used in this step is estimated up to 63×3=189.

b. Determine the In Vivo Efficacy in Vemurafenib-Resistant PDX Tumors Treated with the Combination of Docetaxel with Vemurafenib, Dabrafenib, or Trametinib.

The ideal strategy to overcome acquired vemurafenib-resistance is the upfront use with very effective therapies to prevent its development. Unfortunately, this is not realistic with existing therapy and most patients quickly develop vemurafenib-resistance. Stuart et al recently suggested that intermittent high dosing schedules of single-agent vemurafenib may attenuate the development of drug resistance compared with continuous dosing schedules. However, the psychological impact to patients and the long-term clinical efficacy of this "drug holidays" strategy remain to be seen. Because resistant melanoma tumors often develop addiction to the activated MEK-ERK pathway, a suitable combination of a tubulin inhibitor with a BRAFi/MEKi is still very effective in suppressing tumor growth while the use of single agent may not be sufficient (FIGS. 6 and 7). Therefore, it is important to confirm that the combination of docetaxel with a BRAFi/MEKi induces substantial tumor regressions for vemurafenib-resistant tumors. Such results may translate to prolonged patient survival even when tumors become vemurafenib-resistant.

Similar to the experiment procedures described above, after establishing early stage PDX tumors based on vemurafenib-resistant PDX tumor bearing mice, 63 mice divided into nine groups (one vehicle only group, four single-agent treatment groups, and four combination treatment groups), are used to determine whether the combination of docetaxel with an approved BRAFi or MEKi drug is effective in a vemurafenib-resistant PDX model. Tumor sizes, serial tumor biopsies, terminal blood samples, and major organs are measured or collected to assess efficacy and potential toxicities, similar to described in the previous section. The combination testing is repeated in two additional vemurafenib-resistant PDX tumor models; therefore, 63×3=189 mice are used in this step.

Even though it is expected that these vemurafenib-resistant PDX tumors will be resistant to single agent BRAFi/MEKi or the combination of dabrafefnib+trametinib, as demonstrated in clinical trials and in the results presented above with A375RF21 xenograft models, it is believed that these are valuable references to objectively assess the potential efficacy of the combinations containing docetaxel. Similar to the experiments with vemurafenib-sensitive PDX models, tumor sizes, potential acute toxicity, clinical pathology, and levels of pERK/ERK in tumor biopsies are determined in order to rank the efficacy of these combinations.

Determine Potential Toxicity and Focused Western Blot Analysis to Evaluate Treatment Efficacy and to Identify Potential Biomarkers for Clinical Disease Monitoring.

Determine Potential Toxicities of Combination Treatments in PDX Models:

In addition to closely monitoring the weight and activities of PDX tumor bearing mice during the treatment, blood samples collected at the terminal points are sent to comprehensive clinical pathology analyses (blood chemistry) within 24 h after collection. The complete pathology, chemistry and hematology (complete blood count with differential) profile is assayed and detailed results is provided. The results are analysed for signs of potential indications of toxicity similar to what have been described earlier. For pathological analysis, formalin-fixed tumor tissues are processed to paraffin blocks, and sectioning is stained with hematoxylin and eosin. The slides are scanned to create a digital replica of the entire tissues on a glass microscopic slide using ScanScope® XT (Aperio Technologies, Inc., CA) at 0.25 pixel/μm. The scanning process can allow the tissue images to be displayed and analyzed at different magnifications, closely emulating traditional viewing of tissues with a conventional microscope.

Pathological Assessment of Cell Proliferation and Apoptosis in PDX Tumor Sections.

To assess whether the drug combination maintain the enhanced efficacy, harvested PDX tumors are processed to tumor sections and immunohistochemistry is performed.

For anti proliferative assessment, tumor sections are examined for their reduced pERK levels and Ki67 stains which is a marker for tumor cell proliferation, following standard immunohistochemistry procedures. Melanoma specific markers, S100 and HMB-45, are used in conjunction with H&E stains for determining the proportion of melanoma cells within the tumor sections.

For apoptosis assessment, nuclear morphology is assessed for evidence of nuclear fragmentation by fixing tumor sections, staining sections with Hoechst 33342, and counting nuclei displaying fragmented or normal morphology. Alternatively, nuclear changes are assessed by TUNEL, followed by analyzing apoptotic pathways. Mitochondrial transmembrane potential changes are measured with the flow cytometric MitoScreen kit. Concentration and subcellular distribution (translocation from mitochondria to cytosol) of cytochrome c are assessed by Western blot. Expression of anti-apoptotic proteins Bcl-2 and Bcl-xl; pro-apoptotic proteins Bax and Noxa; and phosphorylation status of pro-apoptotic protein Bad are assessed by Western blot. Activation of initiator caspase 9 and effector caspase 3 are assessed by measuring specific proteolytic cleavage of fluorogenic substrates Ac-LEHD-AFC (caspase 9) and Ac-DEVD-AMC (caspase 3).

Focused Western Blot Analysis to Evaluate Combination Treatment Efficacy and to Identify Potential Biomarkers for Clinical Disease Monitoring.

For PDX tumors that are initially vemurafenib-sensitive, a focused western blot analyses is performed to determine changes in key protein levels that are known to confer BRAFi or MEKi-resistance and identify potential biomarkers useful for future monitoring of therapeutic efficacy using serial tumor biopsies collected during the experiments. In particularly, based on the data presented above, the efforts are focused on examining elements in MAPK, PDGFβ, PI3K/AKT, and apoptotic pathways since they are well known to involve in vemurafenib-resistance. Expression level of proteins of RAS, RAF, RAF, MEK1/2, phospho-MEK1/2 (Ser217/221), ERK1/2, phospho-ERK1/2 (Thr202/Tyr204), AKT, phospho-AKT (Ser473), PDGFβ, cleaved PARP or caspase-3 are analyzed, similar to the work with the A375RF21 model. For PDX tumors that are vemurafenib-resistant, their gene profiles are obtained for P0 tumor determine the baseline resistant mechanisms and monitor the therapeutic efficacy by focused western blot analysis on those proteins responsible for the initial baseline resistance.

In addition, the use of taxanes including docetaxel only gives a modest survival advantage with most patients eventually progressing because of inherent of acquired drug resistance. One of the major resistant mechanisms is mediated by the ABC-transporters that can reduce intracellular concentrations of docetaxel. Therefore, in addition to monitor protein levels responsible for BRAFi/MEKi resistance, the potential development to docetaxel is monitored by examining the expression of key ABC-transporters include P-glycoprotein (Pgp), multidrug resistance protein (MRP), and breast cancer resistant proteins (BCRP), using similar procedures described in previous studies. Protein extractions, western blot and antigen detection are performed according to standard protocols, with modifications depending on the target antigen. Protein levels are accurately quantified by densitometry analysis (average from triplicated experiments).

Expected Results, Pitfalls, and Alternative Approaches.

The combination of docetaxel with a BRAFi or MEKi is expected to be effective against both vemurafenib-sensitive and vemurafenib-resistant PDX models. Because all drugs used in this study have been approved, if proved effective, results from this aim are highly translational and can be tested quickly in clinical to serve as a first-line combination therapy to benefit patients immediately.

The Combination of an ABI (Novel Tubulin Inhibitors) with a BRAFi or MEKi Suppresses Acquired BRAFi-Resistance and Secondary Taxane-Resistance in PDX Tumors.

TABLE 17

ABIs showed excellent potency against all tested melanoma cell lines including highly metastatic and multidrug resistant cell lines.

| | IC$_{50}$ ± SEM (nmol/L) (n = 3) | | | | | | | | |
|---|---|---|---|---|---|---|---|---|---|
| | 17ya | 12cb | 12da | 12fb | Paclitaxel | Vinblastine | Colchicine | ABT-751 | SN-38 |
| A375 | | 31 ± 5 | 9 ± 2 | 52 ± 4 | 12 ± 3 | 1 ± 0.1 | 20 ± 3 | 685 ± 108 | ND |
| A375MA2 | | 44 ± 5 | 8 ± 1 | 55 ± 4 | 8 ± 1 | 1 ± 0.2 | 18 ± 2 | 265 ± 36 | ND |
| B16-F1 | | 63 ± 7 | 46 ± 5 | 73 ± 6 | 17 ± 2 | 5 ± 1 | 29 ± 5 | 2127 ± 351 | ND |
| WM-164 | | 28 ± 3 | 8 ± 2 | 74 ± 9 | 18 ± 3 | 0.6 ± 0.1 | 10 ± 2 | 661 ± 56 | ND |
| MDR1 (P-gp) | | | | | | | | | |
| MDA-MB-435* | 4 ± 1 | 24 ± 2 | 5 ± 1 | 41 ± 2 | 4 ± 1 | 0.4 ± 0.1 | 10 ± 1 | 417 ± 23 | ND |
| MDA-MB-435/LCC6MDR1 | 4 ± 1 (1) | 30 ± 4 (1) | 11 ± 2 (2) | 38 ± 2 (1) | 277 ± 4 (69) | 11 ± 1 (28) | 658 ± 50 (66) | 577 ± 31 (1) | ND |
| OVCAR-8* | 13 ± 1 | 25 ± 2 | 11 ± 1 | 45 ± 2 | 10 ± 0.2 | 2 ± 0.1 | 12 ± 1 | 785 ± 17 | 2 ± 0.2 |
| 20 ± 1 (1.5) MRP | 13 ± 1 (0.5) | 5 ± 0.1 (0.5) | 20 ± 6 (0.4) | 5109 ± 170 (511) | 570 ± 84 (285) | 737 ± 51 (61) | 864 ± 42 (1) | 10 ± 1 (5) | |
| HEK293-pcDNA3.1* | ND | 12 ± 2 | 9 ± 1 | 54 ± 0.3 | 9 ± 0.3 | 5 ± 0.1 | 3 ± 0.4 | 645 ± 153 | 3 ± 0.4 |
| HEK293-MRP1 | ND | 16 ± 2 (1) | 8 ± 1 (0.9) | 33 ± 7 (0.6) | 30 ± 3 (3) | 24 ± 1 (5) | 5 ± 0.1 (2) | 717 ± 28 (1) | 9 ± 0.04 (3) |
| HEK293-MRP2 BCRP | ND | 14 ± 4 (1) | 8 ± 0.3 (0.9) | 39 ± 12 (0.7) | 37 ± 2 (4) | 28 ± 2 (6) | 3 ± 0.3 (1) | 747 ± 7 (1) | 7 ± 0.1 (2) |
| HEK293-482R2 | ND | 17 ± 1 (1) | 8 ± 1 (0.9) | 23 ± 3 (0.4) | 50 ± 1 (6) | 25 ± 1 (5) | 5 ± 0.1 (2) | 653 ± 72 (1) | 123 ± 28 (41) |

Notes:
*parental cell line to drug resistant cell subline;
MDR1 were overexpressed in MDA-MB-435/LCC6MDR1 and NCI/ADR-RES;
MRP1, MRP2 and BCRP were overexpressed in HEK293-MRP1, HEK293-MRP2, and HEK293-482R2.
The resistance indexes (numbers in the parenthesis) were calculated by dividing IC$_{50}$ values on the resistant cell subline by that of the matching parental cell line.
Abbreviations:
N/A, not applicable since they bind to tubulin at different sites.
ND, not determined.

Clinical use of docetaxel could lead to secondary taxane-resistance in the combination of docetaxel with a BRAFi/MEKi treatment. Compared with approved tubulin inhibitors, ABIs bind to a different site in tubulin and have distinct advantages including high potency, acceptable oral bioavailability, excellent pharmacokinetic properties, and effectiveness in overcoming ABC-transporter mediated multidrug resistance (Table 17). Preliminary toxicity studies indicated that ABIs have significantly lower toxicities than existing tubulin inhibitors such as docetaxel or vinblastine. Therefore, in order to develop new generations of combination treatment to overcome potential secondary resistance to the first-line combination containing docetaxel, the efficacy of combinations of a BRAFi/MEKi with two advanced ABIs (compound 12da and compound 17ya) is determined in PDX models. Both ABIs and the approved BRAFi/MEKi are orally active agents. No adverse drug-drug interactions between a tubulin inhibitor and a BRAFi/MEKi has been reported. Therefore, based on A375RF21 xenograft model, co-administration of an ABI with vemurafenib, dabrafenib, or trametinib orally is likely to retain strong synergies in suppressing melanoma tumor growth in PDX tumors.

The same procedures described above are followed as briefly described below:

c. Determine the In Vivo Efficacy in Vemurafenib-Sensitive PDX Tumors Treated with the Combination of an ABI (Compounds 12da and 17ya) with Vemurafenib, Dabrafenib, or Trametinib.

NSG mice (typically 1-2 mice) implanted with small passage two (P2) PDX tumors are utilized for this study. The tumor is grown to about 1,500 mm$^3$ and is propagated to up to five new NSG mice to provide sufficient P3 tumors. The genetic profile and histology of five randomly picked P3 tumors is characterized and verified with data from original P0 tumors to ensure overall genetic and histological fidelity, before tumor pieces are implanted into a large number of mice for subsequent studies (FIG. 27).

Since the pharmacokinetic properties for both ABIs and BRAFi/MEKi have been established, similar to described above, the combination efficacy, potential toxicity, and possible disease monitoring biomarkers are determined in three independent vemurafenib-sensitive PDX models. As results for standard single-agent vemurafenib, dabrafenib, or trametinib treatments are obtained already as described above, when the evaluation of the combination containing docetaxel is finished, the study continues on the combination treatment by including the best efficacy identified in the docetaxel combination as well as the reference combination (dabrafenib+trametinib). Therefore, for compound 12da, small pieces (~3 mm$^3$) of vemurafenib-sensitive P3 tumors are surgically implanted subcutaneously into the flanks of 49 anesthetized nude mice (6-week-old male athymic nude mice). When the tumors reach approximately 100-200 mm$^3$ after 2~3 weeks of implantation, mice are randomized into seven groups (n=7), minimizing weight and tumor size differences: a negative control group with vehicle only (Group 1); one single-agent compound 12da (15 mg/kg [53], Group 2); and five combination treatment groups including continuous daily treatment using dabrafenib+trametinib (reference combination, Group 3), the most efficacious combination containing docetaxel identified above (Group 4), and compound 12da in combinations with vemurafenib, dabrafenib, or trametinib (Group 5-7). Tumors are measured every three days with a caliper, and their volumes are calculated using the formula: (width×length)/2. Tumors are monitored for up to 90 days or until the tumor has completely regressed. Potential development of drug resistance are closely monitored by tumor growth kinetics. Mice weight, activities, and appearance are closely monitored for potential toxicity. Terminal blood samples are sent to blood chemistry analyses and tumor sections are processed for clinical pathology analyses. In addition, serial tumor biopsies from each tumor are taken weekly with a fine needle following reported procedures. Focused western blot analyses on examining elements in the MAPK, PDGFβ-PI3K/AKT, and apoptosis pathways are performed to monitor acquired drug resistance and potential biomarkers for assessing therapeutic efficacy. The experiments are repeated using two additional vemurafenib-sensitive PDX tumors, thus for testing with compound 12da, up to 49×3=147 mice are used. To finish testing with compound 17ya, up to 147×2=294 mice are used.

d. Determine the In Vivo Efficacy in Vemurafenib-Resistant PDX Tumors Treated with the Combination of an ABI (12da or 17ya) with Vemurafenib, Dabrafenib, or Trametinib.

Similar to the experiment procedures briefly described in the above sections the experiments are repeated using three vemurafenib-resistant PDX tumor models and up to 294 mice are used to determine the efficacy in the combination of an ABI (compound 12da or 17ya) with vemurafenib, dabrafenib, or trametinib. Tumor sizes, serial tumor biopsies, terminal blood samples, and major organs are measured or collected to assess efficacy and potential toxicities, similar to described in the previous section. The potential toxicity is determined by monitoring weight loss during experiments and post pathological analyses. Focused western blot analyses are performed to evaluate treatment efficacy and to identify potential biomarkers as detailed above.

Expected Results, Pitfalls, and Alternative Approaches

The combination of an ABI with a BRAFi or MEKi is expected to be effective against both vemurafenib-sensitive and resistant PDX models. Such combinations are expected to be comparable or have better efficacy with those containing docetaxel, but have the benefit to overcome potential secondary drug resistance associated with the use of docetaxel.

The Combination of a Tubulin Inhibitor with a BRAFi or MEKi is Effective in Models of Melanoma Metastasis.

Figure 28:
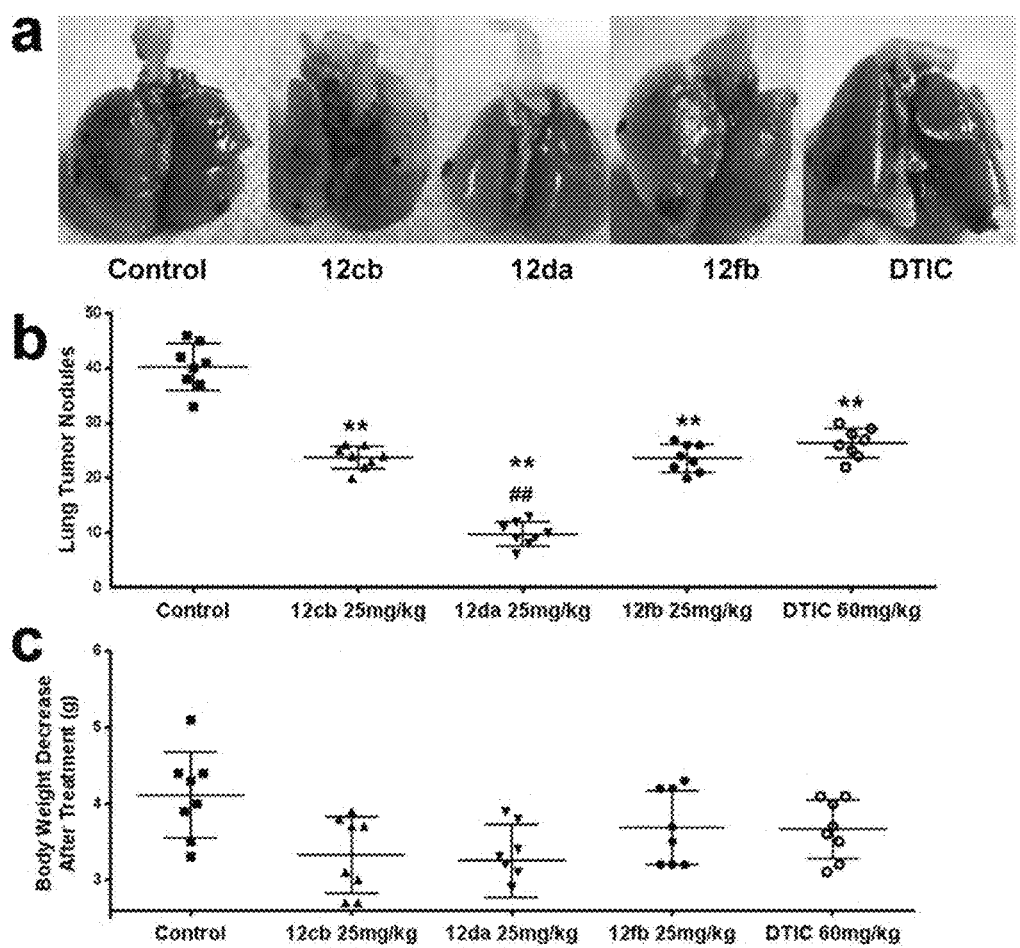
FIG. 28 depicts the inhibition by ABI's 12cb, 12da, and 12fb of metastasis of melanoma to the lungs in mice. Panel A: Representative photos of lungs with melanoma nodules (black dots, n=8 per group). Treatment was i.p. injection 5 days per week for 2 weeks. Panel B: Number of melanoma nodules on each lung. Points: individual nodule number; long line in the middle: mean; short line on the top and bottom: 95% confidence intervals ** and ##: p<0.01. Panel C: Mouse body weight changes during the experiment. Points: means; bars: SD. Control: vehicle solution only.

The major challenge in providing prolonged survival for melanoma patients is to find an effective treatment for melanoma metastasis. Due to the subcutaneous nature, PDX models rarely produce metastasis. Therefore, in addition to evaluating the efficacy of systematically administered drug combinations against melanoma tumors in these subcutaneous PDX model as described above, the combination efficacy in experimental lung metastatic models is determined using nude mice. The lung metastatic model is selected because this is one of the major metastatic sites for malignant melanoma, and has the worst 5-year survival rate among all melanoma metastases. The PI's lab has a well-established protocol to assess melanoma lung metastasis (FIG. 28), and has shown that ABIs as a single agent can effectively suppress melanoma lung metastasis (compound 17ya shown as an example). Similar models have been widely used in the literature. In addition, unlike cells cultured from long-established cell lines such as A375, early passage single-cell suspensions directly isolated from PDX tumors never grow in plastics. Therefore, they are likely to retain tumor heterogeneity, genetic fidelity, and responses to drug treatments expected to cells in the original patient tumors.

Isolation of Single-Cell Suspensions from Early Passage PDX Tumors.

Single-cell suspensions are made from PDX tumors following standard protocols. Briefly, after the NSG mice are purchased (typically 1-2 mice) and implanted with small passage two (P2) PDX tumors, the tumor is grown to about 2,000 mm³. Within 1 hour of surgical removal from the NSG mice, fresh tumors are washed 3 times with DMEM media to avoid contamination (5 minutes each on ice). PDX tumors free of necrotic and connective tissue are minced into small pieces (1×1 mm or smaller) using sterile crossed blades under sterile conditions. Tumor pieces are mixed with ultra-pure collagenase type IV (Gibco, 17104-019) solution at concentration 1 mg/mL in DMEM media and incubated for 1 h at 37° C. with gentle shaking. After digestion, the resulting mixture is filtered through a nylon mesh cell strainer (BD Biosciences, 70 μm pores, 352340) to obtain single-cell suspensions. Cell number is counted with an Auto T4 Cell Counter, pelleted, and re-suspended in DMEM for tail-vein injection. The viability of cells obtained by this method in trypan blue test is typically more than 95%.

Suppression Lung Metastasis Using Vemurafenib-Sensitive or Vemurafenib-Resistant Single-Cell Suspensions.

As the best combinations are already ranked in the previous study described above, the optimal combinations are tested. The approved dabrafenib+trametinib combination is always included as the reference combination. Briefly, seventy-five thousand single cells suspended in 100 μL DMEM produced from a vemurafenib-sensitive or vemurafenib-resistant PDX tumor model are injected into each of the 50 nude mice (6-week-old, either sex) via their tail veins, and mice are divided into five groups (n=10): a negative control group with vehicle only (Group 1); a reference combination treatment group with dabrafenib+trametinib (Group 2); the optimal combination of docetaxel with a BRAFi/MEKi as determined above (Group 3); the optimal combination of compound 12da or 17ya with a BRAFi/MEKi as determined above (Group 4 and 5). The number of mice in each group is increased from 7 to 10 to ensure statistical significance, because of the anticipated higher variation with this experimental lung metastasis model. After 7-10 days of tumor cell injection, mice are treated with the vehicle or drug combinations orally (except docetaxel which is not orally available and is administered via i.v. route) daily for four weeks. At the end of treatment, all mice are sacrificed by CO₂ inhalation followed by cervical dislocation. Mice are dissected to remove the lungs. The number of tumor nodules in the lung is accurately counted, and the efficacy of the treatments is evaluated based on the absence or reduced number of tumor nodules in lung. The melanoma nature of nodules and tumor morphology is also examined after fixation and processing for paraffin embedded sections with following H&E stain. To perform this experiment using cells from the three vemurafenib-sensitive and three vemurafenib-resistant PDX models, up to 50×3×2=300 nude mice are expected to be used.

Expected Results, Pitfalls, and Alternative Approaches

These combinations are expected to be effective in reducing the number of lung metastasis in vemurafenib-sensitive tumors, and to a less extent, in vemurafenib-resistant tumors. The combinations containing a tubulin inhibitor (docetaxel, compound 12da or 17ya) are likely to be more effective than the reference combination of dabrafenib+trametinib, especially for vemurafenib-resistant tumor metastasis. In the unlikely case where single-cell suspensions isolated from PDX tumors fails to form lung metastasis, as an alternative approach, established early passage $BRAF^{V600E}$ human melanoma lines (YUGEN8, YUSAC2, YUKOLI, and YUSIK) are used.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A pharmaceutical composition comprising (a) a tubulin inhibitor (b) at least one of a BRAF inhibitor, and (c) a pharmaceutically acceptable carrier, wherein the tubulin inhibitor is a compound represented by the structure of formula II:

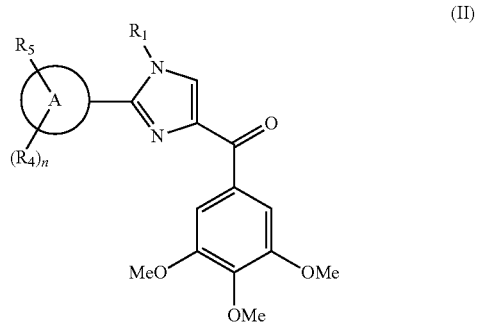

wherein

A is single or fused aromatic or heteroaromatic ring system;

$R_1$ is H, $C_1$-$C_6$ linear or branched alkyl, aryl, phenyl, benzyl, haloalkyl, aminoalkyl, —OCH₂Ph, SO₂-aryl, SO₂-phenyl, —(C=O)-aryl, —(C=O)-phenyl or OH;

$R_4$ and $R_5$ are each independently hydrogen, $C_1$-$C_6$ linear or branched alkyl, $C_1$-$C_6$ linear or branched haloalkyl, $C_1$-$C_6$ linear or branched alkoxy, $C_1$-$C_6$ linear or branched haloalkoxy, F, Cl, Br, I, CF₃, CN, —CH₂CN, NH₂, OH, —OC(O)CF₃, alkylamino, aminoalkyl, —OCH₂Ph, —NHCO— alkyl, COOH, —C(O)Ph, C(O)O-alkyl, C(O)H, —C(O)NH₂ or NO₂; and n is an integer between 1-4;

or its pharmaceutically acceptable salt, N-oxide, hydrate, tautomer or isomer.

2. The composition of claim 1, wherein said compound of formula II is:

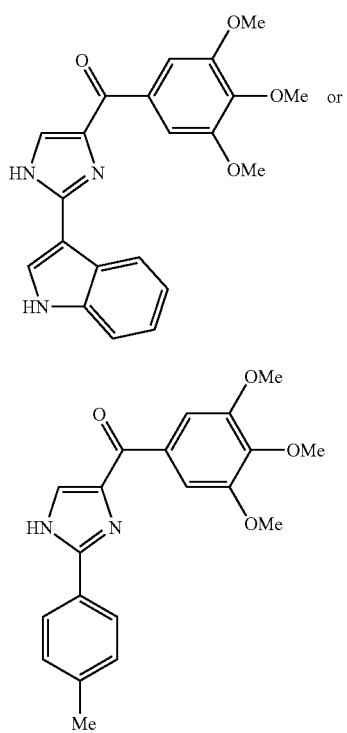

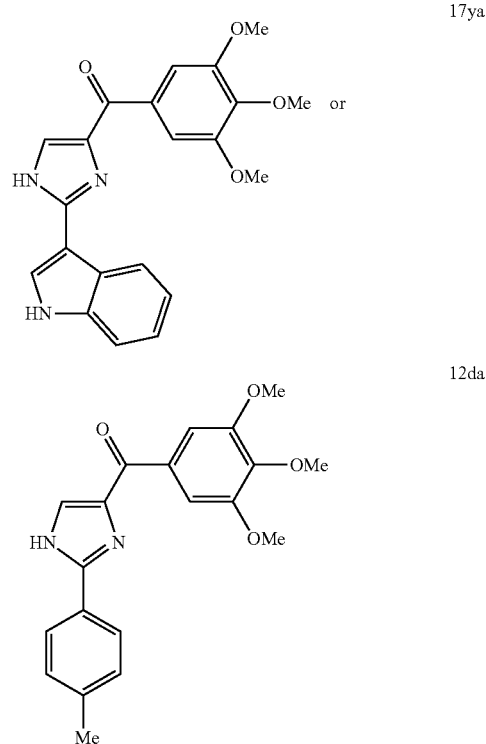

or a pharmaceutically acceptable salt thereof, or a combination thereof.

3. The composition of claim 1, wherein said BRAF inhibitor is vemurafenib, dabrafenib, GDC-0879, PLX-4720, sorafenib tosylate, LGX818 or any combination thereof.

4. The composition of claim 2, comprising a compound represented by the following structure:

or a pharmaceutically acceptable salt thereof, in combination with a BRAF inhibitor and a pharmaceutically acceptable carrier, wherein said BRAF inhibitor is vemurafenib.

\* \* \* \* \*